US011202840B2

(12) United States Patent
Duan et al.

(10) Patent No.: US 11,202,840 B2
(45) Date of Patent: Dec. 21, 2021

(54) MODIFIED DYSTROPHIN PROTEINS

(71) Applicant: THE CURATORS OF THE UNIVERSITY OF MISSOURI, Columbia, MO (US)

(72) Inventors: Dongsheng Duan, Columbia (MO); Yi Lai, Columbia, MO (US); Junling Zhao, Columbia, MO (US); Yongping Yue, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 374 days.

(21) Appl. No.: 16/311,236

(22) PCT Filed: Jun. 21, 2017

(86) PCT No.: PCT/US2017/038418

§ 371 (c)(1),
(2) Date: Dec. 19, 2018

(87) PCT Pub. No.: WO2017/223128

PCT Pub. Date: Dec. 28, 2017

(65) Prior Publication Data

US 2019/0184033 A1 Jun. 20, 2019

Related U.S. Application Data

(60) Provisional application No. 62/352,927, filed on Jun. 21, 2016, provisional application No. 62/357,865, filed on Jul. 1, 2016, provisional application No. 62/367,559, filed on Jul. 27, 2016.

(51) Int. Cl.

| | |
|---|---|
| ***A61K 48/00*** | (2006.01) |
| ***A61K 35/28*** | (2015.01) |
| ***A61K 9/00*** | (2006.01) |
| ***A61P 25/14*** | (2006.01) |
| ***C07K 14/47*** | (2006.01) |
| ***C12N 15/62*** | (2006.01) |
| ***C12N 5/0775*** | (2010.01) |
| ***C12N 15/86*** | (2006.01) |
| ***C12N 15/85*** | (2006.01) |
| *A61K 38/00* | (2006.01) |
| *A61K 35/00* | (2006.01) |

(52) U.S. Cl.

CPC .......... *A61K 48/005* (2013.01); *A61K 9/0019* (2013.01); *A61K 35/28* (2013.01); *A61K 48/00* (2013.01); *A61P 25/14* (2018.01); *C07K 14/4716* (2013.01); *C12N 5/0663* (2013.01); *C12N 15/62* (2013.01); *C12N 15/85* (2013.01); *C12N 15/86* (2013.01); *A61K 35/00* (2013.01); *A61K 38/00* (2013.01); *C07K 2319/00* (2013.01); *C07K 2319/01* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,580,859 | A | 12/1996 | Felgner et al. |
| 2004/0033604 | A1 | 2/2004 | Kobinger et al. |
| 2007/0042462 | A1 | 2/2007 | Hildinger |
| 2008/0044393 | A1 | 2/2008 | White et al. |
| 2008/0249052 | A1 | 10/2008 | Duan et al. |
| 2014/0140969 | A1 | 5/2014 | Beausejour et al. |
| 2014/0234255 | A1 | 8/2014 | Lai et al. |
| 2016/0115488 | A1 | 4/2016 | Zhang et al. |
| 2016/0153004 | A1 | 6/2016 | Zhang et al. |
| 2016/0175462 | A1 | 6/2016 | Zhang et al. |

OTHER PUBLICATIONS

Zhao, et al. (2016) "Dystrophin contains multiple independent membrane-binding domains", Human Molecular Genetics, 25(17): 3647-53. (Year: 2016).*

Li et al., "A highly functional mini-dystrophin/GFP fusion gene for cell and gene therapy studies of Duchenne muscular dystrophy", Human Molecular Genetics, 2006, pp. 1610-1622, vol. 15, No. 10.

Zhang et al. "Novel Mini-Dystrophin Gene Dual Adeno-Associated Virus Vectors Restore Neuronal Nitric Oxide Synthase Expression at the Sarcolemma", Human Gene Therapy (2012) pp. 98-103, vol. 23, No. 1; XP055619093, GB ISSN: 1043-0342, DOI: 101089/hum. 2011.131 *p. 98 col. 2, p. 99 col. 2 para. 2, 3, Fig. 1*.

Legardinier et al., "Mapping of the Lipid-Binding and Stability Properties of the Central Rod Domain of Human Dystrophin", Journal of Molecular Biology, 2009, pp. 546-558, vol. 389.

Legardinier et al., "Sub-Domains of the Dystrophin Rod Domain Display Contrasting Lipid-Binding and Stability Properties", Biochimica et Biophysica Acta, 2008, pp. 672-682, vol. 1784.

Levitt et al., "Definition of an Efficient Synthetic Poly(A) Site", Genes & Development, 1989, pp. 1019-1025, vol. 3.

Liadaki et al., "Co-Detection of GFP and Dystrophin in Skeletal Muscle Tissue Sections", Bio Techniques, 2007, pp. 699-700, vol. 42, No. 6.

(Continued)

*Primary Examiner* — Robert M Kelly

(74) *Attorney, Agent, or Firm* — Thompson Coburn LLP; William A. Holtz

(57) ABSTRACT

Synthetic nucleic acids encoding mini and microdystrophin genes comprising the membrane binding motifs or domains of the R10-R11-R12 region are provided. Also provided are vectors, host cells, and related methods of using the same to treat a subject suffering from Duchenne muscular dystrophy (DMD), Becker muscular dystrophy (BMD) or X-linked dilated cardiomyopathy (XLDC), or for ameliorating one or more adverse effects of DMD, BMD, or XLDC. Also provided are a fusion protein comprising a nNOS binding domain of dystrophin R16-R17 that is operably linked to a syntrophin PDZ domain and synthetic nucleic acids comprising the same that can be used to treat subjects with diseases characterized by loss of sarcolemmal neuronal nitric oxide synthase (nNOS) activity.

24 Claims, 28 Drawing Sheets

Specification includes a Sequence Listing.

(56) References Cited

OTHER PUBLICATIONS

Linder et al., "Palmitoylation: Policing Protein Stability and Traffic", Nature Reviews Molecular Cell Biology, 2007, pp. 74-78, vol. 8, No. 1.
Liu et al., "Adeno-Associated Virus-Mediated Microdystrophin Expression Protects Young mdx Muscle from Contraction-Induced Injury", Mol Ther., 2005, pp. 245-256, vol. 11, No. 2.
Luna et al., "Cytoskeleton-Plasma Membrane Interactions", Science, 1992, pp. 955-964, vol. 258, No. 5084.
Maconochie et al., "The Cysteine-Rich and C-Terminal Domains of Dystrophin are not Required for Normal Costameric Localization in the Mouse", Transgenic Research, 1996, pp. 123-130, vol. 5.
Mariani et al., "A Tightly Membrane-Associated Subpopulation of Spectrin Is $^3$H-Palmitoylated", The Journal of Biological Chemistry, 1993, pp. 12996-13001, vol. 268, No. 17.
Mendell et al., "Dystrophin Immunity in Duchenne's Muscular Dystrophy", The New Englend Journal of Medicine, 2010, pp. 1429-1437, vol. 363, No. 15.
Odom et al., "Gene Therapy of mdx Mice with Large Truncated Dystrophins Generated by Recombination Using rAAV6", Molecular Therapy, 2011, pp. 36-45, vol. 19, No. 1.
Oku et al., "In Silico Screening for Palmitoyl Substrates Reveals a Role for DHHC1/3/10 (zDHHC1/3/11)-Mediated Neurochondrin Palmitoylation in Its Targeting to Rab5-Positive Endosomes", The Journal of Biological Chemistry, 2013, pp. 19816-19829, vol. 299, No. 27.
Petrof et al., "Dystrophin Protects the Sarcolemma from Stresses Developed During Muscle Contraction", Proc. Natl. Acad. Sci. USA, 1993, pp. 3710-3714, vol. 90.
Prior et al., "Spectrum of Small Mutations in the Dystrophin Coding Region", Am. J. Hum. Genet., 1995, pp. 22-33, vol. 57.
Rafael et al., "Forced Expression of Dystrophin Deletion Constructs Reveals Structure-Function Correlations", The Journal of Cell Biology, 1996, pp. 93-102, vol. 134, No. 1.
Rapaport et al., "Dp71, the Nonmuscle product of the Duchenne Musuclar Dystrophy Gene is Associated with the Cell Membrane", FEBS Letters, 1993, pp. 197-202, vol. 328, No. 12.
Recan et al., "Are Cysteine-Rich and COOH-Terminal Domains of Dystrophin Cirical for Sarcolemmal Localization?", J. Clin. Invest., 1992, pp. 712-716, vol. 89.
Ren et al., "CSS-Palm 2.0: An Updated Software for Palmitoylation Sites Prediction", Protein Engineering, Design & Selection, 2008, pp. 639-644, vol. 21, No. 11.
Rumeur et al., "Binding of the Dystrophin Second Repeat to Membrane Di-Oleyl Phospholipids is Dependent Upon Lipid Packing", Biochimica et Biophysica Acta, 2007, pp. 648-654, vol. 1768.
Rumeur et al., "Dystrophin: More Than Just the Sum of its Parts", Biochimica et Biophysica Acta, 2010, pp. 1713-1722, vol. 1804, No. 9.
Rumeur et al., "Interaction of Dystrophin Rod Domain with Membrane Phospholipids", The Journal of Biological Chemistry, 2003, pp. 5993-6001, vol. 278, No. 8.
Rybakova et al., "A New Model for the Interaction of Dystrophin with F-Actin", The Journal of Cell Biology, 1996, pp. 661-672, vol. 135, No. 3.
Sadoulet-Puccio et al., "Dystrobrevin and Dystrophin: An Interaction Through Coiled-Coil Motifs", Proc. Natl. Acad. Sci. USA, 1997, pp. 12413-12418, vol. 94.
Sarkis et al., "Resisting Sarcolemmal Rupture: Dystrophin Repeats Increase Membrane-Actin Stiffness", The FASEB Journal, 2013, pp. 359-367, vol. 27.
Sarkis et al., "Spectrin-Like Repeats 11-15 of Human Dystrophin Show Adaptations to a Lipidic Envrionment", The Journal of Biological Chemistry, 2011, pp. 30481-30491, vol. 286, No. 35.
Sheetz et al., "Continuous Membrane-Cytoskeleton Adhesion Requires Continuous Accommodation to Lipid and Cytoskeleton Dynamics", Annu. Rev. Biophys. Biomol. Struct., 2006, pp. 417-434, vol. 35.
Shin et al., "A Simplified Immune Suppression Scheme Leads to Persistent Micro-Dystrophin Expression in Duchenne Muscular Dystrophy Dogs", Human Gene Therapy, 2012, pp. 202-209, vol. 23.
Shin et al., "Microdystrophin Ameliorates Muscular Dystrophy in the Canine Model of Duchenne Muscular Dystrophy", Molecular Therapy, 2013, pp. 750-757, vol. 21, No. 4.
Shin et al., "Recombinant Adeno-Associated Viral Vector Production and Purification", Methods Mol Biol., 2012, pp. 267-284, vol. 798.
Straub et al., "Animal Models for Musuclar Dystrophy Show Different patterns of Sarcolemmal Disruption", Cell Biology, 1997, pp. 375-385, vol. 139, No. 2.
Suminaga et al., "C-Terminal Truncated Dystrophin Identified in Skeletal Muscle of an Asymptomatic Boy with a Novel Nonsense Mutation of the Dystrophin Gene", Pediatric Research, 2004, pp. 739-743, vol. 56, No. 5.
Sun et al., "Overcoming Adeno-Associated Virus Vector Size Limitation Through Viral DNA Heterodimerization", Nature Medicine, 2000, pp. 599-602, vol. 6, No. 5.
Suzuki et al., "Glycoprotein-Binding Site of Dystrophin is Confined to the Cysteine-Rich Domain and the First Half of the Carboxy-Terminal Domain", Federation of European Biochemical Societies, 1992, pp. 154-160, vol. 308, No. 2.
Suzuki et al., "Mammalian a1- and b1-Syntrophin Bind to the Alternative Splice-Prone Region of the Dystrophin COOH Terminus", The Journal of Cell Biology, 1995, pp. 373-381, vol. 128, No. 3.
Suzuki et al., "Molecular Organization at the Glycoprotein-Complex-Binding Site of Dystrophin", Eur. J. Biochem., 1994, pp. 283-292, vol. 220.
Topinka et al., "N-Terminal Palmitoylation of PSD-95 Regulates Association with Cell Membranes and Interactions with K+ Channel Kv1.4", Neuron, 1998, pp. 125-134, vol. 20.
Wang et al., "Adeno-Associated Virus Vector Carrying Human Minidystrophin Genes Effectively Ameliorates Muscular Dystrophy in mdx Mouse Model", PNAS, 2000, pp. 13714-13719, vol. 97, No. 25.
Wang et al., "Construction and Analysis of Compact Muscle-Specific Promoters for AAV Vectors", Gene Therapy, 2008, pp. 1489-1499, vol. 15.
Wang et al., "Successful Regional Delivery and Long-Term Expression of a Dystrophin Gene in Canine Muscular Dystrophy: A Preclinical Model for Human Therapies", Molecular Therapy, 2012, pp. 1501-1507, vol. 20, No. 8.
Yan et al., "Trans-Splicing Vectors Expand the Utility of Adeno-Associated Virus for Gene Therapy", PNAS, 2000, pp. 6716-6721, vol. 97, No. 12.
Yanai et al., "Palmitoylation of Huntingtin by HIP14 is Essential for Its Trafficking and Function", Nat Neurosci., 2006, pp. 824-831, vol. 9, No. 6.
Yang et al., "Dystrophin Deficiency Compromises Force Production of the Extensor Carpi Ulnaris Muscle in the Canine Model of Duchenne Muscular Dystrophy", PLOS One, 2012, pp. 1-7, vol. 7, No. 9.
Yang et al., "Identification of a-Syntrophin Binding to Syntrophin Triplet, Dystrophin, and Utrophin", The Journal of Biological Chemistry, 1995, pp. 4975-4978, vol. 270, No. 10.
Yoshida et al., "Biochemical Evidence for Association of Dystrobrevin with the Sarcoglycan-Sarcospan Complex as a Basis for Understanding Sarcoglycanopathy", Human Molecular Genetics, 2000, pp. 1033-1040, vol. 9, No. 7.
Yue et al., "C-Terminal-Truncated Microdystrophin Recruits Dystrobrevin and Syntrophin to the Dystrophin-Associated Glycoprotein Complex and Reduces Muscular Dystrophy in Symptomatic Utrophin/Dystrophin Double-Knockout Mice", Mol Ther., 2006, pp. 79-87, vol. 14, No. 1.
Yue et al., "Safe and Bodywide Muscle Transduction in Young Adult Duchenne Muscular Dystrophy Dogs with Adeno-Associated Virus", Human Molecular Genetics, 2015, pp. 5880-5890, vol. 24, No. 20.
Zhang et al., "Dual AAV Therapy Ameliorates Exercise-Induced Muscle Injury and Functional Ischemia in Murine Models of Duchenne Muscular Dystrophy", Human Molecular Genetics, May 15, 2013, pp. 3720-3729, vol. 22.

(56) References Cited

OTHER PUBLICATIONS

Zhong et al., "Next Generation of Adeno-Associated Virus 2 Vectors: Point Mutations in Tyrosines Lead to High-Efficiency Transduction at Lower Doses", PNAS, 2008, pp. 7827-7832, vol. 105, No. 22.
Allen et al., "Absence of Dystrophin Disrupts Skeletal Muscle Signaling: Roles of $Ca^{2}$+, Reactive Oxygen Species, and Nitric Oxide in the Development of Muscular Dystrophy", Physiological Reviews, 2016, pp. 253-305, vol. 96, No. 1.
Amann et al., "A Cluster of Basic Repeats in the Dystrophin Rod Domain Binds F-Actin Through an Electrostatic Interaction", The Journal of Biological Chemistry, 1998, pp. 28419-28423, vol. 273, No. 43.
Bajanca et al., "In Vivo Dynamics of Skeletal Muscle Dystrophin in Zebrafish Embryos Revealed by Improved FRAP Analysis", 2015, pp. 1-32.
Banks et al., "The Polyproline Site in Hinge 2 Influences the Functional Capacity of Truncated Dystrophins", Plos Genetics, 2010, pp. 1-10, vol. 6, No. 5.
Barnabei et al., "Severe Dystrophic Cardiomyopathy Caused by the Enteroviral Protease 2A-Mediated C-Terminal Dystrophin Cleavage Fragment", Science Translational Medicine, 2015, pp. 1-11, vol. 7.
Bennett et al., "An Adaptable Spectrin/Ankyrin-Based Mechanism for Long-Range Organization of Plasma Membranes in Vertebrate Tissues", Current Topics in Membranes, 2016, pp. 143-184, vol. 77.
Bok et al., "Lipid-Binding Role of bII-Spectrin Ankyrin-Binding Domain", Cell Biology International, 2007, pp. 1482-1494, vol. 31.
Bostick et al., "AAV Micro-Dystrophin Gene Therapy Alleviates Stress-Induced Cardiac Death but not Myocardial Fibrosis in > 21-m-Old mdx Mice, an End-Stage Model of Duchenne Muscular Dystrophy Cardiomyopathy", Journal of Molecular and Cellular Cardiology, May 12, 2012, pp. 217-222, vol. 53.
Bostick et al., "Cardiac Expression of a Mini-Dystrophin That Normalizes Skeletal Muscle Force Only Partially Restores Heart Function in Aged Mdx Mice", Molecular Therapy, 2009, pp. 253-261, vol. 17, No. 2.
Bunnell et al., "Destabilization of the Dystrophin-Glycoprotein Complex without Functional Deficits in a-Dystrobrevin Null Muscle", PLOS One, 2008, pp. 1-6, vol. 3, No. 7.
Campbell et al., "Association of Dystrophin and an Integral Membrane Glycoprotein", Nature, 1989, pp. 259-262, vol. 338.
Chandrasekharan et al., "Introduction of a Human-Specific Deletion in Mouse Cmah Increases Disease Severity in the mdx Model of Duchenne Muscular Dystrophy", Sci Transl Med., 2010, pp. 1-34, vol. 2, No. 42.
Constantin, "Dystrophin Complex Functions as a Scaffold for Signalling Proteins", Biochimica et Biophysica Acta, 2014, pp. 635-642, vol. 1838.
Cox et al., "Dp71 can Restore the Dystrophin-Associated Glycoprotein Complex in Muscle but Fails to Prevent Dystrophy", Nature Genetics, 1994, pp. 333-339, vol. 8.
Crawford et al., "Assembly of the Dystrophin-Associated Protein Complex Does Not Require the Dystrophin COOH-Terminal Domain", The Journal of Cell Biology, 2000, pp. 1399-1409, vol. 150, No. 6.
Das et al., "Purification and Biochemical Characterization of a Protein-Palmitoyl Acyltransferase from Human Erythrocytes", The Journal of Biological Chemistry, 1997, pp. 11021-11025, vol. 272, No. 17.
Dewolf et al., "Interaction of Dystrophin Fragments with Model Membranes", Biophysical Journal, 1997, pp. 2599-2604, vol. 72.
Draviam et al., "Mini-Dystrophin Efficiently Incorporates into the Dystrophin Protein Complex in Living Cells", Journal of Muscle Research and Cell Motility, 2006, pp. 53-67, vol. 27.
Duan et al., "Expanding AAV Packaging Capacity with Trans-Splicing or Overlapping Vectors: A Quantitative Comparison", Molecular Therapy, 2001, pp. 383-391, vol. 4, No. 4.
Dunckley et al., "Independent Localization of Dystrophin N- and C-Terminal Regions to the Sarcolemma of mdx Mouse Myofibres In Vivo", Journal of Cell Science, 1994, pp. 1469-1475, vol. 107.
Einbond et al., "Towards Prediction of Cognate Complexes Between the WW Domain and Proline-Rich Ligands", FEBS Letters, 1996, pp. 1-8, vol. 384.
Ervasti et al., "Membrane Organization of the Dystrophin-Glycoprotein Complex", Cell, 1991, pp. 1121-1131, vol. 66.
Fine et al., "Age-Matched Comparison Reveals Early Electrocardiography and Echocardiography Changes in Dystrophin-Deficient Dog", Neuromuscul Disord., 2011, pp. 453-461, vol. 21, No. 7.
Fritz et al., "Expression of Deletion-Containing Dystrophins in mdx Muscle: Implicatons for Gene Therapy and Dystrophin Function", Pediatric Research, 1995, pp. 693-700, vol. 37, No. 6.
Gao et al., "The Dystrophin Complex: Structure, Function, and Implications for Therapy", Compr Physiol., 2015, pp. 1223-1239, vol. 5, No. 3.
Gardner et al., "Restoration of all Dystrophin Protein Interactions by Functional Domains in Trans Does Not Rescue Dystrophy", Gene Therapy, 2006, pp. 744-751, vol. 13.
Ghosh et al., "A Hybrid Vector System Expands Adeno-Associated Viral Vector Packaging Capacity in a Transgene-Independent Manner", Molecular Therapy, 2008, pp. 124-130, vol. 16, No. 1.
Ghosh et al., "Expanding Adeno-Associated Viral Vector Capacity: A Tale of Two Vectors", Biotechnology and Genetic Engineering Reviews, 2007, pp. 165-178, vol. 24.
Halbert et al., "Efficient Mouse Airway Transduction Following Recombination Between AAV Vectors Carrying Parts of a Larger Gene", Nature Biotechnology, 2002, pp. 697-701, vol. 20.
Harper et al., "Modular Flexibility of Dystrophin: Implications for Gene Therapy of Duchenne Muscular Dystrophy", Nature Medicine, 2002, pp. 253-261, vol. 8, No. 3.
Helliwell et al., "A Truncated Dystrophin Lacking the C-Terminal Domains is Localized at the Muscle Membrane", American Journal of Human Genetics, 1992, pp. 508-514, vol. 50.
Hillier et al., "Unexpected Modes of PDZ Domain Scaffolding Revealed by Structure of nNOS-Syntrophin Complex", Science, Apr. 30, 1999, pp. 812-815, vol. 284.
Hir et al., "Cholesterol Favors the Anchorage of Human Dystrophin Repeats 16 to 21 in Membrane at Physiological Surface Pressure", Biochimica et Biophysica Acta, 2014, pp. 1266-1273, vol. 1838, No. 5.
Hoffman et al., "Dystrophin: The Protein Product of the Duchenne Muscular Dystrophy Locus", Cell, 1987, pp. 919-928, vol. 51.
Hoffman et al., "Is the Carboxyl-Terminus of Dystrophin Required for Membrane Association? A Novel, Severe Case of Duchenne Muscular Dystrophy", Annals of Neurology, 1991, pp. 605-610, vol. 30, No. 4.
Huang et al., "Structure of a WW Domain Containing Fragment of Dystrophin in Complex with b-Dystroglycan", Nature Structural Biology, 2000, pp. 634-638, vol. 7, No. 8.
Ipsaro et al., "Structural Basis for Spectrin Recognition by Ankyrin", Blood, 2010, pp. 4093-4101, vol. 115, No. 20.
Ipsaro et al., "Structures of the Spectrin-Ankyrin Interaction Binding Domains", Blood, 2009, pp. 5385-5393, vol. 113, No. 22.
Ishikawa-Sakurai et al., "ZZ Domain is Essentially Required for the Physiological Binding of Dystrophin and Utrophin to b-Dystroglycan", Human Molecular Genetics, 2004, pp. 693-702, vol. 13, No. 7.
Johnson et al., "Identification of New Dystroglycan Complexes in Skeletal Muscle", PLOS One, 2013, pp. 1-17, vol. 8, No. 8.
Johnson et al., "Proteomic Analysis Reveals New Cardiac-Specific Dystrophin-Associated Proteins", PLOS One, 2012, pp. 1-12, vol. 7, No. 8.
Judge et al., "Dissecting the Signaling and Mechanical Functions of the Dystrophin-Glycoprotein Complex", Journal of Cell Science, 2006, pp. 1537-1546, vol. 119.
Judge et al., "Expression of the Dystrophin Isoform Dp116 Preserves Functional Muscle Mass and Extends Lifespan Without Preventing Dystrophy in Severely Dystrophic Mice", Human Molecular Genetics, 2011, pp. 4978-4990, vol. 20, No. 24.
Jung et al., "Identification and Characterization of the Dystrophin Anchoring Site on b-Dystroglycan", The Journal of Biological Chemistry, 1995, pp. 27305-27310, vol. 270, No. 45.

(56) References Cited

OTHER PUBLICATIONS

Koenig et al., "Detailed Analysis of the Repeat Domain of Dystrophin Reveals Four Potential Hinge Segments That May Confer Flexibility", The Journal of Biological Chemistry, 1990, pp. 4560-4566, vol. 265.
Lai et al., "a2 and a3 Helices of Dystrophin R16 and R17 Frame a Microdomain in the a1 Helix of Dystrophin R17 for Neuronal NOS Binding", PNAS, 2013, pp. 525-530, vol. 110, No. 2.
Lai et al., "Dystrophins Carrying Spectrin-Like Repeats 16 and 17 Anchor nNOS to the Sarcolemma and Enhance Exercise Performance in a Mouse Model of Muscular Dystrophy", The Journal of Clinical Investigation, 2009, pp. 624-635, vol. 119, No. 3.
Lai et al., "Efficient In Vivo Gene Expression by Trans-Splicing Adeno-Associated Viral Vectors", Nat Biotechnol., 2005, pp. 1435-1439, vol. 23, No. 11.
Lai et al., "Partial Restoration of Cardiac Function with DPDZ nNOS in Aged mdx Model of Duchenne Cardiomyopathy", Human Molecular Genetics, Jan. 25, 2014, pp. 3189-3199, vol. 23.
Lai et al., "Synthetic Intron Improves Transduction Efficiency of Trans-Splicing Adeno-Associated Viral Vectors", Human Gene Therapy, 2006, pp. 1036-1042, vol. 17, No. 10.

* cited by examiner

Figure 2A,B,C,D

| | | | |
|---|---|---|---|
| NT-H1 | 1-336 NT-H1 GFP | 65.9 kD | YL376 |
| R1-3 | 337-667 R1-3 GFP | 65.7 kD | YL375 |
| R4-6 | 718-1045 R4-6 GFP | 65.5 kD | YL367 |
| R7-9 | 1046-1367 R7-9 GFP | 64.9 kD | YL368 |
| R10-12 | 1368-1676 R10-12 GFP | 62.6 kD | YL369 |
| R13-15 | 1677-1973 R13-15 GFP | 62.4 kD | YL370 |
| R16-19 | 1992-2423 R16-19 GFP | 77.8 kD | YL371 |
| R20-24 | 2471-3040 R20-24 GFP | 94.1 kD | YL372 |
| H4-CR | 3041-3408 H4-CR GFP | 69.9 kD | YL410 |
| CT | 3422-3685 CT GFP | 57 kD | YL411 |

Figure 7A,B

| Domain | Human | Mouse |
|---|---|---|
| R1 | C433 | C435 |
| R2 | C544 | C490, C546 |
| R3 | C569, C650 | C571 |
| R11 | C1505 | C1507 |
| R12 | C1569 | C1571 |
| CT | C3478 | C3469 |

Figure 12

| Position | Peptide | Score | Cutoff | Cluster |
| --- | --- | --- | --- | --- |
| R1 | LLNSRWECLRVASME | 0.929 | 0.196 | Cluster A |
| R3 | QRLTEEQCLFSAWLS | 1.537 | 0.951 | Cluster C |
| R3 | WLDNFARCWDNLVQK | 0.648 | 0.196 | Cluster A |
| R12 | CLKLSRKM | 1.452 | 0.196 | Cluster A |

Figure 24
AAV.R16/17.Syn.GFP.Pal
CMV
R16/17
Syn PDZ
GFP
Pal
SV40 pA
5'-ITR
3'-ITR

Individual Membrane-Binding Domains of Dystrophin

| Membrane Binding | | | | |
|---|---|---|---|---|
| No | NT-H1 | 1-336 NT-H1 GFP | 65.9 kD | YL376 |
| **Yes** | R1-3 | 337-667 R1-3 GFP | 65.7 kD | YL375 |
| No | R4-6 | 718-1045 R4-6 GFP | 65.5 kD | YL367 |
| No | R7-9 | 1046-1367 R7-9 GFP | 64.9 kD | YL368 |
| **Yes** | R10-12 | 1368-1676 R10-12 GFP | 62.6 kD | YL369 |
| No | R13-15 | 1677-1973 R13-15 GFP | 62.4 kD | YL370 |
| No | R16-19 | 1992-2423 R16-19 GFP | 77.8 kD | YL371 |
| No | R20-24 | 2471-3040 R20-24 GFP | 94.1 kD | YL372 |
| **Yes** | H4-CR | 3041-3408 H4-CR GFP | 69.9 kD | YL410 |
| **Yes** | CT | 3422-3685 CT GFP | 57 kD | YL411 |

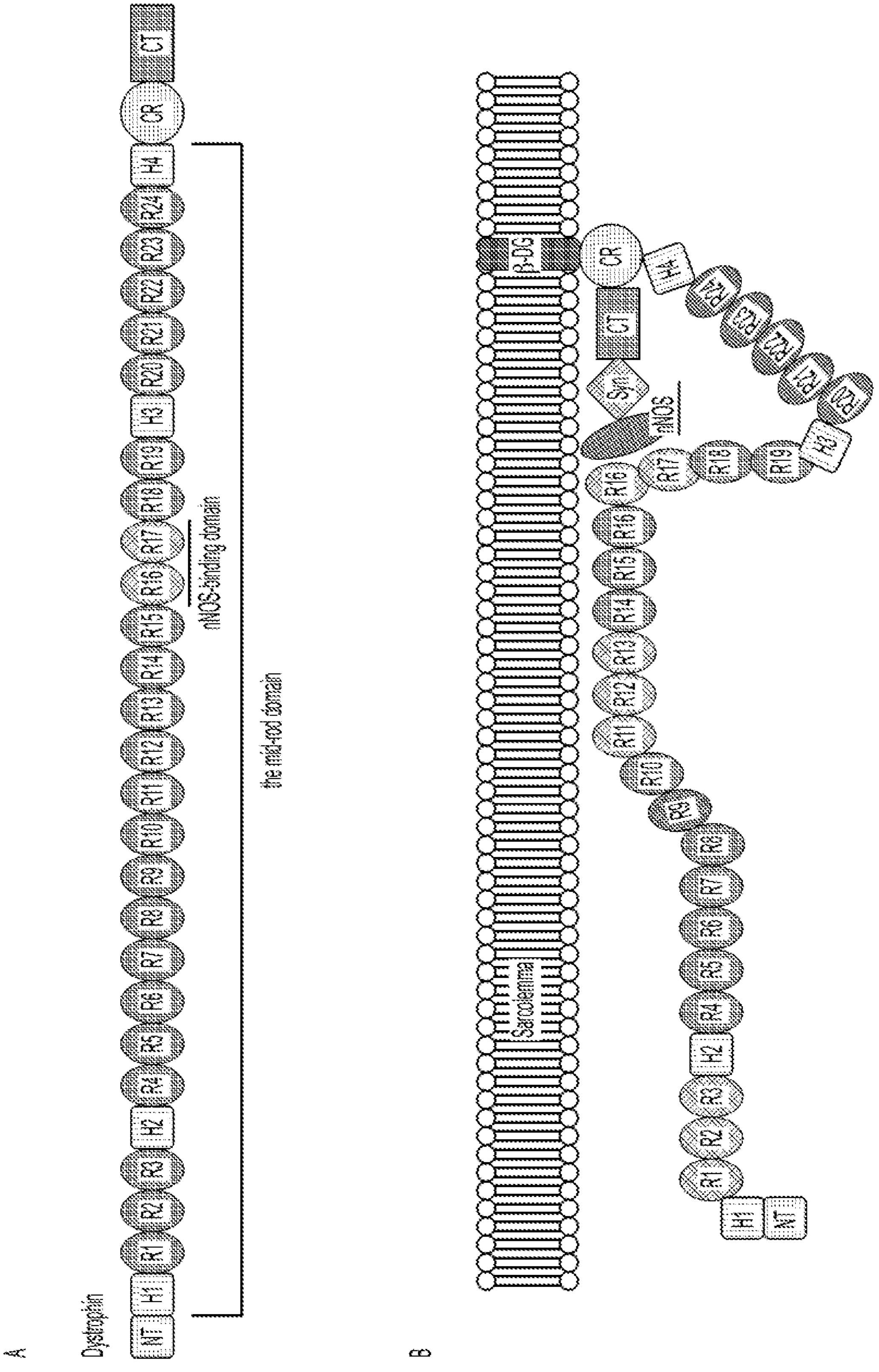
Figure 27A,B

SEQUENCE LISTING

```
<160> NUMBER OF SEQ ID NOS: 67

<210> SEQ ID NO 1
<211> LENGTH: 3685
<212> TYPE: PRT
<213> ORGANISM: Homo sapiens

<400> SEQUENCE: 1

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
```

-continued

```
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575
```

```
Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
    690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
    850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990
```

-continued

```
Gln Ser Gly Leu Tyr Tyr Leu Ser  Thr Thr Val Lys Glu  Met Ser Lys
        995                 1000                 1005

Lys Ala  Pro Ser Glu Ile Ser  Arg Lys Tyr Gln Ser  Glu Phe Glu
    1010                 1015                 1020

Glu Ile  Glu Gly Arg Trp Lys  Lys Leu Ser Ser Gln  Leu Val Glu
    1025                 1030                 1035

His Cys  Gln Lys Leu Glu Glu  Gln Met Asn Lys Leu  Arg Lys Ile
    1040                 1045                 1050

Gln Asn  His Ile Gln Thr Leu  Lys Lys Trp Met Ala  Glu Val Asp
    1055                 1060                 1065

Val Phe  Leu Lys Glu Glu Trp  Pro Ala Leu Gly Asp  Ser Glu Ile
    1070                 1075                 1080

Leu Lys  Lys Gln Leu Lys Gln  Cys Arg Leu Leu Val  Ser Asp Ile
    1085                 1090                 1095

Gln Thr  Ile Gln Pro Ser Leu  Asn Ser Val Asn Glu  Gly Gly Gln
    1100                 1105                 1110

Lys Ile  Lys Asn Glu Ala Glu  Pro Glu Phe Ala Ser  Arg Leu Glu
    1115                 1120                 1125

Thr Glu  Leu Lys Glu Leu Asn  Thr Gln Trp Asp His  Met Cys Gln
    1130                 1135                 1140

Gln Val  Tyr Ala Arg Lys Glu  Ala Leu Lys Gly Gly  Leu Glu Lys
    1145                 1150                 1155

Thr Val  Ser Leu Gln Lys Asp  Leu Ser Glu Met His  Glu Trp Met
    1160                 1165                 1170

Thr Gln  Ala Glu Glu Glu Tyr  Leu Glu Arg Asp Phe  Glu Tyr Lys
    1175                 1180                 1185

Thr Pro  Asp Glu Leu Gln Lys  Ala Val Glu Glu Met  Lys Arg Ala
    1190                 1195                 1200

Lys Glu  Glu Ala Gln Gln Lys  Glu Ala Lys Val Lys  Leu Leu Thr
    1205                 1210                 1215

Glu Ser  Val Asn Ser Val Ile  Ala Gln Ala Pro Pro  Val Ala Gln
    1220                 1225                 1230

Glu Ala  Leu Lys Lys Glu Leu  Glu Thr Leu Thr Thr  Asn Tyr Gln
    1235                 1240                 1245

Trp Leu  Cys Thr Arg Leu Asn  Gly Lys Cys Lys Thr  Leu Glu Glu
    1250                 1255                 1260

Val Trp  Ala Cys Trp His Glu  Leu Leu Ser Tyr Leu  Glu Lys Ala
    1265                 1270                 1275

Asn Lys  Trp Leu Asn Glu Val  Glu Phe Lys Leu Lys  Thr Thr Glu
    1280                 1285                 1290

Asn Ile  Pro Gly Gly Ala Glu  Glu Ile Ser Glu Val  Leu Asp Ser
    1295                 1300                 1305

Leu Glu  Asn Leu Met Arg His  Ser Glu Asp Asn Pro  Asn Gln Ile
    1310                 1315                 1320

Arg Ile  Leu Ala Gln Thr Leu  Thr Asp Gly Gly Val  Met Asp Glu
    1325                 1330                 1335

Leu Ile  Asn Glu Glu Leu Glu  Thr Phe Asn Ser Arg  Trp Arg Glu
    1340                 1345                 1350

Leu His  Glu Glu Ala Val Arg  Arg Gln Lys Leu Leu  Glu Gln Ser
    1355                 1360                 1365

Ile Gln  Ser Ala Gln Glu Thr  Glu Lys Ser Leu His  Leu Ile Gln
    1370                 1375                 1380

Glu Ser  Leu Thr Phe Ile Asp  Lys Gln Leu Ala Ala  Tyr Ile Ala
```

-continued

```
    1385                1390                1395

Asp Lys  Val Asp Ala Ala Gln  Met Pro Gln Glu Ala  Gln Lys Ile
    1400                1405                1410

Gln Ser  Asp Leu Thr Ser His  Glu Ile Ser Leu Glu  Glu Met Lys
    1415                1420                1425

Lys His  Asn Gln Gly Lys Glu  Ala Ala Gln Arg Val  Leu Ser Gln
    1430                1435                1440

Ile Asp  Val Ala Gln Lys Lys  Leu Gln Asp Val Ser  Met Lys Phe
    1445                1450                1455

Arg Leu  Phe Gln Lys Pro Ala  Asn Phe Glu Leu Arg  Leu Gln Glu
    1460                1465                1470

Ser Lys  Met Ile Leu Asp Glu  Val Lys Met His Leu  Pro Ala Leu
    1475                1480                1485

Glu Thr  Lys Ser Val Glu Gln  Glu Val Val Gln Ser  Gln Leu Asn
    1490                1495                1500

His Cys  Val Asn Leu Tyr Lys  Ser Leu Ser Glu Val  Lys Ser Glu
    1505                1510                1515

Val Glu  Met Val Ile Lys Thr  Gly Arg Gln Ile Val  Gln Lys Lys
    1520                1525                1530

Gln Thr  Glu Asn Pro Lys Glu  Leu Asp Glu Arg Val  Thr Ala Leu
    1535                1540                1545

Lys Leu  His Tyr Asn Glu Leu  Gly Ala Lys Val Thr  Glu Arg Lys
    1550                1555                1560

Gln Gln  Leu Glu Lys Cys Leu  Lys Leu Ser Arg Lys  Met Arg Lys
    1565                1570                1575

Glu Met  Asn Val Leu Thr Glu  Trp Leu Ala Ala Thr  Asp Met Glu
    1580                1585                1590

Leu Thr  Lys Arg Ser Ala Val  Glu Gly Met Pro Ser  Asn Leu Asp
    1595                1600                1605

Ser Glu  Val Ala Trp Gly Lys  Ala Thr Gln Lys Glu  Ile Glu Lys
    1610                1615                1620

Gln Lys  Val His Leu Lys Ser  Ile Thr Glu Val Gly  Glu Ala Leu
    1625                1630                1635

Lys Thr  Val Leu Gly Lys Lys  Glu Thr Leu Val Glu  Asp Lys Leu
    1640                1645                1650

Ser Leu  Leu Asn Ser Asn Trp  Ile Ala Val Thr Ser  Arg Ala Glu
    1655                1660                1665

Glu Trp  Leu Asn Leu Leu Leu  Glu Tyr Gln Lys His  Met Glu Thr
    1670                1675                1680

Phe Asp  Gln Asn Val Asp His  Ile Thr Lys Trp Ile  Ile Gln Ala
    1685                1690                1695

Asp Thr  Leu Leu Asp Glu Ser  Glu Lys Lys Lys Pro  Gln Gln Lys
    1700                1705                1710

Glu Asp  Val Leu Lys Arg Leu  Lys Ala Glu Leu Asn  Asp Ile Arg
    1715                1720                1725

Pro Lys  Val Asp Ser Thr Arg  Asp Gln Ala Ala Asn  Leu Met Ala
    1730                1735                1740

Asn Arg  Gly Asp His Cys Arg  Lys Leu Val Glu Pro  Gln Ile Ser
    1745                1750                1755

Glu Leu  Asn His Arg Phe Ala  Ala Ile Ser His Arg  Ile Lys Thr
    1760                1765                1770

Gly Lys  Ala Ser Ile Pro Leu  Lys Glu Leu Glu Gln  Phe Asn Ser
    1775                1780                1785
```

```
Asp Ile  Gln Lys Leu Leu Glu  Pro Leu Glu Ala Glu  Ile Gln Gln
    1790                 1795                 1800

Gly Val  Asn Leu Lys Glu Glu  Asp Phe Asn Lys Asp  Met Asn Glu
    1805                 1810                 1815

Asp Asn  Glu Gly Thr Val Lys  Glu Leu Leu Gln Arg  Gly Asp Asn
    1820                 1825                 1830

Leu Gln  Gln Arg Ile Thr Asp  Glu Arg Lys Arg Glu  Glu Ile Lys
    1835                 1840                 1845

Ile Lys  Gln Gln Leu Leu Gln  Thr Lys His Asn Ala  Leu Lys Asp
    1850                 1855                 1860

Leu Arg  Ser Gln Arg Arg Lys  Lys Ala Leu Glu Ile  Ser His Gln
    1865                 1870                 1875

Trp Tyr  Gln Tyr Lys Arg Gln  Ala Asp Asp Leu Leu  Lys Cys Leu
    1880                 1885                 1890

Asp Asp  Ile Glu Lys Lys Leu  Ala Ser Leu Pro Glu  Pro Arg Asp
    1895                 1900                 1905

Glu Arg  Lys Ile Lys Glu Ile  Asp Arg Glu Leu Gln  Lys Lys Lys
    1910                 1915                 1920

Glu Glu  Leu Asn Ala Val Arg  Arg Gln Ala Glu Gly  Leu Ser Glu
    1925                 1930                 1935

Asp Gly  Ala Ala Met Ala Val  Glu Pro Thr Gln Ile  Gln Leu Ser
    1940                 1945                 1950

Lys Arg  Trp Arg Glu Ile Glu  Ser Lys Phe Ala Gln  Phe Arg Arg
    1955                 1960                 1965

Leu Asn  Phe Ala Gln Ile His  Thr Val Arg Glu Glu  Thr Met Met
    1970                 1975                 1980

Val Met  Thr Glu Asp Met Pro  Leu Glu Ile Ser Tyr  Val Pro Ser
    1985                 1990                 1995

Thr Tyr  Leu Thr Glu Ile Thr  His Val Ser Gln Ala  Leu Leu Glu
    2000                 2005                 2010

Val Glu  Gln Leu Leu Asn Ala  Pro Asp Leu Cys Ala  Lys Asp Phe
    2015                 2020                 2025

Glu Asp  Leu Phe Lys Gln Glu  Glu Ser Leu Lys Asn  Ile Lys Asp
    2030                 2035                 2040

Ser Leu  Gln Gln Ser Ser Gly  Arg Ile Asp Ile Ile  His Ser Lys
    2045                 2050                 2055

Lys Thr  Ala Ala Leu Gln Ser  Ala Thr Pro Val Glu  Arg Val Lys
    2060                 2065                 2070

Leu Gln  Glu Ala Leu Ser Gln  Leu Asp Phe Gln Trp  Glu Lys Val
    2075                 2080                 2085

Asn Lys  Met Tyr Lys Asp Arg  Gln Gly Arg Phe Asp  Arg Ser Val
    2090                 2095                 2100

Glu Lys  Trp Arg Arg Phe His  Tyr Asp Ile Lys Ile  Phe Asn Gln
    2105                 2110                 2115

Trp Leu  Thr Glu Ala Glu Gln  Phe Leu Arg Lys Thr  Gln Ile Pro
    2120                 2125                 2130

Glu Asn  Trp Glu His Ala Lys  Tyr Lys Trp Tyr Leu  Lys Glu Leu
    2135                 2140                 2145

Gln Asp  Gly Ile Gly Gln Arg  Gln Thr Val Val Arg  Thr Leu Asn
    2150                 2155                 2160

Ala Thr  Gly Glu Glu Ile Ile  Gln Gln Ser Ser Lys  Thr Asp Ala
    2165                 2170                 2175
```

-continued

```
Ser Ile  Leu Gln Glu Lys Leu  Gly Ser Leu Asn Leu  Arg Trp Gln
    2180                 2185                 2190

Glu Val  Cys Lys Gln Leu Ser  Asp Arg Lys Lys Arg  Leu Glu Glu
    2195                 2200                 2205

Gln Lys  Asn Ile Leu Ser Glu  Phe Gln Arg Asp Leu  Asn Glu Phe
    2210                 2215                 2220

Val Leu  Trp Leu Glu Glu Ala  Asp Asn Ile Ala Ser  Ile Pro Leu
    2225                 2230                 2235

Glu Pro  Gly Lys Glu Gln Gln  Leu Lys Glu Lys Leu  Glu Gln Val
    2240                 2245                 2250

Lys Leu  Leu Val Glu Glu Leu  Pro Leu Arg Gln Gly  Ile Leu Lys
    2255                 2260                 2265

Gln Leu  Asn Glu Thr Gly Gly  Pro Val Leu Val Ser  Ala Pro Ile
    2270                 2275                 2280

Ser Pro  Glu Glu Gln Asp Lys  Leu Glu Asn Lys Leu  Lys Gln Thr
    2285                 2290                 2295

Asn Leu  Gln Trp Ile Lys Val  Ser Arg Ala Leu Pro  Glu Lys Gln
    2300                 2305                 2310

Gly Glu  Ile Glu Ala Gln Ile  Lys Asp Leu Gly Gln  Leu Glu Lys
    2315                 2320                 2325

Lys Leu  Glu Asp Leu Glu Glu  Gln Leu Asn His Leu  Leu Leu Trp
    2330                 2335                 2340

Leu Ser  Pro Ile Arg Asn Gln  Leu Glu Ile Tyr Asn  Gln Pro Asn
    2345                 2350                 2355

Gln Glu  Gly Pro Phe Asp Val  Gln Glu Thr Glu Ile  Ala Val Gln
    2360                 2365                 2370

Ala Lys  Gln Pro Asp Val Glu  Glu Ile Leu Ser Lys  Gly Gln His
    2375                 2380                 2385

Leu Tyr  Lys Glu Lys Pro Ala  Thr Gln Pro Val Lys  Arg Lys Leu
    2390                 2395                 2400

Glu Asp  Leu Ser Ser Glu Trp  Lys Ala Val Asn Arg  Leu Leu Gln
    2405                 2410                 2415

Glu Leu  Arg Ala Lys Gln Pro  Asp Leu Ala Pro Gly  Leu Thr Thr
    2420                 2425                 2430

Ile Gly  Ala Ser Pro Thr Gln  Thr Val Thr Leu Val  Thr Gln Pro
    2435                 2440                 2445

Val Val  Thr Lys Glu Thr Ala  Ile Ser Lys Leu Glu  Met Pro Ser
    2450                 2455                 2460

Ser Leu  Met Leu Glu Val Pro  Ala Leu Ala Asp Phe  Asn Arg Ala
    2465                 2470                 2475

Trp Thr  Glu Leu Thr Asp Trp  Leu Ser Leu Leu Asp  Gln Val Ile
    2480                 2485                 2490

Lys Ser  Gln Arg Val Met Val  Gly Asp Leu Glu Asp  Ile Asn Glu
    2495                 2500                 2505

Met Ile  Ile Lys Gln Lys Ala  Thr Met Gln Asp Leu  Glu Gln Arg
    2510                 2515                 2520

Arg Pro  Gln Leu Glu Glu Leu  Ile Thr Ala Ala Gln  Asn Leu Lys
    2525                 2530                 2535

Asn Lys  Thr Ser Asn Gln Glu  Ala Arg Thr Ile Ile  Thr Asp Arg
    2540                 2545                 2550

Ile Glu  Arg Ile Gln Asn Gln  Trp Asp Glu Val Gln  Glu His Leu
    2555                 2560                 2565

Gln Asn  Arg Arg Gln Gln Leu  Asn Glu Met Leu Lys  Asp Ser Thr
```

```
    2570                2575                2580

Gln Trp Leu Glu Ala Lys Glu Glu Ala Glu Gln Val Leu Gly Gln
    2585                2590                2595

Ala Arg Ala Lys Leu Glu Ser Trp Lys Glu Gly Pro Tyr Thr Val
    2600                2605                2610

Asp Ala Ile Gln Lys Lys Ile Thr Glu Thr Lys Gln Leu Ala Lys
    2615                2620                2625

Asp Leu Arg Gln Trp Gln Thr Asn Val Asp Val Ala Asn Asp Leu
    2630                2635                2640

Ala Leu Lys Leu Leu Arg Asp Tyr Ser Ala Asp Asp Thr Arg Lys
    2645                2650                2655

Val His Met Ile Thr Glu Asn Ile Asn Ala Ser Trp Arg Ser Ile
    2660                2665                2670

His Lys Arg Val Ser Glu Arg Glu Ala Ala Leu Glu Glu Thr His
    2675                2680                2685

Arg Leu Leu Gln Gln Phe Pro Leu Asp Leu Glu Lys Phe Leu Ala
    2690                2695                2700

Trp Leu Thr Glu Ala Glu Thr Thr Ala Asn Val Leu Gln Asp Ala
    2705                2710                2715

Thr Arg Lys Glu Arg Leu Leu Glu Asp Ser Lys Gly Val Lys Glu
    2720                2725                2730

Leu Met Lys Gln Trp Gln Asp Leu Gln Gly Glu Ile Glu Ala His
    2735                2740                2745

Thr Asp Val Tyr His Asn Leu Asp Glu Asn Ser Gln Lys Ile Leu
    2750                2755                2760

Arg Ser Leu Glu Gly Ser Asp Asp Ala Val Leu Leu Gln Arg Arg
    2765                2770                2775

Leu Asp Asn Met Asn Phe Lys Trp Ser Glu Leu Arg Lys Lys Ser
    2780                2785                2790

Leu Asn Ile Arg Ser His Leu Glu Ala Ser Ser Asp Gln Trp Lys
    2795                2800                2805

Arg Leu His Leu Ser Leu Gln Glu Leu Leu Val Trp Leu Gln Leu
    2810                2815                2820

Lys Asp Asp Glu Leu Ser Arg Gln Ala Pro Ile Gly Gly Asp Phe
    2825                2830                2835

Pro Ala Val Gln Lys Gln Asn Asp Val His Arg Ala Phe Lys Arg
    2840                2845                2850

Glu Leu Lys Thr Lys Glu Pro Val Ile Met Ser Thr Leu Glu Thr
    2855                2860                2865

Val Arg Ile Phe Leu Thr Glu Gln Pro Leu Glu Gly Leu Glu Lys
    2870                2875                2880

Leu Tyr Gln Glu Pro Arg Glu Leu Pro Pro Glu Glu Arg Ala Gln
    2885                2890                2895

Asn Val Thr Arg Leu Leu Arg Lys Gln Ala Glu Glu Val Asn Thr
    2900                2905                2910

Glu Trp Glu Lys Leu Asn Leu His Ser Ala Asp Trp Gln Arg Lys
    2915                2920                2925

Ile Asp Glu Thr Leu Glu Arg Leu Gln Glu Leu Gln Glu Ala Thr
    2930                2935                2940

Asp Glu Leu Asp Leu Lys Leu Arg Gln Ala Glu Val Ile Lys Gly
    2945                2950                2955

Ser Trp Gln Pro Val Gly Asp Leu Leu Ile Asp Ser Leu Gln Asp
    2960                2965                2970
```

-continued

```
His Leu  Glu Lys Val Lys Ala  Leu Arg Gly Glu Ile  Ala Pro Leu
    2975                 2980                 2985

Lys Glu  Asn Val Ser His Val  Asn Asp Leu Ala Arg  Gln Leu Thr
    2990                 2995                 3000

Thr Leu  Gly Ile Gln Leu Ser  Pro Tyr Asn Leu Ser  Thr Leu Glu
    3005                 3010                 3015

Asp Leu  Asn Thr Arg Trp Lys  Leu Leu Gln Val Ala  Val Glu Asp
    3020                 3025                 3030

Arg Val  Arg Gln Leu His Glu  Ala His Arg Asp Phe  Gly Pro Ala
    3035                 3040                 3045

Ser Gln  His Phe Leu Ser Thr  Ser Val Gln Gly Pro  Trp Glu Arg
    3050                 3055                 3060

Ala Ile  Ser Pro Asn Lys Val  Pro Tyr Tyr Ile Asn  His Glu Thr
    3065                 3070                 3075

Gln Thr  Thr Cys Trp Asp His  Pro Lys Met Thr Glu  Leu Tyr Gln
    3080                 3085                 3090

Ser Leu  Ala Asp Leu Asn Asn  Val Arg Phe Ser Ala  Tyr Arg Thr
    3095                 3100                 3105

Ala Met  Lys Leu Arg Arg Leu  Gln Lys Ala Leu Cys  Leu Asp Leu
    3110                 3115                 3120

Leu Ser  Leu Ser Ala Ala Cys  Asp Ala Leu Asp Gln  His Asn Leu
    3125                 3130                 3135

Lys Gln  Asn Asp Gln Pro Met  Asp Ile Leu Gln Ile  Ile Asn Cys
    3140                 3145                 3150

Leu Thr  Thr Ile Tyr Asp Arg  Leu Glu Gln Glu His  Asn Asn Leu
    3155                 3160                 3165

Val Asn  Val Pro Leu Cys Val  Asp Met Cys Leu Asn  Trp Leu Leu
    3170                 3175                 3180

Asn Val  Tyr Asp Thr Gly Arg  Thr Gly Arg Ile Arg  Val Leu Ser
    3185                 3190                 3195

Phe Lys  Thr Gly Ile Ile Ser  Leu Cys Lys Ala His  Leu Glu Asp
    3200                 3205                 3210

Lys Tyr  Arg Tyr Leu Phe Lys  Gln Val Ala Ser Ser  Thr Gly Phe
    3215                 3220                 3225

Cys Asp  Gln Arg Arg Leu Gly  Leu Leu Leu His Asp  Ser Ile Gln
    3230                 3235                 3240

Ile Pro  Arg Gln Leu Gly Glu  Val Ala Ser Phe Gly  Gly Ser Asn
    3245                 3250                 3255

Ile Glu  Pro Ser Val Arg Ser  Cys Phe Gln Phe Ala  Asn Asn Lys
    3260                 3265                 3270

Pro Glu  Ile Glu Ala Ala Leu  Phe Leu Asp Trp Met  Arg Leu Glu
    3275                 3280                 3285

Pro Gln  Ser Met Val Trp Leu  Pro Val Leu His Arg  Val Ala Ala
    3290                 3295                 3300

Ala Glu  Thr Ala Lys His Gln  Ala Lys Cys Asn Ile  Cys Lys Glu
    3305                 3310                 3315

Cys Pro  Ile Ile Gly Phe Arg  Tyr Arg Ser Leu Lys  His Phe Asn
    3320                 3325                 3330

Tyr Asp  Ile Cys Gln Ser Cys  Phe Phe Ser Gly Arg  Val Ala Lys
    3335                 3340                 3345

Gly His  Lys Met His Tyr Pro  Met Val Glu Tyr Cys  Thr Pro Thr
    3350                 3355                 3360
```

```
Thr Ser  Gly Glu Asp Val Arg  Asp Phe Ala Lys Val  Leu Lys Asn
    3365                 3370                 3375

Lys Phe  Arg Thr Lys Arg Tyr  Phe Ala Lys His Pro  Arg Met Gly
    3380                 3385                 3390

Tyr Leu  Pro Val Gln Thr Val  Leu Glu Gly Asp Asn  Met Glu Thr
    3395                 3400                 3405

Pro Val  Thr Leu Ile Asn Phe  Trp Pro Val Asp Ser  Ala Pro Ala
    3410                 3415                 3420

Ser Ser  Pro Gln Leu Ser His  Asp Asp Thr His Ser  Arg Ile Glu
    3425                 3430                 3435

His Tyr  Ala Ser Arg Leu Ala  Glu Met Glu Asn Ser  Asn Gly Ser
    3440                 3445                 3450

Tyr Leu  Asn Asp Ser Ile Ser  Pro Asn Glu Ser Ile  Asp Asp Glu
    3455                 3460                 3465

His Leu  Leu Ile Gln His Tyr  Cys Gln Ser Leu Asn  Gln Asp Ser
    3470                 3475                 3480

Pro Leu  Ser Gln Pro Arg Ser  Pro Ala Gln Ile Leu  Ile Ser Leu
    3485                 3490                 3495

Glu Ser  Glu Glu Arg Gly Glu  Leu Glu Arg Ile Leu  Ala Asp Leu
    3500                 3505                 3510

Glu Glu  Glu Asn Arg Asn Leu  Gln Ala Glu Tyr Asp  Arg Leu Lys
    3515                 3520                 3525

Gln Gln  His Glu His Lys Gly  Leu Ser Pro Leu Pro  Ser Pro Pro
    3530                 3535                 3540

Glu Met  Met Pro Thr Ser Pro  Gln Ser Pro Arg Asp  Ala Glu Leu
    3545                 3550                 3555

Ile Ala  Glu Ala Lys Leu Leu  Arg Gln His Lys Gly  Arg Leu Glu
    3560                 3565                 3570

Ala Arg  Met Gln Ile Leu Glu  Asp His Asn Lys Gln  Leu Glu Ser
    3575                 3580                 3585

Gln Leu  His Arg Leu Arg Gln  Leu Leu Glu Gln Pro  Gln Ala Glu
    3590                 3595                 3600

Ala Lys  Val Asn Gly Thr Thr  Val Ser Ser Pro Ser  Thr Ser Leu
    3605                 3610                 3615

Gln Arg  Ser Asp Ser Ser Gln  Pro Met Leu Leu Arg  Val Val Gly
    3620                 3625                 3630

Ser Gln  Thr Ser Asp Ser Met  Gly Glu Glu Asp Leu  Leu Ser Pro
    3635                 3640                 3645

Pro Gln  Asp Thr Ser Thr Gly  Leu Glu Glu Val Met  Glu Gln Leu
    3650                 3655                 3660

Asn Asn  Ser Phe Pro Ser Ser  Arg Gly Arg Asn Thr  Pro Gly Lys
    3665                 3670                 3675

Pro Met  Arg Glu Asp Thr Met
    3680                 3685
```

<210> SEQ ID NO 2
<211> LENGTH: 11058
<212> TYPE: DNA
<213> ORGANISM: Homo sapiens

<400> SEQUENCE: 2

```
atgctttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180
```

```
aaactgccaa aagaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac agatttcaca ggctgtcacc accactcagc catcactaac acagacaact   2040
gtaatggaaa cagtaactac ggtgaccaca agggaacaga tcctggtaaa gcatgctcaa   2100
gaggaacttc caccaccacc tccccaaaag aagaggcaga ttactgtgga ttctgaaatt   2160
aggaaaaggt tggatgttga tataactgaa cttcacagct ggattactcg ctcagaagct   2220
gtgttgcaga gtcctgaatt tgcaatcttt cggaaggaag gcaacttctc agacttaaaa   2280
gaaaaagtca atgccataga gcgagaaaaa gctgagaagt tcagaaaact gcaagatgcc   2340
agcagatcag ctcaggccct ggtggaacag atggtgaatg agggtgttaa tgcagatagc   2400
atcaaacaag cctcagaaca actgaacagc cggtggatcg aattctgcca gttgctaagt   2460
gagagactta actggctgga gtatcagaac aacatcatcg ctttctataa tcagctacaa   2520
```

-continued

```
caattggagc agatgacaac tactgctgaa aactggttga aaatccaacc caccacccca   2580
tcagagccaa cagcaattaa aagtcagtta aaaatttgta aggatgaagt caaccggcta   2640
tcaggtcttc aacctcaaat tgaacgatta aaaattcaaa gcatagccct gaaagagaaa   2700
ggacaaggac ccatgttcct ggatgcagac tttgtggcct ttacaaatca ttttaagcaa   2760
gtcttttctg atgtgcaggc cagagagaaa gagctacaga caatttttga cactttgcca   2820
ccaatgcgct atcaggagac catgagtgcc atcaggacat gggtccagca gtcagaaacc   2880
aaactctcca tacctcaact tagtgtcacc gactatgaaa tcatggagca gagactcggg   2940
gaattgcagg ctttacaaag ttctctgcaa gagcaacaaa gtggcctata ctatctcagc   3000
accactgtga aagagatgtc gaagaaagcg ccctctgaaa ttagccggaa atatcaatca   3060
gaatttgaag aaattgaggg acgctggaag aagctctcct cccagctggt tgagcattgt   3120
caaaagctag aggagcaaat gaataaactc cgaaaaattc agaatcacat acaaaccctg   3180
aagaaatgga tggctgaagt tgatgttttt ctgaaggagg aatggcctgc ccttggggat   3240
tcagaaattc taaaaaagca gctgaaacag tgcagacttt tagtcagtga tattcagaca   3300
attcagccca gtctaaacag tgtcaatgaa ggtgggcaga agataaagaa tgaagcagag   3360
ccagagtttg cttcgagact tgagacagaa ctcaaagaac ttaacactca gtgggatcac   3420
atgtgccaac aggtctatgc cagaaaggag gccttgaagg gaggtttgga gaaaactgta   3480
agcctccaga aagatctatc agagatgcac gaatggatga cacaagctga agaagagtat   3540
cttgagagag attttgaata taaaactcca gatgaattac agaaagcagt tgaagagatg   3600
aagagagcta aagaagaggc ccaacaaaaa gaagcgaaag tgaaactcct tactgagtct   3660
gtaaatagtg tcatagctca agctccacct gtagcacaag aggccttaaa aaaggaactt   3720
gaaactctaa ccaccaacta ccagtggctc tgcactaggc tgaatgggaa atgcaagact   3780
ttggaagaag tttgggcatg ttggcatgag ttattgtcat acttggagaa agcaaacaag   3840
tggctaaatg aagtagaatt taaacttaaa accactgaaa acattcctgg cggagctgag   3900
gaaatctctg aggtgctaga ttcacttgaa aatttgatgc gacattcaga ggataaccca   3960
aatcagattc gcatattggc acagacccta acagatggcg gagtcatgga tgagctaatc   4020
aatgaggaac ttgagacatt taattctcgt tggagggaac tacatgaaga ggctgtaagg   4080
aggcaaaagt tgcttgaaca gagcatccag tctgcccagg agactgaaaa atccttacac   4140
ttaatccagg agtccctcac attcattgac aagcagttgg cagcttatat tgcagacaag   4200
gtggacgcag ctcaaatgcc tcaggaagcc cagaaaatcc aatctgattt gacaagtcat   4260
gagatcagtt tagaagaaat gaagaaacat aatcagggga aggaggctgc ccaaagagtc   4320
ctgtctcaga ttgatgttgc acagaaaaaa ttacaagatg tctccatgaa gtttcgatta   4380
ttccagaaac cagccaattt tgagctgcgt ctacaagaaa gtaagatgat tttagatgaa   4440
gtgaagatgc acttgcctgc attggaaaca aagagtgtgg aacaggaagt agtacagtca   4500
cagctaaatc attgtgtgaa cttgtataaa agtctgagtg aagtgaagtc tgaagtggaa   4560
atggtgataa agactggacg tcagattgta cagaaaaagc agacggaaaa tcccaaagaa   4620
cttgatgaaa gagtaacagc tttgaaattg cattataatg agctgggagc aaaggtaaca   4680
gaaagaaagc aacagttgga gaaatgcttg aaattgtccc gtaagatgcg aaaggaaatg   4740
aatgtcttga cagaatggct ggcagctaca gatatggaat tgacaaagag atcagcagtt   4800
gaaggaatgc ctagtaattt ggattctgaa gttgcctggg gaaaggctac tcaaaaagag   4860
attgagaaac agaaggtgca cctgaagagt atcacagagg taggagaggc cttgaaaaca   4920
```

```
gttttgggca agaaggagac gttggtggaa gataaactca gtcttctgaa tagtaactgg   4980
atagctgtca cctcccgagc agaagagtgg ttaaatcttt tgttggaata ccagaaacac   5040
atggaaactt ttgaccagaa tgtggaccac atcacaaagt ggatcattca ggctgacaca   5100
cttttggatg aatcagagaa aaagaaaccc cagcaaaaag aagacgtgct taagcgttta   5160
aaggcagaac tgaatgacat acgcccaaag gtggactcta cacgtgacca agcagcaaac   5220
ttgatggcaa accgcggtga ccactgcagg aaattagtag agccccaaat ctcagagctc   5280
aaccatcgat ttgcagccat ttcacacaga attaagactg gaaaggcctc cattcctttg   5340
aaggaattgg agcagtttaa ctcagatata caaaaattgc ttgaaccact ggaggctgaa   5400
attcagcagg gggtgaatct gaaagaggaa gacttcaata aagatatgaa tgaagacaat   5460
gagggtactg taaaagaatt gttgcaaaga ggagacaact tacaacaaag aatcacagat   5520
gagagaaaga gagaggaaat aaagataaaa cagcagctgt tacagacaaa acataatgct   5580
ctcaaggatt tgaggtctca aagaagaaaa aaggctctag aaatttctca tcagtggtat   5640
cagtacaaga ggcaggctga tgatctcctg aaatgcttgg atgacattga aaaaaaatta   5700
gccagcctac ctgagcccag agatgaaagg aaaataaagg aaattgatcg ggaattgcag   5760
aagaagaaag aggagctgaa tgcagtgcgt aggcaagctg agggcttgtc tgaggatggg   5820
gccgcaatgg cagtggagcc aactcagatc cagctcagca agcgctggcg ggaaattgag   5880
agcaaatttg ctcagtttcg aagactcaac tttgcacaaa ttcacactgt ccgtgaagaa   5940
acgatgatgg tgatgactga agacatgcct ttggaaattt cttatgtgcc ttctacttat   6000
ttgactgaaa tcactcatgt ctcacaagcc ctattagaag tggaacaact tctcaatgct   6060
cctgacctct gtgctaagga ctttgaagat ctctttaagc aagaggagtc tctgaagaat   6120
ataaaagata gtctacaaca aagctcaggt cggattgaca ttattcatag caagaagaca   6180
gcagcattgc aaagtgcaac gcctgtggaa agggtgaagc tacaggaagc tctctcccag   6240
cttgatttcc aatgggaaaa agttaacaaa atgtacaagg accgacaagg gcgatttgac   6300
agatctgttg agaaatggcg gcgttttcat tatgatataa agatatttaa tcagtggcta   6360
acagaagctg aacagtttct cagaaagaca caaattcctg agaattggga acatgctaaa   6420
tacaaatggt atcttaagga actccaggat ggcattgggc agcggcaaac tgttgtcaga   6480
acattgaatg caactgggga agaaataatt cagcaatcct caaaaacaga tgccagtatt   6540
ctacaggaaa aattgggaag cctgaatctg cggtggcagg aggtctgcaa acagctgtca   6600
gacagaaaaa agaggctaga agaacaaaag aatatcttgt cagaatttca aagagattta   6660
aatgaatttg ttttatggtt ggaggaagca gataacattg ctagtatccc acttgaacct   6720
ggaaaagagc agcaactaaa agaaaagctt gagcaagtca agttactggt ggaagagttg   6780
cccctgcgcc agggaattct caaacaatta aatgaaactg gaggacccgt gcttgtaagt   6840
gctcccataa gcccagaaga gcaagataaa cttgaaaata agctcaagca gacaaatctc   6900
cagtggataa aggtttccag agctttacct gagaaacaag gagaaattga agctcaaata   6960
aaagaccttg ggcagcttga aaaaaagctt gaagaccttg aagagcagtt aaatcatctg   7020
ctgctgtggt tatctcctat taggaatcag ttggaaattt ataaccaacc aaaccaagaa   7080
ggaccatttg acgttcagga aactgaaata gcagttcaag ctaaacaacc ggatgtggaa   7140
gagattttgt ctaaagggca gcatttgtac aaggaaaaac cagccactca gccagtgaag   7200
aggaagttag aagatctgag ctctgagtgg aaggcggtaa accgtttact tcaagagctg   7260
```

agggcaaagc agcctgacct agctcctgga ctgaccacta ttggagcctc tcctactcag 7320
actgttactc tggtgacaca acctgtggtt actaaggaaa ctgccatctc caaactagaa 7380
atgccatctt ccttgatgtt ggaggtacct gctctggcag atttcaaccg ggcttggaca 7440
gaacttaccg actggctttc tctgcttgat caagttataa aatcacagag ggtgatggtg 7500
ggtgaccttg aggatatcaa cgagatgatc atcaagcaga aggcaacaat gcaggatttg 7560
gaacagaggc gtccccagtt ggaagaactc attaccgctg cccaaaattt gaaaaacaag 7620
accagcaatc aagaggctag aacaatcatt acggatcgaa ttgaaagaat tcagaatcag 7680
tgggatgaag tacaagaaca ccttcagaac cggaggcaac agttgaatga aatgttaaag 7740
gattcaacac aatggctgga agctaaggaa gaagctgagc aggtcttagg acaggccaga 7800
gccaagcttg agtcatggaa ggagggtccc tatacagtag atgcaatcca aaagaaaatc 7860
acagaaacca agcagttggc caaagacctc cgccagtggc agacaaatgt agatgtggca 7920
aatgacttgg ccctgaaact tctccgggat tattctgcag atgataccag aaaagtccac 7980
atgataacag agaatatcaa tgcctcttgg agaagcattc ataaaagggt gagtgagcga 8040
gaggctgctt tggaagaaac tcatagatta ctgcaacagt tcccccctgga cctggaaaag 8100 tttcttgcct ggcttacaga agctgaaaca actgccaatg tcctacagga tgctacccgt 8160
aaggaaaggc tcctagaaga ctccaaggga gtaaaagagc tgatgaaaca atggcaagac 8220
ctccaaggtg aaattgaagc tcacacagat gtttatcaca acctggatga aaacagccaa 8280
aaaatcctga gatccctgga aggttccgat gatgcagtcc tgttacaaag acgtttggat 8340
aacatgaact tcaagtggag tgaacttcgg aaaaagtctc tcaacattag gtcccatttg 8400
gaagccagtt ctgaccagtg gaagcgtctg cacctttctc tgcaggaact tctggtgtgg 8460
ctacagctga aagatgatga attaagccgg caggcaccta ttggaggcga ctttccagca 8520
gttcagaagc agaacgatgt acatagggcc ttcaagaggg aattgaaaac taaagaacct 8580
gtaatcatga gtactcttga gactgtacga atatttctga cagagcagcc tttggaagga 8640
ctagagaaac tctaccagga gcccagagag ctgcctcctg aggagagagc ccagaatgtc 8700
actcggcttc tacgaaagca ggctgaggag gtcaatactg agtgggaaaa attgaacctg 8760
cactccgctg actggcagag aaaaatagat gagacccttg aaagactcca ggaacttcaa 8820
gaggccacgg atgagctgga cctcaagctg cgccaagctg aggtgatcaa gggatcctgg 8880
cagcccgtgg gcgatctcct cattgactct ctccaagatc acctcgagaa agtcaaggca 8940
cttcgaggag aaattgcgcc tctgaaagag aacgtgagcc acgtcaatga ccttgctcgc 9000
cagcttacca ctttgggcat tcagctctca ccgtataacc tcagcactct ggaagacctg 9060
aacaccagat ggaagcttct gcaggtggcc gtcgaggacc gagtcaggca gctgcatgaa 9120
gcccacaggg actttggtcc agcatctcag cactttcttt ccacgtctgt ccagggtccc 9180
tgggagagag ccatctcgcc aaacaaagtg ccctactata tcaaccacga gactcaaaca 9240
acttgctggg accatcccaa aatgacagag ctctaccagt ctttagctga cctgaataat 9300
gtcagattct cagcttatag gactgccatg aaactccgaa gactgcagaa ggccctttgc 9360
ttggatctct tgagcctgtc agctgcatgt gatgccttgg accagcacaa cctcaagcaa 9420
aatgaccagc ccatggatat cctgcagatt attaattgtt tgaccactat ttatgaccgc 9480
ctggagcaag agcacaacaa tttggtcaac gtccctctct gcgtggatat gtgtctgaac 9540
tggctgctga atgtttatga tacgggacga acagggagga tccgtgtcct gtcttttaaa 9600
actggcatca tttccctgtg taaagcacat ttggaagaca agtacagata ccttttcaag 9660

-continued

```
caagtggcaa gttcaacagg attttgtgac cagcgcaggc tgggcctcct tctgcatgat   9720

tctatccaaa ttccaagaca gttgggtgaa gttgcatcct ttgggggcag taacattgag   9780

ccaagtgtcc ggagctgctt ccaatttgct aataataagc cagagatcga agcggccctc   9840

ttcctagact ggatgagact ggaaccccag tccatggtgt ggctgcccgt cctgcacaga   9900

gtggctgctg cagaaactgc caagcatcag gccaaatgta acatctgcaa agagtgtcca   9960

atcattggat tcaggtacag gagtctaaag cactttaatt atgacatctg ccaaagctgc  10020

ttttttctg gtcgagttgc aaaaggccat aaaatgcact atcccatggt ggaatattgc  10080

actccgacta catcaggaga agatgttcga gactttgcca aggtactaaa aaacaaattt  10140

cgaaccaaaa ggtattttgc gaagcatccc cgaatgggct acctgccagt gcagactgtc  10200

ttagaggggg acaacatgga aactcccgtt actctgatca acttctggcc agtagattct  10260

gcgcctgcct cgtcccctca gctttcacac gatgatactc attcacgcat tgaacattat  10320

gctagcaggc tagcagaaat ggaaaacagc aatggatctt atctaaatga tagcatctct  10380

cctaatgaga gcatagatga tgaacatttg ttaatccagc attactgcca aagtttgaac  10440

caggactccc ccctgagcca gcctcgtagt cctgcccaga tcttgatttc cttagagagt  10500

gaggaaagag gggagctaga gagaatccta gcagatcttg aggaagaaaa caggaatctg  10560

caagcagaat atgaccgtct aaagcagcag cacgaacata aaggcctgtc cccactgccg  10620

tcccctcctg aaatgatgcc cacctctccc cagagtcccc gggatgctga gctcattgct  10680

gaggccaagc tactgcgtca acacaaaggc cgcctggaag ccaggatgca aatcctggaa  10740

gaccacaata aacagctgga gtcacagtta cacaggctaa ggcagctgct ggagcaaccc  10800

caggcagagg ccaaagtgaa tggcacaacg gtgtcctctc cttctacctc tctacagagg  10860

tccgacagca gtcagcctat gctgctccga gtggttggca gtcaaacttc ggactccatg  10920

ggtgaggaag atcttctcag tcctccccag gacacaagca cagggttaga ggaggtgatg  10980

gagcaactca acaactcctt ccctagttca agaggaagaa atacccctgg aaagccaatg  11040

agagaggaca caatgtag                                                11058
```

<210> SEQ ID NO 3
<211> LENGTH: 5953
<212> TYPE: DNA
<213> ORGANISM: Artificial Sequence
<220> FEATURE:
<223> OTHER INFORMATION: Synthetic

<400> SEQUENCE: 3

```
atgctttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatgccc tgaacaatgt caacaaggca    240

ctgcgggttt tgcagaacaa taatgttgat ttagtgaata ttggaagtac tgacatcgta    300

gatggaaatc ataaactgac tcttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttggcagcag tcagccacac aacgactgga acatgcattc    600
```

-continued

```
aacatcgcca gatatcaatt aggcatagag aaagtactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gtacatcatc aaatgcacta ttctcaacag atcacggtca    840
gtctagcaca gggatatgag agaacttctt cccctaagcc tcgattcaag agctatgcct    900
acacacaggc tgcttatgtc accacctctg accctacacg gagcccattt ccttcacagc    960
atttggaagc tcctgaagac aagtcatttg gcagttcatt gatggagagt gaagtaaacc   1020
tggaccgtta tcaaacagct ttagaagaag tattatcgtg gcttcttcct gctgaggaca   1080
cattgcaagc acaaggagag atttctaatg atgtggaagt ggtgaaagac cagtttcata   1140
ctcatgaggg gtacatgatg gatttgacag cccatcaggg ccgggttggt aatattctac   1200
aattgggaag taagctgatt ggaacaggaa aattatcaga agatgaagaa actgaagtac   1260
aagagcagat gaatctccta aattcaagat gggaatgcct cagggtagct agcatggaaa   1320
aacaaagcaa tttacataga gttttaatgg atctccagaa tcagaaactg aaagagttga   1380
atgactggct aacaaaaaca gaagaaagaa caaggaaaat ggaggaagag cctcttggac   1440
ctgatcttga agacctaaaa cgccaagtac aacaacataa ggtgcttcaa gaagatctag   1500
aacaagaaca agtcagggtc aattctctca ctcacatggt ggtggtagtt gatgaatcta   1560
gtggagatca cgcaactgct gctttggaag aacaagttta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac aggaaactga aatagcagtt caagctaaac aaccggatgt ggaagagatt   2040
ttgtctaaag ggcagcattt gtacaaggaa aaaccagcca ctcagccagt gaagaggaag   2100
ttagaagatc tgagctctga gtggaaggcg gtaaaccgtt tacttcaaga gctgagggca   2160
aagcagcctg acctagctcc tggactgacc actattggag cctctcctac tcagactgtt   2220
actctggtga cacaacctgt ggttagtaag gaaactgcca tctccaaact agaaatgcca   2280
tcttccttga tgttggaggt acctgctctg gcagatttca acggggcttg gacagaactt   2340
accgagtggc tttctctgct tgatcaagtt ataaaatcac agagggtgat ggtgggtgac   2400
cttgaggata tcaacgagat gatcatcaag cagaaggcaa caatgcagga tttggaacag   2460
aggcgtcccc agttggaaga actcattacc gctgcccaaa atttgaaaaa caagaccagc   2520
aatcaagagg ctagaacaat cattacggat cgaattgaaa gaattcagaa tcagtgggat   2580
gaagtacaag aacaccttca gaaccggagg caacagttga atgaaatgtt aaaggattca   2640
acacaatggc tggaagctaa ggaagaagct gagcaggtct taggacaggg cagagccaag   2700
cttgagtcat ggaaggaggg tccctataca gtagatgcaa tccaaaagaa aatcacagaa   2760
accaagcagt tggccaaaga cctccgccag tggcagacaa atgtagatgt ggcaaatgac   2820
ttggccctga aacttctccg ggattattct gcagatgata ccagaaaagt ccacatgata   2880
acagagaata tcaatgcctc ttggagaagc attcataaaa gggtgagtga gcgagaggct   2940
gctttggaag aaactcatag attactgcaa cagttccccc tggacctgga aaagtttctt   3000
```

gcctggctta cagaagctga aacaactgcc aatgtcctac aggatgctac ccgtaaggaa 3060
aggctcctag aagactccaa gggagtaaaa gagctgatga aacaatggca agacctccaa 3120
ggtgaaattg aagctcacac agatgtttat cacaacctgg atgaaaacag ccaaaaaatc 3180
ctgagatccc tggaaggttc cgatgatgca gtcctgttac aaagacgttt ggataacatg 3240
aacttcaagt ggagtgaact tcggaaaaag tctctcaaca ttaggtccca tttggaagcc 3300
agttctgacc agtggaagcg tctgcacctt tctctgcagg aacttctggt gtggctacag 3360
ctgaaagatg atgaattaag ccggcaggca cctattggag gcgactttcc agcagttcag 3420
aagcagaacg atgtacatag ggccttcaag agggaattga aaactaaaga acctgtaatc 3480
atgagtactc ttgagactgt acgaatattt ctgacagagc agcctttgga aggactagag 3540
aaactctacc aggagcccag agagctgcct cctgaggaga gagcccagaa tgtcactcgg 3600
cttctacgaa agcaggctga ggaggtcaat actgagtggg aaaaattgaa cctgcactcc 3660
gctgactggc agagaaaaat agatgagacc cttgaaagac tccaggaact tcaagaggcc 3720
acggatgagc tggacctcaa gctgcgccaa gctgaggtga tcaagggatc ctggcagccc 3780
gtgggcgatc tcctcattga ctctctccaa gatcacctcg agaaagtcaa ggcacttcga 3840
ggagaaattg cgcctctgaa agagaacgtg agccacgtca atgaccttgc tcgccagctt 3900
accactttgg gcattcagct ctcaccgtat aacctcagca ctctggaaga cctgaacacc 3960
agatggaagc ttctgcaggt ggccgtcgag gaccgagtca ggcagctgca tgaagcccac 4020
agggactttg gtccagcatc tcagcacttt ctttccacgt ctgtccaggg tcggtgggag 4080
agagccatct cgccaaacaa agtgccctac tatatcaacc acgagactca aacaacttgc 4140
tgggaccatc ccaaaatgac agagctctac cagtctttag ctgacctgaa taatgtcaga 4200
ttctcagctt ataggactgc catgaaactc cgaagactgc agaaggccct ttgcttggat 4260
ctcttgagcc tgtcagctgc atgtgatgcc ttggaccagc acaacctcaa gcaaaatgac 4320
cagcccatgg atatcctgca gattattaat tgtttgacca ctatttatga ccgcctggag 4380
caagagcaca acaatttggt caacgtccct ctctgcgtgg atatgtgtct gaactggctg 4440
ctgaatgttt atgatacggg acgaacaggg aggatccgtg tcctgtcttt taaaactggc 4500
atcatttccc tgtgtaaagc acatttggaa gacaagtaca gatacctttt caagcaagtg 4560
gcaagttcaa caggattttg tgaccagcgc aggctgggcc tccttctgca tgattctatc 4620
caaattccaa gacagttggg tgaagttgca tcctttgggg gcagtaacat tgagccaagt 4680
gtccggagct gcttccaatt tgctaataat aagccagaga tcgaagcggc cctcttccta 4740
gactggatga gactggaacc ccagtccatg gtgtggctgc ccgtcctgca cagagtggct 4800
gctgcagaaa ctgccaagca tcaggccaaa tgtaacatct gcaaagagtg tccaatcatt 4860
ggattcaggt acaggagtct aaagcacttt aattatgaca tctgccaaag ctgctttttt 4920
tctggtcgag ttgcaaaagg ccataaaatg cactatccca tggtggaata ttgcactccg 4980
actacatcag gagaagatgt tcgagacttt gccaaggtac taaaaaacaa atttcgaacc 5040
aaaaggtatt ttgcgaagca tccccgaatg ggctacctgc cagtgcagac tgtcttagag 5100
ggggacaaca tggaaactcc cgttactctg atcaacttct ggccagtaga ttctgcgcct 5160
gcctcgtccc ctcagctttc acacgatgat actcattcac gcattgaaca ttatgctagc 5220
aggctagcag aaatggaaaa cagcaatgga tcttatctaa atgatagcat ctctcctaat 5280
gagagcatag atgatgaaca tttgttaatc cagcattact gccaaagttt gaaccaggac 5340 tccccccctga gccagcctcg tagtcctgcc cagatcttga tttccttaga gagtgaggaa 5400
agaggggagc tagagagaat cctagcagat cttgaggaag aaaacaggaa tctgcaagca 5460
gaatatgacc gtctaaagca gcagcacgaa cataaaggcc tgtccccact gccgtcccct 5520
cctgaaatga tgcccacctc tccccagagt ccccgggatg ctgagctcat tgctgaggcc 5580
aagctactgc gtcaacacaa aggccgcctg gaagccagga tgcaaatcct ggaagaccac 5640
aataaacagc tggagtcaca gttacacagg ctaaggcagg tgctggagca accccaggca 5700
gaggccaaag tgaatggcac aacggtgtcc tctccttcta cctctctaca gaggtccgac 5760
agcagtcagc ctatgctgct ccgagtggtt ggcagtcaaa cttcggactc catgggtgag 5820
gaagatcttc tcagtcgtcc ccaggacaca agcacagggt tagaggaggt gatggagcaa 5880
ctcaacaact cctttcccta gttcaagagg aagaaatacc cctggaaagc caatgagaga 5940
ggacacaatg tag 5953

<210> SEQ ID NO 4
<211> LENGTH: 5749
<212> TYPE: DNA
<213> ORGANISM: Artificial Sequence
<220> FEATURE:
<223> OTHER INFORMATION: Synthetic

<400> SEQUENCE: 4
atgcttggtg ggaagaagta gaggactgtt atgaaagaga agatgttcaa aagaaaacat 60
tcacaaaatg ggtaaatgca caattttcta agtttgggaa gcagcatatt gagaacctct 120
tcagtgacct acaggatggg aggcgcctcc tagacctcct cgaaggcctg acagggcaaa 180
aactgccaaa agaaaaagga tccacaagag ttcatgccct gaacaatgtc aacaaggcac 240
tgcgggtttt gcagaacaat aatgttgatt tagtgaatat tggaagtact gacatcgtag 300
atggaaatca taaactgact cttggtttga tttggaatat aatcctccac tggcaggtca 360
aaaatgtaat gaaaaatatc atggctggat tgcaacaaac caacagtgaa aagattctcc 420
tgagctgggt gcgacaatca actcgtaatt atccacaggt taatgtaatc aacttcacca 480
ccagctggtc tgatggcctg gctttgaatg ctctcatcca tagtcatagg ccagacctat 540
ttgactggaa tagtgtggtt tgccagcagt cagccacaca acgactggaa catgcattca 600
acatcgccag atatcaatta ggcatagaga aactactcga tcctgaagat gttgatacca 660
cctatccaga taagaagtcc atctttaatg tacatcacat cactcttcca agttttgcct 720
caacaagtga gcattgaagc catccaggaa gtggaaatgt tgccaaggcc acctaaagtg 780
actaaagaag aacattttca gttacatcat caaatgcact attctcaaca gatcacggtc 840
agtctagcac agggatatga gagaacttct tcccctaagc ctcgattcaa gagctatgcc 900
tacacacagg ctgcttatgt caccacctct gaccctacac ggagcccatt tccttcacag 960
catttggaag ctcctgaaga caagtcattt ggcagttcat tgatggagag tgaagtaaac 1020
ctggaccgtt atcaaacagc tttagaagaa gtattatcgt ggcttctttc tgctgaggac 1080
acattgcaag cacaaggaga gatttctaat gatgtggaag tggtgaaaga ccagtttcat 1140
actcatgagg ggtacatgat ggatttgaca gcccatcagg gccgggttgg taatattcta 1200
caattgggaa gtaagctgat tggaacagga aaattatcag aagatgaaga aactgaagta 1260
caagagcaga tgaatctcct aaattcaaga tgggaatgcc tcagggtagc tagcatggaa 1320
aaacaaagca atttacatag agttttaatg gatctccaga atcagaaact gaaagagttg 1380
aatgactggc taacaaaaac agaagaaaga acaaggaaaa tggaggaaga gcctcttgga 1440

```
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tgggaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac agatttcaca gcagcctgac ctagctcctg gactgaccac tattggagcc   2040
tctcctactc agactgttac tctggtgaca caacctgtgg ttactaagga aactgccatc   2100
tccaaactag aaatgccatc ttccttgatg ttggaggtac ctgctctggc agatttcaac   2160
cgggcttgga cagaacttac cgactggctt tctctgcttg atcaagttat aaaatcacag   2220
agggtgatgg tgggtgacct tgaggatatc aacgagatga tcatcaagca gaaggcaaca   2280
atgcaggatt tggaacagag gcgtccccag ttggaagaac tcattaccgc tgcccaaaat   2340
ttgaaaaaca agaccagcaa tcaagaggct agaacaatca ttacggatcg aattgaaaga   2400
attcagaatc agtgggatga agtacaagaa caccttcaga accggaggca acagttgaat   2460
gaaatgttaa aggattcaac acaatggctg gaagctaagg aagaagctga gcaggtctta   2520
ggacaggcca gagccaagct tgagtcatgg aaggagggtc cctatacagt agatgcaatc   2580
caaaagaaaa tcacagaaac caagcagttg gccaaagacc tccgcgagtg gcagacaaat   2640
gtagatgtgg caaatgactt ggccctgaaa cttctgcggg attattctgc agatgatacc   2700
agaaaagtcc acatgataac agagaatatc aatgcctctt ggagaagcat tcataaaagg   2760
gtgagtgagc gagaggctgc tttggaagaa actcatagat tactgcaaca gttccccctg   2820
gacctggaaa agtttcttgc ctggcttaca gaagctgaaa caactgccaa tgtcctacag   2880
gatgctaccc gtaaggaaag gctcctagaa gactccaagg gagtaaaaga gctgatgaaa   2940
caatggcaag acctccaagg tgaaattgaa gctcacacag atgtttatga caacctggat   3000
gaaaacagcc aaaaaatcct gagatccctg gaaggttccg atgatgcagt cctgttacaa   3060
agacgtttgg ataacatgaa cttcaagtgg agtgaacttc ggaaaaagtc tctcaacatt   3120
aggtcccatt tggaagccag ttctgaccag tggaagcgtc tgcacctttc tctgcaggaa   3180
cttctggtgt ggctacagct gaaagatgat gaattaagcc ggcaggcacc tattggaggc   3240
gactttccag cagttcagaa gcagaacgat gtacataggg ccttcaagag ggaattgaaa   3300
actaaagaac ctgtaatcat gagtactctt gagactgtac gaatatttct gacagagcag   3360
cctttggaag gactagagaa actctaccag gagcccagag agctgcctcc tgaggagaga   3420
gcccagaatg tcactcggct tctacgaaag caggctgagg aggtcaatac tgagtgggaa   3480
aaattgaacc tgcactccgc tgactggcag agaaaaatag atgagaccct tgaaagactc   3540
caggaacttc aagaggccac ggatgagctg gacctcaagc tgcgccaagc tgaggtgatc   3600
aagggatcct ggcagcccgt gggcgatctc ctgattgact ctctccaaga tcacctcgag   3660
aaagtcaagg cacttcgagg agaaattgcg cctctgaaag agaacgtgag cgacgtcaat   3720
gaccttgctc gccagcttac cactttgggc attcagctct caccgtataa cctcagcact   3780
```

```
ctggaagacc tgaacaccag atggaagctt ctgcaggtgg ccgtcgagga ccgagtcagg   3840

cagctgcatg aagcccacag ggactttggt ccagcatctc agcactttct ttccacgtct   3900

gtccagggtc cctgggagag agccatctcg ccaaacaaag tgccctacta tatcaaccac   3960

gagactcaaa caacttgctg ggaccatccc aaaatgacag agctctacca gtctttagct   4020

gacctgaata atgtcagatt ctcagcttat aggactgcca tgaaactccg aagactgcag   4080

aaggcccttt gcttggatct cttgagcctg tcagctgcat gtgatgcctt ggaccagcac   4140

aacctcaagc aaaatgacca gcccatggat atcctgcaga ttattaattg tttgaccact   4200

atttatgacc gcctggagca agagcacaac aatttggtca acgtccctct ctgcgtggat   4260

atgtgtctga actggctgct gaatgtttat gatacgggac gaacagggag gatccgtgtc   4320

ctgtctttaa aagtggcatc atttccctgt gtaaagcaca tttggaagac aagtacagat   4380

accttttcaa gcaagtggca agttcaacag gattttgtga ccagcgcagg ctgggcctcc   4440

ttctgcatga ttctatccaa atccaagaca gttgggtgaa gttgcatcct ttgggggcag   4500

taacattgag ccaagtgtcc ggagctgctt ccaatttgct aataataagc cagagatcga   4560

agcggccctc ttcctagact ggatgagact ggaaccccag tccatggtgt ggctgcccgt   4620

cctgcacaga gtggctgctg gagaaactgc caagcatcag gccaaatgta acatctgcaa   4680

agagtgtcca atcattggat tcaggtacag gagtctaaag cactttaatt atgacatctg   4740

ccaaagctgc ttttttctg gtcgagttgc aaaaggccat aaaatgcact atcccatggt   4800

ggaatattgc actccgacta catcaggaga agatgttcga gactttgcca aggtactaaa   4860

aaacaaattt cgaaccaaaa ggtattttgc gaagcatccc cgaatgggct acctgccagt   4920

gcagactgtc ttagaggggg acaacatgga aacgcctgcc tcgtcccctc agctttcaca   4980

cgatgatact cattcacgca ttgaacatta tgctagcagg ctagcagaaa tggaaaacag   5040

caatggatct tatctaaatg atagcatctc tcctaatgag agcatagatg atgaacattt   5100

gttaatccag cattactgcc aaagtttgaa ccaggactcc cccctgagcc agcctcgtag   5160

tcctgcccag atcttgattt ccttagagag tgaggaaaga ggggagctag agagaatcct   5220

agcagatctt gaggaagaaa acaggaatct gcaagcagaa tatgaccgtc taaagcagca   5280

gcacgaacat aaaggcctgt ccccactgcc gtcccctcct gaaatgatgc ccacctctcc   5340

ccagagtccc cgggatgctg agctcattgc tgaggccaag ctactgcgtc aacacaaagg   5400

ccgcctggaa gccaggatgc aaatcctgga agaccacaat aaacagctgg agtcacagtt   5460

acacaggcta aggcagctgc tggagcaacc ccaggcagag gccaaagtga atggcacaac   5520

ggtgtcctct ccttctacct ctctacagag gtccgacagc agtcagccta tgctgctccg   5580

agtggttggc agtcaaactt cggactccat gggtgaggaa gatcttctca gtcctcccca   5640

ggacacaagc acagggttag aggaggtgat ggagcaactc aacaactcct tccctagttg   5700

aagaggaaga aataccccctg gaaagccaat gagagaggac acaatgtag              5749
```

<210> SEQ ID NO 5
<211> LENGTH: 6397
<212> TYPE: DNA
<213> ORGANISM: Artificial Sequence
<220> FEATURE:
<223> OTHER INFORMATION: Synthetic

<400> SEQUENCE: 5

```
atgctttggt gggaagaagt agaggactgt tatgaaagag aagatgttca aaagaaaaca     60

ttcacaaaat gggtaaatgc acaattttct aagtttggga agcagcatat tgagaacctc    120
```

```
ttcagtgacc tacaggatgg gaggcgcctc ctagacctcc tcgaaggcct gacagggcaa    180
aaactgccaa aagaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac agatttcaca gcaaaagaat atcttgtcag aatttcaaag agatttaaat   2040
gaatttgttt tatggttgga ggaagcagat aacattgcta gtatcccact tgaacctgga   2100
aaagagcagc aactaaaaga aaagcttgag caagtcaagt tactggtgga agagttgccc   2160
ctgcgccagg gaattctcaa acaattaaat gaaactggag gacccgtgct tgtaagtgct   2220
cccataagcc cagaagagca agataaactt gaaaataagc tcaagcagac aaatctccag   2280
tggataaagg tttccagagc tttacctgag aaacaaggag aaattgaagc tcaaataaaa   2340
gaccttgggc agcttgaaaa aaagcttgaa gaccttgaag agcagttaaa tcatctgctg   2400
ctgtggttat ctcgtattag gaatcagttg gaaatttata accaaccaaa ccaagaagga   2460
```

-continued

```
ccatttgacg ttcaggaaac tgaaatagca gttcaagcta aacaaccgga tgtggaagag   2520
attttgtcta aagggcagca tttgtacaag gaaaaaccag ccactgagcc agtgaagagg   2580
aagttagaag atctgagctc tgagtggaag gcggtaaacc gtttacttca agagctgagg   2640
gcaaagcagc ctgacctagc tcctggactg accactattg gagcctctcc tactcagact   2700
gttactctgg tgacacaacc tgtggttact aaggaaactg ccatctccaa actagaaatg   2760
ccatcttcct tgatgttgga ggtacctgct ctggcagatt tcaaccgggc ttggacagaa   2820
cttaccgact ggctttctct gcttgatcaa gttataaaat cacagagggt gatggtgggt   2880
gaccttgagg atatcaacga gatgatcatc aagcagaagg caacaatgca ggatttggaa   2940
cagaggcgtc cccagttgga agaactcatt accgctgccc aaaatttgaa aaacaagacc   3000
agcaatcaag aggctagaac aatcattacg gatcgaattg aaagaattca gaatcagtgg   3060
gatgaagtac aagaacacct tcagaaccgg aggcaacagt tgaatgaaat gttaaaggat   3120
tcaacacaat ggctggaagc taaggaagaa gctgagcagg tcttaggaca ggccagagcc   3180
aagcttgagt catggaagga gggtccctat acagtagatg caatccaaaa gaaaatcaca   3240
gaaaccaagc agttggccaa agacctccgc cagtggcaga caaatgtaga tgtggcaaat   3300
gacttggccc tgaaacttct ccgggattat tctgcagatg ataccagaaa agtccacatg   3360
ataacagaga atatcaatgc ctcttggaga agcattcata aaagggtgag tgagcgagag   3420
gctgctttgg aagaaactca tagattactg caacagttcc ccctggacct ggaaaagttt   3480
cttgcctggc ttacagaagc tgaaacaact gccaatgtcc tacaggatgc tacccgtaag   3540
gaaaggctcc tagaagactc caagggagta aaagagctga tgaaacaatg gcaagacctc   3600
caaggtgaaa ttgaagctca cacagatgtt tatcacaacc tggatgaaaa cagccaaaaa   3660
atcctgagat ccctggaagg ttccgatgat gcagtcctgt tacaaagacg tttggataac   3720
atgaacttca agtggagtga acttcggaaa aagtctctca acattaggtc ccatttggaa   3780
gccagttctg accagtggaa gcgtctgcac ctttctctgc aggaacttct ggtgtggcta   3840
gagctgaaag atgatgaatt aagccggcag gcacctattg gaggcgactt tccagcagtt   3900
cagaagcaga acgatgtaca tagggccttc aagagggaat tgaaaactaa agaacctgta   3960
atcatgagta ctcttgagac tgtacgaata tttctgacag agcagccttt ggaaggacta   4020
gagaaactct accaggagcc cagagagctg cctcctgagg agagagccca gaatgtcact   4080
cggcttctac gaaagcaggc tgaggaggtc aatactgagt gggaaaaatt gaacctgcac   4140
tccgctgact ggcagagaaa aatagatgag acccttgaaa gactccagga acttcaagag   4200
gccacggatg agctggacct caagctgcgc caagctgagg tgatcaaggg atcctggcag   4260
ccggtgggcg atctcctcat tgactctctc caagatcacc tcgagaaagt caaggcactt   4320
cgaggagaaa ttgcgcctct gaaagagaac gtgagccacg tcaatgacct tgctcgccag   4380
cttaccactt tgggcattca gctctcaccg tataacctca gcactctgga agacctgaac   4440
accagatgga agcttctgca ggtggccgtc gaggaccgag tcaggcagct gcatgaagcc   4500
cacagggact ttggtccagc atctcagcac tttctttcca cgtctgtcca gggtccctgg   4560
gagagagcca tctcgccaaa caaagtgccc tactatatca accacgagac tcaaacaact   4620
tgctgggacc atcccaaaat gacagagctc taccagtctt tagctgacct gaataatgtc   4680
agattctcag cttataggac tgccatgaaa ctccgaagac tgcagaaggc cctttgcttg   4740
gatctcttga gcctgtcagc tgcatgtgat gccttggacc agcacaacct caagcaaaat   4800
gaccagccca tggatatcct gcagattatt aattgtttga ccactattta tgaccgcctg   4860
```

-continued

```
gagcaagagc acaacaattt ggtcaacgtc cctctctgcg tggatatgtg tctgaactgg   4920

ctgctgaatg tttatgatac gggacgaaca gggaggatcc gtgtcctgtc ttttaaaact   4980

ggcatcattt ccctgtgtaa agcacatttg gaagacaagt acagatacct tttcaagcaa   5040

gtggcaagtt caacaggatt ttgtgaccag cgcaggctgg gcctccttct gcatgattct   5100

atccaaattc caagacagtt gggtgaagtt gcatcctttg gggggcagtaa cattgagcca   5160

agtgtccgga gctgcttcca atttgctaat aataagccag agatcgaagc ggccctcttc   5220

ctagactgga tgagactgga accccagtcc atggtgtggc tgcccgtcct gcacagagtg   5280

gctgctgcag aaactgccaa gcatcaggcc aaatgtaaca tctgcaaaga gtgtccaatc   5340

attggattca ggtacaggag tctaaagcac tttaattatg acatctgcca aagctgcttt   5400

ttttctggtc gagttgcaaa aggccataaa atgcactatc ccatggtgga atattgcact   5460

ccgactacat caggagaaga tgttcgagac tttgccaagg tactaaaaaa caaatttcga   5520

accaaaaggt attttgcgaa gcatccccga atgggctacc tgccagtgca gactgtctta   5580

gagggggaca acatggaaac gcctgcctcg tcccctcagc tttcacacga tgatactcat   5640

tcacgcattg aacattatgc tagcaggcta gcagaaatgg aaaacagcaa tggatcttat   5700

ctaaatgata gcatctctcc taatgagagc atagatgatg aacatttgtt aatccagcat   5760

tactgccaaa gtttgaacca ggactccccc ctgagccagc ctcgtagtcc tgcccagatc   5820

ttgatttcct tagagagtga ggaaagaggg gagctagaga gaatcctagc agatcttgag   5880

gaagaaaaca ggaatctgca agcagaatat gaccgtctaa agcagcagca cgaacataaa   5940

ggcctgtccc cactgccgtc ccctcctgaa atgatgccca cctctcccca gagtccccgg   6000

gatgctgagc tcattgctga ggccaagcta ctgcgtcaac acaaaggccg cctggaagcc   6060

aggatgcaaa tcctggaaga ccacaataaa cagctggagt cacagttaca caggctaagg   6120

cagctgctgg agcaacccca ggcagaggcc aaagtgaatg gcacaacggt gtcctctcct   6180

tctacctctc tacagaggtc cgacagcagt cagcctatgc tgctccgagt ggttggcagt   6240

caaacttcgg actccatggg tgaggaagat cttctcagtc ctccccagga cacaagcaca   6300

gggtttagag gaggtgatgg agcaactcaa caactccttc cctagttcaa gaggaagaaa   6360

taccccctgga aagccaatga gagaggacac aatgtag                          6397
```

<210> SEQ ID NO 6
<211> LENGTH: 6718
<212> TYPE: DNA
<213> ORGANISM: Artificial Sequence
<220> FEATURE:
<223> OTHER INFORMATION: Synthetic

<400> SEQUENCE: 6

```
atggtttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatgccc tgaacaatgt caacaaggca    240

ctgcgggttt tgcagaacaa taatgttgat ttagtgaata ttggaagtac tgacatcgta    300

gatggaaatc ataaactgac tcttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtaat caacttcacc    480
```

```
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca aacaagatct tcttcaacac tgaagaataa gtcagtgacc cagaagacgg   1920
aagcatggct ggataacttt gcccggtgtt gggataattt agtccaaaaa cttgaaaaga   1980
gtacagcaca gatttcacag tctgttgaga aatggcggcg ttttcattat gatataaaga   2040
tatttaatca gtggctaaca gaagctgaag agtttctcag aaagacacaa attcctgaga   2100
attgggaaca tgctaaatac aaatggtatc ttaaggaact ccaggatggc attgggcagc   2160
ggcaaactgt tgtcagaaca ttgaatgcaa ctggggaaga aataattcag caatcctcaa   2220
aaacagatgc cagtattcta caggaaaaat tgggaagcct gaatctgcgg tggcaggagg   2280
tctgcaaaca gctgtcagac agaaaaaaga ggctagaaga acaaaagaat atcttgtcag   2340
aatttcaaag agatttaaat gaatttgttt tatggttgga ggaagcagat aacattgcta   2400
gtatcccact tgaacctgga aaagagcagc aactaaaaga aaagcttgag caagtcaagt   2460
tactggtgga agagttgccc ctgcgccagg gaattctcaa acaattaaat gaaactggag   2520
gacccgtgct tgtaagtgct cccataagcc cagaagagca agataaactt gaaaataagc   2580
tcaagcagac aaatctccag tggataaagg tttccagagc tttacctgag aaacaaggag   2640
aaattgaagc tcaaataaaa gaccttgggc agcttgaaaa aaagcttgaa gaccttgaag   2700
agcagttaaa tcatctgctg ctgtggttat ctcctattag gaatcagttg gaaatttata   2760
accaaccaaa ccaagaagga ccatttgacg ttcaggaaac tgaaatagca gttcaagcta   2820
aacaaccgga tgtggaagag attttgtcta aagggcagca tttgtacaag gaaaaaccag   2880
```

-continued

```
ccactcagcc agtgaagagg aagttagaag atctgagctc tgagtggaag gcggtaaacc   2940
gtttacttca agagctgagg gcaaagcagc ctgacctagc tcctggactg accactattg   3000
gagcctctcc tactcagact gttactctgg tgacacaacc tgtggttact aaggaaactg   3060
ccatctccaa actagaaatg ccatcttcct tgatgttgga ggtacctgct ctggcagatt   3120
tcaaccgggc ttggacagaa cttaccgact ggctttctct gcttgatcaa gttataaaat   3180
cacagagggt gatggtgggt gaccttgagg atatcaacga gatgatcatc aagcagaagg   3240
caacaatgca ggatttggaa cagaggcgtc cccagttgga agaactcatt accgctgccc   3300
aaaatttgaa aaacaagacc agcaatcaag aggctagaac aatcattacg gatcgaattg   3360
aaagaattca gaatcagtgg gatgaagtac aagaacacct tcagaaccgg aggcaacagt   3420
tgaatgaaat gttaaaggat tcaacacaat ggctggaagc taaggaagaa gctgagcagg   3480
tcttaggaca ggccagagcc aagcttgagt catggaagga gggtccctat acagtagatg   3540
caatccaaaa gaaaatcaca gaaaccaagc agttggccaa agacctccgc cagtggcaga   3600
caaatgtaga tgtggcaaat gacttggccc tgaaacttct ccgggattat tctgcagatg   3660
ataccagaaa agtccacatg ataacagaga atatcaatgc ctcttggaga agcattcata   3720
aaagggtgag tgagcgagag gctgctttgg aagaaactca tagattactg caacagtccc   3780
cctggacctg gaaaagtttc ttgcctggct tacagaagct gaaacaactg ccaatgtcct   3840
acaggatgct acccgtaagg aaaggctcct agaagactcc aagggagtaa aagagctgat   3900
gaaacaatgg caagacctcc aaggtgaaat tgaagctcac acagatgttt atcacaacct   3960
ggatgaaaac agccaaaaaa tcctgagatc cgtggaaggt tccgatgatg cagtcctgtt   4020
acaaagacgt ttggataaca tgaacttcaa gtggagtgaa cttcggaaaa agtctctcaa   4080
cattaggtcc catttggaag ccagttctga ccagtggaag cgtctgcacc tttctctgca   4140
ggaacttctg gtgtggctac agctgaaaga tgatgaatta agccggcagg cacctattgg   4200
aggcgacttt ccagcagttc agaagcagaa cgatgtacat agggccttca agagggaatt   4260
gaaaactaaa gaacctgtaa tcatgagtac tcttgagact gtacgaatat ttctgacaga   4320
gcagcctttg gaaggactag agaaactcta ccaggagccc agagagctgc ctcctgagga   4380
gagagcccag aatgtcactc ggcttctacg aaagcaggct gaggaggtca atactgagtg   4440
ggaaaaattg aacctgcact ccgctgactg gcagagaaaa atagatgaga cccttgaaag   4500
actccaggaa cttcaagagg ccacggatga gctggacctc aagctgcgcc aagctgaggt   4560
gatcaaggga tcctggcagc ccgtgggcga tctcctcatt gactctctcc aagatcacct   4620
cgagaaagtc aaggcacttc gaggagaaat ttgcgcctct gaaagagaac gtgagccacg   4680
tcaatgacct tgctcgccag cttaccactt tgggcattca gctctcaccg tataacctca   4740
gcactctgga agacctgaac accagatgga agcttctgca ggtggccgtc gaggaccgag   4800
tcaggcagct gcatgaagcc cacagggact ttggtccagc atctcagcac tttctttcca   4860
cgtctgtcca gggtccctgg gagagagcca tctcgccaaa caaagtgccc tactatatca   4920
accacgagac tcaaacaact tgctgggacc atcccaaaat gacagagctc taccagtctt   4980
tagctgacct gaataatgtc agattctcag cttataggac tgccatgaaa ctccgaagac   5040
tgcagaaggc cctttgcttg gatctcttga gcctgtcagc tgcatgtgat gccttggacc   5100
agcacaacct caagcaaaat gaccagccca tggatatcct gcagattatt aattgtttga   5160
ccactattta tgaccgcctg gagcaagagc acaacaattt ggtcaacgtc cctctctgcg   5220
```

-continued

```
tggatatgtg tctgaactgg ctgctgaatg tttatgatac gggacgaaca gggaggatcc   5280

gtgtcctgtc ttttaaaact ggcatcattt ccctgtgtaa agcacatttg gaagacaagt   5340

acagatacct tttcaagcaa gtggcaagtt caacaggatt ttgtgaccag cgcaggctgg   5400

gcctccttct gcatgattct atccaaattc caagacagtt gggtgaagtt gcatcctttg   5460

ggggcagtaa cattgagcca agtgtccgga gctgcttcca atttgctaat aataagccag   5520

agatcgaagc ggccctcttc ctagactgga tgagactgga accccagtcc atggtgtggc   5580

tgcccgtcct gcacagagtg gctgctgcag aaactgccaa gcatcaggcc aaatgtaaca   5640

tctgcaaaga gtgtccaatc attggatttc aggtacagga gtctaaagca ctttaattat   5700

gacatctgcc aaagctgctt tttttctggt cgagttgcaa aaggccataa aatgcactat   5760

cccatggtgg aatattgcac tccgactaca tcaggagaag atgttcgaga ctttgccaag   5820

gtactaaaaa acaaatttcg aaccaaaagg tattttgcga agcatccccg aatgggctac   5880

ctgccagtgc agactgtctt agagggggac aacatggaaa cgcctgcctc gtcccctgag   5940

ctttcacacg atgatactca ttcacgcatt gaacatatgc tagcaggcta gcagaaatgg   6000

aaaacagcaa tggatcttat ctaaatgata gcatctctcc taatgagagc atagatgatg   6060

aacattttgt taatccagca ttactgccaa agtttgaacc aggactcccc cctgagccag   6120

cctcgtagtc ctgcccagat cttgatttcc ttagagagtg aggaaagagg ggagctagag   6180

agaatcctag cagatcttga ggaagaaaac aggaatctgc aagcagaata tgaccgtcta   6240

aagcagcagc acgaacataa aggcctgtcc ccactgccgt cccctcctga aatgatgccc   6300

acgtctcccc agagtccccg ggatgctgag ctcattgctg aggccaagct actgcgtcaa   6360

cacaaaggcc gcctggaagc caggatgcaa atcctggaag accacaataa acagctggag   6420

tcacagttac acaggctaag gcagctgctg gagcaacccc aggcagaggc caaagtgaat   6480

ggcacaacgg tgtcctctcc tttctacctc tctacagagg tccgacagca gtcagcctat   6540

gctgctccga gtggttggca gtcaaacttc ggactccatg ggtgaggaag atcttctcag   6600

tcctccccag gacacaagca cagggttaga ggaggtgatg gagcaactca acaactcctt   6660

ccctagttca agaggaagaa atacccctgg aaagccaatg agagaggaca caatgtag     6718
```

<210> SEQ ID NO 7
<211> LENGTH: 7049
<212> TYPE: DNA
<213> ORGANISM: Artificial Sequence
<220> FEATURE:
<223> OTHER INFORMATION: Synthetic

<400> SEQUENCE: 7

```
atgctttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatgccc tgaacaatgt caacaaggca    240

ctgcgggttt tgcagaacaa taatgttgat ttagtgaata ttggaagtac tgacatcgta    300

gatggaaatc ataaactgac tgttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttgccagcag tcagccacac aacgactgga acatgcattc    600
```

```
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtatttgg gagatcgatg   1620
ggcaaacatc tgtagatgga cagaagaccg ctgggttctt ttacaagaca tccttctcaa   1680
atggcaacgt cttactgaag aacagtgcct tttagtgca tggctttcag aaaaagaaga    1740
tgcagtgaac aagattcaca caactggctt taaagatcaa aatgkaatgt tatcaagtct   1800
tcaaaaagtg gccgttttaa aagcggatct agaaaaagaa aagcaatcca tgggcaaact   1860
gtattcactc aaacaagatc ttctttcaac actgaagaat aagtcagtga cccagaagac   1920
ggaagcatgg ctggataact ttgcccggtg ttgggataat ttagtccaaa aacttgaaaa   1980
gagtacagca cagatttcac aggaaatttc ttatgtgcct tctacttatt tgactgaaat   2040
cactcatgtc tcacaagccc tattagaagt ggaacaactt ctcaatgctc ctgacctctg   2100
tgctaaggac tttgaagatc tctttaagca agaggagtct ctgaagaata taaaagatag   2160
tctacaacaa agctcaggtc ggattgacat tattcatagc aagaagacag cagcattgca   2220
aagtgcaacg cctgtggaaa gggtgaagct acaggaagct ctctcccagc ttgatttcca   2280
atgggaaaaa gttaacaaaa tgtacaagga ccgacaaggg cgatttgaca gatctgttga   2340
gaaatggcgg cgttttcatt atgatataaa gatatttaat cagtggctaa cagaagctga   2400
acagtttctc agaaagacac aaattcctga gaattgggaa catgctaaat acaaatggta   2460
tcttaaggaa ctccaggatg gcattgggca gcggcaaact gttgtcagaa cattgaatgc   2520
aactggggaa gaaataattc agcaatcctc aaaaacagat gccagtattc tacaggaaaa   2580
attgggaagc ctgaatctgc ggtggcagga ggtctgcaaa cagctgtcag acagaaaaaa   2640
gaggctagaa gaacaaaaga atatcttgtc agaatttcaa agagatttaa atgaatttgt   2700
tttatggttg gaggaagcag ataacattgc tagtatccca cttgaacctg gaaaagagca   2760
gcaactaaaa gaaaagcttg agcaagtcaa gttactggtg gaagagttgc ccctgcgcca   2820
gggaattctc aaacaattaa atgaaactgg aggacccgtg cttgtaagtg ctcccataag   2880
cccagaagag caagataaac ttgaaaataa gctcaagcag acaaatctcc agtggataaa   2940
```

```
ggtttccaga gctttacctg agaaacaagg agaaattgaa gctcaaataa aagaccttgg   3000
gcagcttgaa aaaaagcttg aagaccttga agagcagtta aatcatctgc tgctgtggtt   3060
atctcctatt aggaatcagt tggaaattta taaccaacca aaccaagaag gaccatttga   3120
cgttcaggaa actgaaatag cagttcaagc taaacaaccg gatgtggaag agattttgtc   3180
taaagggcag catttgtaca aggaaaaacc agccactcag ccagtgaaga ggaagttaga   3240
agatctgagc tctgagtgga aggcggtaaa ccgtttactt caagagctga gggcaaagca   3300
gcctgaccta gctcctggac tgaccactat tggagcctct cctactcaga ctgttactct   3360
ggtgacacaa cctgtggtta ctaaggaaac tgccatctcc aaactagaaa tgccatcttc   3420
cttgatgttg gaggtacctg ctctggcaga tttcaaccgg gcttggacag aacttaccga   3480
ctggctttct ctgcttgatc aagttataaa atcacagagg gtgatggtgg gtgaccttga   3540
ggatatcaac gagatgatca tcaagcagaa ggcaacaatg caggatttgg aacagaggcg   3600
tccccagttg gaagaactca ttaccgctgg ccaaaatttg aaaaacaaga ccagcaatca   3660
agaggctaga acaatcatta cggatcgaat tgaaagaatt cagaatcagt gggatgaagt   3720
acaagaacac cttcagaacc ggaggcaaca gttgaatgaa atgttaaagg attcaacaca   3780
atggctggaa gctaaggaag aagctgagca ggtcttagga caggccagag ccaagcttga   3840
gtcatggaag gagggtccct atacagtaga tgcaatccaa aagaaaatca cagaaaccaa   3900
gcagttggcc aaagacctcc gccagtggca gacaaatgta gatgtggcaa atgacttggc   3960
cctgaaactt ctccgggatt attctgcaga tgataccaga aaagtccaca tgataacaga   4020
gaatatcaat gcctcttgga gaagcattca taaaagggtg agtgagcgag aggctgcttt   4080
ggaagaaact catagattac tgcaacagtt ccccctggac ctggaaaagt ttcttgcctg   4140
gcttacagaa gctgaaacaa ctgccaatgt cctacaggat gctacccgta aggaaaggct   4200
cctagaagac tccaagggag taaaagagct gatgaaacaa tggcaagacc tccaaggtga   4260
aattgaagct cacacagatg tttatcacaa cctggatgaa aacagccaaa aaatcctgag   4320
atccctggaa ggttccgatg atgcagtcct gttacaaaga cgtttggata acatgaactt   4380
caagtggagt gaacttcgga aaaagtctct caacattagg tcccatttgg aagccagttc   4440
tgaccagtgg aagcgtctgc acctttctct gcaggaactt ctggtgtggc tacagctgaa   4500
agatgatgaa ttaagccggc aggcacctat tggaggcgac tttccagcag ttcagaagca   4560
gaacgatgta catagggcct tcaagaggga attgaaaact aaagaacctg taatcatgag   4620
tactcttgag actgtacgaa tatttctgac agagcagcct ttggaaggac tagagaaact   4680
ctaccaggag cccagagagc tgcctcctga ggagagagcc cagaatgtca ctcggcttct   4740
acgaaagcag gctgaggagg tcaatactga gtgggaaaaa ttgaacctgc actccgctga   4800
ctggcagaga aaaatagatg agacccttga aagactccag gaacttcaag aggccacgga   4860
tgagctggac ctcaagctgc gcgaagctga ggtgatcaag ggatcctggc agcccgtggg   4920
cgatctcctc attgactctc tccaagatca cctcgagaaa gtcaaggcac ttcgaggaga   4980
aattgcgcct ctgaaagaga acgtgagcca cgtcaatgac cttgctcgcc agcttaccac   5040
tttgggcatt cagctctcac cgtataacct cagcactctg gaagacctga acaccagatg   5100
gaagcttctg caggtggccg tcgaggaccg agtcaggcag ctgcatgaag cccacaggga   5160
ctttggtcca gcatctcagc actttctttc cacgtctgtc cagggtccct gggagagagc   5220
catctcgcca aacaaagtgc cctactatat caaccacgag actcaaacaa cttgctggga   5280
ccatcccaaa atgacagagc tctaccagtc tttagctgac ctgaataatg tcagattctc   5340
```

agcttatagg actgccatga aactccgaag actgcagaag gccctttgct tggatctctt 5400
gagcctgtca gctgcatgtg atgccttgga ccagcacaac ctcaagcaaa atgaccagcc 5460
catggatatc ctgcagatta ttaattgttt gaccactatt tatgaccgcc tggagcaaga 5520
gcacaacaat ttggtgaacg tgcctctctg cgtggatatg tgtctgaact ggctggtgaa 5580
tgtttatgat acgggacgaa cagggaggat ccgtgtcctg tcttttaaaa ctggcatcat 5640
ttccctgtgt aaagcacatt tggaagacaa gtacagatac cttttcaagc aagtgggaag 5700
ttcaacagga ttttgtgacc agcgcaggct gggcctcctt ctgcatgatt ctatccaaat 5760
tccaagacag ttgggtgaag ttgcatcctt tgggggcagt aacattgagc caagtgtccg 5820
gagctgcttc caatttgcta ataataagcc agagatcgaa gcggccctct tcctagactg 5880
gatgagactg gaaccccagt ccatggtgtg gctgcccgtc ctgcacagag tggctgctgc 5940
agaaactgcc aagcatcagg ccaaatgtaa catctgcaaa gagtgtccaa tcattggatt 6000
caggtacagg agtctaaagc actttaatta tgacatctgc caaagctgct ttttttctgg 6060
tcgagttgca aaaggccata aaatgcacta tcccatggtg gaatattgca ctccgactac 6120
atcaggagaa gatgttcgag actttgccaa ggtactaaaa aacaaatttc gaaccaaaag 6180
gtattttgcg aagcatcccc gaatgggcta cctgccagtg cagactgtct tagaggggga 6240
caacatggaa acgcctgcct cgtcccctca gctttcacag gatgatactc attcacgcat 6300
tgaacattat gctagcaggc tagcagaaat ggaaaacagc aatggatctt tatctaaatg 6360
atagcatctc tcctaatgag agcatagatg atgaacattt gttaatccag cattactgcc 6420
aaagtttgaa ccaggactcc cccctgagcc agcctcgtag tcctgcccag atcttgattt 6480
ccttagagag tgaggaaaga ggggagctag agagaatcct agcagatctt gaggaagaaa 6540
acaggaatct gcaagcagaa tatgaccgtc taaagcagca gcacgaacat aaaggcctgt 6600
ccccactgcc gtcccctcct gaaatgatgc ccacctctcc ccagagtccc cgggatgctg 6660
agctcattgc tgaggccaag ctactgcgtc aacacaaagg ccgcctggaa gccaggatgc 6720
aaatcctgga agaccacaat aaacagctgg agtcacagtt acacaggcta aggcagctgg 6780
tggagcaacc ccaggcagag gccaaagtga atggcacaac ggtgtcctct ccttctacct 6840
ctctacagag gtccgacagc agtcagccta tgctgctccg agtggttggc agtcaaactt 6900
cggactccat gggtgaggaa gatcttctca gtcctcccca ggacacaagc acagggttag 6960
aggaggtgat ggagcaactc aacaactcct tccctagttc aagaggaaga aatacccctg 7020
gaaagccaat gagagaggac acaatgtag 7049

<210> SEQ ID NO 8
<211> LENGTH: 6398
<212> TYPE: DNA
<213> ORGANISM: Artificial Sequence
<220> FEATURE:
<223> OTHER INFORMATION: Synthetic

<400> SEQUENCE: 8
atgctttggt gggaagaagt agaggactgt tatgaaagag aagatgttca aaagaaaaca 60
ttcacaaaat gggtaaatgc acaattttct aagtttggga agcagcatat tgagaacctc 120
ttcagtgacc tacaggatgg gaggcgcctc ctagacctcc tcgaaggcct gacagggcaa 180
aaactgccaa aagaaaaagg atccacaaga gttcatgccc tgaacaatgt caacaaggca 240
ctgcgggttt tgcagaacaa taatgttgat ttagtgaata ttggaagtac tgacatcgta 300

-continued

```
gatggaaatc ataaactgac tcttggtttg atttggaata taatcctcca ctggcaggtc    360
aaaaatgtaa tgaaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggcttgaatg ctctcatcca tagtcatagg ccagacctat    540
ttgactggaa tagtgtggtt tgccagcagt cagccacaca acgactggaa catgcattca    600
acatcgccag atatcaatta ggcatagaga aactactcga tcctgaagat gttgatacca    660
cctatccaga taagaagtcc atcttaatgt acatcacatc actcttccaa gttttgcctc    720
aacaagtgag cattgaagcc atccaggaag tggaaatgtt gccaaggcca cctaaagtga    780
ctaaagaaga acattttcag ttacatcatc aaatgcacta ttctcaacag atcacggtca    840
gtctagcaca gggatatgag agaacttctt cccctaaggc tcgattcaag agctatgcct    900
acacacaggc tgcttatgtc accacctctg accctacacg gagcccattt ccttcacagc    960
atttggaagc tcctgaagac aagtcatttg gcagttcatt gatggagagt gaagtaaacc   1020
tggaccgtta tcaaacagct ttagaagaag tattatcgtg gcttctttct gctgaggaca   1080
cattgcaagc acaaggagag atttctaatg atgtggaagt ggtgaaagac cagtttcata   1140
ctcatgaggg gtacatgatg gatttgacag cccatcaggg ccgggttggt aatattctac   1200
aattgggaag taagctgatt ggaacaggaa aattatcaga agatgaagaa actgaagtac   1260
aagagcagat gaatctccta aattcaagat gggaatgcct cagggtagct agcatggaaa   1320
aacaaagcaa tttacataga gttttaatgg atctccagaa tcagaaactg aaagagttga   1380
atgactggct aacaaaaaca gaagaaagaa caaggaaaat ggaggaagag cctcttggac   1440
ctgatcttga agacctaaaa cgccaagtac aacaacataa ggtgcttcaa gaagatctag   1500
aacaagaaca agtcagggtc aattctctca ctcacatggt ggtggtagtt gatgaatcta   1560
gtggagatca cgcaactgct gctttggaag aacaacttaa ggtattggga gatcgatggg   1620
caaacatctg tagatggaca gaagaccgct gggttctttt acaagacatc cttctcaaat   1680
ggcaacgtct tactgaagaa cagtgccttt ttagtgcatg gctttcagaa aaagaagatg   1740
cagtgaacaa gattcacaca actggcttta aagatcaaaa tgaaatgtta tcaagtcttc   1800
aaaaactggc cgttttaaaa gcggatctag aaaagaaaaa gcaatccatg ggcaaactgt   1860
attcactcaa acaagatctt ctttcaacac tgaagaataa gtcagtgacc cagaagacgg   1920
aagcatggct ggataacttt gcccggtgtt gggataattt agtccaaaaa cttgaaaaga   1980
gtacagcaca gatttcacag gaaatttctt atgtgccttc tacttatttg actgaaatca   2040
ctcatgtctc acaagcccta ttagaagtgg aacaacttct caatgctcct gacctctgtg   2100
ctaaggactt tgaagatctc tttaagcaag aggagtctct gaagaatata aaagatagtc   2160
tacaacaaag ctcaggtcgg attgacatta ttcatagcaa gaagacagca gcattgcaaa   2220
gtgcaacgcc tgtggaaagg gtgaagctac aggaagctct ctcccagctt gatttccaat   2280
gggaaaaagt taacaaaatg tacaaggacc gacaagggcg atttgacaga tctgttgaga   2340
aatggcggcg ttttcattat gatataaaga tatttaatca gtggctaaca gaagctgaac   2400
agtttctcag aaagacacaa attcctgaga attgggaaca tgctaaatac aaatggtatc   2460
ttaaggaact ccaggatggc attgggcagc ggcaaactgt tgtcagaaca ttgaatgcaa   2520
ctggggaaga aataattcag caatcctcaa aaacagatgc cagtattcta caggaaaaat   2580
tgggaagcct gaatctgcgg tggcaggagg tctgcaaaca gctgtcagac agaaaaaaga   2640
ggctagaaga acagcctgac ctagctcctg gactgacgac tattggagcc tctcctactc   2700
```

```
agactgttac tctggtgaca caacctgtgg ttactaagga aactgccatc tccaaactag   2760
aaatgccatc ttccttgatg ttggaggtac ctgctctggc agatttcaac cgggcttgga   2820
cagaacttac cgactggctt tctgtgcttg atcaagttat aaaatcacag agggtgatgg   2880
tgggtgacct tgaggatatc aacgagatga tcatcaagca gaaggcaaca atgcaggatt   2940
tggaacagag gcgtccccag ttggaagaac tcattaccgc tgcccaaaat ttgaaaaaca   3000
agaccagcaa tcaagaggct agaacaatca ttacggatcg aattgaaaga attcagaatc   3060
agtgggatga agtacaagaa caccttcaga accggaggca acagttgaat gaaatgttaa   3120
aggattcaac acaatggctg gaagctaagg aagaagctga gcaggtctta ggacaggcca   3180
gagccaagct tgagtcatgg aaggagggtc cctatacagt agatgcaatc caaaagaaaa   3240
tcacagaaac caaggagttg gccaaagacc tccgccagtg gcagacaaat gtagatgtgg   3300
caaatgactt ggccctgaaa cttgtccggg attattctgc agatgatacc agaaaagtcc   3360
acatgataac agagaatatc aatgcctctt ggagaagcat tcataaaagg gtgagtgagc   3420
gagaggctgc tttggaagaa actcatagat tactgcaaca gttcccccctg gacctggaaa   3480
agtttcttgc ctggcttaca gaagctgaaa caactgccaa tgtcctacag gatgctaccc   3540
gtaaggaaag gctcctagaa gactccaagg gagtaaaaga gctgatgaaa caatggcaag   3600
acctccaagg tgaaatgaag ctcacacaga tgtttatcac aacctggatg aaaacagcca   3660
aaaaatcctg agatccctgg aaggttccga tgatgcagtc ctgttacaag acgthtggat   3720
aacatgaact tcaagtggag tgaacttcgg aaaaagtctc tcaacattag gtcccatttg   3780
gaagccagtt ctgaccagtg gaagcgtctg cacctttctc tgcaggaact tctggtgtgg   3840
ctacagctga aagatgatga attaagccgg caggcaccta ttggaggcga ctttccagca   3900
gttcagaagc agaacgatgt acatagggcc ttcaagaggg aattgaaaac taaagaacct   3960
gtaatcatga gtactcttga gactgtacga atatttctga cagagcagcc tttggaagga   4020
ctagagaaac tctaccagga gcccagagag ctgcctcctg aggagagagc ccagaatgtc   4080
actcggcttc tacgaaagca ggctgaggag gtcaatactg agtgggaaaa attgaacctg   4140
cactccgctg actggcagag aaaaatagat gagacccttg aaagactcca ggaacttcaa   4200
gaggccacgg atgagctgga cctcaagctg cgccaagctg aggtgatcaa gggatcctgg   4260
cagcccgtgg gcgatctcct catgactctc tccaagatca cctcgagaaa gtcaaggcac   4320
ttcgaggaga aattgcgcct ctgaaagaga acgtgagcca cgtcaatgac cttgctcgcc   4380
agcttaccac tttgggcatt cagctctcac cgtataacct cagcactctg gaagacctga   4440
acaccagatg gaagcttctg caggtggccg tcgaggaccg agtcaggcag ctgcatgaag   4500
cccacaggga ctttggtcca gcatctcagc actttctttc cacgtctgtc cagggtccct   4560
gggagagagc catctcgcca aacaaagtgc cctactatat caaccacgag actcaaacaa   4620
cttgctggga ccatcccaaa atgacagagc tctaccagtc tttagctgac ctgaataatg   4680
tcagattctc agcttatagg actgccatga aactccgaag actgcagaag gccctttgct   4740
tggatctctt gagcctgtca gctgcatgtg atgccttgga ccagcacaac ctcaagcaaa   4800
atgaccagcc catggatatc ctgcagatta ttaattgttt gaccactatt tatgaccgcc   4860
tggagcaaga gcacaacaat ttggtcaacg tccctctctg cgtggatatg tgtctgaact   4920
ggctgctgaa tgtttatgat acgggacgaa cagggaggat ccgtgtcctg tcttttaaaa   4980
ctggcatcat ttccctgtgt aaagcacatt tggaagacaa gtacagatac cttttcaagc   5040
```

```
aagtggcaag ttcaacagga ttttgtgacc agcgcaggct gggcctcctt ctgcatgatt   5100
ctatccaaat tccaagacag ttgggtgaag ttgcatcctt tgggggcagt aacattgagc   5160
caagtgtccg gagctgcttc caatttgcta ataataagcc agagatcgaa gcggccctct   5220
tcctagactg gatgagactg gaaccccagt ccatggtgtg gctgcccgtc ctgcacagag   5280
tggctgctgc agaaactgcc aagcatcagg ccaaatgtaa catctgcaaa gagtgtccaa   5340
tcattggatt caggtacagg agtctaaagc actttaatta tgacatctgc caaagctgct   5400
tttttctgg tcgagttgca aaaggccata aaatgcacta tcccatggtg gaatattgca    5460
ctccgactac atcaggagaa gatgttcgag actttgccaa ggtactaaaa aacaaatttc   5520
gaaccaaaag gtattttgcg aagcatcccc gaatgggcta cctgccagtg cagactgtct   5580
tagaggggga caacatggaa acgcctgcct cgtcccctca gctttcacac gatgatactc   5640
attcacgcat tgaacattat gctagcaggc tagcagaaat ggaaaacagc aatggatctt   5700
atctaaatga tagcatctct cctaatgaga gcatagatga tgaacatttg ttaatccagc   5760
attactgcca aagtttgaac caggactccc ccctgagcca gcctcgtagt cctgcccaga   5820
tcttgatttc cttagagagt gaggaaagag gggagctaga gagaatccta gcagatcttg   5880
aggaagaaaa caggaatctg caagcagaat atgaccgtct aaagcagcag cacgaacata   5940
aaggcctgtc cccactgccg tcccctcctg aaatgatgcc cacctctccc cagagtcccc   6000
gggatgctga gctcattgct gaggccaagc tactgcgtca acacaaaggc cgcgtggaag   6060
ccaggatgca aatcctggaa gaccacaata aacagctgga gtcacagtta cacaggctaa   6120
ggcagctgct ggagcaaccc caggcagagg ccaaagtgaa tggcacaacg gtgtcctctc   6180
cttctacctc tctacagagg tccgacagca gtcagcctat gctgctccga gtggttggca   6240
gtcaaacttc ggactccatg ggtgaggaag atcttctcag tcctccccag gacacaagca   6300
cagggttaga ggaggtgatg gagcaactca acaactcctt ccctagttca agaggaagaa   6360
atacccctgg aaagccaatg agagaggaca caatgtag                           6398
```

<210> SEQ ID NO 9
<211> LENGTH: 6078
<212> TYPE: DNA
<213> ORGANISM: Artificial Sequence
<220> FEATURE:
<223> OTHER INFORMATION: Synthetic

<400> SEQUENCE: 9

```
atgctttggt gggaagaagt agaggactgt tatgaaagag aagatgttca aaagaaaaca     60
ttcacaaaat gggtaaatgc acaattttct aagtttggga agcagcatat tgagaacctc    120
ttcagtgacc tacaggatgg gaggcgcctc ctagacctcc tcgaaggcct gacagggcaa    180
aaactgccaa aagaaaaagg atccacaaga gttcatgccc tgaagaatgt caacaaggca    240
ctgcgggttt tgcagaacaa taatgttgat ttagtgaata ttggaagtac tgagatcgta    300
gatggaaatc ataaactgac tcttggtttg atttggaata taatcctcca ctggcaggtc    360
aaaaatgtaa tgaaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
```

```
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt gggataattt agtccaaaaa cttgaaaaga   1980
gtacagcaca gatttcacag gaaattctta tgtgccttct acttatttga ctgaaatcac   2040
tcatgtctca caagccctat tagaagtgga acaacttctc aatgctcctg acctctgtgc   2100
taaggacttt gaagatctct ttaagcaaga ggagtctctg aagaatataa aagatagtct   2160
acaacaaagc tcaggtcgga ttgacattat tcatagcaag aagacagcag cattgcaaag   2220
tgcaacgcct gtggaaaggg tgaagctaca ggaagctctc tcccagcttg atttccaatg   2280
ggaaaaagtt aacaaaatgt acaaggaccg acaagggcga tttgacagac agcctgacct   2340
agctcctgga ctgaccacta ttggagcctc tcctactcag actgttactc tggtgacaca   2400
acctgtggtt actaaggaaa ctgccatctc caaactagaa atgccatctt ccttgatgtt   2460
ggaggtacct gctctggcag atttcaaccg ggcttggaca gaacttaccg actggctttc   2520
tctgcttgat caagttataa aatcacagag ggtgatggtg ggtgaccttg aggatatcaa   2580
cgagatgatc atcaagcaga aggcaacaat gcaggatttg gaacagaggc gtccccagtt   2640
ggaagaactc attaccgctg cccaaaattt gaaaaacaag accagcaatc aagaggctag   2700
aacaatcatt acggatcgaa ttgaaagaat tcagaatcag tgggatgaag tacaagaaca   2760
ccttcagaac cggaggcaac agttgaatga aatgttaaag gattcaacac aatggctgga   2820
agctaaggaa gaagctgagc aggtcttagg acaggccaga gccaagcttg agtcatggaa   2880
ggagggtccc tatacagtag atgcaatcca aaagaaaatc acagaaacca agcagttggc   2940
caaagacctc cgccagtggc agacaaatgt agatgtggca aatgacttgg ccctgaaact   3000
tctccgggat tattctgcag atgataccag aaaagtccac atgataacag agaatatcaa   3060
```

-continued

```
tgcctcttgg agaagcattc ataaaagggt gagtgagcga gaggctgctt tggaagaaac   3120
tcatagatta ctgcaacagt tccccctgga cctggaaaag tttcttgcct ggcttacaga   3180
agctgaaaca actgccaatg tcctacagga tgctacccgt aaggaaaggc tcctagaaga   3240
ctccaaggga gtaaaagagc tgatgaaaca atggcaagac ctccaaggtg aaattgaagc   3300
tcacacagat gtttatcaca acctggatga aaacagccaa aaaatcctga gatccctgga   3360
aggttccgat gatgcagtcc tgttacaaag acgtttggat aacatgaact tcaagtggag   3420
tgaacttcgg aaaaagtctc tcaacattag gtcccatttg gaagccagtt ctgaccagtg   3480
gaagcgtctg cacctttctc tgcaggaact tctggtgtgg ctacagctga aagatgatga   3540
attaagccgg caggcaccta ttggaggcga ctttccagca gttcagaagc agaacgatgt   3600
acatagggcc ttcaagaggg aattgaaaac taaagaacct gtaatcatga gtactctgag   3660
actgtacgaa tatttctgac agagcagcct ttggaaggac tagagaaact ctaccaggag   3720
cccagagagc tgcctcctga ggagagagcc cagaatgtca ctcggcttct acgaaagcag   3780
gctgaggagg tcaatactga gtgggaaaaa ttgaacctgc actccgctga ctggcagaga   3840
aaaatagatg agacccttga aagactccag gaacttcaag aggccacgga tgagctggac   3900
ctcaagctgc gccaagctga ggtgatcaag ggatcctggc agcccgtggg cgatctcctc   3960
attgactctc tccaagatca cctcgagaaa gtcaaggcac ttcgaggaga aattgcgcct   4020
ctgaaagaga acgtgagcca cgtcaatgac cttgctcgcc agcttaccac tttggggatt   4080
cagctctcac cgtataacct cagcactctg gaagacctga acaccagatg gaagcttctg   4140
caggtggccg tcgaggacgg agtcaggcag gtgcatgaag cccacaggga ctttggtcca   4200
gcatgtcagc actttctttc cacgtctgtc cagggtccct gggagagagc catctcgcca   4260
aacaaagtgc cctactatat caaccacgag actcaaacaa cttgctggga ccatcccaaa   4320
atgacagagc tctaccagtc tttagctgac ctgaataatg tcagattctc agcttatagg   4380
actgccatga aactccgaag actgcagaag gccctttgct tggatctctt gagcctgtca   4440
gctgcatgtg atgccttgga ccagcacaac ctcaagcaaa atgaccagcc catggatatc   4500
ctgcagatta ttaattgttt gaccactatt tatgaccgcc tggagcaaga gcacaacaat   4560
ttggtcaacg tccctctctg cgtggatatg tgtctgaact ggctgctgaa tgtttatgat   4620
acgggacgaa cagggaggat ccgtgtcctg tcttttaaaa ctggcatcat ttccctgtgt   4680
aaagcacatt tggaagacaa gtacagatac cttttcaagc aagtggcaag ttcaacagga   4740
ttttgtgacc agcgcaggct gggcctcctt ctgcatgatt ctatccaaat tccaagacag   4800
ttgggtgaag ttgcatcctt tgggggcagt aacattgagc caagtgtccg gagctgcttc   4860
caatttgcta ataataagcc agagatcgaa gcggccctct tcctagactg gatgagactg   4920
gaaccccagt ccatggtgtg gctgcccgtc ctgcacagag tggctgctgc agaaactgcc   4980
aagcatcagg ccaaatgtaa catctgcaaa gagtgtccaa tcattggatt caggtacagg   5040
agtctaaagc actttaatta tgacatctgc caaagctgct ttttttctgg tcgagttgca   5100
aaaggccata aaatgcacta tcccatggtg gaatattgca ctccgactac atcaggagaa   5160
gatgttcgag actttgccaa ggtactaaaa aacaaatttc gaagcaaaag gtattttgcg   5220
aagcatcccc gaatgggcta cctgccagtg cagactgtct tagaggggga caacatggaa   5280
acgcctgcct cgtcccctca gctttcacac gatgatactc attcacgcat tgaacattat   5340
gctagcaggc tagcagaaat ggaaaacagc aatggatctt atctaaatga tagcatctct   5400
cctaatgaga gcatagatga tgaacatttg ttaatccagc attactgcca aagtttgaac   5460
```

```
caggactccc ccctgagcca gcctcgtagt cctgcccaga tcttgatttc cttagagagt   5520

gaggaaagag gggagctaga gagaatccta gcagatcttg aggaagaaaa caggaatctg   5580

caagcagaat atgaccgtct aaagcagcag cacgaacata aaggcctgtc cccactgccg   5640

tcccctcctg aaatgatgcc cacctctccc cagagtcccc gggatgctga gctcattgct   5700

gaggccaagc tactgcgtca acacaaaggc cgccctggaag ccaggatgca aatcctggaa   5760

gaccacaata aacagctgga gtcacagtta cacaggctaa ggcagctgct ggagcaaccc   5820

caggcagagg ccaaagtgaa tggcacaacg gtgtcctctc cttctacctc tctacagagg   5880

tccgacagca gtcagcctat gctgctccga gtggttggca gtcaaacttc ggactccatg   5940

ggtgaggaag atcttctcag tcctccccag gacacaagca cagggttaga ggaggtgatg   6000

gagcaactca acaactcctt ccctagttga agaggaagaa atacccctgg aaagccaatg   6060

agagaggaca caatgtag                                                  6078
```

```
<210> SEQ ID NO 10
<211> LENGTH: 6264
<212> TYPE: DNA
<213> ORGANISM: Artificial Sequence
<220> FEATURE:
<223> OTHER INFORMATION: Synthetic

<400> SEQUENCE: 10

atgctttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatgccc tgaacaatgt caacaaggca    240

ctgcgggttt tgcagaacaa taatgttgat ttagtgaata ttggaagtac tgacatcgta    300

gatggaaatc ataaactgac tcttggtttg atttggaata taatcctcca ctggcaggtc    360

aaaaatgtaa tgaaaaatat gatggctgga ttgcaacaaa ccaacagtga aaagattctc    420

ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttgccagcag tcagccacac aacgactgga acatgcattc    600

aacatcgcca gatatcaatt aggcatagag aaactactcg atcctgaaga tgttgatacc    660

acctatccag ataagaagtc catcttaatg tacatcacat cactcttcca agttttgcct    720

caacaagtga gcattgaagc catccaggaa gtggaaatgt tgccaaggcc acctaaagtg    780

actaaagaag aacattttca gttacatcat caaatgcact attctcaaca gatcacggtc    840

agtctagcac agggatatga gagaacttct tcccctaagc ctcgattcaa gagctatgcc    900

tacacacagg ctgcttatgt caccacctct gaccctacac ggagcccatt tccttcacag    960

catttggaag ctcctgaaga caagtcattt ggcagttcat tgatggagag tgaagtaaac   1020

ctggaccgtt atcaaacagc tttagaagaa gtattatcgt ggcttctttc tgctgaggac   1080

acattgcaag cacaaggaga gatttctaat gatgtggaag tggtgaaaga ccagtttcat   1140

actcatgagg ggtacatgat ggatttgaca gcccatcagg gccgggttgg taatattcta   1200

caattgggaa gtaagctgat tggaacagga aaattatca gaagatgaag aaactgaagt    1260

acaagagcag atgaatctcc taaattcaag atgggaatgc ctcagggtag ctagcatgga   1320

aaaacaaagc aatttacata gagttttaat ggatctccag aatcagaaac tgaaagagtt   1380
```

gaatgactgg ctaacaaaaa cagaagaaag aacaaggaaa atggaggaag agcctcttgg 1440
acctgatctt gaagacctaa aacgccaagt acaacaacat aaggtgcttc aagaagatct 1500
agaacaagaa caagtcaggg tcaattctct cactcacatg gtggtggtag ttgatgaatc 1560
tagtggagat cacgcaactg ctgctttgga agaacaactt aaggtattgg gagatcgatg 1620
ggcaaacatc tgtagatgga cagaagaccg ctgggttctt ttacaagaca tccttctcaa 1680
atggcaacgt cttactgaag aacagtgcct ttttagtgca tggctttcag aaaaagaaga 1740
tgcagtgaac aagattcaca caactggctt taaagatcaa aatgaaatgt tatcaagtct 1800
tcaaaaactg gccgttttaa aagcggatct agaaaagaaa aagcaatcca tgggcaaact 1860
gtattcactc aaacaagatc ttctttcaac actgaagaat aagtcagtga cccagaagac 1920
ggaagcatgg ctggataact ttgcccggtg ttgggataat ttagtccaaa aacttgaaaa 1980
gagtacagca cagatttcac aggaaatttc ttatgtgcct tctacttatt tgactgaaat 2040
cactcatgtc tcacaagccc tattagaagt ggaacaactt ctcaatgctc ctgacctctg 2100
tgctaaggac tttgaagatc tctttaagca agaggagtct ctgaagaata taaaagatag 2160
tctacaacaa agctcaggtc ggattgacat tattcatagc aagaagacag cagcattgca 2220
aagtgcaacg cctgtggaaa gggtgaagct acaggaagct ctctcccagc ttgatttcca 2280
atgggaaaaa gttaacaaaa tgtacaagga cggacaaggg cgatttgaca gatctgttga 2340
gaaatggcgg cgttttcatt atgatataaa gatatttaat cagtggctaa cagaagctga 2400
acagtttctc agaaagacac aaattcctga gaattgggaa catgctaaat acaaatggta 2460
tcttaaggaa ctccaggatg gcattgggca gcggcaaact gttgtcagaa cattgaatgc 2520
aactggggaa gaaataattc agcaatcctc aaaaacagat gccagtattc tacaggaaaa 2580
attgggaagc ctgaatctgc ggtggcagga ggtctgcaaa cagctgtcag acagaaaaaa 2640
gaggctagaa gaacaaaaga atatcttgtc agaatttcaa agagatttaa atgaatttgt 2700
tttatggttg gaggaagcag ataacattgc tagtatccca cttgaacctg gaaaagagca 2760
gcaactaaaa gaaaagcttg agcaagtcaa gttactggtg gaagagttgc ccctgcgcca 2820
gggaattctc aaacaattaa atgaaactgg aggacccgtg cttgtaagtg ctcccataag 2880
cccagaagag caagataaac ttgaaaataa gctcaagcag acaaatctcc agtggataaa 2940
ggtttccaga gctttacctg agaaacaagg agaaattgaa gctcaaataa aagaccttgg 3000
gcagcttgaa aaaaagcttg aagaccttga agagcagtta aatcatctgc tgctgtggtt 3060
atctcctatt aggaatcagt tggaaattta taaccaacca aaccaagaag gaccatttga 3120
cgttcaggaa actgaaatag cagttcaagc taaacaaccg gatgtggaag agattttgtc 3180
taaagggcag catttgtaca aggaaaaacc agccactcag ccagtgaaga ggaagttaga 3240
agatctgagc tctgagtgga aggcggtaaa ccgtttactt caagagctga gggcaaagca 3300
gcctgaccta gctcctggac tgaccactat tggagcctct cctactcaga ctgttactct 3360
ggtgacacaa cctgtggtta ctaaggaaac tgccatctcc aaactagaaa tgccatcttc 3420
cttgatgttg gaggtacctg ctctggcaga tttcaaccgg gcttggacag aacttaccga 3480
ctggctttct ctgcttgatc aagttataaa atcacagagg gtgatggtgg gtgaccttga 3540
ggatatcaac gagatgatca tcaagcagaa ggcaacaatg caggatttgg aacagaggcg 3600
tccccagttg gaagaactca ttaccgctgc ccaaaatttg aaaaacaaga ccagcaatca 3660
agaggctaga acaatcatta cggatcgaat tgaaagaatt cagaatcagt gggatgaagt 3720
acaagaacac cttcagaacc ggaggcaaca gttgaatgaa atgttaaagg attcaacaca 3780
atggctggaa gctaaggaag aagctgagca ggtcttagga caggccagag ccaagcttga 3840
gtcatggaag gagggtccct atacagtaga tgcaatccaa aagaaaatca cagaaaccaa 3900
gcagttggcc aaagacctcc gccagtggca gacaaatgta gatgtggcaa atgacttggc 3960
cctgaaactt ctccgggatt attctgcaga tgataccaga aaagtccaca tgataacaga 4020
gaatatcaat gcctcttgga gaagcattca taaaagggtg agtgagcgag aggctgcttt 4080
ggaagaaact catagattac tgcaacagtt cccccctggac ctggaaaagt ttcttgcctg 4140
gcttacagaa gctgaaacaa ctgccaatgt cctacaggat gctacccgta aggaaaggct 4200
cctagaagac tccaagggag taaaagagct gatgaaacaa tggcaagacc tccaaggtga 4260
aattgaagct cacacagatg tttatcacaa cctggatgaa aacagccaaa aaatcctgag 4320
atccctggaa ggttccgatg atgcagtcct gttacaaaga cgtttggata acatgaactt 4380
caagtggagt gaacttcgga aaaagtctct caacattagg tcccatttgg aagccagttc 4440
tgaccagtgg aagcgtctgc acctttctct gcaggaactt ctggtgtggc tacagctgaa 4500
agatgatgaa ttaagccggc aggcacctat tggaggcgac tttccagcag ttcagaagca 4560
gaacgatgta catagggcct tcaagaggga attgaaaact aaagaacctg taatcatgag 4620
tactctgaga ctgtacgaat atttctgaca gagcagcctt tggaaggact agagaaactc 4680
taccaggagc ccagagagct gcctcctgag gagagagccc agaatgtcac tcggcttcta 4740
cgaaagcagg ctgaggaggt caatactgag tgggaaaaat tgaacctgca ctccgctgac 4800
tggcagagaa aaatagatga gacccttgaa agactccagg aacttcaaga ggccacggat 4860
gagctggacc tcaagctgcg ccaagctgag gtgatcaagg gatcctggca gcccgtgggc 4920
gatctcctca ttgactctct ccaagatcac ctcgagaaag tcaaggcact tcgaggagaa 4980
attgcgcctc tgaaagagaa cgtgagccac gtcaatgacc ttgctcgcca gcttaccact 5040
ttgggcattc agctctcacc gtataacctc agcactctgg aagacctgaa caccagatgg 5100
aagcttctgc aggtggccgt cgaggaccga gtcaggcagc tgcatgaagc ccacagggac 5160
tttggtccag catctcagca ctttctttcc acgtctgtcc agggtccctg ggagagagcc 5220
atctcgccaa acaaagtgcc ctactatatc aaccacgaga ctcaaacaac ttgctgggac 5280
catcccaaaa tgacagagct ctaccagtct ttagctgacc tgaataatgt cagattctca 5340
gcttatagga ctgccatgaa actccgaaga ctgcagaagg ccctttgctt ggatctcttg 5400
agcctgtcag ctgcatgtga tgccttggac cagcacaacc tcaagcaaaa tgaccagccc 5460
atggatatcc tgcagattat taattgtttg accactattt atgaccgcct ggagcaagag 5520
cacaacaatt tggtcaacgt ccctctctgc gtggatatgt gtctgaactg gctgctgaat 5580
gtttatgata cgggacgaac agggaggatc cgtgtcctgt cttttaaaac tggcatcatt 5640
tccctgtgta aagcacattt ggaagacaag tacagatacc ttttcaagca agtggcaagt 5700
tcaacaggat tttgtgacca gcgcaggctg ggcctccttc tgcatgattc tatccaaatt 5760
ccaagacagt tgggtgaagt tgcatccttt gggggcagta acattgagcc aagtgtccgg 5820
agctgcttcc aatttgctaa taataagcca gagatcgaag cggccctctt cctagactgg 5880
atgagactgg aaccccagtc catggtgtgg ctgcccgtcc tgcacagagt ggctgctgca 5940
gaaactgcca agcatcaggc caaatgtaac atctgcaaag agtgtccaat cattggattc 6000
aggtacagga gtctaaagca ctttaattat gacatctgcc aaagctgctt tttttctggt 6060
cgagttgcaa aaggccataa aatgcactat cccatggtgg aatattgcac tccgactaca 6120
tcaggagaag atgttcgaga ctttgccaag gtactaaaaa acaaatttcg aaccaaaagg 6180
tattttgcga agcatccccg aatgggctac ctgccagtgc agactgtctt agagggggac 6240
aacatggaaa ctgacacaat gtag 6264

<210> SEQ ID NO 11
<211> LENGTH: 4078
<212> TYPE: DNA
<213> ORGANISM: Artificial Sequence
<220> FEATURE:
<223> OTHER INFORMATION: Synthetic

<400> SEQUENCE: 11
atgctttggt gggaagaagt agaggactgt tatgaaagag aagatgttca aaagaaaaca 60
ttcacaaaat gggtaaatgc acaattttct aagtttggga agcagcatat tgagaacctc 120
ttcagtgacc tacaggatgg gaggcgcctc ctagacctcc tcgaaggcct gacagggcaa 180
aaactgccaa aagaaaaagg atccacaaga gttcatgccc tgaacaatgt caacaaggca 240
ctgcgggttt tgcagaacaa taatgttgat ttagtgaata ttggaagtac tgacatcgta 300
gatggaaatc ataaactgac tcttggtttg atttggaata taatcctcca ctggcaggtc 360
aaaaatgtaa tgaaaaatat catggctgga ttgcaacaaa ccaacagtga aaagattctc 420
ctgagctggg tccgacaatc aactcgtaat tatccagagg ttaatgtaat caacttcacc 480
accagctggt ctgatggcct ggctttgaat gctctcatcc atagtcatag gccagaccta 540
tttgactgga atagtgtggt ttgccagcag tcagccacac aacgactgga acatgcattc 600
aacatcgcca gatatcaatt aggcatagag aaactactcg atcctgaaga tgttgatacc 660
acctatccag ataagaagtc catcttaatg tacatcacat cactcttcca agttttgcct 720
caacaagtga gcattgaagc catccaggaa gtggaaatgt tgccaaggcc acctaaagtg 780
actaaagaag aacattttca gttacatcat caaatgcact attctcaaca gatcacggtc 840
agtctagcac agggatatga gagaacttct tcccctaagc ctcgattcaa gagctatgcc 900
tacacacagg ctgcttatgt caccacctct gaccctacac ggagcccatt tccttcacag 960
catttggaag ctcctgaaga caagtcattt ggcagttcat tgatggagag tgaagtaaac 1020
ctggaccgtt atcaaacagc tttagaagaa gtattatcgt ggcttctttc tgctgaggac 1080
acattgcaag cacaaggaga gatttctaat gatgtggaag tggtgaaaga ccagtttcat 1140
actcatgagg ggtacatgat ggatttgaca gcccatcagg gccgggttgg taatattcta 1200
caattgggaa gtaagctgat tggaacagga aaattatcag aagatgaaga aactgaagta 1260
caagagcaga tgaatctcct aaattcaaga tgggaatgcc tcagggtagc tagcatggaa 1320
aaacaaagca atttacatag agaaatttct tatgtgcctt ctacttattt gactgaaatc 1380
actcatgtct cacaagccct attagaagtg gaacaacttc tcaatgctcc tgacctctgt 1440
gctaaggact ttgaagatct ctttaagcaa gaggagtctc tgaagaatat aaaagatagt 1500
ctacaacaaa gctcaggtcg gattgacatt attcatagca agaagacagc agcattgcaa 1560
agtgcaacgc ctgtggaaag ggtgaagcta caggaagctc tctcccagct tgatttcgaa 1620
tgggaaaaag ttaacaaaat gtacaaggac cgacaagggc gatttgacag atctgttgag 1680
aaatggcggc gttttcatta tgatataaag atatttaatc agtggctaac agaagctgaa 1740
cagtttctca gaaagacaca aattcctgag aattgggaac atgctaaata caaatggtat 1800
cttaaggaac tccaggatgg cattgggcag cggcaaactg ttgtcagaac attgaatgca 1860
actggggaag aaataattca gcaatcctca aaaacagatg ccagtattct acaggaaaaa 1920

```
ttgggaagcc tgaatctgcg gtggcaggag gtctgcaaac agctgtcaga cagaaaaaag   1980
aggctagaag aacaaaagaa tatcttgtca gaatttcaaa gagatttaaa tgaatttgtt   2040
ttatggttgg aggaagcaga taacattgct agtatcccac ttgaacctgg aaaagagcag   2100
caactaaaag aaaagcttga gcaagtcaag ttactggtgg aagagttgcc cctgcgccag   2160
ggaattctca aacaattaaa tgaaactgga ggacccgtgc ttgtaagtgc tcccataagc   2220
ccagaagagc aagataaact tgaaaataag ctcaagcaga caaatctcca gtggataaag   2280
gtttccagag ctttacgtga gaaagaagga gaaattgaag ctcaaataaa agaccttggg   2340
cagcttgaaa aaaagcttga agaccttgaa gagcagttaa atcatctgct gctgtggtta   2400
tctcctatta ggaatcagtt ggaaatttat aaccaaccaa accaagaagg accatttgac   2460
gttcaggaaa ctgaaatagc agtcaagcta aacaaccgga tgtggaagag attttgtcta   2520
aagggcagca tttgtacaag gaaaaaccag ccactcagcc agtgaagagg aagttagaag   2580
atctgagctc tgagtggaag gcggtaaacc gtttacttca agagctgagg gcaaagaccc   2640
ttgaaagact ccaggaactt caagaggcca cggatgagct ggacctcaag ctgcgccaag   2700
ctgaggtgat caagggatcc tggcagcccg tgggcgatct cctcattgac tctctccaag   2760
atcacctcga gaaagtcaag gcacttcgag gagaaattgc gcctctgaaa gagaacgtga   2820
gccacgtcaa tgaccttgct cgccagctac cactttgggc attcagctct caccgtataa   2880
cctcagcact ctggaagacc tgaacaccag atggaagctt ctgcaggtgg ccgtcgagga   2940
ccgagtcagg cagctgcatg aagcccacag ggactttggt ccagcatctc agcactttct   3000
ttccacgtct gtccagggtc cctgggagag agccatctcg ccaaacaaag tgccctacta   3060
tatcaaccac gagactcaaa caacttgctg ggaccatccc aaaatgacag agctctacca   3120
gtctttagct gacctgaata atgtcagatt ctcagcttat aggactgcca tgaaactccg   3180
aagactgcag aaggcccttt gcttggatct cttgagcctg tcagctgcat gtgatgcctt   3240
ggaccagcac aacctcaagc aaaatgacca gcccatggat atcctgcaga ttattaattg   3300
tttgagcact atttatgacc gcctggagca agagcacaac aatttggtca acgtccctct   3360
ctgcgtggat atgtgtctga actggctgct gaatgtttat gatacgggac gaacagggag   3420
gatccgtgtc ctgtctttta aaactggcat catttccctg tgtaaagcac atttggaaga   3480
caagtacaga taccttttca agcaagtggc aagttcaaca ggattttgtg accagcgcag   3540
gctgggcctc cttctgcatg attctatcca aattccaaga cagttgggtg aagttgcatc   3600
ctttgggggc agtaacattg agccaagtgt ccggagctgc ttccaatttg ctaataataa   3660
gccagagatc gaagcggccc tcttcctaga ctggatgaga ctggaacccc agtccatggt   3720
gtggctgccc gtcctgcaca gagtggctgc tgcagaaact gccaagcatc aggccaaatg   3780
taacatctgc aaagagtgtc caatcattgg attcaggtac aggagtctaa agcactttaa   3840
ttatgacatc tgccaaagct gctttttttc tggtcgagtt gcaaaaggcc ataaaatgca   3900
ctatcccatg gtggaatatt gcactccgac tacatcagga gaagatgttc gagactttgc   3960
caaggtacta aaaaacaaat ttcgaaccaa aaggtatttt gcgaagcatc cccgaatggg   4020
ctacctgcca gtgcagactg tcttagaggg ggacaacatg gaaactgaca caatgtag     4078
```

```
<210> SEQ ID NO 12
<211> LENGTH: 3761
<212> TYPE: DNA
<213> ORGANISM: Artificial Sequence
<220> FEATURE:
```

<223> OTHER INFORMATION: Synthetic

<400> SEQUENCE: 12
atgctttggt gggaagaagt agaggactgt tatgaaagag aagatgttca aaagaaaaca 60
ttcacaaaat gggtaaatgc acaattttct aagtttggga agcagcatat tgagaacctc 120
ttcagtgacc tacaggatgg gaggcgcctc ctagacctcc tcgaaggcct gacagggcaa 180
aaactgccaa aagaaaaagg atccacaaga gttcatgccc tgaacaatgt caacaaggca 240
ctgcgggttt tgcagaacaa taatgttgat ttagtgaata ttggaagtac tgacatcgta 300
gatggaaatc ataaactgac tcttggtttg atttggaata taatcctcca ctggcaggtc 360
aaaaatgtaa tgaaaaatat catggctgga ttgcaacaaa ccaacagtga aaagattctc 420
ctgagctggg tccgacaatc aactcgtaat tatccacagg taatgtaatc aacttcacca 480
ccagctggtc tgatggcctg gctttgaatg ctctcatcca tagtcatagg ccagacctat 540
ttgactggaa tagtgtggtt tgccagcagt cagccacaca acgactggaa catgcattca 600
acatcgccag atatcaatta ggcatagaga aactactcga tcctgaagat gttgatacca 660
cctatccaga taagaagtcc atcttaatgt acatcacatc actcttccaa gttttgcctc 720
aacaagtgag cattgaagcc atccaggaag tggaaatgtt gccaaggcca cctaaagtga 780
ctaaagaaga acattttcag ttacatcatc aaatgcacta ttctcaacag atcacggtca 840
gtctagcaca gggatatgag agaacttctt cccctaagcc tcgattcaag agctatgcct 900
acacacaggc tgcttatgtc accacctctg accctacacg gagcccattt ccttcacagc 960
atttggaagc tcctgaagac aagtcatttg gcagttcatt gatggagagt gaagtaaacc 1020
tggaccgtta tcaaacagct ttagaagaag tattatcgtg gcttctttct gctgaggaca 1080
cattgcaagc acaaggagag atttctaatg atgtggaagt ggtgaaagac cagtttcata 1140
ctcatgaggg gtacatgatg gatttgacag cccatcaggg ccgggttggt aatattctac 1200
aattgggaag taagctgatt ggaacaggaa aattatcaga agatgaagaa actgaagtac 1260
aagagcagat gaatctccta aattcaagat gggaatgcct cagggtagct agcatggaaa 1320
aacaaagcaa tttacataga gttttaatgg atctccagaa tcagaaactg aaagagttga 1380
atgactggct aacaaaaaca gaagaaagaa caaggaaaat ggaggaagag cctcttggac 1440
ctgatcttga agacctaaaa cgccaagtac aacaacataa ggtgcttcaa gaagatctag 1500
aacaagaaca agtcagggtc aattctctca ctcacatggt ggtggtagtt gatgaatcta 1560
gtggagatca cgcaactgct gctttggaag aacaacttaa ggtattggga gatcgatggg 1620
caaacatctg tagatggaca gaagaccgct gggttctttt acaagacgaa atttcttatg 1680
tgccttctac ttatttgact gaaatcactc atgtctcaca agccctatta gaagtggaac 1740
aacttctcaa tgctcctgac ctctgtgcta aggactttga agatctcttt aagcaagagg 1800
agtctctgaa gaatataaaa gatagtctac aacaaagctc aggtcggatt gacattattc 1860
atagcaagaa gacagcagca ttgcaaagtg caacgcctgt ggaaagggtg aagctacagg 1920
aagctctctc ccagcttgat ttccaatggg aaaaagttaa caaaatgtac aaggaccgac 1980
aagggcgatt tgacagatct gttgagaaat ggcggcgttt tcattatgat ataaagatat 2040
ttaatcagtg gctaacagaa gctgaacagt ttctcagaaa gacacaaatt cctgagaatt 2100
gggaacatgc taaatacaaa tggtatctta aggaactcca ggatggcatt gggcagcggc 2160
aaactgttgt cagaacattg aatgcaactg ggaagaaat aattcagcaa tcctcaaaaa 2220
cagatgccag tattctacag gaaaaattgg gaagcctgaa tctgcggtgg caggaggtct 2280
gcaaacagct gtcagacaga aaaaagaggc tagaagaaac ccttgaaaga ctccaggaac 2340
ttcaagaggc cacggatgag ctggacctca agctgcgcca agctgaggtg atcaagggat 2400
cctggcagcc cgtgggcgat ctcctcattg actctctcca agatcacctc gagaaagtca 2460
aggcacttcg aggagaaatt gcgcctctga aagagaacgt gagccacgtc aatgaccttg 2520
ctcgccagct taccactttg ggcattcagc tctcaccgta taacctcagc actctggaag 2580
acctgaacac cagatggaag cttctgcagg tggccgtcga ggaccgagtc aggcagctgc 2640
atgaagccca cagggacttt ggtccagcat ctcagcactt tctttccacg tctgtccagg 2700
gtccctggga gagagccatc tcgccaaaca aagtgcccta ctatatcaac cacgagactc 2760
aaacaacttg ctgggaccat cccaaaatga cagagctcta ccagtcttta gctgacctga 2820
ataatgtcag attctcagct tataggactg ccatgaaact ccgaagactg cagaaggccc 2880
tttgcttgga tctcttgagc ctgtcagctg catgtgatgc cttggaccag cacaacctca 2940
agcaaaatga ccagcccatg gatatcctgc agattattaa ttgtttgacc actatttatg 3000
accgcctgga gcaagagcac aacaatttgg tcaacgtccc tctctgcgtg gatatgtgtc 3060
tgaactggct gctgaatgtt tatgatacgg gacgaacagg gaggatccgt gtcctgtctt 3120
ttaaaactgg catcatttcc ctgtgtaaag cacatttgga agacaagtac agataccttt 3180
tcaagcaagt ggcaagttca acaggatttt gtgaccagcg caggctgggc ctccttctgc 3240
atgattctat ccaaattcca agacagttgg gtgaagttgc atcctttggg ggcagtaaca 3300
ttgagccaag tgtccggagc tgcttccaat ttgctaataa taagccagag atcgaagcgg 3360
ccctcttcct agactggatg agactggaac cccagtccat ggtgtggctg cccgtcctgc 3420
acagagtggc tgctgcagaa actgccaagc atcaggccaa atgtaacatc tgcaaagagt 3480
gtccaatcat tggattcagg tacaggagtc taaagcactt taattatgac atctgccaaa 3540
gctgcttttt ttctggtcga gttgcaaaag gccataaaat gcactatccc atggtggaat 3600
attgcactcc gactacatca ggagaagatg ttcgagactt tgccaaggta ctaaaaaaca 3660
aatttcgaac caaaaggtat tttgcgaagc atccccgaat gggctacctg ccagtgcaga 3720
ctgtcttaga gggggacaac atggaaactg acacaatgta g 3761

<210> SEQ ID NO 13
<211> LENGTH: 3434
<212> TYPE: DNA
<213> ORGANISM: Artificial Sequence
<220> FEATURE:
<223> OTHER INFORMATION: Synthetic

<400> SEQUENCE: 13
atgctttggt gggaagaagt agaggactgt tatgaaagag aagatgttca aaagaaaaca 60
ttcacaaaat gggtaaatgc acaattttct aagtttggga agcagcatat tgagaacctc 120
ttcagtgacc tacaggatgg gaggcgcctc ctagacctcc tcgaaggcct gacagggcaa 180
aaactgccaa aagaaaaagg atccacaaga gttcatgccc tgaacaatgt caacaaggca 240
ctgcgggttt tgcagaacaa taatgttgat ttagtgaata ttggaagtac tgacatcgta 300
gatggaaatc ataaactgac tcttggtttg atttggaata taatcctcca ctggcaggtc 360
aaaaatgtaa tgaaaaatat catggctgga ttgcaacaaa ccaacagtga aaagattctc 420
ctgagctggg tccgacaatc aactcgtaat tatccacagg ttaatgtaat caacttcacc 480
accagctggt ctgatggcct ggctttgaat gctctcatcc atagtcatag gccagaccta 540

```
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca attacataga gaaatttctt atgtgccttc tacttatttg actgaaatca   1380
ctcatgtctc acaagcccta ttagaagtgg aacaacttct caatgctcct gacctctgtg   1440
ctaaggactt tgaagatctc tttaagcaag aggagtctct gaagaatata aaagatagtc   1500
tacaacaaag ctcaggtcgg attgacatta ttcatagcaa gaagacagca gcattgcaaa   1560
gtgcaacgcc tgtggaaagg gtgaagctac aggaagctct ctcccagctt gatttccaat   1620
gggaaaaagt taacaaaatg tacaaggacc gacaagggcg atttgacaga tctgttgaga   1680
aatggcggcg ttttcattat gatataaaga tatttaatca gtggctaaca gaagctgaac   1740
agtttctcag aaagacacaa attcctgaga attgggaaca tgctaaatac aaatggtatc   1800
ttaaggaact ccaggatggc attgggcagc ggcaaactgt tgtcagaaca ttgaatgcaa   1860
ctggggaaga aataattcag caatcctcaa aaacagatgc cagtattcta caggaaaaat   1920
tgggaagcct gaatctgcgg tggcaggagg tctgcaaaca gctgtcagac agaaaaaaga   1980
ggctagaaga aacccttgaa agactccagg aacttcaaga ggccacggat gagctggacc   2040
tcaagctgcg ccaagctgag gtgatcaagg gatcctggca gcccgtgggc gatctcctca   2100
ttgactctct ccaagatcac ctcgagaaag tcaaggcact tcgaggagaa attgcgcctc   2160
tgaaagagaa cgtgagccac gtcaatgacc ttgctcgcca gcttaccact ttgggcattc   2220
agctctcacc gtataacctc agcactctgg aagacctgaa caccagatgg aagcttctgc   2280
aggtggccgt cgaggaccga gtcaggcagc tgcatgaagc ccacagggac tttggtccag   2340
catctcagca ctttctttcc acgtctgtcc agggtccctg ggagagagcc atctcgccaa   2400
acaaagtgcc ctactatatc aaccacgaga ctcaaacaac ttgctgggac gatcccaaaa   2460
tgacagagct ctaccagtct ttagctgacc tgaataatgt cagattctca gcttatagga   2520
ctgccatgaa actccgaaga ctgcagaagg ccctttgctt ggatctcttg agcctgtcag   2580
ctgcatgtga tgccttggac cagcacaacc tcaagcaaaa tgaccagccc atggatatcc   2640
tgcagattat taattgtttg accactattt atgaccgcct ggagcaagag cacaacaatt   2700
tggtcaacgt ccctctctgc gtggatatgt gtctgaactg gctgctgaat gtttatgata   2760
cgggacgaac agggaggatc cgtgtcctgt cttttaaaac tggcatcatt tccctgtgta   2820
aagcacattt ggaagacaag tacagatacc ttttcaagca agtggcaagt tcaacaggat   2880
tttgtgacca gcgcaggctg ggcctccttc tgcatgattc tatccaaatt ccaagacagt   2940
```

tgggtgaagt tgcatccttt gggggcagta acattgagcc aagtgtccgg agctgcttcc 3000
aatttgctaa taataagcca gagatcgaag cggccctctt cctagactgg atgagactgg 3060
aaccccagtc catggtgtgg ctgcccgtcc tgcacagagt ggctgctgca gaaactgcca 3120
agcatcaggc caaatgtaac atctgcaaag agtgtccaat cattggattc aggtacagga 3180
gtctaaagca ctttaattat gacatctgcc aaagctgctt tttttctggt cgagttgcaa 3240
aaggccataa aatgcactat cccatggtgg aatattgcac tccgactaca tcaggagaag 3300
atgttcgaga ctttgccaag gtactaaaaa acaaatttcg aaccaaaagg tattttgcga 3360
agcatccccg aatgggctac ctgccagtgc agactgtctt agagggggac aacatggaaa 3420
ctgacacaat gtag 3434

<210> SEQ ID NO 14
<211> LENGTH: 3439
<212> TYPE: DNA
<213> ORGANISM: Artificial Sequence
<220> FEATURE:
<223> OTHER INFORMATION: Synthetic

<400> SEQUENCE: 14
atgctttggt gggaagaagt agaggactgt tatgaaagag aagatgttca aaagaaaaca 60
ttcacaaaat gggtaaatgc acaattttct aagtttggga agcagcatat tgagaacctc 120
ttcagtgacc tacaggatgg gaggcgcctc ctagacctcc tcgaaggcct gacagggcaa 180
aaactgccaa aagaaaaagg atccacaaga gttcatgccc tgaacaatgt caacaaggca 240
ctgcgggttt tgcagaacaa taatgttgat ttagtgaata ttggaagtac tgacatcgta 300
gatggaaatc ataaactgac tcttggtttg atttggaata taatcctcca ctggcaggtc 360
aaaaatgtaa tgaaaaatat catggctgga ttgcaacaaa ccaacagtga aaagattctc 420
ctgagctggg tccgacaatc aactcgtaat tatccacagg ttaatgtaat caacttcacc 480
accagctggt ctgatggcct ggctttgaat gctctcatcc atagtcatag gccagaccta 540
tttgactgga atagtgtggt ttggcagcag tcagccacac aacgactgga acatgcattc 600
aacatcgcca gatatcaatt aggcatagag aaactactcg atcctgaaga tgttgatacc 660
acctatccag ataagaagtc catcttaatg tacatcacat cactcttcca agttttgcct 720
caacaagtga gcatgaagcc atccaggaag tggaaatgtt gccaaggcca cctaaagtga 780
ctaaagaaga acattttcag ttacatcatc aaatgcacta ttctcaacag atcacggtca 840
gtctagcaca gggatatgag agaacttctt cccctaagcc tcgattcaag agctatgcct 900
acacacaggc tgcttatgtc accacctctg accctacacg gagcgcattt ccttcacagc 960
atttggaagc tcctgaagac aagtcatttg gcagttcatt gatggagagt gaagtaaacc 1020
tggaccgtta tcaaacagct ttagaagaag tattatcgtg gcttctttct gctgaggaca 1080
cattgcaagc acaaggagag atttctaatg atgtggaagt ggtgaaagac cagtttcata 1140
ctcatgaggg gtacatgatg gatttgacag cccatcaggg ccgggttggt aatattctac 1200
aattgggaag taagctgatt ggaacaggaa aattatcaga agatgaagaa actgaagtac 1260
aagagcagat gaatctccta aattcaagat gggaatgcct cagggtagct agcatggaaa 1320
aacaaagcaa tttacataga gttttaatgg atctccagaa tcagaaactg aaagagttga 1380
atgactggct aacaaaaaca gaagaaagaa caaggaaaat ggaggaagag cctcttggac 1440
ctgatcttga agacctaaaa cgccaagtac aacaacataa ggtgcttcaa gaagatctag 1500
aacaagaaca agtcagggtc aattctctca ctcacatggt ggtggtagtt gatgaatcta 1560
gtggagatca cgcaactgct gctttggaag aacaacttaa ggtattggga gatcgatggg 1620
caaacatctg tagatggaca gaagaccgct gggttctttt acaagacgaa atttcttatg 1680
tgccttctac ttatttgact gaaatcactc atgtctcaca agccctatta gaagtggaac 1740
aacttctcaa tgctcctgac ctctgtgcta aggactttga agatctcttt aagcaagagg 1800
agtctctgaa gaatataaaa gatagtctac aacaaagctc aggtcggatt gacattattc 1860
atagcaagaa gacagcagca ttgcaaagtg caacgcctgt ggaaagggtg aagctacagg 1920
aagctctctc ccagcttgat ttccaatggg aaaaagttaa caaaatgtac aaggaccgac 1980
aagggcgatt tgacagaacc cttgaaagac tccaggaact tcaagaggcc acggatgagc 2040
tggacctcaa gctgcgccaa gctgaggtga tcaagggatc ctggcagccc gtgggcgatc 2100
tcctcattga ctctctccaa gatcacctcg agaaagtcaa ggcacttcga ggagaaattg 2160
cgcctctgaa agagaacgtg agccacgtca atgaccttgc tcgccagctt accactttgg 2220
gcattcagct ctcaccgtat aacctcagca ctctggaaga cctgaacacc agatggaagc 2280
ttctgcaggt ggccgtcgag gaccgagtca ggcagctgca tgaagcccac agggactttg 2340
gtccagcatc tcagcacttt ctttccacgt ctgtccaggg tccctgggag agagccatct 2400
cgccaaacaa agtgccctac tatatcaacc acgagactca aacaacttgc tgggaccatc 2460
ccaaaatgac agagctctac cagtctttag ctgacctgaa taatgtcaga ttctcagctt 2520
ataggactgc catgaaactc cgaagactgc agaaggccct ttgcttggat ctcttgagcc 2580
tgtcagctgc atgtgatgcc ttggaccagc acaacctcaa gcaaaatgac cagcccatgg 2640
atatcctgca gattattaat tgtttgacca ctatttatga ccgcctggag caagagcaca 2700
acaatttggt caacgtccct ctctgcgtgg atatgtgtct gaactggctg ctgaatgttt 2760
atgatacggg acgaacaggg aggatccgtg tcctgtcttt taaaactggc atcatttccc 2820
tgtgtaaagc acatttggaa gacaagtaca gataccttttt caagcaagtg gcaagtcaac 2880
aggattttgt gaccagcgca ggctgggcct ccttctgcat gattctatcc aaattccaag 2940
acagttgggt gaagttgcat cctttggggg cagtaacatt gaggcaagtg tccggagctg 3000
cttccaattt gctaataata agccagagat cgaagcggcc ctcttcctag actggatgag 3060
actggaaccc cagtccatgg tgtggctgcc cgtcctgcac agagtggctg ctgcagaaac 3120
tgccaagcat caggccaaat gtaacatctg caaagagtgt ccaatcattg gattcaggta 3180
caggagtcta aagcacttta attatgacat ctgccaaagc tgcttttttt ctggtcgagt 3240
tgcaaaaggc cataaaatgc actatcccat ggtggaatat tgcactccga ctacatcagg 3300
agaagatgtt cgagactttg ccaaggtact aaaaaacaaa tttcgaacca aaaggtattt 3360
tgcgaagcat ccccgaatgg gctacctgcc agtgcagact gtcttagagg gggacaacat 3420
ggaaactgac acaatgtag 3439

<210> SEQ ID NO 15
<211> LENGTH: 8312
<212> TYPE: DNA
<213> ORGANISM: Artificial Sequence
<220> FEATURE:
<223> OTHER INFORMATION: Synthetic

<400> SEQUENCE: 15
cattaatgaa tcggccaacg cgcggggaga ggcggtttgc gtattgggcg ctcttccgct 60
tcctcgctca ctgactcgct gcgctcggtc gttcggctgc ggcgagcggt atcagctcac 120

-continued tcaaaggcgg taatacggtt atccacagaa tcaggggata acgcaggaaa gaacatgtga 180
gcaaaaggcc agcaaaaggc caggaaccgt aaaaaggccg cgttgctggc gtttttccata 240 ggctccgccc ccctgacgag catcacaaaa atcgacgctc aagtcagagg tggcgaaacc 300
cgacaggact ataaagatac caggcgtttc cccctggaag ctccctcgtg cgctctcctg 360
ttccgaccct gccgcttacc ggatacctgt ccgcctttct cccttcggga agcgtggcgc 420
tttctcatag ctcacgctgt aggtatctca gttcggtgta ggtcgttcgc tccaagctgg 480
gctgtgtgca cgaacccccc gttcagcccg accgctgcgc cttatccggt aactatcgtc 540
ttgagtccaa cccggtaaga cacgacttat cgccactggc agcagccact ggtaacagga 600
ttagcagagc gaggtatgta ggcggtgcta cagagttctt gaagtggtgg cctaactacg 660
gctacactag aaggacagta tttggtatct gcgctctgct gaagccagtt accttcggaa 720
aaagagttgg tagctcttga tccggcaaac aaaccaccgc tggtagcggt ggtttttttg 780
tttgcaagca gcagattacg cgcagaaaaa aaggatctca agaagatcct ttgatctttt 840
ctacggggtc tgacgctcag tggaacgaaa actcacgtta agggattttg gtcatgagat 900
tatcaaaaag gatcttcacc tagatccttt taaattaaaa atgaagtttt aaatcaatct 960
aaagtatata tgagtaaact tggtctgaca gttaccaatg cttaatcagt gaggcaccta 1020
tctcagcgat ctgtctattt cgttcatcca tagttgcctg actccccgtc gtgtagataa 1080
ctacgatacg ggagggctta ccatctggcc ccagtgctgc aatgataccg cgagacccac 1140
gctgaccggc tccagattta tcagcaataa accagccagc cggaagggcc gagcgcagaa 1200
gtggtcctgc aagtttatcc gcctccatcc agtgtattaa ttgttgccgg gaagctagag 1260
taagtagttc gccagttaat agtttgcgca acgttgttgc cattgctaca ggcatcgtgg 1320
tgtcaggctc gtcgtttggt atggcttcat tcagctccgg ttcccaacga tcaaggcgag 1380
ttacatgatc ccccatgttg tgcaaaaaag cggttagctc cttcggtcct ccgatcgttg 1440
tcagaagtaa gttggccgca gtgttatcac tcatggttat ggcagcactg cataattctc 1500
ttactgtcat gccatccgta agatgctttt ctgtgactgg tgagtactca accaagtcat 1560
tctgagaata gtgtatgcgg cgaccgagtt gctcttgccc ggcgtcaata cgggataata 1620
ccgcgccaca tagcagaact ttaaaagtgc tcatcattgg aaaacgttct tcggggcgaa 1680
aactctcaag gatcttaccg ctgttgagat ccagtcgatg taacccactc gtgcacccaa 1740
ctgatcttca gcatctttta ctttcaccag cgtttctggg tgagcaaaaa caggaaggca 1800
aaatgccgca aaaaagggaa taagggcgac acggaaatgt tgatactcat actcttcctt 1860
tttcaatatt attgaagcat ttatcagggt tattgtctca tgagcggata catatttgaa 1920
tgtatttaga aaaataaaca aataggggtt ccgcgcacat ttccccgaaa agtgccacct 1980
gacgtctaag aaaccattat tatcatgaca ttaacctata aaaataggcg tatcacgagg 2040
ccctttcgtc tcgcgcgttt cggtgatgac ggtgaaaacc tctgacacat gcagctcccg 2100
gagacggtca cagcttgtct gtaagcggat gccgggagca gacaagcccg tcagggcgcg 2160
tcagcgggtg ttggcgggtg tcggggctgg cttaactatg cggcatcaga gcagattgta 2220
ctgagagtgc accatatgcg gtgtgaaata ccgcacagat gcgtaaggag aaaataccgc 2280
atcaggaatt ccaacatcca ataaatcata caggcaaggc aaagaattag caaaattaag 2340
caataaagcc tcagagcata aagctaaatc ggttgtacca aaaacattat gaccctgtaa 2400
tacttttgcg ggagaagcct ttatttcaac gcaaggataa aaatttttag aaccctcata 2460

```
tattttaaat gcaatgcctg agtaatgtgt aggtaaagat tcaaacgggt gagaaaggcc   2520
ggagacagtc aaatcaccat caatatgata ttcaaccgtt ctagctgata aattcatgcc   2580
ggagagggta gctatttttg agaggtctct acaaaggcta tcaggtcatt gcctgagagt   2640
ctggagcaaa caagagaatc gatgaacggt aatcgtaaaa ctagcatgtc aatcatatgt   2700
accccggttg ataatcagaa aagccccaaa aacaggaaga ttgtataagc aaatatttaa   2760
attgtaaacg ttaatatttt gttaaaattc gcgttaaatt tttgtaaatc agctcatttt   2820
ttaaccaata ggccgaaatc ggcaaaatcc cttataaatc aaaagaatag accgagatag   2880
ggttgagtgt tgttccagtt tggaacaaga gtccactatt aaagaacgtg gactccaacg   2940
tcaaagggcg aaaaaccgtc tatcagggcg atggcccact acgtgaacca tcaccctaat   3000
caagtttttt ggggtcgagg tgccgtaaag cactaaatcg gaaccctaaa gggagccccc   3060
gatttagagc ttgacgggga aagccggcga acgtggcgag aaaggaaggg aagaaagcga   3120
aaggagcggg cgctagggcg ctggcaagtg tagcggtcac gctgcgcgta accaccacac   3180
ccgccgcgct taatgcgccg ctacagggcg cgtactatgg ttgctttgac gagcaggtat   3240
aacgtgcttt cctcgttaga atcagagcgg gagctaaaca ggaggccgat taaagggatt   3300
ttagacagga acggtacgcc agaatcctga gaagtgtttt tataatcagt gaggccaccg   3360
agtaaaagag tctgtcgatc acgcaaatta accgttgtcg caatacttct ttgattagta   3420
ataacatcac ttgcctgagt agaagaactc aaactatcgg ccttgctggt aatatccaga   3480
acaatattac cgccagccat tgcaagagga aaaacgctca tggaaatacc tacattttga   3540
cgctcaatcg tctggaattc cattcgccat tcaggctgcg caactgttgg gaagggcgat   3600
cggtgcgggc ctcttcgcta ttacgccagc tggcgcgctc gctcgctcac tgaggccgcc   3660
cgggcaaagc ccgggcgtcg ggcgaccttt ggtcgcccgg cctcagtgag cgagcgagcg   3720
cgcagagagg gagtggccaa ctccatcact aggggttcct tgtagttaat gattaacccg   3780
ccatgctact tatctacggc cgcggtaccg cgttacataa cttacggtaa atggcccgcc   3840
tggctgaccg cccaacgacc cccgcccatt gacgtcaata atgacgtatg ttcgcatagt   3900
aacgccaata gggactttcc attgacgtca atgggtggag tatttacggt aaactgccca   3960
cttggcagta catcaagtgt atcatatgcc aagtacgccc cctattgacg tcaatgacgg   4020
taaatggccc gcctggcatt atgcccagta catgacctta tgggactttc ctacttggca   4080
gtacatctac gtattagtca tcgctattac catggtgatg cggttttggc agtacatcaa   4140
tgggcgtgga tagcggtttg actcacgggg atttccaagt ctccacccca ttgacgtcaa   4200
tgggagtttg ttttggcacc aaaatcaacg ggactttcca aaatgtcgta acaactccgc   4260
cccattgacg caaatgggcg gtaggcgtgt acggtgggag gtctatataa gcagagctcg   4320
tttagtgaac cgtctagacg gccgcggttt tttttatcgc tgccttgata tacactttcc   4380
accatgcttt ggtgggaaga agtagaggac tgttatgaaa gagaagatgt tcaaaagaaa   4440
acattcacaa aatgggtaaa tgcacaattt tctaagtttg ggaagcagca tattgagaac   4500
ctcttcagtg acctacagga tgggaggggc ctcctagacc tcctcgaagg cctgacaggg   4560
caaaaactgc caaaagaaaa aggatccaca agagttcatg ccctgaacaa tgtcaacaag   4620
gcactgcggg ttttgcagaa caataatgtt gatttagtga atattggaag tactgacatc   4680
gtagatggaa atcataaact gactcttggt ttgatttgga atataatcct ccactggcag   4740
gtcaaaaatg taatgaaaaa tatcatggct ggattgcaac aaaccaacag tgaaaagatt   4800
ctcctgagct gggtccgaca atcaactcgt aattatccac aggttaatgt aatcaacttc   4860
```

-continued accaccagct ggtctgatgg cctggctttg aatgctctca tccatagtca taggccagac 4920
ctatttgact ggaatagtgt ggtttgccag cagtcagcca cacaacgact ggaacatgca 4980
ttcaacatcg ccagatatca attaggcata gagaaactac tcgatcctga agatgttgat 5040
accacctatc cagataagaa gtccatctta atgtacatca catcactctt ccaagttttg 5100
cctcaacaag tgagcattga agccatccag gaagtggaaa tgttgccaag gccacctaaa 5160
gtgactaaag aagaacattt tcagttacat catcaaatgc actattctca acagatcacg 5220
gtcagtctag cacagggata tgagagaact tcttccccta agcctcgatt caagagctat 5280
gcctacacac aggctgctta tgtcaccacc tctgacccta cacggagccc atttccttca 5340
cagcatttgg aagctcctga agacaagtca tttggcagtt cattgatgga gagtgaagta 5400
aacctggacc gttatcaaac agctttagaa gaagtattat cgtggcttct ttctgctgag 5460
gacacattgc aagcacaagg agagatttct aatgatgtgg aagtggtgaa agaccagttt 5520
catactcatg aggggtacat gatggatttg acagcgcatc agggccgggt tggtaatatt 5580
ctacaattgg gaagtaagct gattggaaca ggaaaattat cagaagatga agaaactgaa 5640
gtacaagagc agatgaatct cctaaattca agatgggaat gcctcagggt agctagcatg 5700
gaaaaacaaa gcaatttaca tagagaaatt tcttatgtgc cttctactta tttgactgaa 5760
atcactcatg tctcacaagc cctattagaa gtggaacaac ttctcaatgc tcctgacctc 5820
tgtgctaagg actttgaaga tctctttaag caagaggagt ctctgaagaa tataaaagat 5880
agtctacaac aaagctcagg tcggattgac attattcata gcaagaagac agcagcattg 5940
caaagtgcaa cgcctgtgga aagggtgaag ctacaggaag ctctctccga gcttgatttc 6000
caatgggaaa aagttaacaa aatgtacaag gaccgacaag ggcgatttga cagatctgtt 6060
gagaaatggc ggcgttttca ttatgatata aagatattta atcagtggct aacagaagct 6120
gaacagtttc tcagaaagag acaaattcct gagaattggg aacatgctaa atacaaatgg 6180
tatcttaagg aactccagga tggcattggg cagcggcaaa ctgttgtcag aacattgaat 6240
gcaactgggg aagaaataat tcagcaatcc tcaaaaacag atgccagtat tctacaggaa 6300
aaattgggaa gcctgaatct gcggtggcag gaggtctgca aacagctgtc agacagaaaa 6360
aagaggctag aagaaaccct tgaaagactc caggaacttc aagaggccac ggatgaggtg 6420
gacctcaagc tgcgccaagc tgaggtgatc aagggatcct ggcagcccgt gggcgatctc 6480
ctcattgact ctctccaaga tcacctcgag aaagtcaagg cacttcgagg agaaattgcg 6540
cctctgaaag agaacgtgag ccacgtcaat gaccttgctc gccagcttac cactttgggc 6600
attcagctct caccgtataa cctcagcact ctggaagacc tgaacaccag atggaagctt 6660
ctgcaggtgg ccgtcgagga ccgagtcagg cagctgcatg aagcccacag ggactttggt 6720
ccagcatctc agcactttct ttccacgtct gtccagggtc cctgggagag agccatctcg 6780
ccaaacaaag tgccctacta tatcaaccac gagactcaaa caacttgctg ggaccatccc 6840
aaaatgacag agctctacca gtctttagct gacctgaata atgtcagatt ctcagcttat 6900
aggactgcca tgaaactccg aagactgcag aaggcccttt gcttggatct cttgagcctg 6960
tcagctgcat gtgatgcctt ggaccagcac aacctcaagc aaaatgacca gcccatggat 7020
atcctgcaga ttattaattg tttgaccact atttatgacc gcctggagca agagcacaac 7080
aatttggtca acgtccctct ctgcgtggat atgtgtctga actggctgct gaatgtttat 7140
gatacgggac gaacagggag gatccgtgtc ctgtctttta aaactggcat catttccctg 7200

```
tgtaaagcac atttggaaga caagtacaga tacctttca agcaagtggc aagttcaaca   7260

ggattttgtg accagcgcag gctgggcctc cttctgcatg attctatcca aattccaaga   7320

cagttgggtg aagttgcatc ctttggggc agtaacattg agccaagtgt ccggagctgc   7380

ttccaatttg ctaataataa gccagagatc gaagcggccc tcttcctaga ctggatgaga   7440

ctggaacccc agtccatggt gtggctgccc gtcctgcaca gagtggctgc tgcagaaact   7500

gccaagcatc aggccaaatg taacatctgc aaagagtgtc caatcattgg attcaggtac   7560

aggagtctaa agcactttaa ttatgacatc tgccaaagct gctttttttc tggtcgagtt   7620

gcaaaaggcc ataaaatgca ctatcccatg gtggaatatt gcactccgac tacatcagga   7680

gaagatgttc gagactttgc caaggtacta aaaaacaaat ttcgaaccaa aaggtatttt   7740

gcgaagcatc cccgaatggg ctacctgcca gtgcagactg tcttagaggg ggacaacatg   7800

gaaactgaca caatgtagga agtcttttcc acatggcaga tgatttgggc agagcgatgg   7860

agtccttagt atcagtcatg acagatgaag aaggagcaga ataaatgttt tacaactcct   7920

gattcccgca tgcggccgat ccagacatga taagatacat tgatgagttt ggacaaacca   7980

caactagaat gcagtgaaaa aaatgcttta tttgtgaaat ttgtgatgct attgctttat   8040

ttgtaaccat tataagctgc aataaacaag ttaacaacaa caattgcatt cattttatgt   8100

ttcaggttca gggggaggtg tgggaggttt tttgcggccg tagataagta gcatggcggg   8160

ttaatcatta actacaagga acccctagtg atggagttgg ccactccctc tctgcgcgct   8220

cgctcgctca ctgaggccgg gcgaccaaag gtcgcccgac gcccgggctt tgcccgggcg   8280

gcctcagtga gcgagcgagc gcgcagctgc tg                                8312
```

<210> SEQ ID NO 16
<211> LENGTH: 8293
<212> TYPE: DNA
<213> ORGANISM: Artificial Sequence
<220> FEATURE:
<223> OTHER INFORMATION: Synthetic

<400> SEQUENCE: 16

```
cattaatgaa tcggccaacg cgcggggaga ggcggtttgc gtattgggcg ctcttccgct     60

tcctcgctca ctgactcgct gcgctcggtc gttcggctgc ggcgagcggt atcagctcac    120

tcaaaggcgg taatacggtt atccacagaa tcaggggata acgcaggaaa gaacatgtga    180

gcaaaaggcc agcaaaaggc caggaaccgt aaaaaggccg cgttgctggc gtttttccat    240

aggctccgcc cccctgacga gcatcacaaa aatcgacgct caagtcagag gtggcgaaac    300

ccgacaggac tataaagata ccaggcgttt ccccctggaa gctccctcgt gcgctctcct    360

gttccgaccc tgccgcttac cggatacctg tccgcctttc tcccttcggg aagcgtggcg    420

ctttctcata gctcacgctg taggtatctc agttcggtgt aggtcgttcg ctccaagctg    480

ggctgtgtgc acgaaccccc cgttcagccc gaccgctgcg ccttatccgg taactatcgt    540

cttgagtcca acccggtaag acacgactta tcgccactgg cagcagccac tggtaacagg    600

attagcagag cgaggtatgt aggcggtgct acagagttct tgaagtggtg gcctaactac    660

ggctacacta gaaggacagt atttggtatc tgcgctctgc tgaagccagt taccttcgga    720

aaaagagttg gtagctcttg atccggcaaa caaaccaccg ctggtagcgg tggttttttt    780

gtttgcaagc agcagattac gcgcagaaaa aaaggatctc aagaagatcc tttgatcttt    840

tctacggggt ctgacgctca gtggaacgaa aactcacgtt aagggatttt ggtcatgaga    900

ttatcaaaaa ggatcttcac ctagatcctt ttaaattaaa aatgaagttt taaatcaatc    960
```

taaagtatat atgagtaaac ttggtctgac agttaccaat gcttaatcag tgaggcacct 1020
atctgagcga tctgtctatt tcgttcatcc atagttgcct gactccccgt cgtgtagata 1080
actacgatac gggagggctt accatctggc cccagtgctg caatgatacc gcgagaccca 1140
cgctgaccgg ctccagattt atcagcaata aaccagccag ccggaagggc cgagcgcaga 1200
agtggtcctg caactttatc cgcctccatc cagtctatta attgttgccg ggaagctaga 1260
gtaagtagtt cgccagttaa tagtttgcgc aacgttgttg ccattgctac aggcatcgtg 1320
gtgtcacgct cgtcgtttgg tatggcttca ttcagctccg gttcccaacg atcaaggcga 1380
gttacatgat cccccatgtt gtgcaaaaaa gcggttagct ccttcggtcc tccgatcgtt 1440
gtcagaagta agttggccgc agtgttatca ctcatggtta tggcagcact gcataattct 1500
cttactgtca tgccatccgt aagatgcttt tctgtgactg gtgagtactc aaccaagtca 1560
ttctgagaat agtgtatgcg gcgaccgagt tgctcttgcc cggcgtcaat aggggataat 1620
accgcgccac atagcagaac tttaaaagtg ctcatcattg gaaaacgttc ttcggggcga 1680
aaactctcaa ggatcttacc gctgttgaga tccagttcga tgtaacccac tcgtgcaccc 1740
aactgatctt cagcatcttt tactttcacc agcgtttctg ggtgagcaaa aacaggaagg 1800
caaaatgccg caaaaaaggg aataagggcg acacggaaat gttgaatact catactcttc 1860
ctttttcaat attattgaag catttatcag ggttattgtc tcatgagcgg atacatattt 1920
gaatgtattt agaaaaataa acaaataggg gttccgcgca catttccccg aaaagtgcca 1980
cctgacgtct aagaaaccat tattatcatg acattaacct ataaaaatag gcgtatcacg 2040
aggccctttc gtctcgcgcg tttcggtgat gacggtgaaa acctctgaca catgcagctc 2100
ccggagacgg tcacagcttg tctgtaagcg gatgccggga gcagacaagc ccgtcagggc 2160
gcgtcagcgg gtgttggcgg gtgtcggggc tggcttaact atgcggcatc agagcagatt 2220
gtactgagag tgcaccatat gcggtgtgaa ataccgcaca gatgcgtaag gagaaaatac 2280
cgcatcagga attccaacat ccaataaatc atacaggcaa ggcaaagaat tagcaaaatt 2340
aagcaataaa gcctcagagc ataaagctaa atcggttgta ccaaaaacat tatgaccctg 2400
taatactttt gcgggagaag cctttatttc aacgcaagga taaaaatttt tagaaccctc 2460
atatatttta aatgcaatgc ctgagtaatg tgtaggtaaa gattcaaacg ggtgagaaag 2520
gccggagaca gtcaaatcac catcaatatg atattcaacc gttctagctg ataaattcat 2580
gccggagagg gtagctattt ttgagaggtc tctacaaagg ctatcaggtc attgcctgag 2640
agtctggagc aaacaagaga atcgatgaac ggtaatcgta aaactagcat gtcaatcata 2700
tgtaccccgg ttgataatca gaaaagcccc aaaaacagga agattgtata agcaaatatt 2760
taaattgtaa acgttaatat tttgttaaaa ttcgcgttaa atttttgtta aatcagctca 2820
tttttaacc aataggccga aatcggcaaa atcccttata aatcaaaaga atagaccgag 2880
atagggttga gtgttgttcc agtttggaac aagagtccac tattaaagaa cgtggactcc 2940
aacgtcaaag ggcgaaaaac cgtctatcag ggcgatggcc cactacgtga accatcaccc 3000
taatcaagtt ttttggggtc gaggtgccgt aaagcactaa atcggaaccc taaagggagc 3060
ccccgattta gagcttgacg gggaaagccg gcgaacgtgg cgagaaagga agggaagaaa 3120
gcgaaaggag cgggcgctag ggcgctggca agtgtagcgg tcacgctgcg cgtaaccacc 3180
acacccgccg cgcttaatgc gccgctacag ggcgcgtact atggttgctt tgacgagcac 3240
gtataacgtg ctttcctcgt tagaatcaga gcgggagcta aacaggaggc cgattaaagg 3300

-continued

```
gattttagac aggaacggta cgccagaatc ctgagaagtg tttttataat cagtgaggcc   3360
accgagtaaa agagtctgtc catcacgcaa attaaccgtt gtcgcaatac ttcttgatta   3420
gtaataacat cacttgcctg agtagaagaa ctcaaactat cggccttgct ggtaatatcc   3480
agaacaatat taccgccagc cattgcaaca ggaaaaacgc tcatggaaat acctacattt   3540
tgacgctcaa tcgtctggaa ttccattcgc cattcaggct gcgcaactgt tgggaagggc   3600
gatcggtgcg ggcctcttcg ctattacgcc agctggcgcg ctcgctcgct cactgaggcc   3660
gccggggcaa agcccgggcg tcgggcgacc tttggtcgcc cggcctcagt gagcgagcga   3720
gcgcgcagag agggagtggc caactccatc actaggggtt ccttgtagtt aatgattaac   3780
ccgccatgct acttatctac ggccgcggta ccactcacgg ggatttccaa gtctccaccc   3840
cattgacgtc aatgggagtt tgttttggca ccaaaatcaa cgggactttc caaaatgtcg   3900
taataacccc gccccgttga cgcaaatggg cggtaggcgt gtacggtggg aggtctatat   3960
aagcagagct cgtttagtga accgtctcta gacggccgcg gtttttttta tcgctgcctt   4020
gatatacact ttccaccatg ctttggtggg aagaagtaga ggactgttat gaaagagaag   4080
atgttcaaaa gaaaacattc acaaaatggg taaatgcaca attttctaag tttgggaagc   4140
agcatattga gaacctcttc agtgacctac aggatgggag gcgcctccta gacctcctcg   4200
aaggcctgac agggcaaaaa ctgccaaaag aaaaaggatc cacaagagtt catgccctga   4260
acaatgtcaa caaggcactg cgggttttgc agaacaataa tgttgattta gtgaatattg   4320
gaagtactga catcgtagat ggaaatcata aactgactct tggtttgatt tggaatataa   4380
tcctccactg gcaggtcaaa aatgtaatga aaaatatcat ggctggattg caacaaacca   4440
acagtgaaaa gattctcctg agctgggtcc gacaatcaac tcgtaattat ccacaggtta   4500
atgtaatcaa cttcaccacc agctggtctg atggcctggc tttgaatgct ctcatccata   4560
gtcataggcc agacctattt gactggaata gtgtggtttg ccagcagtca gccacacaac   4620
gactggaaca tgcattcaac atcgccagat atcaattagg catagagaaa ctactcgatc   4680
ctgaagatgt tgataccacc tatccagata agaagtccat cttaatgtac atcacatcac   4740
tcttccaagt tttgcctcaa caagtgagca ttgaagccat ccaggaagtg gaaatgttgc   4800
caaggccacc taaagtgact aaagaagaac attttcagtt acatcatcaa atgcactatt   4860
ctcaacagat cacggtcagt ctagcacagg gatatgagag aagttcttcc cctaagcctc   4920
gattcaagag ctatgcctac acacaggctg cttatgtcac cacctctgac cctacacgga   4980
gcccatttcc ttcacagcat ttggaagctc ctgaagacaa gtcatttggc agttcattga   5040
tggagagtga agtaaacctg gaccgttatc aaacagcttt agaagaagta ttatcgtggc   5100
ttctttctgc tgaggacaca ttgcaagcac aaggagagat ttctaatgat gtggaagtgg   5160
tgaaagacca gtttcatact catgaggggt acatgatgga tttgacagcc catcagggcc   5220
gggttggtaa tattctacaa ttgggaagta agctgattgg aacaggaaaa ttatcagaag   5280
atgaagaaac tgaagtacaa gagcagatga atctcctaaa ttcaagatgg gaatgcctca   5340
gggtagctag catggaaaaa caaagcaatt tacatagagt tttaatggat ctccagaatc   5400
agaaactgaa agagttgaat gactggctaa caaaaacaga agaaagaaca aggaaaatgg   5460
aggaagagcc tcttggacct gatcttgaag acctaaaacg gcaagtacaa caacataagg   5520
tgcttcaaga agatctagaa caagaacaag tcagggtcaa ttctctcact cacatggtgg   5580
tggtagttga tgaatctagt ggagatcacg caactgctgc tttggaagaa caacttaagg   5640
tattgggaga tcgatgggca aacatctgta gatggacaga agaccgctgg gttcttttac   5700
```

aagacgaaat ttcttatgtg ccttctactt atttgactga aatcactcat gtctcacaag 5760
ccctattaga agtggaacaa cttctcaatg ctcctgacct ctgtgctaag gactttgaag 5820
atctctttaa gcaagaggag tctctgaaga atataaaaga tagtctacaa caaagctcag 5880
gtcggattga cattattcat agcaagaaga cagcagcatt gcaaagtgca acgcctgtgg 5940
aaagggtgaa gctacaggaa gctctctccc agcttgattt ccaatgggaa aaagttaaca 6000
aaatgtacaa ggaccgacaa gggcgatttg acagatctgt tgagaaatgg cggcgttttc 6060
attatgatat aaagatattt aatcagtggc taacagaagc tgaacagttt ctcagaaaga 6120
cacaaattcc tgagaattgg gaacatgcta aatacaaatg gtatcttaag gaactccagg 6180
atggcattgg gcagcggcaa actgttgtca gaacattgaa tgcaactggg gaagaaataa 6240
ttcagcaatc gtcaaaaaca gatgccagta ttctacagga aaaattggga agcctgaatc 6300
tgcggtggca ggaggtctgc aaacagctgt cagacagaaa aaagaggcta gaagaaaccc 6360
ttgaaagact ccaggaactt caagaggcca cggatgagct ggacctcaag ctgcgccaag 6420
ctgaggtgat caagggatcc tggcagcccg tgggcgatct cctcattgac tctctccaag 6480
atcacctcga gaaagtcaag gcacttcgag gagaaattgc gcctctgaaa gagaacgtga 6540
gccacgtcaa tgaccttgct cgccagctta ccactttggg cattcaggtc tcacggtata 6600
acctcagcac tctggaagac ctgaacacca gatggaagct tctgcaggtg gccgtcgagg 6660
accgagtcag gcagctgcat gaagcccaca gggactttgg tccagcatct cagcactttc 6720
tttccacgtc tgtccagggt ccctgggaga gagccatctc gccaaacaaa gtgccctact 6780
atatcaacca cgagactcaa acaacttgct gggaccatcc caaaatgaca gagctctacc 6840
agtctttagc tgacctgaat aatgtcagat tctcagctta taggactgcc atgaaactcc 6900
gaagactgca gaaggccctt tgcttggatc tcttgagcct gtcagctgca tgtgatgcct 6960
tggaccagca caacctcaag caaaatgacc agcccatgga tatcctgcag attattaatt 7020
gtttgaccac tatttatgac cgcctggagc aagagcacaa caatttggtc aacgtccctc 7080
tctgcgtgga tatgtgtctg aactggctgc tgaatgttta tgatacggga cgaacaggga 7140
ggatccgtgt cctgtctttt aaaactggca tcatttccct gtgtaaagca catttggaag 7200
acaagtacag ataccttttc aagcaagtgg caagttcaac aggattttgt gaccagcgca 7260
ggctgggcct ccttctgcat gattctatcc aaattccaag acagttgggt gaagttgcat 7320
cctttggggg cagtaacatt gagccaagtg tccggagctg cttccaattt gctaataata 7380
agccagagat cgaagcggcc ctcttcctag actggatgag actggaaccg cagtccatgg 7440
tgtggctgcc cgtcctgcac agagtggctg ctgcagaaac tgccaagcat caggccaaat 7500
gtaacatctg caaagagtgt ccaatcattg gattcaggta caggagtcta aagcacttta 7560
attatgacat ctgccaaagc tgcttttttt ctggtcgagt tgcaaaaggc cataaaatgc 7620
actatcccat ggtggaatat tgcactccga ctacatcagg agaagatgtt cgagactttg 7680
ccaaggtact aaaaaacaaa tttcgaacca aaaggtattt tgcgaagcat ccccgaatgg 7740
gctacctgcc agtgcagact gtcttagagg gggacaacat ggaaactgac acaatgtagg 7800
aagtcttttc cacatggcag atgatttggg cagagcgatg gagtccttag tatcagtcat 7860
gacagatgaa gaaggagcag aataaatgtt ttacaactcc tgattcccgc atgcggccga 7920
tccagacatg ataagataca ttgatgagtt tggacaaacc acaactagaa tgcagtgaaa 7980
aaaatgcttt atttgtgaaa tttgtgatgc tattgcttta tttgtaacca ttataagctg 8040

-continued

```
caataaacaa gttaacaaca acaattgcat tcattttatg tttcaggttc agggggaggt   8100

gtgggaggtt ttttgcggcc gtagataagt agcatggcgg gttaatcatt aactacaagg   8160

aacccctagt gatggagttg gccactccct ctctgcgcgc tcggtcgctc actgaggccg   8220

ggcgaccaaa ggtcgcccga cgcccgggct ttgcccgggc ggcctcagtg agcgagcgag   8280

cgcgcagctg ctg                                                       8293
```

```
<210> SEQ ID NO 17
<211> LENGTH: 756
<212> TYPE: DNA
<213> ORGANISM: Homo sapiens

<400> SEQUENCE: 17

atgctttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatggcc tgaacaatgt caacaaggca    240

ctgcgggttt tgcagaacaa taatgttgat ttagtgaata ttggaagtac tgacatcgta    300

gatggaaatc ataaactgac tcttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttgccagcag tcagccacac aacgactgga acatgcattc    600

aacatcgcca gatatcaatt aggcatagag aaactactcg atcctgaaga tgttgatacc    660

acctatccag ataagaagtc catcttaatg tacatcacat cactcttcca agttttgcct    720

caacaagtga gcattgaagc catccaggaa gtggaa                              756
```

```
<210> SEQ ID NO 18
<211> LENGTH: 252
<212> TYPE: DNA
<213> ORGANISM: Homo sapiens

<400> SEQUENCE: 18

atgttgccaa ggccacctaa agtgactaaa gaagaacatt ttcagttaca tcatcaaatg     60

cactattctc aacagatcac ggtcagtcta gcacagggat atgagagaac ttcttcccct    120

aagcctcgat tcaagagcta tgcctacaca caggctgctt atgtcaccac ctctgaccct    180

acacggagcc catttccttc acagcatttg gaagctcctg aagacaagtc atttggcagt    240

tcattgatgg ag                                                        252
```

```
<210> SEQ ID NO 19
<211> LENGTH: 333
<212> TYPE: DNA
<213> ORGANISM: Homo sapiens

<400> SEQUENCE: 19

agtgaagtaa acctggaccg ttatcaaaca gctttagaag aagtattatc gtggcttctt     60

tctgctgagg acacattgca agcacaagga gagatttcta atgatgtgga agtggtgaaa    120

gaccagtttc atactcatga ggggtacatg atggatttga cagcccatca gggccgggtt    180

ggtaatattc tacaattggg aagtaagctg attggaacag gaaaattatc agaagatgaa    240

gaaactgaag tacaagagca gatgaatctc ctaaattcaa gatgggaatg cctcagggta    300
```

gctagcatgg aaaaacaaag caatttacat aga 333

<210> SEQ ID NO 20
<211> LENGTH: 327
<212> TYPE: DNA
<213> ORGANISM: Homo sapiens

<400> SEQUENCE: 20
gttttaatgg atctccagaa tcagaaactg aaagagttga atgactggct aacaaaaaca 60
gaagaaagaa caaggaaaat ggaggaagag cctcttggac ctgatcttga agacctaaaa 120
cgccaagtac aacaacataa ggtgcttcaa gaagatctag aacaagaaca agtcagggtc 180
aattctctca ctcacatggt ggtggtagtt gatgaatcta gtggagatca cgcaactgct 240
gctttggaag aacaacttaa ggtattggga gatcgatggg caaacatctg tagatggaca 300
gaagaccgct gggttctttt acaagac 327

<210> SEQ ID NO 21
<211> LENGTH: 333
<212> TYPE: DNA
<213> ORGANISM: Homo sapiens

<400> SEQUENCE: 21
atccttctca aatggcaacg tcttactgaa gaacagtgcc tttttagtgc atggctttca 60
gaaaaagaag atgcagtgaa caagattcac acaactggct ttaaagatca aaatgaaatg 120
ttatcaagtc ttcaaaaact ggccgtttta aaagcggatc tagaaaagaa aaagcaatcc 180
atgggcaaac tgtattcact caaacaagat cttctttcaa cactgaagaa taagtcagtg 240
acccagaaga cggaagcatg gctggataac tttgcccggt gttgggataa tttagtccaa 300
aaacttgaaa agagtacagc acagatttca cag 333

<210> SEQ ID NO 22
<211> LENGTH: 150
<212> TYPE: DNA
<213> ORGANISM: Homo sapiens

<400> SEQUENCE: 22
gctgtcacca ccactcagcc atcactaaca cagacaactg taatggaaac agtaactacg 60
gtgaccacaa gggaacagat cctggtaaag catgctcaag aggaacttcc accaccacct 120
ccccaaaaga agaggcagat tactgtggat 150

<210> SEQ ID NO 23
<211> LENGTH: 262
<212> TYPE: DNA
<213> ORGANISM: Homo sapiens

<400> SEQUENCE: 23
tctgaaatta ggaaaaggtt ggatgttgat ataactgaac ttcacagctg gattactcgc 60
tcagaagctg tgttgcagag tcctgaattt gcaatctttc ggaaggaagg caacttctca 120
gacttaaaag aaaaagtcaa tgccatagag cgagaaaaag ctgagaagtt cagaaaactg 180
caagatgcca gcagatcagc tcaggccctg gtggaacaga tggtgaatga gggtgttaat 240
gcagatagca tcaaacaagc ct 262

<210> SEQ ID NO 24
<211> LENGTH: 389
<212> TYPE: DNA

<213> ORGANISM: Homo sapiens

<400> SEQUENCE: 24
cagaacaact gaacagccgg tggatcgaat tctgccagtt gctaagtgag agacttaact 60
ggctggagta tcagaacaac atcatcgctt tctataatca gctacaacaa ttggagcaga 120
tgacaactac tgctgaaaac tggttgaaaa tccaacccac caccccatca gagccaacag 180
caattaaaag tcagttaaaa atttgtaagg atgaagtcaa ccggctatca ggtcttcaac 240
ctcaaattga acgattaaaa attcaaagca tagccctgaa agagaaagga caaggaccca 300
tgttcctgga tgcagacttt gtggccttta caaatcattt taagcaagtc ttttctgatg 360
tgcaggccag agagaaagag ctacagaca 389

<210> SEQ ID NO 25
<211> LENGTH: 333
<212> TYPE: DNA
<213> ORGANISM: Homo sapiens

<400> SEQUENCE: 25
atttttgaca ctttgccacc aatgcgctat caggagacca tgagtgccat caggacatgg 60
gtccagcagt cagaaaccaa actctccata cctcaactta gtgtcaccga ctatgaaatc 120
atggagcaga gactcgggga attgcaggct ttacaaagtt ctctgcaaga gcaacaaagt 180
ggcctatact atctcagcac cactgtgaaa gagatgtcga agaaagcgcc ctctgaaatt 240
agccggaaat atcaatcaga atttgaagaa attgagggac gctggaagaa gctctcctcc 300
cagctggttg agcattgtca aaagctagag gag 333

<210> SEQ ID NO 26
<211> LENGTH: 327
<212> TYPE: DNA
<213> ORGANISM: Homo sapiens

<400> SEQUENCE: 26
caaatgaata aactccgaaa aattcagaat cacatacaaa ccctgaagaa atggatggct 60
gaagttgatg tttttctgaa ggaggaatgg cctgcccttg gggattcaga aattctaaaa 120
aagcagctga aacagtgcag acttttagtc agtgatattc agacaattca gcccagtcta 180
aacagtgtca atgaaggtgg gcagaagata aagaatgaag cagagccaga gtttgcttcg 240
agacttgaga cagaactcaa agaacttaac actcagtggg atcacatgtg ccaacaggtc 300
tatgccagaa aggaggcctt gaaggga 327

<210> SEQ ID NO 27
<211> LENGTH: 327
<212> TYPE: DNA
<213> ORGANISM: Homo sapiens

<400> SEQUENCE: 27
ggtttggaga aaactgtaag cctccagaaa gatctatcag agatgcacga atggatgaca 60
caagctgaag aagagtatct tgagagagat tttgaatata aaactccaga tgaattacag 120
aaagcagttg aagagatgaa gagagctaaa gaagaggccc aacaaaaaga agcgaaagtg 180
aaactcctta ctgagtctgt aaatagtgtc atagctcaag ctccacctgt agcacaagag 240
gccttaaaaa aggaacttga aactctaacc accaactacc agtggctctg cactaggctg 300
aatgggaaat gcaagacttt ggaagaa 327

<210> SEQ ID NO 28
<211> LENGTH: 312
<212> TYPE: DNA
<213> ORGANISM: Homo sapiens

<400> SEQUENCE: 28
gtttgggcat gttggcatga gttattgtca tacttggaga aagcaaacaa gtggctaaat 60
gaagtagaat ttaaacttaa aaccactgaa aacattcctg gcggagctga ggaaatctct 120
gaggtgctag attcacttga aaatttgatg cgacattcag aggataaccc aaatcagatt 180
cgcatattgg cacagaccct aacagatggc ggagtcatgg atgagctaat caatgaggaa 240
cttgagacat ttaattctcg ttggagggaa ctacatgaag aggctgtaag gaggcaaaag 300
ttgcttgaac ag 312

<210> SEQ ID NO 29
<211> LENGTH: 288
<212> TYPE: DNA
<213> ORGANISM: Homo sapiens

<400> SEQUENCE: 29
agcatccagt ctgcccagga gactgaaaaa tccttacact taatccagga gtccctcaca 60
ttcattgaca agcagttggc agcttatatt gcagacaagg tggacgcagc tcaaatgcct 120
caggaagccc agaaaatcca atctgatttg acaagtcatg agatcagttt agaagaaatg 180
aagaaacata atcaggggaa ggaggctgcc caaagagtcc tgtctcagat tgatgttgca 240
cagaaaaaat tacaagatgt ctccatgaag tttcgattat tccagaaa 288

<210> SEQ ID NO 30
<211> LENGTH: 315
<212> TYPE: DNA
<213> ORGANISM: Homo sapiens

<400> SEQUENCE: 30
ccagccaatt ttgagctgcg tctacaagaa agtaagatga ttttagatga agtgaagatg 60
cacttgcctg cattggaaac aaagagtgtg gaacaggaag tagtacagtc acagctaaat 120
cattgtgtga acttgtataa aagtctgagt gaagtgaagt ctgaagtgga aatggtgata 180
aagactggac gtcagattgt acagaaaaag cagacggaaa atcccaaaga acttgatgaa 240
agagtaacag ctttgaaatt gcattataat gagctgggag caaaggtaac agaaagaaag 300
caacagttgg agaaa 315

<210> SEQ ID NO 31
<211> LENGTH: 324
<212> TYPE: DNA
<213> ORGANISM: Homo sapiens

<400> SEQUENCE: 31
tgcttgaaat tgtcccgtaa gatgcgaaag gaaatgaatg tcttgacaga atggctggca 60
gctacagata tggaattgac aaagagatca gcagttgaag gaatgcctag taatttggat 120
tctgaagttg cctggggaaa ggctactcaa aaagagattg agaaacagaa ggtgcacctg 180
aagagtatca cagaggtagg agaggccttg aaaacagttt tgggcaagaa ggagacgttg 240
gtggaagata aactcagtct tctgaatagt aactggatag ctgtcacctc ccgagcagaa 300
gagtggttaa atcttttgtt ggaa 324

<210> SEQ ID NO 32

<211> LENGTH: 306
<212> TYPE: DNA
<213> ORGANISM: Homo sapiens

<400> SEQUENCE: 32
taccagaaac acatggaaac ttttgaccag aatgtggacc acatcacaaa gtggatcatt 60
caggctgaca cacttttgga tgaatcagag aaaaagaaac cccagcaaaa agaagacgtg 120
cttaagcgtt taaaggcaga actgaatgac atacgcccaa aggtggactc tacacgtgac 180
caagcagcaa acttgatggc aaaccgcggt gaccactgca ggaaattagt agagccccaa 240
atctcagagc tcaaccatcg atttgcagcc atttcacaca gaattaagac tggaaaggcc 300
tccatt 306

<210> SEQ ID NO 33
<211> LENGTH: 288
<212> TYPE: DNA
<213> ORGANISM: Homo sapiens

<400> SEQUENCE: 33
cctttgaagg aattggagca gtttaactca gatatacaaa aattgcttga accactggag 60
gctgaaattc agcagggggt gaatctgaaa gaggaagact tcaataaaga tatgaatgaa 120
gacaatgagg gtactgtaaa agaattgttg caaagaggag acaacttaca acaaagaatc 180
acagatgaga gaaagagaga ggaaataaag ataaaacagc agctgttaca gacaaaacat 240
aatgctctca aggatttgag gtctcaaaga agaaaaaagg ctctagaa 288

<210> SEQ ID NO 34
<211> LENGTH: 297
<212> TYPE: DNA
<213> ORGANISM: Homo sapiens

<400> SEQUENCE: 34
atttctcatc agtggtatca gtacaagagg caggctgatg atctcctgaa atgcttggat 60
gacattgaaa aaaaattagc cagcctacct gagcccagag atgaaaggaa aataaaggaa 120
attgatcggg aattgcagaa gaagaaagag gagctgaatg cagtgcgtag gcaagctgag 180
ggcttgtctg aggatggggc cgcaatggca gtggagccaa ctcagatcca gctcagcaag 240
cgctggcggg aaattgagag caaatttgct cagtttcgaa gactcaactt tgcacaa 297

<210> SEQ ID NO 35
<211> LENGTH: 384
<212> TYPE: DNA
<213> ORGANISM: Homo sapiens

<400> SEQUENCE: 35
attcacactg tccgtgaaga aacgatgatg gtgatgactg aagacatgcc tttggaaatt 60
tcttatgtgc cttctactta tttgactgaa atcactcatg tctcacaagc cctattagaa 120
gtggaacaac ttctcaatgc tcctgacctc tgtgctaagg actttgaaga tctctttaag 180
caagaggagt ctctgaagaa tataaaagat agtctacaac aaagctcagg tcggattgac 240
attattcata gcaagaagac agcagcattg caaagtgcaa cgcctgtgga aagggtgaag 300
ctacaggaag ctctctccca gcttgatttc caatgggaaa aagttaacaa aatgtacaag 360
gaccgacaag ggcgatttga caga 384

<210> SEQ ID NO 36
<211> LENGTH: 321

<212> TYPE: DNA
<213> ORGANISM: Homo sapiens

<400> SEQUENCE: 36
tctgttgaga aatggcggcg ttttcattat gatataaaga tatttaatca gtggctaaca 60
gaagctgaac agtttctcag aaagacacaa attcctgaga attgggaaca tgctaaatac 120
aaatggtatc ttaaggaact ccaggatggc attgggcagc ggcaaactgt tgtcagaaca 180
ttgaatgcaa ctggggaaga aataattcag caatcctcaa aaacagatgc cagtattcta 240
caggaaaaat tgggaagcct gaatctgcgg tggcaggagg tctgcaaaca gctgtcagac 300
agaaaaaaga ggctagaaga a 321

<210> SEQ ID NO 37
<211> LENGTH: 330
<212> TYPE: DNA
<213> ORGANISM: Homo sapiens

<400> SEQUENCE: 37
caaaagaata tcttgtcaga atttcaaaga gatttaaatg aatttgtttt atggttggag 60
gaagcagata acattgctag tatcccactt gaacctggaa aagagcagca actaaaagaa 120
aagcttgagc aagtcaagtt actggtggaa gagttgcccc tgcgccaggg aattctcaaa 180
caattaaatg aaactggagg acccgtgctt gtaagtgctc ccataagccc agaagagcaa 240
gataaacttg aaaataagct caagcagaca aatctccagt ggataaaggt ttccagagct 300
ttacctgaga aacaaggaga aattgaagct 330

<210> SEQ ID NO 38
<211> LENGTH: 315
<212> TYPE: DNA
<213> ORGANISM: Homo sapiens

<400> SEQUENCE: 38
caaataaaag accttgggca gcttgaaaaa aagcttgaag accttgaaga gcagttaaat 60
catctgctgc tgtggttatc tcctattagg aatcagttgg aaatttataa ccaaccaaac 120
caagaaggac catttgacgt tcaggaaact gaaatagcag ttcaagctaa acaaccggat 180
gtggaagaga ttttgtctaa agggcagcat ttgtacaagg aaaaaccagc cactcagcca 240
gtgaagagga agttagaaga tctgagctct gagtggaagg cggtaaaccg tttacttcaa 300
gagctgaggg caaag 315

<210> SEQ ID NO 39
<211> LENGTH: 141
<212> TYPE: DNA
<213> ORGANISM: Homo sapiens

<400> SEQUENCE: 39
cagcctgacc tagctcctgg actgaccact attggagcct ctcctactca gactgttact 60
ctggtgacac aacctgtggt tactaaggaa actgccatct ccaaactaga aatgccatct 120
tccttgatgt tggaggtacc t 141

<210> SEQ ID NO 40
<211> LENGTH: 321
<212> TYPE: DNA
<213> ORGANISM: Homo sapiens

<400> SEQUENCE: 40

-continued gctctggcag atttcaaccg ggcttggaca gaacttaccg actggctttc tctgcttgat 60
caagttataa aatcacagag ggtgatggtg ggtgaccttg aggatatcaa cgagatgatc 120
atcaagcaga aggcaacaat gcaggatttg gaacagaggc gtccccagtt ggaagaactc 180
attaccgctg cccaaaattt gaaaaacaag accagcaatc aagaggctag aacaatcatt 240
acggatcgaa ttgaaagaat tcagaatcag tgggatgaag tacaagaaca ccttcagaac 300
cggaggcaac agttgaatga a 321

<210> SEQ ID NO 41
<211> LENGTH: 327
<212> TYPE: DNA
<213> ORGANISM: Homo sapiens

<400> SEQUENCE: 41
atgttaaagg attcaacaca atggctggaa gctaaggaag aagctgagca ggtcttagga 60
caggccagag ccaagcttga gtcatggaag gagggtccct atacagtaga tgcaatccaa 120
aagaaaatca cagaaaccaa gcagttggcc aaagacctcc gccagtggca gacaaatgta 180
gatgtggcaa atgacttggc cctgaaactt ctccgggatt attctgcaga tgataccaga 240
aaagtccaca tgataacaga gaatatcaat gcctcttgga gaagcattca taaaagggtg 300
agtgagcgag aggctgcttt ggaagaa 327

<210> SEQ ID NO 42
<211> LENGTH: 348
<212> TYPE: DNA
<213> ORGANISM: Homo sapiens

<400> SEQUENCE: 42
actcatagat tactgcaaca gttccccctg gacctggaaa agtttcttgc ctggcttaca 60
gaagctgaaa caactgccaa tgtcctacag gatgctaccc gtaaggaaag gctcctagaa 120
gactccaagg gagtaaaaga gctgatgaaa caatggcaag acctccaagg tgaaattgaa 180
gctcacacag atgtttatca caacctggat gaaaacagcc aaaaaatcct gagatccctg 240
gaaggttccg atgatgcagt cctgttacaa agacgtttgg ataacatgaa cttcaagtgg 300
agtgaacttc ggaaaaagtc tctcaacatt aggtcccatt tggaagcc 348

<210> SEQ ID NO 43
<211> LENGTH: 387
<212> TYPE: DNA
<213> ORGANISM: Homo sapiens

<400> SEQUENCE: 43
agttctgacc agtggaagcg tctgcacctt tctctgcagg aacttctggt gtggctacag 60
ctgaaagatg atgaattaag ccggcaggca cctattggag gcgactttcc agcagttcag 120
aagcagaacg atgtacatag ggccttcaag agggaattga aaactaaaga acctgtaatc 180
atgagtactc ttgagactgt acgaatattt ctgacagagc agcctttgga aggactagag 240
aaactctacc aggagcccag agagctgcct cctgaggaga gagcccagaa tgtcactcgg 300
cttctacgaa agcaggctga ggaggtcaat actgagtggg aaaaattgaa cctgcactcc 360
gctgactggc agagaaaaat agatgag 387

<210> SEQ ID NO 44
<211> LENGTH: 327
<212> TYPE: DNA
<213> ORGANISM: Homo sapiens

<400> SEQUENCE: 44
acccttgaaa gactccagga acttcaagag gccacggatg agctggacct caagctgcgc 60
caagctgagg tgatcaaggg atcctggcag cccgtgggcg atctcctcat tgactctctc 120
caagatcacc tcgagaaagt caaggcactt cgaggagaaa ttgcgcctct gaaagagaac 180
gtgagccacg tcaatgacct tgctcgccag cttaccactt tgggcattca gctctcaccg 240
tataacctca gcactctgga agacctgaac accagatgga agcttctgca ggtggccgtc 300
gaggaccgag tcaggcagct gcatgaa 327

<210> SEQ ID NO 45
<211> LENGTH: 216
<212> TYPE: DNA
<213> ORGANISM: Homo sapiens

<400> SEQUENCE: 45
gcccacaggg actttggtcc agcatctcag cactttcttt ccacgtctgt ccagggtccc 60
tgggagagag ccatctcgcc aaacaaagtg ccctactata tcaaccacga gactcaaaca 120
acttgctggg accatcccaa aatgacagag ctctaccagt ctttagctga cctgaataat 180
gtcagattct cagcttatag gactgccatg aaactc 216

<210> SEQ ID NO 46
<211> LENGTH: 888
<212> TYPE: DNA
<213> ORGANISM: Homo sapiens

<400> SEQUENCE: 46
cgaagactgc agaaggccct ttgcttggat ctcttgagcc tgtcagctgc atgtgatgcc 60
ttggaccagc acaacctcaa gcaaaatgac cagcccatgg atatcctgca gattattaat 120
tgtttgacca ctatttatga ccgcctggag caagagcaca acaatttggt caacgtccct 180
ctctgcgtgg atatgtgtct gaactggctg ctgaatgttt atgatacggg acgaacaggg 240
aggatccgtg tcctgtcttt taaaactggc atcatttccc tgtgtaaagc acatttggaa 300
gacaagtaca gataccttttt caagcaagtg gcaagttcaa caggattttg tgaccagcgc 360
aggctgggcc tccttctgca tgattctatc caaattccaa gacagttggg tgaagttgca 420
tcctttgggg gcagtaacat tgagccaagt gtccggagct gcttccaatt tgctaataat 480
aagccagaga tcgaagcggc cctcttccta gactggatga gactggaacc ccagtccatg 540
gtgtggctgc ccgtcctgca cagagtggct gctgcagaaa ctgccaagca tcaggccaaa 600
tgtaacatct gcaaagagtg tccaatcatt ggattcaggt acaggagtct aaagcacttt 660
aattatgaca tctgccaaag ctgctttttt tctggtcgag ttgcaaaagg ccataaaatg 720
cactatccca tggtggaata ttgcactccg actacatcag gagaagatgt tcgagacttt 780
gccaaggtac taaaaaacaa atttcgaacc aaaaggtatt ttgcgaagca tccccgaatg 840
ggctacctgc cagtgcagac tgtcttagag ggggacaaca tggaaact 888

<210> SEQ ID NO 47
<211> LENGTH: 834
<212> TYPE: DNA
<213> ORGANISM: Homo sapiens

<400> SEQUENCE: 47
cccgttactc tgatcaactt ctggccagta gattctgcgc ctgcctcgtc cctcagctt 60

```
tcacacgatg atactcattc acgcattgaa cattatgcta gcaggctagc agaaatggaa    120

aacagcaatg gatcttatct aaatgatagc atctctccta atgagagcat agatgatgaa    180

catttgttaa tccagcatta ctgccaaagt ttgaaccagg actccccccct gagccagcct    240

cgtagtcctg cccagatctt gatttcctta gagagtgagg aaagagggga gctagagaga    300

atcctagcag atcttgagga agaaaacagg aatctgcaag cagaatatga ccgtctaaag    360

cagcagcacg aacataaagg cctgtcccca ctgccgtccc ctcctgaaat gatgcccacc    420

tctccccaga gtccccggga tgctgagctc attgctgagg ccaagctact gcgtcaacac    480

aaaggccgcc tggaagccag gatgcaaatc ctggaagacc acaataaaca gctggagtca    540

cagttacaca ggctaaggca gctgctggag caacccgagg cagaggccaa agtgaatggc    600

acaacggtgt cctctccttc tacctctcta cagaggtccg acagcagtca gcctatgctg    660

ctccgagtgg ttggcagtca aacttcggac tccatgggtg aggaagatct tctcagtcct    720

ccccaggaca caagcacagg gttagaggag gtgatggagc aactcaacaa ctccttccct    780

agttcaagag gaagaaatac ccctggaaag ccaatgagag aggacacaat gtag          834


<210> SEQ ID NO 48
<211> LENGTH: 11044
<212> TYPE: DNA
<213> ORGANISM: Canis familiaris

<400> SEQUENCE: 48

atgctttggt gggaagaagt agaggactgt tatgaaagag aagatgttca aaagaaaaca     60

ttcacaaaat gggtaaatgc acagttttct aagtttggga agcagcacat agagaacctc    120

ttcagtgacc tacaggatgg gagacgcctc ctagaccttt tggaaggcct gacagggcaa    180

aaactgccaa aagaaaaagg atccacaaga gttcatgccc tgaacaatgt caacaaggca    240

ctgcgcgtct tgcagaaaaa taatgttgat ttagtgaaca ttggaagtac tgacatagta    300

gatggaaatc acaaactgac tcttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtcat taacttcacc    480

accagctggt ctgatggcct ggctttgaac gctctcatcc acagtcatag gccagacctg    540

tttgattgga atagtgtggt ttgccagcag tcagccacac aacgcctgga acatgcattc    600

aacattgcca aatatcaatt aggcatagag aaactgcttg atcctgaaga tgttgccacc    660

acttatccag ataagaagtc catcttaatg tatatcacat cactcttcca agttttgcct    720

caacaagtga gcattgaagc catccaggaa gtggaaatgt tgccaaggcc atctcaagtt    780

actagagaag aacattttca gatacatcat caaatgcact attctcaaca gatcacagtc    840

agtctagcac agggatatga acgagcccct tcctttccta agcctcggtt caagagctat    900

gcctacacac aggctgctta tgtcaccact tctgacccca cacggagccc acttccttca    960

cagcatttgg aaactcctga agacaagtca tttggccggt cattgacaga gaccgaagca   1020

aacctggaca gttatcaaac agctttggaa gaagtactct cgtggcttct ttcagctgag   1080

gatgcactgc aagcccaagg agagatttct aatgatgtcg aagaagtgaa agaacaattt   1140

catactcatg agggatatat gatggacttg acatcccatc agggacgggt cggtaatgtt   1200

ctccaactgg gaagtcaact gattggaaca gggaaattat cagaagatga agaaaccgaa   1260

gtgcaggaac aaatgaatct cctcaattca agatgggaat gcctcagggt agctagcatg   1320

gaaaaacaaa gcaatttaca taaagttcta atggatctcc agaatcagca actgaaagag   1380
```

ttaaatgact ggctaaccaa aacagaagag agaacaagga aaatggagaa ggagcccctt 1440
ggacctgata ttgaagacct aaaacgccaa gtacaacaac ataaggtgct tcaagaagac 1500
ttagaacagg aacaagtcag ggtcaattcc ctcactcata tggtggtggt agtcgatgaa 1560
tctagtggag accatgcaac tgctgctttg gaagaacaac ttaaggtact gggagatcga 1620
tgggcaaaca tctgtaggtg gacagaagat cgctgggttc ttttacaaga catcctccta 1680
aaatggcagc gttttactga agaacagtgc ctttttagtg catggctttc ggagaaggaa 1740
gatgcagtga acaagattca cacaactggc tttaaggatc aaagtgaagt gttatcaaat 1800
cttcagaaac tggctgtctt aaaaacagat ctggaaaaga agaagcaaac catggacaaa 1860
ctctgctcac tcaaccaaga ccttctttca gcgctgaaaa acacagtggt agcccacaag 1920
atggaagcat ggctggacaa ctttgcccag cgctgggata atttagtcca gaaacttgaa 1980
aaaagttcag cacagatttc acaggctgtc accaccactc agccatcact aacacagaca 2040
actgtaatgg aaacagtaac tatggtgacc acgagggaac acatcttggt aaagcatgcc 2100
caagaggaac tgccaccacc acccccctcag aagaagaggc agattatcgt ggattctgaa 2160
attaggaaaa ggttggatgt cgatataact gaacttcaca gttggattac tcgttcagaa 2220
gctgtgttgc agagtcctga atttgcaatc tatcggaagg aaggcaactt ctcagacctt 2280
aaagaaaaag tcaatgccat agagcgagaa aaagccgaga agttcagaaa actgcaagat 2340
gccagcagat cagctcaggc cctggtggaa cagatggtga atgagggtgt taatgctgac 2400
agcatcaaac aagcctccga acaactgaac agccggtgga tagagttctg ccaattgcta 2460
agcgagagac ttaactggct ggagtatcag aacaacatca tcactttcta taatcagcta 2520
caacaattgg agcagatgac aactactgct gaaaactggt tgaaaaccca gcctaccacc 2580
acatcagagc caacagcaat taaaagccag ttaaaaattt gtaaggatga aatcaaccga 2640
ctgtcagctc ttcagcctca aatcgagcga ttaaaaattc aaagcatagc cctgaaagag 2700
aaaggacaag ggccaatgtt cctggatgca gactttgtgg cctttacaaa tcattttaac 2760
caagtctttg ctgatgtgca ggcaagagaa aaagagctac aaacaatttt tgacagtttg 2820
ccacccatgc gctatcagga gactatgagt accatcctga catggatcca gcagtcagaa 2880
accaaactct ctatacctca ggttactgtc actgaatatg acatcatgga acagagactc 2940
ggagagctac aggctttaca aagctctctg caagagcaac aaaatggcct aaactatctc 3000
agcaccactg tgaaagagat gtcaaagaaa gcaccactgt ctgatattag tcggaaatat 3060
caatcagaat ttgaagagat tgagggacgt tggaagaagc tgtcttccca gctggttgaa 3120
cattgtcaaa agttggagga gcaaatggct aaacttcgaa aaattcagaa tcacataaaa 3180
actctgaaga aatggatcac tgaagtcgat gttttcctga aggaggaatg gcctgccctt 3240
ggggattcag aaattctgaa aagacagctg aaacagtgca ggcttttagt caatgacatt 3300
cagaccatcc agcctagtct caacagtgtc aatgaagggg ctcagaagat gaagaatgaa 3360
gcagaaccag agtttgctgg cagacttgag acagagctcc gagaacttaa cacccagtgg 3420
gattacatgt gccgccaggt ctatgccagg aaggaagcct taaaaggagg ttttggataa 3480
aactgtaagt cttcagaaag atctgtcaga gatgcatgag tggatgacac aagctgaaga 3540
agaataccta gagagagatt tcgaatacaa gacccctgat gaattacaga cagcagttga 3600
agagatgaag agagctaaag aagaggccca gcaaaaagaa gcaaaagtga aactcctaac 3660
cgagtccgtc aatagtgtca tagctcaggc tccacctgca gcacaagagg ccttaaaaaa 3720
ggaacttgac actctcacca ccaactacca gtggctctgc accaggctca atggcaaatg 3780
caagaccttg gaagaagttt gggcgtgctg gcatgagtta ttgtcctact tggagaaggc 3840
aaacaagtgg ctaagtgaag tagaagtcaa gcttaaaacc actgaaaata tttctggggg 3900
agctgaggaa atcgccgagg tgcttgattc gcttgaaaat ttgatgcaac attcagagga 3960
taacccgaat cagattcgca tattggcaca gaccttgaca gatggtggag tcatggatga 4020
actgatcaat gaggagcttg agacatttaa ttctcgttgg agagaactcc atgaagaggc 4080
tgtgaggagg caaaagttgc ttgagcagag tatccagtcg gcccaggaga tagaaaaatc 4140
cttgcactta attcaggagt ccctctcttc cattgacaag cagttggcag cttatattgc 4200
tgacaaagtg gatgcagctc agatgcctca ggaagcccag aaaatccaat cagatttgac 4260
aagtcatgag atcagtttag aagaaatgaa gaaacataac cagggaaagg agactgccca 4320
aagggtacta tcccaaattg atgtggcaca gaaaaaattg caggatgttt ccatgaagtt 4380
tcgattattc cagaagccag ccaattttga gcagcgccta caagaaagta aaatgatttt 4440
agatgaagtg aagatgcatt tacctgcgtt ggaaacaaag agtgtggaac aggaagtagt 4500
acagtcacag ttaaatcatt gtgtgaactt gtataaaagt ctgagtgaag tgaagtctga 4560
agtggaaatg gtaataaaaa ctggacgtca gattgtacag aagaagcaga cggaaaaccc 4620
gaaagagctt gatgaaagag ttacagcttt gaaattgcat tataatgagc tgggagcaaa 4680
ggtgacagaa agaaagcaac agttggaaaa atgcttgaaa ttgtcccgta agatgcgaaa 4740
ggaaatgaat gccctgacag aatggctggc agctacagat atggaactga caaagagatc 4800
ggcagttgaa ggaatgccta gtaatttgga ttctgaagtt gcctggggaa aggctactca 4860
gaaagagatt gagaaacaga aggttcacct aaagagtgtc acagaggtag gagaggcctt 4920
gaaaacggtt ttgggcaaga aggaaatgtt ggtggaagat aaactgagtc ttctgaatag 4980
taactggata gccgtcactt cccgagcaga agagtggtta aaccttttat tggaatacca 5040
gaaacacatg gaaacttttg accagaatgt ggattacatc acaaactgga tcattcaggc 5100
tgatgcactt ttggatgaat ctgagaaaaa gaaacctcag caaaaagaag acatacttaa 5160
gcgtttaaag gctgaaatga atgacatacg tccaaaggtg gattctacac gtgaccaagc 5220
agcaaacctg atggcaaacc gcggcgacca ctgcaggaaa gtagtagagc ccaaaatctc 5280
agagctcaac catcgatttg cagccatttc tcacagaatt aagactggaa aggcctccat 5340
tcctttgaag gaattggagc agtttaactc agatatacaa aaattgcttg aaccactgga 5400
ggctgaaatt cagcaggggg tgaatctgaa agaggaagac ttcaataaag atatgagtga 5460
agacaatgag ggtactgtaa aagaattgtt gcaaagagga gacaacttac aacaaagaat 5520
cacagatgag agaaagcgag aggaaataaa gataaaacaa cagctgttac agacaaaaca 5580
taatgctctc aaggatttga ggtctcaaag aagaaaaaag gctctagaaa tttctcacca 5640
gtggtatcag tacaagaggc aggctgatga tctcctgaaa tgcttggatg acattgaaaa 5700
aaaattagcc agcctacctg aacccagaga tgaaaggaaa ataaaggaaa ttgatcgtga 5760
attgcagaag aagaaagagg agctgaatgc agtgcgtagg caagctgagg gcttgtctga 5820
ggatggggcc gcaatggcag tggagccaac tcagatccag ctcagcaagc gctggcggga 5880
aattgagagc aaatttgctc agtttcgaag actcaacttt gcacaaattc acactgtcca 5940
tgaagagtca gtggtggcga tgactgaaga catgcctttg gaaatttctt atgtgccttc 6000
tacttacctg actgagatca ctcatgtctc acaagcccta tcagaagtgg aagagcttct 6060
taatgctccc gacctttgtg ctcaagattt tgaagatctc tttaaacaag aggaatcctt 6120

```
gaagaacata aaagacagcc tgcaacaaat ctcaggtcgg attgacatca ttcacaataa   6180
aaagacagca gcattgcaca gtgccactcc tgcagaaagg gcaaagctcc aggaagctct   6240
ctcacggctt gatttccaat gggaaagagt taacaatatg tacaaggacc gacaagggag   6300
atttgacaga tctgtggaaa aatggcggcg gtttcattat gatatgaaga tacttaatca   6360
atggctaaca gaagctgaac agtttctcaa aaagacacaa attcctgaga attgggaaca   6420
tgccaaatac aaatggtatc ttaaggaact ccaggatggc attggacagc ggcaaagtgt   6480
tgtcagggta ttgaatgcaa ctggggaaga aataattcaa cagtcctcaa aaacagatgc   6540
cagtattctc caagaaaaac tgggaagcct gaatctgcgg tggcaggagg tctgcaaaca   6600
gctggcagaa agaaaaaaga ggctagagga acagaagaat atcttgtcag aatttcaaag   6660
agatgtaaat gaatttgttt tatggttgga agaagcggat aacgttgcta atattccact   6720
tgaacctgga aatgagcagc agctaaaaga aaaacttgaa caagtcaagt tactggcaga   6780
agagttgccc ctgcgccagg gaattctaaa acaattaaat gaaactggag gaacagtgct   6840
tgtaagtgct cccctaagcc cagaagagca agataaactt gaaaataagc tcaagcagac   6900
aaatcttcag tggataaagg tttctagaaa tctgcctgag aagcaagaag aaattgaggc   6960
acacgtaaaa gaccttggac agctggaaga gcagttaaat catctgcttc tatggctgtc   7020
tcctattagg aatcagttgg aaatttacaa tcagccaaat caaacaggac catttgacat   7080
caaggaaatt gaagtagcag ttcaagctaa acagccggat gtggaaggga ttttgtctaa   7140
agggcagcat ttgtacaagg aaaaaccagc cactcagcca gcgaagagaa agctggaaga   7200
tctcagctct gattggaagg tggtaactca gttgcttcaa gagctgcggg caaagcaacc   7260
tggcccagct cctggactga ccactgtcag agcccctccc agtcagactg ttactctggt   7320
gacacaaccc gcggttacca aggaaactgc catctccaaa ctagaaatgc catcttcatt   7380
gctgttggag gtacctgcac tggcagattt caaccgagct tggacagaac ttaccgactg   7440
gctgtctctg cttgatcgag ttataaaatc acagagggtg atggtgggtg atcttgaaga   7500
cattaacgag atgatcatca agcagaaggc aacgctgcag gatttggaac agaggcgccc   7560
ccagttggaa gaactcatta ccgctgccca gaatttgaaa aacaagacca gcaatcaaga   7620
ggctagaaca atcattactg atcgaattga aagaattcag agtcagtggg atgaagtaca   7680
ggaacatctt cagaaccgga ggctacagtt gactgaaatg ttaaaggatt ccacacaatg   7740
gctggaagct aaagaggagg ctgagcaggt gttggggcag gccagagcca agcttgagtc   7800
atggaaggag gctccctaca cagtagatgc aatccaaaag aaaatcacag aaaccaagca   7860
gttggccaaa gacctccgcc agtggcagat aaatgtagat gttgcaaatg atttggcact   7920
gaaacttctc cgagattatt ctgcagatga taccagaaaa gtacacatga taacagagaa   7980
catcaatgcc tcttgggcaa gcatccataa aagattgagt gagcgagagg ctgctctgga   8040
agaaacccac agattactgc aacagttccc cttggacctg gagaagttcc ttgcctggct   8100
tacagaagcc gaaacaactg ccaacgtcct gcaggatgcc acccataagg aaaggcttct   8160
agaagattcc aagggagtaa gagagctgat gaaacaatgg caagacctcc aaggagaaat   8220
cgaagctcac acagatatct atcacaacct ggacgaaaat ggccaaaaag tcctgagatc   8280
cctggaaggt tctgacgatg cagccttgtt gcaaagacgt ttggataaca tgaacttcaa   8340
gtggagcgaa cttcggaaaa agtctctcaa cattaggtct cacttggaag ccagttctga   8400
ccagtggaag cgtctgcacc tttctcttca ggaacttctg gtatggctcc agctgaaaga   8460
```

-continued

```
tgatgagtta agccggcagg cacccattgg aggagacttt ccagcggtgc agaagcagaa   8520
tgatgtacac agggccttca agagggaatt gaaaacgaaa gaacctgtaa tcatgagtac   8580
tcttgagact gtacgaatat ttctgacaga gcagccttta gaaggactag agaaactcta   8640
ccaggagccc agagagctgc ctcctgaaga gagagcccag aatgtcacac ggctcctacg   8700
aaagcaagct gaggaggtca acactcagtg ggaaaaactg aacgtgcact ctgcagactg   8760
gcagagaaaa atagacgagg ccctcgaaag actccaggag cttcaggaag caacagatga   8820
gctggatctc aaactacgtc aggcagaggt gatcaaagga tcctggcagc ctgtgggtga   8880
cctcctcatt gactctctcc aagatcacct cgaaaaagtc aaggcgcttc gaggagaaat   8940
tacacctctg aaagagaatg tcagctacgt caatgacctt gctcgccaac tcactacgtt   9000
gggcattcag ctgtcaccat ataacctcaa cactctggaa gacctgaaca ccagatggaa   9060
gcttctgcag gtggccattg aggaccgcat caggcagctg catgaagcgc acagggactt   9120
tggaccagcc tcccagcact tcctttccac ttctgtccag ggtccctggg agagagccat   9180
ctcaccaaac aaagtgccct actatatcaa ccacgagacc caaacaactt gctgggacca   9240
tcccaaaatg acagagctct accagtcttt agctgacctg aataatgtca ggttctcagc   9300
ttacaggact gccatgaaac tccgaagact gcagaaggcc ctttgcttgg atctcttgag   9360
cctatcggct gcatgcgatg ccttggacca gcacaacctc aagcaaaatg accagcccat   9420
ggatatcctg caggtcatta actgtctgac cactatttat gatcgcctag agcaagagca   9480
caacaatctg gtcaacgtcc ctctctgcgt ggatatgtgt ctcaattggc tgctgaatgt   9540
ttatgacacg ggacgaacgg ggaggatccg ggtcctgtct tttaaaactg gcatcatttc   9600
tctgtgtaaa gcccatttgg aagacaagta cagatacctc ttcaagcaag tggcaagttc   9660
gacaggattt tgtgaccagc gcaggctggg cctcctcctg catgactcta tccagatccc   9720
aagacagttg ggtgaagtcg catcgttcgg gggcagtaac attgagccga gtgtcaggag   9780
ctgcttccag tttgctaata ataagcctga gatcgaagcg gccctcttcc tagactggat   9840
gcgcctggag ccccagtcca tggtgtggct gcctgtcctg caccgagtgg ctgccgcgga   9900
aactgccaag caccaggcca agtgcaacat ctgcaaggag tgtcccatca tcggattcag   9960
gtacaggagt ctaaagcact ttaattatga catctggcaa agttgctttt tttctggtcg  10020
agttgcaaaa ggccataaaa tgcactatcc catggtggaa tactgcactc cgactacatc  10080
gggagaagat gtccgtgact ttgccaaggt actaaaaaac aaatttcgaa ccaaaaggta  10140
ttttgcgaag catccccgaa tgggctacct gccagtgcag actgtcttag agggggacaa  10200
catggaaact cctgtcactc tgatcaactt ctggccggta gattctgcgc ctgcctcgtc  10260
ccctcagctt tcacacgatg atactcattc acgcattgag cattatgcta gcaggctaaa  10320
aaaaatggaa aacagcaatg gatcttatct aaatgatagc atctctccta atgagagcat  10380
agatgatgaa catttgttaa tccagcatta ctggcgaagt ttgaaccagg aatccccccct  10440
gagccagcct cgtagtcctg cccagatctt gatttcctta gagagtgagg aaagagggga  10500
gctagagaga atcctagcag atcttgaggg gagaaacaga aatctgcaag cagagtatga  10560
tcgtctaaag cagcagcatg aacacaaagg cctgtcccca ctgccatccc ctcctgaaat  10620
gatgcctact tctccccaaa gtccccggga tgctgagctc atcgctgagg ccaagctgct  10680
gcgtcaacac aaaggccgcc tggaagccag gatgcaaatc cttgaagacc ataacaaaca  10740
actggaatcc cagttacaca ggctcaggca gctgctggag caaccccagg cagaggccaa  10800
ggtgaatggt acaacggtgt cttctccttc tacctctctt cagaggtcag atagcagtca  10860
```

gcctatgctg ctccgggtgg tcggcagtca gacttcagaa tccatgggcg aggaagacct 10920
gctcagccct ccccaggaca caagcacagg gttagaggaa gtgatggagc agctcaacca 10980
ctccttccct agttccagag gaagaaatac ccctgggaag ccaatgagag aggacacaat 11040
gtag 11044

<210> SEQ ID NO 49
<211> LENGTH: 3680
<212> TYPE: PRT
<213> ORGANISM: Canis familiaris

<400> SEQUENCE: 49

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Lys Tyr Gln Leu Gly
        195                 200                 205

Ile Glu Lys Leu Leu Asp Pro Glu Asp Val Ala Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Ser Gln Val Thr Arg Glu Glu His Phe Gln Ile His His Gln Met
            260                 265                 270

His Tyr Ser Gln Gln Ile Thr Val Ser Leu Ala Gln Gly Tyr Glu Arg
        275                 280                 285

Ala Pro Ser Phe Pro Lys Pro Arg Phe Lys Ser Tyr Ala Tyr Thr Gln
    290                 295                 300

Ala Ala Tyr Val Thr Thr Ser Asp Pro Thr Arg Ser Pro Leu Pro Ser
305                 310                 315                 320

Gln His Leu Glu Thr Pro Glu Asp Lys Ser Phe Gly Arg Ser Leu Thr
                325                 330                 335

```
Glu Thr Glu Ala Asn Leu Asp Ser Tyr Gln Thr Ala Leu Glu Glu Val
            340                 345                 350

Leu Ser Trp Leu Leu Ser Ala Glu Asp Ala Leu Gln Ala Gln Gly Glu
        355                 360                 365

Ile Ser Asn Asp Val Glu Glu Val Lys Glu Gln Phe His Thr His Glu
    370                 375                 380

Gly Tyr Met Met Asp Leu Thr Ser His Gln Gly Arg Val Gly Asn Val
385                 390                 395                 400

Leu Gln Leu Gly Ser Gln Leu Ile Gly Thr Gly Lys Leu Ser Glu Asp
                405                 410                 415

Glu Glu Thr Glu Val Gln Glu Gln Met Asn Leu Leu Asn Ser Arg Trp
            420                 425                 430

Glu Cys Leu Arg Val Ala Ser Met Glu Lys Gln Ser Asn Leu His Lys
        435                 440                 445

Val Leu Met Asp Leu Gln Asn Gln Gln Leu Lys Glu Leu Asn Asp Trp
    450                 455                 460

Leu Thr Lys Thr Glu Glu Arg Thr Arg Lys Met Glu Lys Glu Pro Leu
465                 470                 475                 480

Gly Pro Asp Ile Glu Asp Leu Lys Arg Gln Val Gln Gln His Lys Val
                485                 490                 495

Leu Gln Glu Asp Leu Glu Gln Glu Gln Val Arg Val Asn Ser Leu Thr
            500                 505                 510

His Met Val Val Val Val Asp Glu Ser Ser Gly Asp His Ala Thr Ala
        515                 520                 525

Ala Leu Glu Glu Gln Leu Lys Val Leu Gly Asp Arg Trp Ala Asn Ile
    530                 535                 540

Cys Arg Trp Thr Glu Asp Arg Trp Val Leu Leu Gln Asp Ile Leu Leu
545                 550                 555                 560

Lys Trp Gln Arg Phe Thr Glu Glu Gln Cys Leu Phe Ser Ala Trp Leu
                565                 570                 575

Ser Glu Lys Glu Asp Ala Val Asn Lys Ile His Thr Thr Gly Phe Lys
            580                 585                 590

Asp Gln Ser Glu Val Leu Ser Asn Leu Gln Lys Leu Ala Val Leu Lys
        595                 600                 605

Thr Asp Leu Glu Lys Lys Lys Gln Thr Met Asp Lys Leu Cys Ser Leu
    610                 615                 620

Asn Gln Asp Leu Leu Ser Ala Leu Lys Asn Thr Val Val Ala His Lys
625                 630                 635                 640

Met Glu Ala Trp Leu Asp Asn Phe Ala Gln Arg Trp Asp Asn Leu Val
                645                 650                 655

Gln Lys Leu Glu Lys Ser Ser Ala Gln Ile Ser Gln Ala Val Thr Thr
            660                 665                 670

Thr Gln Pro Ser Leu Thr Gln Thr Thr Val Met Glu Thr Val Thr Met
        675                 680                 685

Val Thr Thr Arg Glu His Ile Leu Val Lys His Ala Gln Glu Glu Leu
    690                 695                 700

Pro Pro Pro Pro Pro Gln Lys Lys Arg Gln Ile Ile Val Asp Ser Glu
705                 710                 715                 720

Ile Arg Lys Arg Leu Asp Val Asp Ile Thr Glu Leu His Ser Trp Ile
                725                 730                 735

Thr Arg Ser Glu Ala Val Leu Gln Ser Pro Glu Phe Ala Ile Tyr Arg
            740                 745                 750
```

```
Lys Glu Gly Asn Phe Ser Asp Leu Lys Glu Lys Val Asn Ala Ile Glu
        755                 760                 765

Arg Glu Lys Ala Glu Lys Phe Arg Lys Leu Gln Asp Ala Ser Arg Ser
    770                 775                 780

Ala Gln Ala Leu Val Glu Gln Met Val Asn Glu Gly Val Asn Ala Asp
785                 790                 795                 800

Ser Ile Lys Gln Ala Ser Glu Gln Leu Asn Ser Arg Trp Ile Glu Phe
                805                 810                 815

Cys Gln Leu Leu Ser Glu Arg Leu Asn Trp Leu Glu Tyr Gln Asn Asn
            820                 825                 830

Ile Ile Thr Phe Tyr Asn Gln Leu Gln Gln Leu Glu Gln Met Thr Thr
        835                 840                 845

Thr Ala Glu Asn Trp Leu Lys Thr Gln Pro Thr Thr Thr Ser Glu Pro
    850                 855                 860

Thr Ala Ile Lys Ser Gln Leu Lys Ile Cys Lys Asp Glu Ile Asn Arg
865                 870                 875                 880

Leu Ser Ala Leu Gln Pro Gln Ile Glu Arg Leu Lys Ile Gln Ser Ile
                885                 890                 895

Ala Leu Lys Glu Lys Gly Gln Gly Pro Met Phe Leu Asp Ala Asp Phe
            900                 905                 910

Val Ala Phe Thr Asn His Phe Asn Gln Val Phe Ala Asp Val Gln Ala
        915                 920                 925

Arg Glu Lys Glu Leu Gln Thr Ile Phe Asp Ser Leu Pro Pro Met Arg
    930                 935                 940

Tyr Gln Glu Thr Met Ser Thr Ile Leu Thr Trp Ile Gln Gln Ser Glu
945                 950                 955                 960

Thr Lys Leu Ser Ile Pro Gln Val Thr Val Thr Glu Tyr Asp Ile Met
                965                 970                 975

Glu Gln Arg Leu Gly Glu Leu Gln Ala Leu Gln Ser Ser Leu Gln Glu
            980                 985                 990

Gln Gln Asn Gly Leu Asn Tyr Leu  Ser Thr Thr Val Lys  Glu Met Ser
        995                 1000                1005

Lys Lys  Ala Pro Leu Ser Asp  Ile Ser Arg Lys Tyr  Gln Ser Glu
    1010                 1015                 1020

Phe Glu  Glu Ile Glu Gly Arg  Trp Lys Lys Leu Ser  Ser Gln Leu
    1025                 1030                 1035

Val Glu  His Cys Gln Lys Leu  Glu Glu Gln Met Ala  Lys Leu Arg
    1040                 1045                 1050

Lys Ile  Gln Asn His Ile Lys  Thr Leu Lys Lys Trp  Ile Thr Glu
    1055                 1060                 1065

Val Asp  Val Phe Leu Lys Glu  Glu Trp Pro Ala Leu  Gly Asp Ser
    1070                 1075                 1080

Glu Ile  Leu Lys Arg Gln Leu  Lys Gln Cys Arg Leu  Leu Val Asn
    1085                 1090                 1095

Asp Ile  Gln Thr Ile Gln Pro  Ser Leu Asn Ser Val  Asn Glu Gly
    1100                 1105                 1110

Ala Gln  Lys Met Lys Asn Glu  Ala Glu Pro Glu Phe  Ala Gly Arg
    1115                 1120                 1125

Leu Glu  Thr Glu Leu Arg Glu  Leu Asn Thr Gln Trp  Asp Tyr Met
    1130                 1135                 1140

Cys Arg  Gln Val Tyr Ala Arg  Lys Glu Ala Leu Lys  Gly Gly Leu
    1145                 1150                 1155

Asp Lys  Thr Val Ser Leu Gln  Lys Asp Leu Ser Glu  Met His Glu
```

```
    1160                1165                1170

Trp Met  Thr Gln Ala Glu Glu  Glu Tyr Leu Glu Arg  Asp Phe Glu
    1175                1180                1185

Tyr Lys  Thr Pro Asp Glu Leu  Gln Thr Ala Val Glu  Glu Met Lys
    1190                1195                1200

Arg Ala  Lys Glu Glu Ala Gln  Gln Lys Glu Ala Lys  Val Lys Leu
    1205                1210                1215

Leu Thr  Glu Ser Val Asn Ser  Val Ile Ala Gln Ala  Pro Pro Ala
    1220                1225                1230

Ala Gln  Glu Ala Leu Lys Lys  Glu Leu Asp Thr Leu  Thr Thr Asn
    1235                1240                1245

Tyr Gln  Trp Leu Cys Thr Arg  Leu Asn Gly Lys Cys  Lys Thr Leu
    1250                1255                1260

Glu Glu  Val Trp Ala Cys Trp  His Glu Leu Leu Ser  Tyr Leu Glu
    1265                1270                1275

Lys Ala  Asn Lys Trp Leu Ser  Glu Val Glu Val Lys  Leu Lys Thr
    1280                1285                1290

Thr Glu  Asn Ile Ser Gly Gly  Ala Glu Glu Ile Ala  Glu Val Leu
    1295                1300                1305

Asp Ser  Leu Glu Asn Leu Met  Gln His Ser Glu Asp  Asn Pro Asn
    1310                1315                1320

Gln Ile  Arg Ile Leu Ala Gln  Thr Leu Thr Asp Gly  Gly Val Met
    1325                1330                1335

Asp Glu  Leu Ile Asn Glu Glu  Leu Glu Thr Phe Asn  Ser Arg Trp
    1340                1345                1350

Arg Glu  Leu His Glu Glu Ala  Val Arg Arg Gln Lys  Leu Leu Glu
    1355                1360                1365

Gln Ser  Ile Gln Ser Ala Gln  Glu Ile Glu Lys Ser  Leu His Leu
    1370                1375                1380

Ile Gln  Glu Ser Leu Ser Ser  Ile Asp Lys Gln Leu  Ala Ala Tyr
    1385                1390                1395

Ile Ala  Asp Lys Val Asp Ala  Ala Gln Met Pro Gln  Glu Ala Gln
    1400                1405                1410

Lys Ile  Gln Ser Asp Leu Thr  Ser His Glu Ile Ser  Leu Glu Glu
    1415                1420                1425

Met Lys  Lys His Asn Gln Gly  Lys Glu Thr Ala Gln  Arg Val Leu
    1430                1435                1440

Ser Gln  Ile Asp Val Ala Gln  Lys Lys Leu Gln Asp  Val Ser Met
    1445                1450                1455

Lys Phe  Arg Leu Phe Gln Lys  Pro Ala Asn Phe Glu  Gln Arg Leu
    1460                1465                1470

Gln Glu  Ser Lys Met Ile Leu  Asp Glu Val Lys Met  His Leu Pro
    1475                1480                1485

Ala Leu  Glu Thr Lys Ser Val  Glu Gln Glu Val Val  Gln Ser Gln
    1490                1495                1500

Leu Asn  His Cys Val Asn Leu  Tyr Lys Ser Leu Ser  Glu Val Lys
    1505                1510                1515

Ser Glu  Val Glu Met Val Ile  Lys Thr Gly Arg Gln  Ile Val Gln
    1520                1525                1530

Lys Lys  Gln Thr Glu Asn Pro  Lys Glu Leu Asp Glu  Arg Val Thr
    1535                1540                1545

Ala Leu  Lys Leu His Tyr Asn  Glu Leu Gly Ala Lys  Val Thr Glu
    1550                1555                1560
```

Arg Lys Gln Gln Leu Glu Lys Cys Leu Lys Leu Ser Arg Lys Met
1565 1570 1575

Arg Lys Glu Met Asn Ala Leu Thr Glu Trp Leu Ala Ala Thr Asp
1580 1585 1590

Met Glu Leu Thr Lys Arg Ser Ala Val Glu Gly Met Pro Ser Asn
1595 1600 1605

Leu Asp Ser Glu Val Ala Trp Gly Lys Ala Thr Gln Lys Glu Ile
1610 1615 1620

Glu Lys Gln Lys Val His Leu Lys Ser Val Thr Glu Val Gly Glu
1625 1630 1635

Ala Leu Lys Thr Val Leu Gly Lys Lys Glu Met Leu Val Glu Asp
1640 1645 1650

Lys Leu Ser Leu Leu Asn Ser Asn Trp Ile Ala Val Thr Ser Arg
1655 1660 1665

Ala Glu Glu Trp Leu Asn Leu Leu Leu Glu Tyr Gln Lys His Met
1670 1675 1680

Glu Thr Phe Asp Gln Asn Val Asp Tyr Ile Thr Asn Trp Ile Ile
1685 1690 1695

Gln Ala Asp Ala Leu Leu Asp Glu Ser Glu Lys Lys Lys Pro Gln
1700 1705 1710

Gln Lys Glu Asp Ile Leu Lys Arg Leu Lys Ala Glu Met Asn Asp
1715 1720 1725

Ile Arg Pro Lys Val Asp Ser Thr Arg Asp Gln Ala Ala Asn Leu
1730 1735 1740

Met Ala Asn Arg Gly Asp His Cys Arg Lys Val Val Glu Pro Lys
1745 1750 1755

Ile Ser Glu Leu Asn His Arg Phe Ala Ala Ile Ser His Arg Ile
1760 1765 1770

Lys Thr Gly Lys Ala Ser Ile Pro Leu Lys Glu Leu Glu Gln Phe
1775 1780 1785

Asn Ser Asp Ile Gln Lys Leu Leu Glu Pro Leu Glu Ala Glu Ile
1790 1795 1800

Gln Gln Gly Val Asn Leu Lys Glu Glu Asp Phe Asn Lys Asp Met
1805 1810 1815

Ser Glu Asp Asn Glu Gly Thr Val Lys Glu Leu Leu Gln Arg Gly
1820 1825 1830

Asp Asn Leu Gln Gln Arg Ile Thr Asp Glu Arg Lys Arg Glu Glu
1835 1840 1845

Ile Lys Ile Lys Gln Gln Leu Leu Gln Thr Lys His Asn Ala Leu
1850 1855 1860

Lys Asp Leu Arg Ser Gln Arg Arg Lys Lys Ala Leu Glu Ile Ser
1865 1870 1875

His Gln Trp Tyr Gln Tyr Lys Arg Gln Ala Asp Asp Leu Leu Lys
1880 1885 1890

Cys Leu Asp Asp Ile Glu Lys Lys Leu Ala Ser Leu Pro Glu Pro
1895 1900 1905

Arg Asp Glu Arg Lys Ile Lys Glu Ile Asp Arg Glu Leu Gln Lys
1910 1915 1920

Lys Lys Glu Glu Leu Asn Ala Val Arg Arg Gln Ala Glu Gly Leu
1925 1930 1935

Ser Glu Asp Gly Ala Ala Met Ala Val Glu Pro Thr Gln Ile Gln
1940 1945 1950

```
Leu Ser  Lys Arg Trp Arg Glu  Ile Glu Ser Lys Phe  Ala Gln Phe
    1955                 1960                 1965

Arg Arg  Leu Asn Phe Ala Gln  Ile His Thr Val His  Glu Glu Ser
    1970                 1975                 1980

Val Val  Ala Met Thr Glu Asp  Met Pro Leu Glu Ile  Ser Tyr Val
    1985                 1990                 1995

Pro Ser  Thr Tyr Leu Thr Glu  Ile Thr His Val Ser  Gln Ala Leu
    2000                 2005                 2010

Ser Glu  Val Glu Glu Leu Leu  Asn Ala Pro Asp Leu  Cys Ala Gln
    2015                 2020                 2025

Asp Phe  Glu Asp Leu Phe Lys  Gln Glu Glu Ser Leu  Lys Asn Ile
    2030                 2035                 2040

Lys Asp  Ser Leu Gln Gln Ile  Ser Gly Arg Ile Asp  Ile Ile His
    2045                 2050                 2055

Asn Lys  Lys Thr Ala Ala Leu  His Ser Ala Thr Pro  Ala Glu Arg
    2060                 2065                 2070

Ala Lys  Leu Gln Glu Ala Leu  Ser Arg Leu Asp Phe  Gln Trp Glu
    2075                 2080                 2085

Arg Val  Asn Asn Met Tyr Lys  Asp Arg Gln Gly Arg  Phe Asp Arg
    2090                 2095                 2100

Ser Val  Glu Lys Trp Arg Arg  Phe His Tyr Asp Met  Lys Ile Leu
    2105                 2110                 2115

Asn Gln  Trp Leu Thr Glu Ala  Glu Gln Phe Leu Lys  Lys Thr Gln
    2120                 2125                 2130

Ile Pro  Glu Asn Trp Glu His  Ala Lys Tyr Lys Trp  Tyr Leu Lys
    2135                 2140                 2145

Glu Leu  Gln Asp Gly Ile Gly  Gln Arg Gln Ser Val  Val Arg Val
    2150                 2155                 2160

Leu Asn  Ala Thr Gly Glu Glu  Ile Ile Gln Gln Ser  Ser Lys Thr
    2165                 2170                 2175

Asp Ala  Ser Ile Leu Gln Glu  Lys Leu Gly Ser Leu  Asn Leu Arg
    2180                 2185                 2190

Trp Gln  Glu Val Cys Lys Gln  Leu Ala Glu Arg Lys  Lys Arg Leu
    2195                 2200                 2205

Glu Glu  Gln Lys Asn Ile Leu  Ser Glu Phe Gln Arg  Asp Val Asn
    2210                 2215                 2220

Glu Phe  Val Leu Trp Leu Glu  Glu Ala Asp Asn Val  Ala Asn Ile
    2225                 2230                 2235

Pro Leu  Glu Pro Gly Asn Glu  Gln Gln Leu Lys Glu  Lys Leu Glu
    2240                 2245                 2250

Gln Val  Lys Leu Leu Ala Glu  Glu Leu Pro Leu Arg  Gln Gly Ile
    2255                 2260                 2265

Leu Lys  Gln Leu Asn Glu Thr  Gly Gly Thr Val Leu  Val Ser Ala
    2270                 2275                 2280

Pro Leu  Ser Pro Glu Glu Gln  Asp Lys Leu Glu Asn  Lys Leu Lys
    2285                 2290                 2295

Gln Thr  Asn Leu Gln Trp Ile  Lys Val Ser Arg Asn  Leu Pro Glu
    2300                 2305                 2310

Lys Gln  Glu Glu Ile Glu Ala  His Val Lys Asp Leu  Gly Gln Leu
    2315                 2320                 2325

Glu Glu  Gln Leu Asn His Leu  Leu Leu Trp Leu Ser  Pro Ile Arg
    2330                 2335                 2340

Asn Gln  Leu Glu Ile Tyr Asn  Gln Pro Asn Gln Thr  Gly Pro Phe
```

```
    2345                2350                2355

Asp Ile  Lys Glu Ile Glu Val  Ala Val Gln Ala Lys  Gln Pro Asp
    2360                2365                2370

Val Glu  Gly Ile Leu Ser Lys  Gly Gln His Leu Tyr  Lys Glu Lys
    2375                2380                2385

Pro Ala  Thr Gln Pro Ala Lys  Arg Lys Leu Glu Asp  Leu Ser Ser
    2390                2395                2400

Asp Trp  Lys Val Val Thr Gln  Leu Leu Gln Glu Leu  Arg Ala Lys
    2405                2410                2415

Gln Pro  Gly Pro Ala Pro Gly  Leu Thr Thr Val Arg  Ala Pro Pro
    2420                2425                2430

Ser Gln  Thr Val Thr Leu Val  Thr Gln Pro Ala Val  Thr Lys Glu
    2435                2440                2445

Thr Ala  Ile Ser Lys Leu Glu  Met Pro Ser Ser Leu  Leu Leu Glu
    2450                2455                2460

Val Pro  Ala Leu Ala Asp Phe  Asn Arg Ala Trp Thr  Glu Leu Thr
    2465                2470                2475

Asp Trp  Leu Ser Leu Leu Asp  Arg Val Ile Lys Ser  Gln Arg Val
    2480                2485                2490

Met Val  Gly Asp Leu Glu Asp  Ile Asn Glu Met Ile  Ile Lys Gln
    2495                2500                2505

Lys Ala  Thr Leu Gln Asp Leu  Glu Gln Arg Arg Pro  Gln Leu Glu
    2510                2515                2520

Glu Leu  Ile Thr Ala Ala Gln  Asn Leu Lys Asn Lys  Thr Ser Asn
    2525                2530                2535

Gln Glu  Ala Arg Thr Ile Ile  Thr Asp Arg Ile Glu  Arg Ile Gln
    2540                2545                2550

Ser Gln  Trp Asp Glu Val Gln  Glu His Leu Gln Asn  Arg Arg Leu
    2555                2560                2565

Gln Leu  Thr Glu Met Leu Lys  Asp Ser Thr Gln Trp  Leu Glu Ala
    2570                2575                2580

Lys Glu  Glu Ala Glu Gln Val  Leu Gly Gln Ala Arg  Ala Lys Leu
    2585                2590                2595

Glu Ser  Trp Lys Glu Ala Pro  Tyr Thr Val Asp Ala  Ile Gln Lys
    2600                2605                2610

Lys Ile  Thr Glu Thr Lys Gln  Leu Ala Lys Asp Leu  Arg Gln Trp
    2615                2620                2625

Gln Ile  Asn Val Asp Val Ala  Asn Asp Leu Ala Leu  Lys Leu Leu
    2630                2635                2640

Arg Asp  Tyr Ser Ala Asp Asp  Thr Arg Lys Val His  Met Ile Thr
    2645                2650                2655

Glu Asn  Ile Asn Ala Ser Trp  Ala Ser Ile His Lys  Arg Leu Ser
    2660                2665                2670

Glu Arg  Glu Ala Ala Leu Glu  Glu Thr His Arg Leu  Leu Gln Gln
    2675                2680                2685

Phe Pro  Leu Asp Leu Glu Lys  Phe Leu Ala Trp Leu  Thr Glu Ala
    2690                2695                2700

Glu Thr  Thr Ala Asn Val Leu  Gln Asp Ala Thr His  Lys Glu Arg
    2705                2710                2715

Leu Leu  Glu Asp Ser Lys Gly  Val Arg Glu Leu Met  Lys Gln Trp
    2720                2725                2730

Gln Asp  Leu Gln Gly Glu Ile  Glu Ala His Thr Asp  Ile Tyr His
    2735                2740                2745
```

```
Asn Leu  Asp Glu Asn Gly Gln  Lys Val Leu Arg Ser  Leu Glu Gly
    2750                 2755                 2760

Ser Asp  Asp Ala Ala Leu Leu  Gln Arg Arg Leu Asp  Asn Met Asn
    2765                 2770                 2775

Phe Lys  Trp Ser Glu Leu Arg  Lys Lys Ser Leu Asn  Ile Arg Ser
    2780                 2785                 2790

His Leu  Glu Ala Ser Ser Asp  Gln Trp Lys Arg Leu  His Leu Ser
    2795                 2800                 2805

Leu Gln  Glu Leu Leu Val Trp  Leu Gln Leu Lys Asp  Asp Glu Leu
    2810                 2815                 2820

Ser Arg  Gln Ala Pro Ile Gly  Gly Asp Phe Pro Ala  Val Gln Lys
    2825                 2830                 2835

Gln Asn  Asp Val His Arg Ala  Phe Lys Arg Glu Leu  Lys Thr Lys
    2840                 2845                 2850

Glu Pro  Val Ile Met Ser Thr  Leu Glu Thr Val Arg  Ile Phe Leu
    2855                 2860                 2865

Thr Glu  Gln Pro Leu Glu Gly  Leu Glu Lys Leu Tyr  Gln Glu Pro
    2870                 2875                 2880

Arg Glu  Leu Pro Pro Glu Glu  Arg Ala Gln Asn Val  Thr Arg Leu
    2885                 2890                 2895

Leu Arg  Lys Gln Ala Glu Glu  Val Asn Thr Gln Trp  Glu Lys Leu
    2900                 2905                 2910

Asn Val  His Ser Ala Asp Trp  Gln Arg Lys Ile Asp  Glu Ala Leu
    2915                 2920                 2925

Glu Arg  Leu Gln Glu Leu Gln  Glu Ala Thr Asp Glu  Leu Asp Leu
    2930                 2935                 2940

Lys Leu  Arg Gln Ala Glu Val  Ile Lys Gly Ser Trp  Gln Pro Val
    2945                 2950                 2955

Gly Asp  Leu Leu Ile Asp Ser  Leu Gln Asp His Leu  Glu Lys Val
    2960                 2965                 2970

Lys Ala  Leu Arg Gly Glu Ile  Thr Pro Leu Lys Glu  Asn Val Ser
    2975                 2980                 2985

Tyr Val  Asn Asp Leu Ala Arg  Gln Leu Thr Thr Leu  Gly Ile Gln
    2990                 2995                 3000

Leu Ser  Pro Tyr Asn Leu Asn  Thr Leu Glu Asp Leu  Asn Thr Arg
    3005                 3010                 3015

Trp Lys  Leu Leu Gln Val Ala  Ile Glu Asp Arg Ile  Arg Gln Leu
    3020                 3025                 3030

His Glu  Ala His Arg Asp Phe  Gly Pro Ala Ser Gln  His Phe Leu
    3035                 3040                 3045

Ser Thr  Ser Val Gln Gly Pro  Trp Glu Arg Ala Ile  Ser Pro Asn
    3050                 3055                 3060

Lys Val  Pro Tyr Tyr Ile Asn  His Glu Thr Gln Thr  Thr Cys Trp
    3065                 3070                 3075

Asp His  Pro Lys Met Thr Glu  Leu Tyr Gln Ser Leu  Ala Asp Leu
    3080                 3085                 3090

Asn Asn  Val Arg Phe Ser Ala  Tyr Arg Thr Ala Met  Lys Leu Arg
    3095                 3100                 3105

Arg Leu  Gln Lys Ala Ile Cys  Leu Asp Leu Leu Ser  Leu Ser Ala
    3110                 3115                 3120

Ala Cys  Asp Ala Leu Asp Gln  His Asn Leu Lys Gln  Asn Asp Gln
    3125                 3130                 3135
```

```
Pro Asn  Asp Ile Leu Gln Val  Ile Asn Cys Leu Thr  Thr Ile Tyr
    3140                 3145                 3150

Asp Arg  Leu Glu Gln Glu His  Asn Asn Leu Val Asn  Val Pro Leu
    3155                 3160                 3165

Cys Val  Asp Met Cys Leu Asn  Trp Leu Leu Asn Val  Tyr Asp Thr
    3170                 3175                 3180

Gly Arg  Thr Gly Arg Ile Arg  Val Leu Ser Phe Lys  Thr Gly Ile
    3185                 3190                 3195

Ile Ser  Leu Cys Lys Ala His  Leu Glu Asp Lys Tyr  Arg Tyr Leu
    3200                 3205                 3210

Phe Lys  Gln Val Ala Ser Ser  Thr Gly Phe Cys Asp  Gln Arg Arg
    3215                 3220                 3225

Leu Gly  Leu Leu Leu His Asp  Ser Ile Gln Ile Pro  Arg Gln Leu
    3230                 3235                 3240

Gly Glu  Val Ala Ser Phe Gly  Gly Ser Asn Ile Glu  Pro Ser Val
    3245                 3250                 3255

Arg Ser  Cys Phe Gln Phe Ala  Asn Asn Lys Pro Glu  Ile Glu Ala
    3260                 3265                 3270

Ala Leu  Phe Leu Asp Trp Met  Arg Leu Glu Pro Gln  Ser Met Val
    3275                 3280                 3285

Trp Leu  Pro Val Leu His Arg  Val Ala Ala Ala Glu  Thr Ala Lys
    3290                 3295                 3300

His Gln  Ala Lys Cys Asn Ile  Cys Lys Glu Cys Pro  Ile Ile Gly
    3305                 3310                 3315

Phe Arg  Tyr Arg Ser Leu Lys  His Phe Asn Tyr Asp  Ile Cys Gln
    3320                 3325                 3330

Ser Cys  Phe Phe Ser Gly Arg  Val Ala Lys Gly His  Lys Met His
    3335                 3340                 3345

Tyr Pro  Met Val Glu Tyr Cys  Thr Pro Thr Thr Ser  Gly Glu Asp
    3350                 3355                 3360

Val Arg  Asp Phe Ala Lys Val  Leu Lys Asn Lys Phe  Arg Thr Lys
    3365                 3370                 3375

Arg Tyr  Phe Ala Lys His Pro  Arg Met Gly Tyr Leu  Pro Val Gln
    3380                 3385                 3390

Thr Val  Leu Glu Gly Asp Asn  Met Glu Thr Pro Val  Thr Leu Ile
    3395                 3400                 3405

Asn Phe  Trp Pro Val Asp Ser  Ala Pro Ala Ser Ser  Pro Gln Leu
    3410                 3415                 3420

Ser His  Asp Asp Thr His Ser  Arg Ile Glu His Tyr  Ala Ser Arg
    3425                 3430                 3435

Leu Lys  Lys Met Glu Asn Ser  Asn Gly Ser Tyr Leu  Asn Asp Ser
    3440                 3445                 3450

Ile Ser  Pro Asn Glu Ser Ile  Asp Asp Glu His Leu  Leu Ile Gln
    3455                 3460                 3465

His Tyr  Trp Arg Ser Leu Asn  Gln Glu Ser Pro Leu  Ser Gln Pro
    3470                 3475                 3480

Arg Ser  Pro Ala Gln Ile Leu  Ile Ser Leu Glu Ser  Glu Glu Arg
    3485                 3490                 3495

Gly Glu  Leu Glu Arg Ile Leu  Ala Asp Leu Glu Gly  Arg Asn Arg
    3500                 3505                 3510

Asn Leu  Gln Ala Glu Tyr Asp  Arg Leu Lys Gln Gln  His Glu His
    3515                 3520                 3525

Lys Gly  Leu Ser Pro Leu Pro  Ser Pro Pro Glu Met  Met Pro Thr
```

```
    3530                3535                3540

Ser Pro  Gln Ser Pro Arg Asp  Ala Glu Leu Ile Ala  Glu Ala Lys
    3545                3550                3555

Leu Leu  Arg Gln His Lys Gly  Arg Leu Glu Ala Arg  Met Gln Ile
    3560                3565                3570

Leu Glu  Asp His Asn Lys Gln  Leu Glu Ser Gln Leu  His Arg Leu
    3575                3580                3585

Arg Gln  Leu Leu Glu Gln Pro  Gln Ala Glu Ala Lys  Val Asn Gly
    3590                3595                3600

Thr Thr  Val Ser Ser Pro Ser  Thr Ser Leu Gln Arg  Ser Asp Ser
    3605                3610                3615

Ser Gln  Pro Met Leu Leu Arg  Val Val Gly Ser Gln  Thr Ser Glu
    3620                3625                3630

Ser Met  Gly Glu Glu Asp Leu  Leu Ser Pro Pro Gln  Asp Thr Ser
    3635                3640                3645

Thr Gly  Leu Glu Glu Val Met  Glu Gln Leu Asn His  Ser Phe Pro
    3650                3655                3660

Ser Ser  Arg Gly Arg Asn Thr  Pro Gly Lys Pro Met  Arg Glu Asp
    3665                3670                3675

Thr Met
    3680


<210> SEQ ID NO 50
<211> LENGTH: 251
<212> TYPE: PRT
<213> ORGANISM: Homo sapiens

<400> SEQUENCE: 50

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Val Met Lys Asn Ile Met Ala
        115                 120                 125

Gly Leu Gln Gln Thr Asn Ser Glu Lys Ile Leu Leu Ser Trp Val Arg
    130                 135                 140

Gln Ser Thr Arg Asn Tyr Pro Gln Val Asn Val Ile Asn Phe Thr Thr
145                 150                 155                 160

Ser Trp Ser Asp Gly Leu Ala Leu Asn Ala Leu Ile His Ser His Arg
                165                 170                 175

Pro Asp Leu Phe Asp Trp Asn Ser Val Val Cys Gln Gln Ser Ala Thr
            180                 185                 190

Gln Arg Leu Glu His Ala Phe Asn Ile Ala Arg Tyr Gln Leu Gly Ile
        195                 200                 205
```

```
Glu Lys Leu Leu Asp Pro Glu Asp Val Asp Thr Thr Tyr Pro Asp Lys
    210                 215                 220

Lys Ser Ile Leu Met Tyr Ile Thr Ser Leu Phe Gln Val Leu Pro Gln
225                 230                 235                 240

Gln Val Ser Ile Glu Ala Ile Gln Glu Val Glu
                245                 250


<210> SEQ ID NO 51
<211> LENGTH: 2860
<212> TYPE: PRT
<213> ORGANISM: Homo sapiens

<400> SEQUENCE: 51

Met Leu Pro Arg Pro Pro Lys Val Thr Lys Glu Glu His Phe Gln Leu
1               5                   10                  15

His His Gln Met His Tyr Ser Gln Gln Ile Thr Val Ser Leu Ala Gln
            20                  25                  30

Gly Tyr Glu Arg Thr Ser Ser Pro Lys Pro Arg Phe Lys Ser Tyr Ala
        35                  40                  45

Tyr Thr Gln Ala Ala Tyr Val Thr Thr Ser Asp Pro Thr Arg Ser Pro
    50                  55                  60

Phe Pro Ser Gln His Leu Glu Ala Pro Glu Asp Lys Ser Phe Gly Ser
65                  70                  75                  80

Ser Leu Met Glu Ser Glu Val Asn Leu Asp Arg Tyr Gln Thr Ala Leu
                85                  90                  95

Glu Glu Val Leu Ser Trp Leu Leu Ser Ala Glu Asp Thr Leu Gln Ala
            100                 105                 110

Gln Gly Glu Ile Ser Asn Asp Val Glu Val Val Lys Asp Gln Phe His
        115                 120                 125

Thr His Glu Gly Tyr Met Met Asp Leu Thr Ala His Gln Gly Arg Val
    130                 135                 140

Gly Asn Ile Leu Gln Leu Gly Ser Lys Leu Ile Gly Thr Gly Lys Leu
145                 150                 155                 160

Ser Glu Asp Glu Glu Thr Glu Val Gln Glu Gln Met Asn Leu Leu Asn
                165                 170                 175

Ser Arg Trp Glu Cys Leu Arg Val Ala Ser Met Glu Lys Gln Ser Asn
            180                 185                 190

Leu His Arg Val Leu Met Asp Leu Gln Asn Gln Lys Leu Lys Glu Leu
        195                 200                 205

Asn Asp Trp Leu Thr Lys Thr Glu Glu Arg Thr Arg Lys Met Glu Glu
    210                 215                 220

Glu Pro Leu Gly Pro Asp Leu Glu Asp Leu Lys Arg Gln Val Gln Gln
225                 230                 235                 240

His Lys Val Leu Gln Glu Asp Leu Glu Gln Glu Gln Val Arg Val Asn
                245                 250                 255

Ser Leu Thr His Met Val Val Val Val Asp Glu Ser Ser Gly Asp His
            260                 265                 270

Ala Thr Ala Ala Leu Glu Glu Gln Leu Lys Val Leu Gly Asp Arg Trp
        275                 280                 285

Ala Asn Ile Cys Arg Trp Thr Glu Asp Arg Trp Val Leu Leu Gln Asp
    290                 295                 300

Ile Leu Leu Lys Trp Gln Arg Leu Thr Glu Glu Gln Cys Leu Phe Ser
305                 310                 315                 320

Ala Trp Leu Ser Glu Lys Glu Asp Ala Val Asn Lys Ile His Thr Thr
                325                 330                 335
```

```
Gly Phe Lys Asp Gln Asn Glu Met Leu Ser Ser Leu Gln Lys Leu Ala
            340                 345                 350

Val Leu Lys Ala Asp Leu Glu Lys Lys Lys Gln Ser Met Gly Lys Leu
        355                 360                 365

Tyr Ser Leu Lys Gln Asp Leu Leu Ser Thr Leu Lys Asn Lys Ser Val
    370                 375                 380

Thr Gln Lys Thr Glu Ala Trp Leu Asp Asn Phe Ala Arg Cys Trp Asp
385                 390                 395                 400

Asn Leu Val Gln Lys Leu Glu Lys Ser Thr Ala Gln Ile Ser Gln Ala
                405                 410                 415

Val Thr Thr Thr Gln Pro Ser Leu Thr Gln Thr Thr Val Met Glu Thr
            420                 425                 430

Val Thr Thr Val Thr Thr Arg Glu Gln Ile Leu Val Lys His Ala Gln
        435                 440                 445

Glu Glu Leu Pro Pro Pro Pro Pro Gln Lys Lys Arg Gln Ile Thr Val
    450                 455                 460

Asp Ser Glu Ile Arg Lys Arg Leu Asp Val Asp Ile Thr Glu Leu His
465                 470                 475                 480

Ser Trp Ile Thr Arg Ser Glu Ala Val Leu Gln Ser Pro Glu Phe Ala
                485                 490                 495

Ile Phe Arg Lys Glu Gly Asn Phe Ser Asp Leu Lys Glu Lys Val Asn
            500                 505                 510

Ala Ile Glu Arg Glu Lys Ala Glu Lys Phe Arg Lys Leu Gln Asp Ala
        515                 520                 525

Ser Arg Ser Ala Gln Ala Leu Val Glu Gln Met Val Asn Glu Gly Val
    530                 535                 540

Asn Ala Asp Ser Ile Lys Gln Ala Ser Glu Gln Leu Asn Ser Arg Trp
545                 550                 555                 560

Ile Glu Phe Cys Gln Leu Leu Ser Glu Arg Leu Asn Trp Leu Glu Tyr
                565                 570                 575

Gln Asn Asn Ile Ile Ala Phe Tyr Asn Gln Leu Gln Gln Leu Glu Gln
            580                 585                 590

Met Thr Thr Thr Ala Glu Asn Trp Leu Lys Ile Gln Pro Thr Thr Pro
        595                 600                 605

Ser Glu Pro Thr Ala Ile Lys Ser Gln Leu Lys Ile Cys Lys Asp Glu
    610                 615                 620

Val Asn Arg Leu Ser Gly Leu Gln Pro Gln Ile Glu Arg Leu Lys Ile
625                 630                 635                 640

Gln Ser Ile Ala Leu Lys Glu Lys Gly Gln Gly Pro Met Phe Leu Asp
                645                 650                 655

Ala Asp Phe Val Ala Phe Thr Asn His Phe Lys Gln Val Phe Ser Asp
            660                 665                 670

Val Gln Ala Arg Glu Lys Glu Leu Gln Thr Ile Phe Asp Thr Leu Pro
        675                 680                 685

Pro Met Arg Tyr Gln Glu Thr Met Ser Ala Ile Arg Thr Trp Val Gln
    690                 695                 700

Gln Ser Glu Thr Lys Leu Ser Ile Pro Gln Leu Ser Val Thr Asp Tyr
705                 710                 715                 720

Glu Ile Met Glu Gln Arg Leu Gly Glu Leu Gln Ala Leu Gln Ser Ser
                725                 730                 735

Leu Gln Glu Gln Gln Ser Gly Leu Tyr Tyr Leu Ser Thr Thr Val Lys
            740                 745                 750
```

```
Glu Met Ser Lys Lys Ala Pro Ser Glu Ile Ser Arg Lys Tyr Gln Ser
        755                 760                 765

Glu Phe Glu Glu Ile Glu Gly Arg Trp Lys Lys Leu Ser Ser Gln Leu
    770                 775                 780

Val Glu His Cys Gln Lys Leu Glu Glu Gln Met Asn Lys Leu Arg Lys
785                 790                 795                 800

Ile Gln Asn His Ile Gln Thr Leu Lys Lys Trp Met Ala Glu Val Asp
                805                 810                 815

Val Phe Leu Lys Glu Glu Trp Pro Ala Leu Gly Asp Ser Glu Ile Leu
            820                 825                 830

Lys Lys Gln Leu Lys Gln Cys Arg Leu Leu Val Ser Asp Ile Gln Thr
        835                 840                 845

Ile Gln Pro Ser Leu Asn Ser Val Asn Glu Gly Gly Gln Lys Ile Lys
    850                 855                 860

Asn Glu Ala Glu Pro Glu Phe Ala Ser Arg Leu Glu Thr Glu Leu Lys
865                 870                 875                 880

Glu Leu Asn Thr Gln Trp Asp His Met Cys Gln Gln Val Tyr Ala Arg
                885                 890                 895

Lys Glu Ala Leu Lys Gly Gly Leu Glu Lys Thr Val Ser Leu Gln Lys
            900                 905                 910

Asp Leu Ser Glu Met His Glu Trp Met Thr Gln Ala Glu Glu Glu Tyr
        915                 920                 925

Leu Glu Arg Asp Phe Glu Tyr Lys Thr Pro Asp Glu Leu Gln Lys Ala
    930                 935                 940

Val Glu Glu Met Lys Arg Ala Lys Glu Glu Ala Gln Gln Lys Glu Ala
945                 950                 955                 960

Lys Val Lys Leu Leu Thr Glu Ser Val Asn Ser Val Ile Ala Gln Ala
                965                 970                 975

Pro Pro Val Ala Gln Glu Ala Leu Lys Lys Glu Leu Glu Thr Leu Thr
            980                 985                 990

Thr Asn Tyr Gln Trp Leu Cys Thr  Arg Leu Asn Gly Lys  Cys Lys Thr
        995                 1000                1005

Leu Glu  Glu Val Trp Ala Cys  Trp His Glu Leu Leu  Ser Tyr Leu
    1010                 1015                1020

Glu Lys  Ala Asn Lys Trp Leu  Asn Glu Val Glu Phe  Lys Leu Lys
    1025                 1030                1035

Thr Thr  Glu Asn Ile Pro Gly  Gly Ala Glu Glu Ile  Ser Glu Val
    1040                 1045                1050

Leu Asp  Ser Leu Glu Asn Leu  Met Arg His Ser Glu  Asp Asn Pro
    1055                 1060                1065

Asn Gln  Ile Arg Ile Leu Ala  Gln Thr Leu Thr Asp  Gly Gly Val
    1070                 1075                1080

Met Asp  Glu Leu Ile Asn Glu  Glu Leu Glu Thr Phe  Asn Ser Arg
    1085                 1090                1095

Trp Arg  Glu Leu His Glu Glu  Ala Val Arg Arg Gln  Lys Leu Leu
    1100                 1105                1110

Glu Gln  Ser Ile Gln Ser Ala  Gln Glu Thr Glu Lys  Ser Leu His
    1115                 1120                1125

Leu Ile  Gln Glu Ser Leu Thr  Phe Ile Asp Lys Gln  Leu Ala Ala
    1130                 1135                1140

Tyr Ile  Ala Asp Lys Val Asp  Ala Ala Gln Met Pro  Gln Glu Ala
    1145                 1150                1155

Gln Lys  Ile Gln Ser Asp Leu  Thr Ser His Glu Ile  Ser Leu Glu
```

```
    1160                1165                1170

Glu Met  Lys Lys His Asn Gln  Gly Lys Glu Ala Ala  Gln Arg Val
    1175                1180                1185

Leu Ser  Gln Ile Asp Val Ala  Gln Lys Lys Leu Gln  Asp Val Ser
    1190                1195                1200

Met Lys  Phe Arg Leu Phe Gln  Lys Pro Ala Asn Phe  Glu Leu Arg
    1205                1210                1215

Leu Gln  Glu Ser Lys Met Ile  Leu Asp Glu Val Lys  Met His Leu
    1220                1225                1230

Pro Ala  Leu Glu Thr Lys Ser  Val Glu Gln Glu Val  Val Gln Ser
    1235                1240                1245

Gln Leu  Asn His Cys Val Asn  Leu Tyr Lys Ser Leu  Ser Glu Val
    1250                1255                1260

Lys Ser  Glu Val Glu Met Val  Ile Lys Thr Gly Arg  Gln Ile Val
    1265                1270                1275

Gln Lys  Lys Gln Thr Glu Asn  Pro Lys Glu Leu Asp  Glu Arg Val
    1280                1285                1290

Thr Ala  Leu Lys Leu His Tyr  Asn Glu Leu Gly Ala  Lys Val Thr
    1295                1300                1305

Glu Arg  Lys Gln Gln Leu Glu  Lys Cys Leu Lys Leu  Ser Arg Lys
    1310                1315                1320

Met Arg  Lys Glu Met Asn Val  Leu Thr Glu Trp Leu  Ala Ala Thr
    1325                1330                1335

Asp Met  Glu Leu Thr Lys Arg  Ser Ala Val Glu Gly  Met Pro Ser
    1340                1345                1350

Asn Leu  Asp Ser Glu Val Ala  Trp Gly Lys Ala Thr  Gln Lys Glu
    1355                1360                1365

Ile Glu  Lys Gln Lys Val His  Leu Lys Ser Ile Thr  Glu Val Gly
    1370                1375                1380

Glu Ala  Leu Lys Thr Val Leu  Gly Lys Lys Glu Thr  Leu Val Glu
    1385                1390                1395

Asp Lys  Leu Ser Leu Leu Asn  Ser Asn Trp Ile Ala  Val Thr Ser
    1400                1405                1410

Arg Ala  Glu Glu Trp Leu Asn  Leu Leu Leu Glu Tyr  Gln Lys His
    1415                1420                1425

Met Glu  Thr Phe Asp Gln Asn  Val Asp His Ile Thr  Lys Trp Ile
    1430                1435                1440

Ile Gln  Ala Asp Thr Leu Leu  Asp Glu Ser Glu Lys  Lys Lys Pro
    1445                1450                1455

Gln Gln  Lys Glu Asp Val Leu  Lys Arg Leu Lys Ala  Glu Leu Asn
    1460                1465                1470

Asp Ile  Arg Pro Lys Val Asp  Ser Thr Arg Asp Gln  Ala Ala Asn
    1475                1480                1485

Leu Met  Ala Asn Arg Gly Asp  His Cys Arg Lys Leu  Val Glu Pro
    1490                1495                1500

Gln Ile  Ser Glu Leu Asn His  Arg Phe Ala Ala Ile  Ser His Arg
    1505                1510                1515

Ile Lys  Thr Gly Lys Ala Ser  Ile Pro Leu Lys Glu  Leu Glu Gln
    1520                1525                1530

Phe Asn  Ser Asp Ile Gln Lys  Leu Leu Glu Pro Leu  Glu Ala Glu
    1535                1540                1545

Ile Gln  Gln Gly Val Asn Leu  Lys Glu Glu Asp Phe  Asn Lys Asp
    1550                1555                1560
```

Met Asn Glu Asp Asn Glu Gly Thr Val Lys Glu Leu Leu Gln Arg
1565 1570 1575

Gly Asp Asn Leu Gln Gln Arg Ile Thr Asp Glu Arg Lys Arg Glu
1580 1585 1590

Glu Ile Lys Ile Lys Gln Gln Leu Leu Gln Thr Lys His Asn Ala
1595 1600 1605

Leu Lys Asp Leu Arg Ser Gln Arg Arg Lys Lys Ala Leu Glu Ile
1610 1615 1620

Ser His Gln Trp Tyr Gln Tyr Lys Arg Gln Ala Asp Asp Leu Leu
1625 1630 1635

Lys Cys Leu Asp Asp Ile Glu Lys Lys Leu Ala Ser Leu Pro Glu
1640 1645 1650

Pro Arg Asp Glu Arg Lys Ile Lys Glu Ile Asp Arg Glu Leu Gln
1655 1660 1665

Lys Lys Lys Glu Glu Leu Asn Ala Val Arg Arg Gln Ala Glu Gly
1670 1675 1680

Leu Ser Glu Asp Gly Ala Ala Met Ala Val Glu Pro Thr Gln Ile
1685 1690 1695

Gln Leu Ser Lys Arg Trp Arg Glu Ile Glu Ser Lys Phe Ala Gln
1700 1705 1710

Phe Arg Arg Leu Asn Phe Ala Gln Ile His Thr Val Arg Glu Glu
1715 1720 1725

Thr Met Met Val Met Thr Glu Asp Met Pro Leu Glu Ile Ser Tyr
1730 1735 1740

Val Pro Ser Thr Tyr Leu Thr Glu Ile Thr His Val Ser Gln Ala
1745 1750 1755

Leu Leu Glu Val Glu Gln Leu Leu Asn Ala Pro Asp Leu Cys Ala
1760 1765 1770

Lys Asp Phe Glu Asp Leu Phe Lys Gln Glu Glu Ser Leu Lys Asn
1775 1780 1785

Ile Lys Asp Ser Leu Gln Gln Ser Ser Gly Arg Ile Asp Ile Ile
1790 1795 1800

His Ser Lys Lys Thr Ala Ala Leu Gln Ser Ala Thr Pro Val Glu
1805 1810 1815

Arg Val Lys Leu Gln Glu Ala Leu Ser Gln Leu Asp Phe Gln Trp
1820 1825 1830

Glu Lys Val Asn Lys Met Tyr Lys Asp Arg Gln Gly Arg Phe Asp
1835 1840 1845

Arg Ser Val Glu Lys Trp Arg Arg Phe His Tyr Asp Ile Lys Ile
1850 1855 1860

Phe Asn Gln Trp Leu Thr Glu Ala Glu Gln Phe Leu Arg Lys Thr
1865 1870 1875

Gln Ile Pro Glu Asn Trp Glu His Ala Lys Tyr Lys Trp Tyr Leu
1880 1885 1890

Lys Glu Leu Gln Asp Gly Ile Gly Gln Arg Gln Thr Val Val Arg
1895 1900 1905

Thr Leu Asn Ala Thr Gly Glu Glu Ile Ile Gln Gln Ser Ser Lys
1910 1915 1920

Thr Asp Ala Ser Ile Leu Gln Glu Lys Leu Gly Ser Leu Asn Leu
1925 1930 1935

Arg Trp Gln Glu Val Cys Lys Gln Leu Ser Asp Arg Lys Lys Arg
1940 1945 1950

-continued

```
Leu Glu  Glu Gln Lys Asn Ile  Leu Ser Glu Phe Gln  Arg Asp Leu
    1955                 1960                 1965

Asn Glu  Phe Val Leu Trp Leu  Glu Glu Ala Asp Asn  Ile Ala Ser
    1970                 1975                 1980

Ile Pro  Leu Glu Pro Gly Lys  Glu Gln Gln Leu Lys  Glu Lys Leu
    1985                 1990                 1995

Glu Gln  Val Lys Leu Leu Val  Glu Glu Leu Pro Leu  Arg Gln Gly
    2000                 2005                 2010

Ile Leu  Lys Gln Leu Asn Glu  Thr Gly Gly Pro Val  Leu Val Ser
    2015                 2020                 2025

Ala Pro  Ile Ser Pro Glu Glu  Gln Asp Lys Leu Glu  Asn Lys Leu
    2030                 2035                 2040

Lys Gln  Thr Asn Leu Gln Trp  Ile Lys Val Ser Arg  Ala Leu Pro
    2045                 2050                 2055

Glu Lys  Gln Gly Glu Ile Glu  Ala Gln Ile Lys Asp  Leu Gly Gln
    2060                 2065                 2070

Leu Glu  Lys Lys Leu Glu Asp  Leu Glu Glu Gln Leu  Asn His Leu
    2075                 2080                 2085

Leu Leu  Trp Leu Ser Pro Ile  Arg Asn Gln Leu Glu  Ile Tyr Asn
    2090                 2095                 2100

Gln Pro  Asn Gln Glu Gly Pro  Phe Asp Val Gln Glu  Thr Glu Ile
    2105                 2110                 2115

Ala Val  Gln Ala Lys Gln Pro  Asp Val Glu Glu Ile  Leu Ser Lys
    2120                 2125                 2130

Gly Gln  His Leu Tyr Lys Glu  Lys Pro Ala Thr Gln  Pro Val Lys
    2135                 2140                 2145

Arg Lys  Leu Glu Asp Leu Ser  Ser Glu Trp Lys Ala  Val Asn Arg
    2150                 2155                 2160

Leu Leu  Gln Glu Leu Arg Ala  Lys Gln Pro Asp Leu  Ala Pro Gly
    2165                 2170                 2175

Leu Thr  Thr Ile Gly Ala Ser  Pro Thr Gln Thr Val  Thr Leu Val
    2180                 2185                 2190

Thr Gln  Pro Val Val Thr Lys  Glu Thr Ala Ile Ser  Lys Leu Glu
    2195                 2200                 2205

Met Pro  Ser Ser Leu Met Leu  Glu Val Pro Ala Leu  Ala Asp Phe
    2210                 2215                 2220

Asn Arg  Ala Trp Thr Glu Leu  Thr Asp Trp Leu Ser  Leu Leu Asp
    2225                 2230                 2235

Gln Val  Ile Lys Ser Gln Arg  Val Met Val Gly Asp  Leu Glu Asp
    2240                 2245                 2250

Ile Asn  Glu Met Ile Ile Lys  Gln Lys Ala Thr Met  Gln Asp Leu
    2255                 2260                 2265

Glu Gln  Arg Arg Pro Gln Leu  Glu Glu Leu Ile Thr  Ala Ala Gln
    2270                 2275                 2280

Asn Leu  Lys Asn Lys Thr Ser  Asn Gln Glu Ala Arg  Thr Ile Ile
    2285                 2290                 2295

Thr Asp  Arg Ile Glu Arg Ile  Gln Asn Gln Trp Asp  Glu Val Gln
    2300                 2305                 2310

Glu His  Leu Gln Asn Arg Arg  Gln Gln Leu Asn Glu  Met Leu Lys
    2315                 2320                 2325

Asp Ser  Thr Gln Trp Leu Glu  Ala Lys Glu Glu Ala  Glu Gln Val
    2330                 2335                 2340

Leu Gly  Gln Ala Arg Ala Lys  Leu Glu Ser Trp Lys  Glu Gly Pro
```

2345 2350 2355

Tyr Thr Val Asp Ala Ile Gln Lys Lys Ile Thr Glu Thr Lys Gln
2360 2365 2370

Leu Ala Lys Asp Leu Arg Gln Trp Gln Thr Asn Val Asp Val Ala
2375 2380 2385

Asn Asp Leu Ala Leu Lys Leu Leu Arg Asp Tyr Ser Ala Asp Asp
2390 2395 2400

Thr Arg Lys Val His Met Ile Thr Glu Asn Ile Asn Ala Ser Trp
2405 2410 2415

Arg Ser Ile His Lys Arg Val Ser Glu Arg Glu Ala Ala Leu Glu
2420 2425 2430

Glu Thr His Arg Leu Leu Gln Gln Phe Pro Leu Asp Leu Glu Lys
2435 2440 2445

Phe Leu Ala Trp Leu Thr Glu Ala Glu Thr Thr Ala Asn Val Leu
2450 2455 2460

Gln Asp Ala Thr Arg Lys Glu Arg Leu Leu Glu Asp Ser Lys Gly
2465 2470 2475

Val Lys Glu Leu Met Lys Gln Trp Gln Asp Leu Gln Gly Glu Ile
2480 2485 2490

Glu Ala His Thr Asp Val Tyr His Asn Leu Asp Glu Asn Ser Gln
2495 2500 2505

Lys Ile Leu Arg Ser Leu Glu Gly Ser Asp Asp Ala Val Leu Leu
2510 2515 2520

Gln Arg Arg Leu Asp Asn Met Asn Phe Lys Trp Ser Glu Leu Arg
2525 2530 2535

Lys Lys Ser Leu Asn Ile Arg Ser His Leu Glu Ala Ser Ser Asp
2540 2545 2550

Gln Trp Lys Arg Leu His Leu Ser Leu Gln Glu Leu Leu Val Trp
2555 2560 2565

Leu Gln Leu Lys Asp Asp Glu Leu Ser Arg Gln Ala Pro Ile Gly
2570 2575 2580

Gly Asp Phe Pro Ala Val Gln Lys Gln Asn Asp Val His Arg Ala
2585 2590 2595

Phe Lys Arg Glu Leu Lys Thr Lys Glu Pro Val Ile Met Ser Thr
2600 2605 2610

Leu Glu Thr Val Arg Ile Phe Leu Thr Glu Gln Pro Leu Glu Gly
2615 2620 2625

Leu Glu Lys Leu Tyr Gln Glu Pro Arg Glu Leu Pro Pro Glu Glu
2630 2635 2640

Arg Ala Gln Asn Val Thr Arg Leu Leu Arg Lys Gln Ala Glu Glu
2645 2650 2655

Val Asn Thr Glu Trp Glu Lys Leu Asn Leu His Ser Ala Asp Trp
2660 2665 2670

Gln Arg Lys Ile Asp Glu Thr Leu Glu Arg Leu Gln Glu Leu Gln
2675 2680 2685

Glu Ala Thr Asp Glu Leu Asp Leu Lys Leu Arg Gln Ala Glu Val
2690 2695 2700

Ile Lys Gly Ser Trp Gln Pro Val Gly Asp Leu Leu Ile Asp Ser
2705 2710 2715

Leu Gln Asp His Leu Glu Lys Val Lys Ala Leu Arg Gly Glu Ile
2720 2725 2730

Ala Pro Leu Lys Glu Asn Val Ser His Val Asn Asp Leu Ala Arg
2735 2740 2745

```
Gln Leu  Thr Thr Leu Gly Ile  Gln Leu Ser Pro Tyr  Asn Leu Ser
    2750                 2755                 2760

Thr Leu  Glu Asp Leu Asn Thr  Arg Trp Lys Leu Leu  Gln Val Ala
    2765                 2770                 2775

Val Glu  Asp Arg Val Arg Gln  Leu His Glu Ala His  Arg Asp Phe
    2780                 2785                 2790

Gly Pro  Ala Ser Gln His Phe  Leu Ser Thr Ser Val  Gln Gly Pro
    2795                 2800                 2805

Trp Glu  Arg Ala Ile Ser Pro  Asn Lys Val Pro Tyr  Tyr Ile Asn
    2810                 2815                 2820

His Glu  Thr Gln Thr Thr Cys  Trp Asp His Pro Lys  Met Thr Glu
    2825                 2830                 2835

Leu Tyr  Gln Ser Leu Ala Asp  Leu Asn Asn Val Arg  Phe Ser Ala
    2840                 2845                 2850

Tyr Arg  Thr Ala Met Lys Leu
    2855                 2860


<210> SEQ ID NO 52
<211> LENGTH: 296
<212> TYPE: PRT
<213> ORGANISM: Homo sapiens

<400> SEQUENCE: 52

Arg Arg Leu Gln Lys Ala Leu Cys Leu Asp Leu Leu Ser Leu Ser Ala
1               5                   10                  15

Ala Cys Asp Ala Leu Asp Gln His Asn Leu Lys Gln Asn Asp Gln Pro
            20                  25                  30

Met Asp Ile Leu Gln Ile Ile Asn Cys Leu Thr Thr Ile Tyr Asp Arg
        35                  40                  45

Leu Glu Gln Glu His Asn Asn Leu Val Asn Val Pro Leu Cys Val Asp
    50                  55                  60

Met Cys Leu Asn Trp Leu Leu Asn Val Tyr Asp Thr Gly Arg Thr Gly
65                  70                  75                  80

Arg Ile Arg Val Leu Ser Phe Lys Thr Gly Ile Ile Ser Leu Cys Lys
                85                  90                  95

Ala His Leu Glu Asp Lys Tyr Arg Tyr Leu Phe Lys Gln Val Ala Ser
            100                 105                 110

Ser Thr Gly Phe Cys Asp Gln Arg Arg Leu Gly Leu Leu Leu His Asp
        115                 120                 125

Ser Ile Gln Ile Pro Arg Gln Leu Gly Glu Val Ala Ser Phe Gly Gly
    130                 135                 140

Ser Asn Ile Glu Pro Ser Val Arg Ser Cys Phe Gln Phe Ala Asn Asn
145                 150                 155                 160

Lys Pro Glu Ile Glu Ala Ala Leu Phe Leu Asp Trp Met Arg Leu Glu
                165                 170                 175

Pro Gln Ser Met Val Trp Leu Pro Val Leu His Arg Val Ala Ala Ala
            180                 185                 190

Glu Thr Ala Lys His Gln Ala Lys Cys Asn Ile Cys Lys Glu Cys Pro
        195                 200                 205

Ile Ile Gly Phe Arg Tyr Arg Ser Leu Lys His Phe Asn Tyr Asp Ile
    210                 215                 220

Cys Gln Ser Cys Phe Phe Ser Gly Arg Val Ala Lys Gly His Lys Met
225                 230                 235                 240

His Tyr Pro Met Val Glu Tyr Cys Thr Pro Thr Thr Ser Gly Glu Asp
```

```
                245                 250                 255

Val Arg Asp Phe Ala Lys Val Leu Lys Asn Lys Phe Arg Thr Lys Arg
            260                 265                 270

Tyr Phe Ala Lys His Pro Arg Met Gly Tyr Leu Pro Val Gln Thr Val
        275                 280                 285

Leu Glu Gly Asp Asn Met Glu Thr
    290                 295


<210> SEQ ID NO 53
<211> LENGTH: 277
<212> TYPE: PRT
<213> ORGANISM: Homo sapiens

<400> SEQUENCE: 53

Pro Val Thr Leu Ile Asn Phe Trp Pro Val Asp Ser Ala Pro Ala Ser
1               5                   10                  15

Ser Pro Gln Leu Ser His Asp Asp Thr His Ser Arg Ile Glu His Tyr
            20                  25                  30

Ala Ser Arg Leu Ala Glu Met Glu Asn Ser Asn Gly Ser Tyr Leu Asn
        35                  40                  45

Asp Ser Ile Ser Pro Asn Glu Ser Ile Asp Asp Glu His Leu Leu Ile
    50                  55                  60

Gln His Tyr Cys Gln Ser Leu Asn Gln Asp Ser Pro Leu Ser Gln Pro
65                  70                  75                  80

Arg Ser Pro Ala Gln Ile Leu Ile Ser Leu Glu Ser Glu Glu Arg Gly
                85                  90                  95

Glu Leu Glu Arg Ile Leu Ala Asp Leu Glu Glu Glu Asn Arg Asn Leu
            100                 105                 110

Gln Ala Glu Tyr Asp Arg Leu Lys Gln Gln His Glu His Lys Gly Leu
        115                 120                 125

Ser Pro Leu Pro Ser Pro Pro Glu Met Met Pro Thr Ser Pro Gln Ser
    130                 135                 140

Pro Arg Asp Ala Glu Leu Ile Ala Glu Ala Lys Leu Leu Arg Gln His
145                 150                 155                 160

Lys Gly Arg Leu Glu Ala Arg Met Gln Ile Leu Glu Asp His Asn Lys
                165                 170                 175

Gln Leu Glu Ser Gln Leu His Arg Leu Arg Gln Leu Leu Glu Gln Pro
            180                 185                 190

Gln Ala Glu Ala Lys Val Asn Gly Thr Thr Val Ser Ser Pro Ser Thr
        195                 200                 205

Ser Leu Gln Arg Ser Asp Ser Ser Gln Pro Met Leu Leu Arg Val Val
    210                 215                 220

Gly Ser Gln Thr Ser Asp Ser Met Gly Glu Glu Asp Leu Leu Ser Pro
225                 230                 235                 240

Pro Gln Asp Thr Ser Thr Gly Leu Glu Glu Val Met Glu Gln Leu Asn
                245                 250                 255

Asn Ser Phe Pro Ser Ser Arg Gly Arg Asn Thr Pro Gly Lys Pro Met
            260                 265                 270

Arg Glu Asp Thr Met
        275


<210> SEQ ID NO 54
<211> LENGTH: 15
<212> TYPE: PRT
<213> ORGANISM: Homo sapiens
```

<400> SEQUENCE: 54

Leu Leu Asn Ser Arg Trp Glu Cys Leu Arg Val Ala Ser Met Glu
1 5 10 15

<210> SEQ ID NO 55
<211> LENGTH: 15
<212> TYPE: PRT
<213> ORGANISM: Homo sapiens

<400> SEQUENCE: 55

Gln Arg Leu Thr Glu Glu Gln Cys Leu Phe Ser Ala Trp Leu Ser
1 5 10 15

<210> SEQ ID NO 56
<211> LENGTH: 15
<212> TYPE: PRT
<213> ORGANISM: Homo sapiens

<400> SEQUENCE: 56

Trp Leu Asp Asn Phe Ala Arg Cys Trp Asp Asn Leu Val Gln Lys
1 5 10 15

<210> SEQ ID NO 57
<211> LENGTH: 8
<212> TYPE: PRT
<213> ORGANISM: Homo sapiens

<400> SEQUENCE: 57

Cys Leu Lys Leu Ser Arg Lys Met
1 5

<210> SEQ ID NO 58
<211> LENGTH: 110
<212> TYPE: PRT
<213> ORGANISM: Homo sapiens

<400> SEQUENCE: 58

Glu Ile Ser Tyr Val Pro Ser Thr Tyr Leu Thr Glu Ile Thr His Val
1 5 10 15

Ser Gln Ala Leu Leu Glu Val Glu Gln Leu Leu Asn Ala Pro Asp Leu
20 25 30

Cys Ala Lys Asp Phe Glu Asp Leu Phe Lys Gln Glu Glu Ser Leu Lys
35 40 45

Asn Ile Lys Asp Ser Leu Gln Gln Ser Ser Gly Arg Ile Asp Ile Ile
50 55 60

His Ser Lys Lys Thr Ala Ala Leu Gln Ser Ala Thr Pro Val Glu Arg
65 70 75 80

Val Lys Leu Gln Glu Ala Leu Ser Gln Leu Asp Phe Gln Trp Glu Lys
85 90 95

Val Asn Lys Met Tyr Lys Asp Arg Gln Gly Arg Phe Asp Arg
100 105 110

<210> SEQ ID NO 59
<211> LENGTH: 21
<212> TYPE: PRT
<213> ORGANISM: Homo sapiens

<400> SEQUENCE: 59

Pro Ser Thr Tyr Leu Thr Glu Ile Thr His Val Ser Gln Ala Leu Leu
1 5 10 15

Glu Val Glu Gln Leu

20

<210> SEQ ID NO 60
<211> LENGTH: 309
<212> TYPE: PRT
<213> ORGANISM: Homo sapiens

<400> SEQUENCE: 60

Ser Ile Gln Ser Ala Gln Glu Thr Glu Lys Ser Leu His Leu Ile Gln
1 5 10 15

Glu Ser Leu Thr Phe Ile Asp Lys Gln Leu Ala Ala Tyr Ile Ala Asp
20 25 30

Lys Val Asp Ala Ala Gln Met Pro Gln Glu Ala Gln Lys Ile Gln Ser
35 40 45

Asp Leu Thr Ser His Glu Ile Ser Leu Glu Glu Met Lys Lys His Asn
50 55 60

Gln Gly Lys Glu Ala Ala Gln Arg Val Leu Ser Gln Ile Asp Val Ala
65 70 75 80

Gln Lys Lys Leu Gln Asp Val Ser Met Lys Phe Arg Leu Phe Gln Lys
85 90 95

Pro Ala Asn Phe Glu Leu Arg Leu Gln Glu Ser Lys Met Ile Leu Asp
100 105 110

Glu Val Lys Met His Leu Pro Ala Leu Glu Thr Lys Ser Val Glu Gln
115 120 125

Glu Val Val Gln Ser Gln Leu Asn His Cys Val Asn Leu Tyr Lys Ser
130 135 140

Leu Ser Glu Val Lys Ser Glu Val Glu Met Val Ile Lys Thr Gly Arg
145 150 155 160

Gln Ile Val Gln Lys Lys Gln Thr Glu Asn Pro Lys Glu Leu Asp Glu
165 170 175

Arg Val Thr Ala Leu Lys Leu His Tyr Asn Glu Leu Gly Ala Lys Val
180 185 190

Thr Glu Arg Lys Gln Gln Leu Glu Lys Cys Leu Lys Leu Ser Arg Lys
195 200 205

Met Arg Lys Glu Met Asn Val Leu Thr Glu Trp Leu Ala Ala Thr Asp
210 215 220

Met Glu Leu Thr Lys Arg Ser Ala Val Glu Gly Met Pro Ser Asn Leu
225 230 235 240

Asp Ser Glu Val Ala Trp Gly Lys Ala Thr Gln Lys Glu Ile Glu Lys
245 250 255

Gln Lys Val His Leu Lys Ser Ile Thr Glu Val Gly Glu Ala Leu Lys
260 265 270

Thr Val Leu Gly Lys Lys Glu Thr Leu Val Glu Asp Lys Leu Ser Leu
275 280 285

Leu Asn Ser Asn Trp Ile Ala Val Thr Ser Arg Ala Glu Glu Trp Leu
290 295 300

Asn Leu Leu Leu Glu
305

<210> SEQ ID NO 61
<211> LENGTH: 331
<212> TYPE: PRT
<213> ORGANISM: Homo sapiens

<400> SEQUENCE: 61

Ser Glu Val Asn Leu Asp Arg Tyr Gln Thr Ala Leu Glu Glu Val Leu

```
1               5                   10                  15

Ser Trp Leu Leu Ser Ala Glu Asp Thr Leu Gln Ala Gln Gly Glu Ile
            20                  25                  30

Ser Asn Asp Val Glu Val Val Lys Asp Gln Phe His Thr His Glu Gly
        35                  40                  45

Tyr Met Met Asp Leu Thr Ala His Gln Gly Arg Val Gly Asn Ile Leu
    50                  55                  60

Gln Leu Gly Ser Lys Leu Ile Gly Thr Gly Lys Leu Ser Glu Asp Glu
65                  70                  75                  80

Glu Thr Glu Val Gln Glu Gln Met Asn Leu Leu Asn Ser Arg Trp Glu
                85                  90                  95

Cys Leu Arg Val Ala Ser Met Glu Lys Gln Ser Asn Leu His Arg Val
            100                 105                 110

Leu Met Asp Leu Gln Asn Gln Lys Leu Lys Glu Leu Asn Asp Trp Leu
        115                 120                 125

Thr Lys Thr Glu Glu Arg Thr Arg Lys Met Glu Glu Glu Pro Leu Gly
    130                 135                 140

Pro Asp Leu Glu Asp Leu Lys Arg Gln Val Gln Gln His Lys Val Leu
145                 150                 155                 160

Gln Glu Asp Leu Glu Gln Glu Gln Val Arg Val Asn Ser Leu Thr His
                165                 170                 175

Met Val Val Val Val Asp Glu Ser Ser Gly Asp His Ala Thr Ala Ala
            180                 185                 190

Leu Glu Glu Gln Leu Lys Val Leu Gly Asp Arg Trp Ala Asn Ile Cys
        195                 200                 205

Arg Trp Thr Glu Asp Arg Trp Val Leu Leu Gln Asp Ile Leu Leu Lys
    210                 215                 220

Trp Gln Arg Leu Thr Glu Glu Gln Cys Leu Phe Ser Ala Trp Leu Ser
225                 230                 235                 240

Glu Lys Glu Asp Ala Val Asn Lys Ile His Thr Thr Gly Phe Lys Asp
                245                 250                 255

Gln Asn Glu Met Leu Ser Ser Leu Gln Lys Leu Ala Val Leu Lys Ala
            260                 265                 270

Asp Leu Glu Lys Lys Lys Gln Ser Met Gly Lys Leu Tyr Ser Leu Lys
        275                 280                 285

Gln Asp Leu Leu Ser Thr Leu Lys Asn Lys Ser Val Thr Gln Lys Thr
    290                 295                 300

Glu Ala Trp Leu Asp Asn Phe Ala Arg Cys Trp Asp Asn Leu Val Gln
305                 310                 315                 320

Lys Leu Glu Lys Ser Thr Ala Gln Ile Ser Gln
                325                 330


<210> SEQ ID NO 62
<211> LENGTH: 4
<212> TYPE: PRT
<213> ORGANISM: Homo sapiens

<400> SEQUENCE: 62

Gly Gly Ser Gly
1


<210> SEQ ID NO 63
<211> LENGTH: 4
<212> TYPE: PRT
<213> ORGANISM: Homo sapiens
```

<400> SEQUENCE: 63

Gly Gly Gly Ser
1

<210> SEQ ID NO 64
<211> LENGTH: 5
<212> TYPE: PRT
<213> ORGANISM: Homo sapiens

<400> SEQUENCE: 64

Gly Gly Gly Gly Ser
1 5

<210> SEQ ID NO 65
<211> LENGTH: 4
<212> TYPE: PRT
<213> ORGANISM: Homo sapiens

<400> SEQUENCE: 65

Gly Ser Ala Thr
1

<210> SEQ ID NO 66
<211> LENGTH: 96
<212> TYPE: PRT
<213> ORGANISM: Mus musculus

<400> SEQUENCE: 66

Leu Leu Leu Gln Arg Arg Arg Val Thr Val Arg Lys Ala Asp Ala Gly
1 5 10 15

Gly Leu Gly Ile Ser Ile Lys Gly Gly Arg Glu Asn Lys Met Pro Ile
20 25 30

Leu Ile Ser Lys Ile Phe Lys Gly Leu Ala Ala Asp Gln Thr Glu Ala
35 40 45

Leu Phe Val Gly Asp Ala Ile Leu Ser Val Asn Gly Glu Asp Leu Ser
50 55 60

Ser Ala Thr His Asp Glu Ala Val Gln Ala Leu Lys Lys Thr Gly Lys
65 70 75 80

Glu Val Val Leu Glu Val Lys Tyr Met Lys Glu Val Ser Pro Tyr Phe
85 90 95

<210> SEQ ID NO 67
<211> LENGTH: 96
<212> TYPE: PRT
<213> ORGANISM: Homo sapiens

<400> SEQUENCE: 67

Leu Leu Leu Gln Arg Arg Arg Val Thr Val Arg Lys Ala Asp Ala Gly
1 5 10 15

Gly Leu Gly Ile Ser Ile Lys Gly Gly Arg Glu Asn Lys Met Pro Ile
20 25 30

Leu Ile Ser Lys Ile Phe Lys Gly Leu Ala Ala Asp Gln Thr Glu Ala
35 40 45

Leu Phe Val Gly Asp Ala Ile Leu Ser Val Asn Gly Glu Asp Leu Ser
50 55 60

Ser Ala Thr His Asp Glu Ala Val Gln Val Leu Lys Lys Thr Gly Lys
65 70 75 80

Glu Val Val Leu Glu Val Lys Tyr Met Lys Asp Val Ser Pro Tyr Phe
85 90 95

MODIFIED DYSTROPHIN PROTEINS

CROSS REFERENCE TO RELATED APPLICATIONS

This is a U.S. National Phase application of PCT/US2017/038418, filed on Jun. 21, 2017, which claims the benefit of U.S. Provisional Patent Application No. 62/367,559, filed on Jul. 27, 2016; U.S. Provisional Patent Application No. 62/357,865, filed on Jul. 1, 2016; and U.S. Provisional Patent Application No. 62/352,927, filed on Jun. 21, 2016, each of which is incorporated herein by reference in its entirety.

STATEMENT REGARDING FEDERALLY-SPONSORED RESEARCH AND DEVELOPMENT

This invention was made with government support under NS090634 and AR067985 awarded by the National Institute of Health and with W81XWH-14-1-0302 awarded by the U.S. Army Medical Research and Materiel Command. The government has certain rights in the invention.

INCORPORATION OF SEQUENCE LISTINGS

A sequence listing containing the file named "17UMC006_SEQ LST_TC167044_ST25.txt", which is 263,001 bytes (measured in MS-Windows®), contains 67 sequences, and was created on Jun. 14, 2017, is provided herewith via the USPTO's EFS system, and is incorporated herein by reference in its entirety.

BACKGROUND

Dystrophin is an essential cytoskeletal protein in the muscle. It constitutes a primary linkage between the extracellular matrix (ECM) and the actin cytoskeleton (1, 2). In muscle cells, dystrophin plays an important role in maintaining membrane integrity and preventing membrane rupture. Loss of dystrophin, as seen in Duchenne muscular dystrophy (DMD) (3), leads to sarcolemmal leakage, myofiber degeneration and necrosis. Full-length dystrophin is a large rod-shaped protein. It contains four functional domains including N-terminus (NT), the mid-rod domain, the cysteine-rich (CR) domain and C-terminus (CT). The mid-rod domain consists of 24 spectrin-like repeats. Four hinges (H) are interspersed in the mid-rod domain (4). Dystrophin NT and spectrin-like repeats R11-17 bind to cytoskeletal filamentous actin (5, 6). The CR domain anchors dystrophin to the muscle membrane via interaction with the transmembrane protein β-dystroglycan (7-9). β-dystroglycan further connects with basal lamina proteins to complete the axis from the ECM to the cytoskeleton (10). This mechanical linkage protects the muscle membrane from contraction-induced damages. In this well-established model, the dystrophin CR domain is solely responsible for dystrophin membrane binding (FIG. 1).

Despite compelling evidence suggesting that the CR domain mediates dystrophin-sarcolemma interaction, case reports from some rare-occurring patients suggest that dystrophin can bind to the sarcolemma through CR domain-independent mechanisms. In these patients, biochemical and genetic analyses confirmed a complete deletion of the CR domain. Yet, immunostaining showed clear sarcolemmal localization of the truncated dystrophin protein (FIG. 2B) (11-13).

SUMMARY

Synthetic nucleic acid molecules encoding a synthetic mini-dystrophin gene or micro-dystrophin gene encoding a synthetic, non-full length dystrophin protein comprising: (i) an N-terminal (NT) domain of the dystrophin protein or a modified N-terminal domain of the dystrophin protein; (ii) at least two membrane binding motifs (MBM) independently selected from the group consisting of an MBM of an R1-R2-R3 membrane binding domain (MBD), an MBM of a CR membrane binding domain, and an MBM of a CT membrane binding domain; (iii) an MBM of an R10-R11-R12 MBD; and (iv) an nNOS binding domain of R16-R17; wherein the domains and the MBM are arranged from N to C terminus in the order in which they occur in a wild-type dystrophin protein and are operably linked are provided. Synthetic nucleic acid molecules encoding a synthetic mini-dystrophin gene or micro-dystrophin gene encoding a synthetic, non-full length dystrophin protein comprising: (i) an N-terminal (NT) domain of the dystrophin protein or a modified N-terminal domain of the dystrophin protein; (ii) at least two membrane binding motifs (MBM) independently selected from the group consisting of an MBM of an R1-R2-R3 membrane binding domain (MBD), an MBM of a CR membrane binding domain, and an MBM of a CT membrane binding domain; (iii) an MBM of an R10-R11-R12 MBD; and (iv) an nNOS binding domain of R16-R17 that is operably linked to a syntrophin PDZ domain; wherein the dystrophin domains and the MBM are arranged from N to C terminus in the order in which they occur in a wild-type dystrophin protein and are operably linked are also provided. A synthetic nucleic acid molecule comprising a sequence encoding a fusion protein comprising a nNOS binding domain of dystrophin R16-R17 that is operably linked to a syntrophin PDZ domain are also provided. In certain embodiments, the nNOS binding domain of dystrophin R16-R17 is operably linked to a syntrophin PDZ domain with a hinge region in the fusion protein. In certain embodiments, the nNOS binding domain of dystrophin R16-R17 is operably linked to a syntrophin PDZ domain with a hinge region selected from the group consisting of a synthetic hinge, a semi-synthetic hinge, dystrophin H1, dystrophin H2, dystrophin H3, dystrophin H4, and variants thereof In certain embodiments, the MBM of R1-R2-R3 comprises at least one S-palmitoylation site peptide selected from the group consisting of SEQ ID NO: 54, SEQ ID NO: 55, and SEQ ID NO:56. In certain embodiments, the R3 repeat or R2-R3 repeats are absent from the non-full length dystrophin protein. In certain embodiments, the R1, R2, R3, R1 and R2, R2 and R3, or R1, R2, and R3 repeats are present in the non-full length dystrophin protein. In certain embodiments, the MBM of R10-R11-R12 comprises an S-palmitoylation site peptide of SEQ ID NO:57. In certain embodiments, the R10 repeat, the R11 repeat, the R12 repeat, the R10-R11 repeats, the R11-R12, or the R10 and R12 repeats are present in the non-full length dystrophin protein. In certain embodiments, the R17 domain is present in the non-full length dystrophin protein. In certain embodiments, the n-terminal alpha helix of the R16 domain (SEQ ID NO:59) or a portion thereof is absent from the non-full length dystrophin protein. In certain embodiments, alpha-helix 2 and alpha-helix 3 of the R16 domain is present and alpha-helix 1, alpha-helix 2, and alpha-helix 3 of the R17 domain is present in the non-full length dystrophin protein. In certain embodiments, alpha-helix 2 and alpha-helix 3 of the R16 domain is present and alpha-helix 1, alpha-helix 2, and alpha-helix 3 of the R17 domain is present in the non-full length dystrophin protein. In certain embodiments, the N-terminal helix one of the R16 domain is substituted with the MBM of the R1-R2-R3 MBD or with the MBM of the R10-R11-R12 MBD. In certain embodiments, the R16 domain and the R17 domain are present in the non-full length dystrophin protein. In certain embodiments, the MBM of the CR membrane binding domain is absent, wherein the CR membrane binding domain is absent, or wherein the CR domain is absent from the non-full length dystrophin protein. In certain embodiments, the MBM of the CT MBD comprises residues 3422 to 3535 of SEQ ID NO: 1. In certain embodiments, the MBM of the CT MBD comprises residues 3501 to 3685 of SEQ ID NO:1. In certain embodiments, at least one domain and at least one MBM are operably linked with a hinge region selected from the group consisting of a synthetic hinge, a semi-synthetic hinge, dystrophin H1, dystrophin H2, dystrophin H3, dystrophin H4, and variants thereof. In certain embodiments, the dystrophin H1 hinge or a variant thereof operably links the C-terminus of the NT domain to the N-terminus of an MBM or domain containing an MBM, wherein the dystrophin H2 hinge or a variant thereof operably links the C-terminus of a MBM or domain containing an MBM to the N-terminus of another MBM or domain containing another MBM, wherein the dystrophin H3 hinge or a variant thereof operably links the C-terminus of an MBM or domain containing an MBM to the N-terminus of another MBM or domain containing another MBM, wherein the dystrophin H4 hinge or a variant thereof operably links the C-terminus of an MBM to the N-terminus of the CR MBM or the CR domain, or any combination thereof. In certain embodiments, the dystrophin H4 hinge or a variant thereof operably links the C-terminus of an MBM to the N-terminus of the CR MBM or the CR domain. In certain embodiments of any of the aforementioned synthetic nucleic acid molecules, the mini- or micro-dystrophin gene is between 5 kb to about 8 kb in length or less than 5 kb in length, respectively. In certain embodiments of any of the aforementioned synthetic nucleic acid molecules, the mini- or micro-dystrophin gene is operably linked to a heterologous promoter, a heterologous 5' untranslated region (UTR), a heterologous 3' UTR, a heterologous polyadenylation site, or any combination thereof. In certain embodiments of any of the aforementioned synthetic nucleic acid molecules, the molecule is integrated within an endogenous dystrophin gene locus in an X-chromosome.

Lentiviral vectors comprising any of the aforementioned synthetic nucleic acid molecules, wherein the nucleic acid molecule is operably linked to an expression cassette, 5' and 3' long terminal repeats (LTR), and a psi sequence in the lentiviral vector are also provided.

Single recombinant adeno-associated virus (AAV) vector comprising any of the aforementioned synthetic nucleic acid molecules, wherein said nucleic acid molecule is operably linked to an expression cassette and viral inverted terminal repeats (ITRs) in the AAVare also provided.

Dual recombinant AAV vector system, comprising two AAV vectors, wherein one of the two AAV vectors comprises a part of the nucleic acid molecule of any one of the aforementioned synthetic nucleic acid molecules, and the other vector comprises the remaining part of said nucleic acid molecule, wherein the two vectors further comprise sequences that permit recombination with each other to produce said nucleic acid in full length, and wherein the nucleic acid in full length is operably linked to an expression cassette and viral ITRs.

Composition comprising any one of the aforementioned synthetic nucleic acid molecules or vectors and a pharmaceutically acceptable carrier are also provided. In certain embodiments, the synthetic nucleic acid molecule is operably linked to an expression cassette, 5' and 3' long terminal repeats (LTR), and a psi sequence in a lentiviral vector. In certain embodiments, the nucleic acid molecule is operably linked to an expression cassette and viral inverted terminal repeats (ITRs) in an AAV. In certain embodiments, the composition comprises the aforementioned dual recombinant AAV vector system.

Isolated host cells comprising any one of the aforementioned synthetic nucleic acid molecules or vectors are also provided. In certain embodiments, the nucleic acid molecule is integrated within an endogenous dystrophin gene locus in a chromosome of the host cell. In certain embodiments, the nucleic acid molecule is operably linked to an expression cassette, 5' and 3' long terminal repeats (LTR), and a psi element in a lentiviral vector. In certain embodiments, the nucleic acid molecule is operably linked to an expression cassette and ITRs in an AAV. In certain embodiments, the host cell is a myogenic stem cell.

Methods for the treating or ameliorating one or more adverse effects of Duchenne muscular dystrophy (DMD), Becker muscular dystrophy (BMD), X-linked dilated cardiomyopathy (XLDC), age-related muscle atrophy, cancer cachexia, or other neuromuscular disorders characterized by loss of sarcolemmal neuronal nitric oxide synthase (nNOS) activity in a subject in need thereof comprising the step of administering to the subject a therapeutically effective amount of: (i) any one of the aforementioned synthetic nucleic acid molecules; (ii) the aforementioned lentiviral vectors; (iii) the aforementioned AAV vectors; (iv) any one of the aforementioned compositions; or (iv) any one of the aforementioned host cells to a subject in need thereof. In certain embodiments, the administration is by injection into muscle, systemic delivery, or local delivery. In certain embodiments, the host cell is a stem cell or myogenic stem cell. In certain embodiments, the host cell is derived from an autologous cell of the subject. In certain aforementioned methods, a defective endogenous dystrophin gene of the host cell or a defective portion thereof is edited to provide the synthetic nucleic acid molecule within the host cell's X-chromosome.

Use of (i) any one of the aforementioned synthetic nucleic acid molecules; (ii) the aforementioned lentiviral vectors; (iii) the aforementioned AAV vectors; (iv) any one of the aforementioned compositions; or (iv) any one of the aforementioned host cells for making a composition for administration to a subject suffering from Duchenne muscular dystrophy (DMD), Becker muscular dystrophy (BMD), X-linked dilated cardiomyopathy (XLDC) age-related muscle atrophy, cancer cachexia, or other neuromuscular disorders characterized by loss of sarcolemmal neuronal nitric oxide synthase (nNOS) activity is also provided.

Use of (i) any one of the aforementioned synthetic nucleic acid molecules; (ii) the aforementioned lentiviral vectors; (iii) the aforementioned AAV vectors; (iv) any one of the aforementioned compositions; or (iv) any one of the aforementioned host cells for treating a subject suffering from Duchenne muscular dystrophy (DMD), Becker muscular dystrophy (BMD) or X-linked dilated cardiomyopathy (XLDC), or for ameliorating one or more adverse effects of DMD, BMD, XLDC, age-related muscle atrophy, cancer cachexia, or other neuromuscular disorders characterized by loss of sarcolemmal neuronal nitric oxide synthase (nNOS) activity is also provided.

BRIEF DESCRIPTION OF THE DRAWINGS

FIG. 12. Position of cysteine residues in R1-3, R10-12 and CT is conserved between human and mouse dystrophin.

FIG. 13. Identification of potential palmitoylated site peptides in R1-3 and R10-12 by CSS-Palm 2.0 program. The predicted palmitoylation sites are the sole cysteine residues in the sequences. From top to bottom, the palmitoylation site peptide sequences are LLNSRWECLRVASME (SEQ ID NO:54), QRLTEEQCLFSAWLS (SEQ ID NO:55), WLDNFARCWDNLVQK (SEQ ID NO:56), and CLKLSRKM (SEQ ID NO:57).

FIG. 27. A. Dystrophin functional domains and dystrophin nNOS-binding domain. Dystrophin is composed of four functional domains: NT: N-terminus; the mid rod domain; CR: cysteine-rich domain; and CT: C-terminus. The mid-rod domain contains 24 spectrin-like repeats and four hinge (H) regions. Dystrophin spectrin-like repeats 16 and 17 (R16/17) are identified as the nNOS-binding domain. B. Sarcolemmal localization of nNOS is dependent on interactions with dystrophin R16/17 and syntrophin. Both dystrophin R16/17 and Syntrophin (Syn) bind to nNOS. The interaction of nNOS with dystrophin R16/17 and syntrophin anchors nNOS to the sarcolemma. Syn: Syntrophin; DG: Dystroglycan.

DETAILED DESCRIPTION

Figure 1:
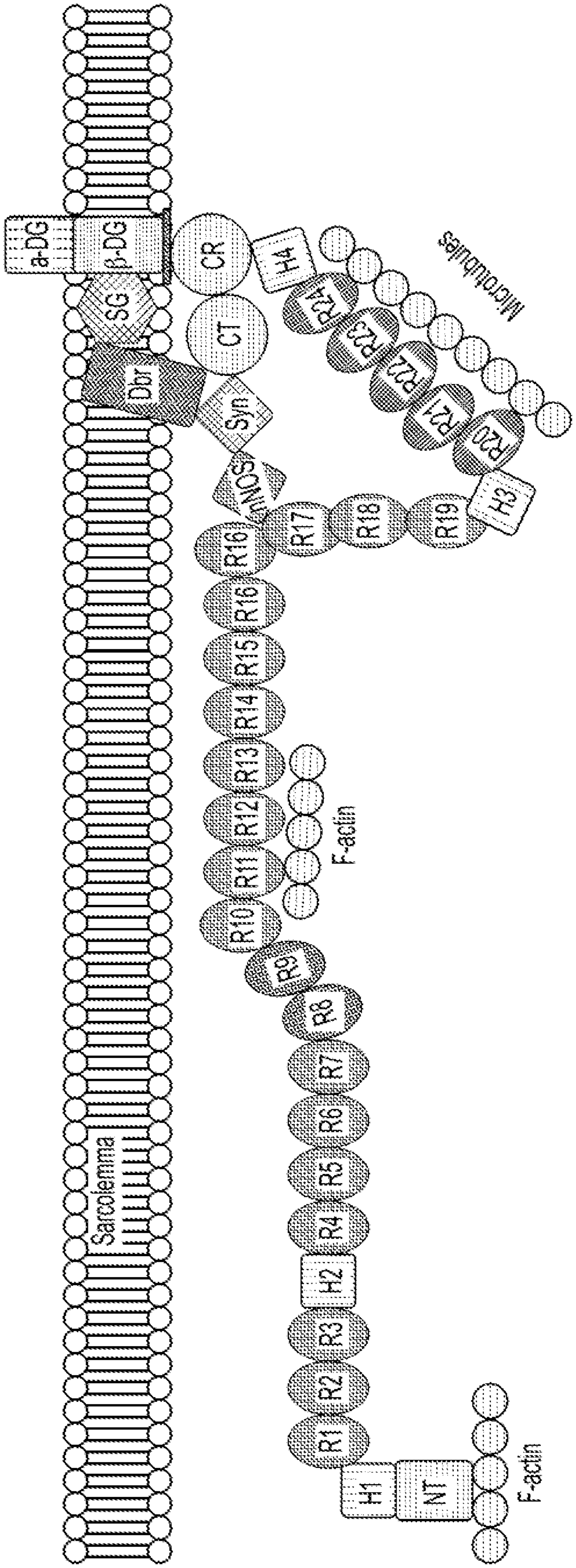
FIG. 1. The classic model of dystrophin-sarcolemma interaction. Numerous studies suggest that dystrophin binds to the sarcolemma via its CR domain (1-8). See Supplementary References provided herein for full citation.

The present disclosure identifies a novel series of dystrophin minigenes and microgenes that are small enough to be packaged into AAV or lentiviral vectors, and yet retain functions of a full-length, wild type dystrophin gene, including, but not limited to, the membrane binding functions and signal functions (such as sarcolemmal nNOS-related functions), needed for protecting muscle from dystrophic injury. The present disclosure recognizes that the inclusion of membrane binding motifs and/or the entire membrane binding domains contained in the spectrin repeats R10-R11-R12 of the mid-rod domain of a dystrophin protein in a synthetic mini/micro-dystrophin gene provide useful membrane binding functions. Mini or micro-dystrophin genes retaining the membrane binding motifs or membrane binding domains of the R10-R11-R12 can exhibit improved membrane binding and biological activity in comparison to mini or micro-dystrophin genes that lack the membrane binding motifs or membrane binding domains of the R10-R11-R12.

By "domain" is meant a portion of a protein structure. For example, the "N-terminal domain" or "NT" of a human dystrophin protein, as referred to herein, includes amino acid residues from approximately 1 to approximately 252, particularly, from amino acid residues methionine 1 to glutamate 252 of SEQ ID NO: 1, more particularly, amino acid sequence encoded by a nucleotide sequence as set forth in SEQ ID NO: 17. Similarly, the "mid-rod domain" or "rod domain" of a dystrophin protein, as referred to herein, includes amino acid residues approximately from 253 to approximately 3112 of SEQ ID NO: 1, particularly, from amino acid residues methionine 253 to leucine 3112 as set forth in SEQ ID NO: 1; the "cysteine-rich domain" or "CR" of a dystrophin protein, as referred to herein, includes amino acid residues from approximately 3113 to approximately 3408 of SEQ ID NO: 1, particularly, from amino acid residues arginine 3113 to threonine 3048 as set forth in SEQ ID NO: 1, more particularly, amino acid sequence encoded by a nucleotide sequence as set forth in SEQ ID NO: 46 and the "C-terminal domain" or "CT" of a dystrophin protein, as referred to herein, includes amino acid residues from approximately 3409 to 3685 of SEQ ID NO: 1, particularly, from amino acid residues proline 3409 to methionine 3685 as set forth in SEQ ID NO: 47.

By "dystrophin microgene" or "micro-dystrophin gene" or "microgene" is meant a nucleic acid molecule that is 5 kb or less in length and encodes a modified or non-full-length dystrophin polypeptide (also referred to as micro-dystrophin in the present application) that retains the N-terminal domain, the cysteine-rich domain, two or more repeats of the mid-rod domain, and two or more hinges of the mid-rod domain of a full-length dystrophin protein. By "micro-dystrophin" is meant a modified or non-full-length dystrophin protein molecule that retains biological function of a full-length dystrophin protein and the coding sequence of which is 5 kb or less.

By "dystrophin minigene," "mini-dystrophin gene" or "minigene" is meant a nucleic acid molecule that is more than 5 kb in length but less than the full-length of dystrophin coding sequence, between 5 kb to about 10 kb in length, about 5 kb to about 8 kb in length, or about 7 kb in length, and encodes a modified or non-full-length dystrophin polypeptide (also referred to as mini-dystrophin in the present application) that retains the N-terminal domain, the cysteine-rich domain, two or more repeats (also referred to by R and a number, e.g., R16 means repeat number 16) of the mid-rod domain, and two or more hinges of the mid-rod domain of a full-length dystrophin protein. By "mini-dystrophin" is meant a modified or non-full-length dystrophin protein molecule that retains the biological functions of a full-length dystrophin protein and the coding sequence of which is more than 5 kb in length but less than the full-length of dystrophin coding sequence.

By "biological functions" of a dystrophin protein is meant functions which include, but are not limited, at least one of providing a mechanical link between the sarcolemma, cytoskeleton or the extracellular matrix and/or providing a signaling function such as recruiting nNOS to the sarcolemma.

By "modified" in connection with dystrophin gene or dystrophin protein is meant a wild-type (or naturally-occurring) full-length dystrophin gene or dystrophin protein molecule is changed so that the modified dystrophin gene or dystrophin protein molecule does not include the full-length coding sequence of a dystrophin gene or the full-length amino acid sequence of a dystrophin protein, yet retain or substantially retain certain biological functions of a full-length gene or protein.

By "modified N-terminal domain" is meant an N-terminal domain that is different in structure and/or sequence from that of wild type or naturally occurred but retain the function of a wild type or naturally occurred N-terminus. By "modifications or variations" is meant any changes to a nucleic acid molecule or polypeptide, such as by mutation, that retains substantial function of the nucleic acid molecule or polypeptides and/or is substantially homologous with, or similar/identical to, the nucleic acid molecule or polypeptide.

In the classic model, dystrophin stabilizes the sarcolemma by interacting with a transmembrane protein β-dystroglycan and the F-actin cytoskeleton via its CR and NT domains, respectively. β-dystroglycan further connects with basal lamina proteins to complete the axis from the extracellular matrix (ECM) to intracellular cytoskeleton. However, this model completely ignores the direct interaction between dystrophin and membrane lipid bilayer, a major mechanism underlying spectrin-mediated membrane stabilization (Luna & Hitt, A. L. *Science* 258, 955-964 (1992); Le Rumeur et al. *Biochim. Biophys. Acta* 1804, 1713-1722 (2010); Sheetz, et al. *Annu Rev Biophys Biomol Struct* 35, 417-434 (2006)). Several lines of evidence suggest that dystrophin-lipid bilayer interaction can play a critical role for sarcolemma protection. First, in vitro studies suggest that the rod domain can contain putative lipid binding regions (LBRs) in R1-3 and R4-19 (Luna & Hitt, A. L. *Science* 258, 955-964 (1992); Le Rumeur et al. *Biochim. Biophys. Acta* 1804, 1713-1722 (2010); Sheetz, et al. *Annu Rev Biophys Biomol Struct* 35, 417-434 (2006)). Second, deletion of all putative rod domain LBRs abolishes the ability of dystrophin to protect muscle (Harper, S. Q. et al. *Nat. Med.* 8, 253-261 (2002)). Third, a series of in vitro studies demonstrated that binding of dystrophin LBRs to phospholipids considerably contributes to stiffness and stability of lipid monolayer (Sarkis, J. et al. *FASEB J.* 27, 359-367 (2013); Sarkis, J. et al. *J. Biol. Chem.* (2011)).

To better understand how dystrophin interacts with the sarcolemma in the absence of the CR domain, a comprehensive in vivo screening for alternative membrane binding domains (MBDs) in dystrophin was performed. The R1-3, R10-12 and CT domains were identified as new dystrophin MBDs in mouse muscle. We further confirmed that these MBDs are conserved in dog muscle. To determine whether these MBDs are functionally equivalent, we evaluated their ability to establish the dystrophin-associated glycoprotein complex (DGC) at the sarcolemma. Our results showed that only the CR domain and CT are capable of restoring the DGC. We also evaluated these newly discovered MBDs in the heart. We found that R1-3 and CT interact with the sarcolemma in cardiac muscle. Taken together, our studies suggest that dystrophin-sarcolemma interaction is much more complex than it has been perceived. Without seeking to be limited by theory, a new model to explain how dystrophin stabilizes the sarcolemma is proposed. In this model, dystrophin maintains sarcolemmal stability through two distinctive mechanisms: (i) dystrophin stabilizes the muscle membrane through the cytoskeleton (F-actin)-NT-CR-ECM axis; (ii) dystrophin strengthens the sarcolemma through the membrane association of its lipid binding regions LBRs. Both mechanisms involve the binding of dystrophin to the muscle membrane. Through the close association with the muscle membrane, dystrophin then tethers intracellular cytoskeleton to the sarcolemma, and stabilizes and strengthens the sarcolemma.

It is well established that dystrophin interacts with a congregation of cellular proteins (FIG. 3) (Johnson, E. K. et al. *PLoS One* 8, e73224 (2013); Johnson, E. K. et al. *PLoS One* 7, e43515 (2012); Allen, D. G. et al. *Physiol. Rev.* 96, 253-305 (2016); Constantin, B. Dystrophin complex functions as a scaffold for signaling proteins. *Biochim. Biophys. Acta* 1838, 635-642 (2014); Gao, Q. Q. & McNally, E. M. *Compr Physiol* 5, 1223-1239 (2015)). Besides the well known dystrophin-associated glycoprotein complex (DGC) (which includes dystroglycans, nNOS, syntrophin, dystrobrevins, sarcoglycans and sarcospan), dystrophin also interacts with cytoskeleton proteins (such as actin, tubulin, keratin, synemin and plectin), signaling proteins (such as Grb2, PAR-1b, cypher and ahnak1), channel proteins (such as TRPC1, TRPC4 and Nav1.5), caveolae proteins (such as caveolin-3 and cavin-1), tripartite motif proteins (e.g. myospryn) and chaperones (e.g. CRYAB). R10-12 belongs to the second actin-binding domain of dystrophin, and the CT-domain has the syntrophin and dystrobrevin binding motifs (Sadoulet-Puccio, et al. *Proc. Natl. Acad. Sci. USA* 94, 12413-12418 (1997). In certain embodiments provided herein, protein binding determinants in R10-R12 (F-actin), R16-R17 (nNOS), CR (beta-dystroglycan), and/or in CT (sarcoglycan, dystrobrevin, syntropin) are retained in the synthetic mini and micro dystrophin proteins and nucleic acids encoding the same that are provided herein.

In certain embodiments, the synthetic nucleic acid molecules provided herein comprise membrane binding motifs or membrane binding domains from the R10-R11-R12 regions of dystrophin that can be coupled with at least two membrane binding motifs or membrane binding domains from the R1-R2-R3, CR, and CT regions of dystrophin protein.

Membrane binding motifs of the R1-R2-R3 region used in the synthetic mini or micro dystrophins provided herein include, but are not limited to, the S-palmitoylation site peptide of SEQ ID NO: 54, SEQ ID NO: 55, and SEQ ID NO:56. In certain embodiments, the membrane binding domain of the R1-R2-R3 region used in the synthetic mini or micro dystrophins comprises the R1 repeat or the R1 and the R2 repeats.

Membrane binding motifs of the R10-R11-R12 region used in the synthetic mini or micro dystrophins provided herein include, but are not limited to, the S-palmitoylation site peptide of SEQ ID NO:57. In certain embodiments, the membrane binding domains of R10-R11-R12 can comprise any one of the R10 repeat, the R11 repeat, the R12 repeat, the R10-R11 repeats, the R11-R12, or the R10 and R12 repeats.

Membrane binding motifs of the CT domain used in the synthetic mini or micro dystrophins provided herein include, but are not limited to, the MBM of the CT MBD comprises residues 3422 to 3535 of SEQ ID NO: 1 or residues 3501 to 3685 of SEQ ID NO:1.

In certain embodiments, the synthetic nucleic acid molecules provided herein can comprise a nNOS binding domain of R16-R17. Such nNOS binding domains of the R16-R17 domains can comprise an R16-R17 peptide wherein the N-terminal alpha-helix of R16 (i.e., the sequence PSTYLTEITHVSQALLEVEQL (SEQ ID NO: 59) has been deleted where alpha-helices 2 and 3 of both of R16 and R17 are present. In certain embodiments, the N-terminal helix one of the R16 domain is substituted with the MBM of the R1-R2-R3 MBD or with the MBM of the R10-R11-R12 MBD. The remaining alpha-helices 2 and 3 of both of R16 and R17 along with the alpha-helix 1 of R17 that binds nNOS binding alpha-helix in vitro are sufficient to provide for in vivo nNOS binding (Lai, Y., et al., *Proc. Natl. Acad. Sci. USA* 110, 525-530 (2013).

In certain embodiments, the aforementioned dystrophin NT domain, repeats (e.g., R1, R2, R3, R10, R11, R12, R16, R17), CR domain, and CT domain are operably linked with a hinge region selected from the group consisting of a synthetic hinge, a semi-synthetic hinge, dystrophin H1, dystrophin H2, dystrophin H3, dystrophin H4, and variants thereof. A synthetic hinge can comprise or consist of one, two, or three, four, five or more "Gly-Gly-Ser-Gly" (SEQ ID NO:62) units. Other useful synthetic hinges that can be used include, but are not limited to: (i) [Gly-Ser]x linkers where x=2-10; (ii) one, two, or three, four, five or more "Gly-Gly-Gly-Ser" (SEQ ID NO:63) units; (iii) one, two, or three, four, five or more "Gly-Gly-Gly-Gly-Ser" (SEQ ID NO:64) units; (iv) one, two, or three, four, five or more "Ser-Glu-Gly" units; (v) one, two, or three, four, five or more "Gly-Ser-Ala-Thr" (SEQ ID NO:65) units; and (vi) any combination of (i)-(v) and/or of one, two, or three, four, five or more "Gly-Gly-Ser-Gly" (SEQ ID NO:62) units. A semi-sythetic hinge can comprise a dystrophin H1, H2, H3, or H4 hinge or portion thereof that incorporates a synthetic hinge.

Nucleic acids that encode the aforementioned syntrophin PDZ domain and/or dystrophin NT domain, repeats (e.g,. R1, R2, R3, R10, R11, R12, R16, R17), CR domain, and CT domain that can be used include, but are not limited to, the nucleic acids provided in the sequence listing provided herein as well as by degenerate versions of those sequences that encode the same dystrophin polypeptide sequences. In certain embodiments, synthetic nucleic acids provided herein encode variants of the sequences of the aforementioned syntrophin PDZ domain and/or dystrophin NT domain, repeats (e.g,. R1, R2, R3, R10, R11, R12, R16, R17), CR domain, and CT domain, or polypeptides contained therein that are listed in the sequence listing provided herewith or that are encoded by the nucleic acids listed in the sequence listing that: (i) exhibit at least 85%, 90%, 95%, 98%, or 99% sequence identity to the polypeptide sequence or encoded polypeptide sequence; (ii) contain 1, 2, 3, 4, 5, 6, or 7 conservative amino acid substitutions, insertions, or deletions; or (iii) incorporate one or more allelic variants of the sequence found in individuals with functional syntrophin PDZ domain or dystrophin genes that do not exhibit disease associated with loss or reductions in syntrophin PDZ domain or dystrophin activity.

In certain embodiments, the present disclosure provides vectors that can deliver the synthetic nucleic acid molecules encoding the micro or mini dystrophins or other fusion proteins provided herein. Any vector suitable for the purpose is contemplated by the present disclosure. In particular, the present disclosure provides a series of recombinant adeno-associated viral vectors (AAVs) and lentiviral vectors to deliver the nucleic acid molecules of the present disclosure (mini/micro-dystrophin genes) that exhibit improved membrane binding and biological activity. In certain embodiments, recombinant AAV vector (single vector or dual vectors) in accordance with the present disclosure includes any one of the nucleic acid molecule of the present disclosure (the mini/micro-dystrophin genes) that exhibit improved membrane binding and biological activity, operably linked to an expression cassette (a promoter and a polyA) and viral inverted terminal repeats (ITRs).

Numerous expression cassettes and vectors can be used with the micro and minidystrophin genes provided herein. By "expression cassette" is meant a complete set of control sequences including, but not limited to, initiation, promoter and termination sequences which function in a cell when they flank a structural gene in the proper reading frame. Expression cassettes frequently contain an assortment of restriction sites suitable for cleavage and insertion of any structural gene, e.g., the microgene or minigene of the present disclosure. In certain embodiments, the cloned gene will have a start codon in the correct reading frame for the structural synthetic dystrophin-encoding sequence. In addition, the expression cassette for the present disclosure can in certain embodiments includes, but not limited to, a constitutive promoter sequence, e.g., a CMV, RSV, CMV, SV40, CAG, CK6, or MCK promoters, at one end to cause the gene to be transcribed, and a poly-A recognition sequence at the other end for proper processing and transport of the messenger RNA. Examples of such a useful (empty) expression cassette into which the microgene of the present disclosure can be inserted are pcis.RSVmcs, pcis.CMVmcs, pcis-.CMVmcs-intron, pcis.SV40mcs, pcis.SV40mcs-intron, pcis.CK6mcs, and pcis.CAGmcs as described in Yue et al (Yue & Duan 2002 Biotechniques 33(3):672-678). Examples of such a useful (empty) expression cassette into which the minigene of the present disclosure can be inserted are pDD188, pDD293 and pDD295 as described in Duan et al (Duan, Yue and Engelhardt 2003 Methods in Molecular Biology 219:29-51) and pAG15, and pAG21 as described in Ghosh et al (Ghosh, Yue, Lai and Duan 2008 Molecular Therapy 16:124-130). In certain embodiments, the expression cassette will provide for a muscle-specific promoter that is operably linked to the nucleic acid encoding the synthetic dystrophin. In certain embodiments, a muscle creatine kinase (MCK) promoter or variant thereof that retains muscle-specific activity is operably linked to the nucleic acid encoding the synthetic dystrophin (Wang et al.; Gene Ther. 2008 Nov; 15(22):1489-99). In certain embodiments, a muscle creatine kinase, troponin I, a skeletal alpha-actin, a desmin muscle-specific promoter or a derivative or chimera thereof is used (US20110212529, incorporated herein by reference in its entirety with respect to these promoters). Other useful muscle-specific promoters that can be used include, but are not limited to, CK5, CK6, CK7, CK8, myoglobin, CSK, Pitx3, and HAS promoters, derivatives thereof, or chimeras thereof. Other useful expression cassettes that can be used in certain vectors in conjunction with the mini and microdystrophin gene expression cassettes include, but are not limited to, expression cassetes that incorporate one or more selectable marker genes, such as a kanamycin, chlorosulfuron, phosphonothricin, hygromycin, or methotrexate resistance gene.

The term "vector" refers to a DNA or RNA sequence which is able to replicate and express a foreign gene in a host cell. Typically, vector has one or more endonuclease recognition sites which can be cut in a predictable fashion by use of the appropriate enzyme. Such vectors are can further comprise additional structural gene sequences imparting markers for identifying and separating transformed cells. Useful markers/selection agents include, but are not limited to, kanamycin, chlorosulfuron, phosphonothricin, hygromycin and methotrexate. A cell in which the foreign genetic material in a vector is functionally expressed has been "transformed" by the vector and is referred to as a "transformant." Useful vectors include, but are not limited to, a nAAV vector, by which is a single-stranded DNA molecule which derives from the genome of Adeno-associated viruses but is non-pathogenic.

The expression cassette containing a minigene or microgene operably linked to the control sequences can be ligated into a suitable vector for delivery. In certain embodiments, AAV and lentiviral vectors containing replication and control sequences compatible with the host cell are used. A suitable vector, such as a single AAV vector will typically carry viral inverted terminal repeats (ITR) at the ends, the promoters, and microgene and polyA site.

By "dual vector system" meant a vector system composed of two vectors, e.g., AAV vectors, in which system both vector carry a part of a gene or sequence to be delivered and the entire gene is reconstituted by interaction between the two vectors. In one embodiment, the two vectors of dual vector system, e.g., AAV dual vector system, of the present disclosure are trans-splicing vectors (ts vectors, e.g., tsAAV vectors). In another embodiment, the two vectors of dual vector system, e.g., AAV dual vector system, of the present disclosure are hybrid vectors (e.g., hybrid AAV vectors). Trans-splicing AAV vectors typically carry (in addition to what are presented in a single AAV vector) a splicing donor signal and a splicing acceptor signal. Hybrid AAV vector will typically carry (in addition to what are presented in a single AAV vector and in the trans-splicing vector) a homologous overlapping sequence, such as from the middle one-third of human placental alkaline phosphotase gene. A lentiviral vector will typically carry the 5' long terminal repeats (LTR), the 3' LTR and the packaging signal.

By "operably linked" is meant that a nucleic acid molecule or polypeptide is placed in a functional relationship with another nucleic acid molecule or polypeptide. For example, expression cassette (a promoter and a polyA) is operably linked to a mini/micro-dystrophin gene if the expression cassette provided for transcription and polyadenylation of the sequence.

Dual AAV vectors of the present disclosure have large, e.g., at least 10 kb, packaging capacity. Three classical dual vectors are the cis-activation, trans-splicing (ts) and overlapping vectors (reviewed in Duan, D., Z. Yan, and J. F. Engelhardt. 2006. Expanding the capacity of AAV vectors, p. pp 525-32. In M. E. Bloom, S. F. Cotmore, R. M. Linden, C. R. Parrish, and J. R. Kerr (ed.), Parvoviruses. Hodder Arnold; Distributed in the U.S.A. by Oxford University Press, London, N.Y. Ghosh, A., and D. Duan. 2007. Expending Adeno-associated Viral Vector Capacity: A Tale of Two Vectors. Biotechnology and Genetic Engineering Reviews 24: 165-177, 2007.) The ts and overlapping vectors can deliver the 6 kb minigene. In tsAAV, a large therapeutic gene is split into a donor vector and an acceptor vector. The donor vector carries the 5' part of the gene and a splicing donor signal. The acceptor vector carries a splicing acceptor signal and the 3' part of the gene. Expression is achieved by AAV inverted terminal repeat (ITR)-mediated intermolecular recombination and subsequent splicing of the recombinant genome (FIG. 4) See Duan, D., Y. Yue, and J. F. Engelhardt. 2001. Expanding AAV Packaging Capacity With Trans-splicing Or Overlapping Vectors: A Quantitative Comparison. Mol Ther 4:383-91, Sun, L., J. Li, and X. Xiao. 2000. Overcoming adeno-associated virus vector size limitation through viral DNA heterodimerization. Nat. Med. 6:599-602, and Yan, Z., Y. Zhang, D. Duan, and J. F. Engelhardt. 2000. From the Cover: Trans-splicing vectors expand the utility of adeno-associated virus for gene therapy. Proc. Natl. Acad. Sci. USA 97:6716-6721.

Figure 4:
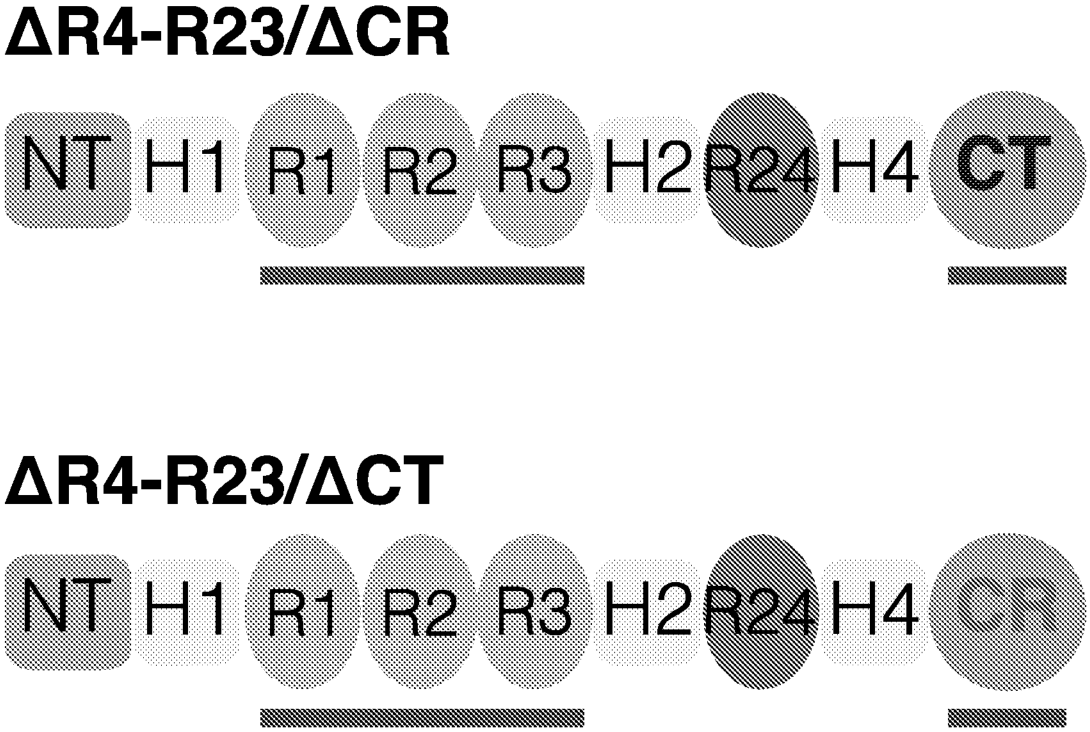
FIG. 4. The CR domain in ΔR4-R23/ΔCT is replaced with the CT domain. The membrane binding is marked by underlining.

In the overlapping vectors, a large therapeutic gene is split into an upstream vector and a downstream vector. The upstream and the downstream vectors share a region of homology (Duan, D., Y. Yue, and J. F. Engelhardt. 2001., Halbert, C. L., J. M. Allen, and A. D. Miller. 2002. Efficient mouse airway transduction following recombination between AAV vectors carrying parts of a larger gene. Nat Biotechnol 20:697-701.) Transgene reconstitution is achieved through homologous recombination (FIG. 4). By rational vector design, such as optimizing the gene splitting site, the transduction efficiency from tsAAV vectors can reach that of a single AAV vector (Lai et al 2005 Nature Biotechnique; Lai et al 2006 Human Gene Therapy). Furthermore, systemic delivery of the tsAAV vectors has been shown to efficiently transduce whole body muscle in rodents (Ghosh, Yue, Long, Bostic and Duan 2007 Molecular Therapy 16:124-130). tsAAV-mediated minigene therapy was demonstrated to reduce muscle pathology, improve muscle force and prevent contraction-induced injury in a single mdx muscle (Lai, Y., D. Li, Y. Yue, and D. Duan. 2007. Design of trans-splicing adeno-associated viral vectors for Duchenne muscular dystrophy gene therapy. Method in Molecular Medicine:In-press., Lai, Y., Y. Yue, M. Liu, and D. Duan. 2006. Synthetic intron improves transduction efficiency of transsplicing adeno-associated viral vectors. Hum Gene Ther 17:1036-42, and Lai, Y., Y. Yue, M. Liu, A. Ghosh, J. F. Engelhardt, J. S. Chamberlain, and D. Duan. 2005. Efficient in vivo gene expression by trans-splicing adeno-associated viral vectors. Nat Biotechnol 23:1435-9.)

Besides the classic dual AAV vectors, a hybrid AAV dual vector system has been developed recently (Ghosh, Yue, Lai and Duan 2008 Molecular Therapy 16:124-130). The tsAAV is highly dependent on the optimal gene splitting site. This limitation is overcome in the hybrid vector system. In hybrid AAV vectors, transgene reconstitution can be achieved either through the traditional trans-splicing pathway as described in the tsAAV vectors or through homologous recombination via a highly recombinogenic foreign DNA sequence.

Accordingly, in still another embodiment, the present disclosure is directed to a method for the treatments of DMD, BMD and/or XLDC in a subject by administering to the subject a therapeutically effective amount of the minigene and/or microgene of the present disclosure, by administering a vector carrying the minigene and/or microgene, by administering to the subject a therapeutically effective amount of a AAV vector containing the minigene and/or microgene of the present disclosure. The term "subject" refers to any mammalian (e.g., human) or avian subject.

One route of the administration accordance with the method of the present disclosure includes, but is not limited to, local or regional muscle injection or forms of delivery to improve local muscle function in patients, systemic delivery (such as intravenous, intra-artery, intraperitoneal) to all or most muscles in a region or in the whole body in patients, in vitro infection of myogenic stem cells with AAV or lentiviral vector followed by local and/or systemic delivery.

By "therapeutically effective amount" is meant an amount high enough to significantly positively modify the condition to be treated but low enough to avoid serious side effects (at reasonable benefit/risk ratio) within the scope of sound medical judgment. The therapeutically effective amount will vary with the particular condition being treated, or the condition of the subject being treated and his/her physical condition, as well as the type of preparation, vector, or composition being used.

In a particular embodiment, the present disclosure contemplates intravascular administration. For example, in AAV-9 gene therapy with micro-dystrophin gene containing R16 and R17, the dosage to newborn mice (1 week or younger in age) is about 0.5 to about 1.5.times.10e11 vg particles/gram body weight or about 50 to about 75 .mu.l/gram body weight; the dosage to young mice (1 week to 1 month in age) is about 0.5 to about 1.5.times.10e11 vg particles/gram body weight or about 75 to about 200 .mu.l/gram body weight; the dosage to adult mice (1 to 20-month-old) is about 0.5 to about 1.5.times.10e11 vg particles/gram body weight or about 200 to about 400 .mu.l/gram body weight; the dosage for newborn dog (three days or younger in age) is about 0.5 to about 2.times.10e11 vg particles/gram body weight or about 10 to about 25 .mu.l/gram body weight; the dosage for young dog (3 days to 3 months in age) is about 0.5 to about 2.times.10e11 vg particles/gram body weight or about 10 to about 25 .mu.l/gram body weight; the dosage for adult dog (3-month-old or older) is about 1 to about 3.times.10e11 vg particles/gram body weight or about 15 to about 30 .mu.l/gram body weight.

According to the present disclosure, after engineering the membrane binding motifs or membrane binding domains of the R10-R11-R12 repeat into the mini/micro dystrophin protein encoding sequence, the resultant synthetic nucleic acid molecule can be incorporated into non-viral and/or viral gene therapy vectors, and/or cell therapy for the treatment of dystrophin deficient diseases such as DMD, BMD and XLDC. The present disclosure provides a series of AAV mini/micro-dystrophin vectors that can exhibit improved membrane binding and biological activity in a dystrophin-deficient muscle. An recombinant AAV vector includes, but is not limited to, any one of the mini/micro-dystrophin genes provided herein, an expression cassette (a promoter and a polyA), and viral inverted terminal repeats (ITRs).

In yet another embodiment, the present disclosure is directed to a pharmaceutical composition containing one or more of the AAV vectors and lentiviral vectors of the present disclosure and unmodified plasmid DNA molecules and a pharmaceutically acceptable carrier.

Pharmaceutical formulations, dosages and routes of administration for nucleic acids are generally disclosed, for example, in U.S. Pat. No. 5,580,859 to Felgner et al. Both local and systemic administration are contemplated by the present disclosure. In certain embodiments where the molecules of the disclosure are employed for prophylactic purposes, agents of the disclosure are amenable to chronic use, such as by systemic administration. One or more suitable unit dosage forms comprising the therapeutic agents of the disclosure, which can optionally be formulated for sustained release, can be administered by a variety of routes including, but not limited to, oral, parenteral, including by rectal, transdermal, subcutaneous, intravenous, intramuscular, intraperitoneal, intrathoracic, intrapulmonary, and intranasal routes. The formulations can, where appropriate, be conveniently presented in discrete unit dosage forms and can be prepared. Such methods can include the step of bringing into association the synthetic dystrophin encoding nucleic acid or synthetic dystrophin with liquid carriers, solid matrices, semi-solid carriers, finely divided solid carriers or combinations thereof, and then, optionally, introducing or shaping the product into the delivery system.

In certain embodiments where a synthetic dystrophin encoding nucleic acid, synthetic dystrophins, or vectors comprising or encoding the same are prepared for oral administration, they can be combined with a pharmaceutically acceptable carrier, diluent or excipient to form a pharmaceutical formulation, or unit dosage form.

By "pharmaceutically acceptable" is meant the carrier, diluent, excipient, and/or salt is compatible with the other ingredients of the formulation, and not deleterious to the recipient thereof. The active ingredient for oral administration can be present as a powder or as granules; as a solution, a suspension or an emulsion; or in achievable base such as a synthetic resin for ingestion of the active ingredients from a chewing gum. The active ingredient can also be presented as a bolus, electuary or paste.

Pharmaceutical formulations containing the a therapeutic agent of this disclosure including, but not limited to, synthetic dystrophin encoding nucleic acids, synthetic dystrophins, vectors or viral vector particle comprising or encoding the same, can be prepared. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The therapeutic agents of the disclosure can also be formulated as elixirs or solutions for convenient oral administration or as solutions appropriate for parenteral administration, for instance by intramuscular, subcutaneous or intravenous routes.

The pharmaceutical formulations of the therapeutic agents of the disclosure can also take the form of an aqueous or anhydrous solution or dispersion, or alternatively the form of an emulsion or suspension.

Thus, the therapeutic agent of this disclosure can be formulated for parenteral administration (e.g., by injection, for example, bolus injection or continuous infusion) and can be presented in unit dose form in ampules, pre-filled syringes, small volume infusion containers or in multi-dose containers with an added preservative. The active ingredients can take such forms as suspensions, solutions, or emulsions in oily or aqueous vehicles, and can contain formulatory agents such as suspending, stabilizing and/or dispersing agents. Alternatively, the active ingredients can be in powder form, obtained by aseptic isolation of sterile solid or by lyophilization from solution, for constitution with a suitable vehicle, e.g., sterile, pyrogen-free water, before use.

The compositions according to the disclosure can also contain thickening agents such as cellulose and/or cellulose derivatives. They can also contain gums such as xanthan, guar or carbo gum or gum arabic, or alternatively polyethylene glycols, bentones and montmorillonites, and the like.

In certain embodiments, an adjuvant chosen from antioxidants, surfactants, other preservatives, film-forming, keratolytic or comedolytic agents, perfumes and colorings can be added to the composition. Also, other active ingredients can be added, whether for the conditions described or some other condition.

The local delivery of the pharmaceutical composition of the present disclosure can also be by a variety of techniques which administer the agent at or near the site of disease. Examples of site-specific or targeted local delivery techniques are not intended to be limiting but to be illustrative of the techniques available. Examples include local delivery catheters, such as an infusion or in-dwelling catheter, e.g., a needle infusion catheter, shunts and stents or other implantable devices, site specific carriers, direct injection, or direct applications.

In particular, for delivery of a vector of the disclosure to a tissue such as muscle, any physical or biological method that will introduce the vector into the muscle tissue of a host animal can be employed. Vector means both a bare recombinant vector and vector DNA packaged into viral coat proteins to form a viral vector particle. Simply dissolving an AAV vector in phosphate buffered saline (PBS) or in N-2-Hydroxyethylpiperazine-N'-2-ethanesulfonic acid (HEPES) buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). The pharmaceutical compositions can be prepared as injectable formulations or as topical formulations to be delivered to the muscles by transdermal transport. Numerous formulations for both intramuscular injection and transdermal transport have been previously developed and can be used in the practice of the disclosure. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. In certain embodiments, such aqueous solutions can be buffered and the liquid diluent first rendered isotonic with saline or glucose. Solutions of the synthetic nucleic acid or vector as a free acid (DNA contains acidic phosphate groups) or a pharmacologically acceptable salt can be prepared in water suitably mixed with a surfactant such as hydroxypropylcellulose. A dispersion of AAV viral particles can also be prepared in glycerol, liquid polyethylene glycols and mixtures thereof and in oils. Under ordinary conditions of storage and use, these preparations contain a preservative to prevent the growth of microorganisms.

In certain embodiments, the Pharmaceutical forms or compositions suitable for injectable use include, but are not limited to, sterile aqueous solutions or dispersions and sterile powders for the extemporaneous preparation of sterile injectable solutions or dispersions. In certain embodiments, the form is sterile and fluid to the extent that easy syringability exists. It is typically stable under the conditions of manufacture and storage and is preserved against the contaminating action of microorganisms such as bacteria and fungi. In certain embodiments, the carrier can be a solvent or dispersion medium containing, for example, water, ethanol, polyol (for example, glycerol, propylene glycol, liquid polyethylene glycol and the like), suitable mixtures thereof, and vegetable oils. In certain embodiments, the proper fluidity can be maintained, for example, by the use of a coating such as lecithin, by the maintenance of a given particle size in the case of a dispersion and by the use of surfactants. In certain embodiments, the prevention of the action of microorganisms can be brought about by various antibacterial and antifungal agents that include, but are not limited to, parabens, chlorobutanol, phenol, sorbic acid, thimerosal and the like. In certain embodiments, isotonic agents, for example, sugars or sodium chloride are included. Prolonged absorption of the injectable compositions can be brought about by use of agents delaying absorption, for example, aluminum monostearate and gelatin.

In certain embodiments, sterile injectable solutions are prepared by incorporating the synthetic nucleic acid or vector in the desired amount in the appropriate solvent with various of the other ingredients enumerated above, followed by filtered sterilization. In certain embodiments, dispersions are prepared by incorporating the sterilized active ingredient into a sterile vehicle which contains the basic dispersion medium and the other ingredients from those enumerated above. In the case of sterile powders for the preparation of sterile injectable solutions, the preferred methods of preparation are vacuum drying and the freeze drying technique which yield a powder of the active ingredient plus any additional ingredient from the previously sterile-filtered solution thereof.

Also provided herein are methods and resultant host cells wherein a defective endogenous dystrophin gene of the host cell or a defective portion thereof is edited to provide the synthetic nucleic acid molecule within the host cell's X-chromosome. Such methods of gene editing include, but are not limited to, those that employ a clustered regularly interspaced short palindromic repeats (CRISPR)-associated (Cas)-guide RNA or source thereof and a Cas endonuclease or source thereof, wherein the guide RNA and Cas endonuclease can form a complex that can introduce a double strand break at a target site in a nuclear genome of the host cell that provides for incorporation of the synthetic nucleic acid or portion thereof into the endogenous dystrophin locus. Methods that can be adapted for this purpose are disclosed in US Patent Application publications US20160175462, US20160115488, and US20160153004, which are each incorporated herein by reference in their entireties.

ABBREVIATIONS

DMD: Duchenne muscular dystrophy
CR: Cysteine-rich
NT: N-terminus
CT: C-terminus
R: Spectrin-like repeat
DGC: Dystrophin-associated glycoprotein complex
ECM: Extracellular matrix
H: Hinge region
MBD: Membrane binding domain
GFP: Green fluorescent protein
TA: Tibialis anterior
AAV: Adeno-associated virus To the extent to which any of the preceding abbreviations or definitions is inconsistent with abbreviations or definitions provided in any patent or non-patent reference incorporated herein by reference, any patent or non-patent reference cited herein, or in any patent or non-patent reference found elsewhere, it is understood that the preceding definition will be used herein.

Non-limiting embodiments provided herein include:

Embodiment 1. A synthetic nucleic acid molecule encoding a synthetic mini-dystrophin gene or micro-dystrophin gene encoding a synthetic, non-full length dystrophin protein comprising: (i) an N-terminal (NT) domain of the dystrophin protein or a modified N-terminal domain of the dystrophin protein; (ii) at least two membrane binding motifs (MBM) independently selected from the group consisting of an MBM of an R1-R2-R3 membrane binding domain (MBD), an MBM of a CR membrane binding domain, and an MBM of a CT membrane binding domain; (iii) an MBM of an R10-R11-R12 MBD; and (iv) an nNOS binding domain of R16-R17; wherein the domains and the MBM are arranged from N to C terminus in the order in which they occur in a wild-type dystrophin protein and are operably linked.

Embodiment 2. The synthetic nucleic acid molecule of embodiment 1, wherein the MBM of R1-R2-R3 comprises at least one S-palmitoylation site peptide selected from the group consisting of SEQ ID NO: 54, SEQ ID NO: 55, and SEQ ID NO:56.

Embodiment 3. The synthetic nucleic acid molecule of embodiment 1, wherein R3 repeat or R2-R3 repeats are absent from the non-full length dystrophin protein.

Embodiment 4. The synthetic nucleic acid molecule of embodiment 1, wherein the R1, R2, R3, R1 and R2, R2 and R3, or R1, R2, and R3 repeats are present in the non-full length dystrophin protein.

Embodiment 5. The synthetic nucleic acid molecule of embodiment 1, wherein the MBM of R10-R11-R12 comprises an S-palmitoylation site peptide of SEQ ID NO:57.

Embodiment 6. The synthetic nucleic acid molecule of embodiment 1, wherein the R10 repeat, the R11 repeat, the R12 repeat, the R10-R11 repeats, the R11-R12, or the R10 and R12 repeats are present in the non-full length dystrophin protein.

Embodiment 7. The synthetic nucleic acid molecule of embodiment 1, wherein the R17 domain is present in the non-full length dystrophin protein.

Embodiment 8. The synthetic nucleic acid molecule of embodiment 1, wherein the n-terminal alpha helix of the R16 domain (SEQ ID NO:59) or a portion thereof is absent from the non-full length dystrophin protein.

Embodiment 9. The synthetic nucleic acid molecule of embodiment 8, wherein alpha-helix 2 and alpha-helix 3 of the R16 domain is present and alpha-helix 1, alpha-helix 2, and alpha-helix 3 of the R17 domain is present in the non-full length dystrophin protein.

Embodiment 10. The synthetic nucleic acid molecule of embodiment 8, wherein alpha-helix 2 and alpha-helix 3 of the R16 domain is present and alpha-helix 1, alpha-helix 2, and alpha-helix 3 of the R17 domain is present in the non-full length dystrophin protein.

Embodiment 11. The synthetic nucleic acid molecule of embodiment 8, wherein N-terminal helix one of the R16 domain is substituted with the MBM of the R1-R2-R3 MBD or with the MBM of the R10-R11-R12 MBD.

Embodiment 12. The synthetic nucleic acid molecule of embodiment 1, wherein the R16 domain and the R17 domain are present in the non-full length dystrophin protein.

Embodiment 13. The synthetic nucleic acid molecule of embodiment 1, wherein the MBM of the CR membrane binding domain is absent, wherein the CR membrane binding domain is absent, or wherein the CR domain is absent from the non-full length dystrophin protein.

Embodiment 14. The synthetic nucleic acid molecule of embodiment 1, wherein the MBM of the CT MBD comprises residues 3422 to 3535 of SEQ ID NO: 1.

Embodiment 15. The synthetic nucleic acid molecule of embodiment 1, wherein the MBM of the CT MBD comprises residues 3501 to 3685 of SEQ ID NO:1.

Embodiment 16. The synthetic nucleic acid of embodiment 1, wherein at least one domain and at least one MBM are operably linked with a hinge region selected from the group consisting of a synthetic hinge, a semi-synthetic hinge, dystrophin H1, dystrophin H2, dystrophin H3, dystrophin H4, and variants thereof.

Embodiment 17. The synthetic nucleic acid of embodiment 1, wherein the dystrophin H1 hinge or a variant thereof operably links the C-terminus of the NT domain to the N-terminus of an MBM or domain containing an MBM, wherein the dystrophin H2 hinge or a variant thereof operably links the C-terminus of a MBM or domain containing an MBM to the N-terminus of another MBM or domain containing another MBM, wherein the dystrophin H3 hinge or a variant thereof operably links the C-terminus of an MBM or domain containing an MBM to the N-terminus of another MBM or domain containing another MBM, wherein the dystrophin H4 hinge or a variant thereof operably links the C-terminus of an MBM to the N-terminus of the CR MBM or the CR domain, or any combination thereof.

Embodiment 18. The synthetic nucleic acid of embodiment 1, wherein the dystrophin H4 hinge or a variant thereof operably links the C-terminus of an MBM to the N-terminus of the CR MBM or the CR domain.

Embodiment 19. The synthetic nucleic acid molecule of any one of embodiments 1 to 18, wherein the mini- or micro-dystrophin gene is between 5 kb to about 8 kb in length or less than 5 kb in length, respectively.

Embodiment 20. The synthetic nucleic acid molecule of any one of embodiments 1 to 18, wherein the mini- or micro-dystrophin gene is operably linked to a heterologous promoter, a heterologous 5' untranslated region (UTR), a heterologous 3' UTR, a heterologous polyadenylation site, or any combination thereof.

Embodiment 21. The synthetic nucleic acid molecule of any one of embodiments 1 to 18, wherein said molecule is integrated within an endogenous dystrophin gene locus in an X-chromosome.

Embodiment 22. A lentiviral vector comprising the synthetic nucleic acid molecule of any one of embodiments 1 to 20, wherein the nucleic acid molecule is operably linked to an expression cassette, 5' and 3' long terminal repeats (LTR), and a psi sequence in the lentiviral vector.

Embodiment 23. A single recombinant adeno-associated virus (AAV) vector comprising the nucleic acid of any one of embodiments 1 to 20, wherein said nucleic acid molecule is operably linked to an expression cassette and viral inverted terminal repeats (ITRs) in the AAV.

Embodiment 24. A dual recombinant AAV vector system, comprising two AAV vectors, wherein one of the two AAV vectors comprises a part of the nucleic acid molecule of any one of embodiments 1 to 20, and the other vector comprises the remaining part of said nucleic acid molecule, wherein the two vectors further comprise sequences that permit recombination with each other to produce said nucleic acid in full length, and wherein the nucleic acid in full length is operably linked to an expression cassette and viral ITRs.

Embodiment 25. A composition comprising the synthetic nucleic acid molecule of any one of embodiments 1 to 20 and a pharmaceutically acceptable carrier.

Embodiment 26. The composition of embodiment 25, wherein the nucleic acid molecule is operably linked to an expression cassette, 5' and 3' long terminal repeats (LTR), and a psi sequence in a lentiviral vector.

Embodiment 27. The composition of embodiment 25, wherein said nucleic acid molecule is operably linked to an expression cassette and viral inverted terminal repeats (ITRs) in an AAV Embodiment 28. The composition of embodiment 25 comprising the dual recombinant AAV vector system of embodiment 24.

Embodiment 29. An isolated host cell comprising the synthetic nucleic acid molecule of any one of embodiments 1 to 21.

Embodiment 30. The host cell of embodiment 29, wherein said nucleic acid molecule is integrated within an endogenous dystrophin gene locus in a chromosome of the host cell.

Embodiment 31. The host cell of embodiment 29, wherein the nucleic acid molecule is operably linked to an expression cassette, 5' and 3' long terminal repeats (LTR), and a psi element in a lentiviral vector.

Embodiment 32. The host cell of embodiment 29, wherein said nucleic acid molecule is operably linked to an expression cassette and ITRs in an AAV.

Embodiment 33. The host cell of embodiment 29, wherein the host cell is a myogenic stem cell.

Embodiment 34. A method for the treating or ameliorating one or more adverse effects of Duchenne muscular dystrophy (DMD), Becker muscular dystrophy (BMD) or X-linked dilated cardiomyopathy (XLDC) in a subject in need thereof comprising the step of administering to the subject a therapeutically effective amount of: (i) the synthetic nucleic acid molecule of any one of embodiments 1 to 21; (ii) the lentiviral vector of embodiment 22; (iii) the AAV vector of embodiment 23; (iv) the composition of any one of embodiments 25 to 28; or (iv) the host cell of any one of embodiments 29 to 33 to a subject in need thereof.

Embodiment 35. The method of embodiment 34, wherein the administration is by injection into muscle, systemic delivery, or local delivery.

Embodiment 36. The method of embodiment 34, wherein the host cell is a stem cell or myogenic stem cell.

Embodiment 37. The method of embodiment 34 or 36, wherein the host cell is derived from an autologous cell of the subject.

Embodiment 38. The method of any one of embodiments 34, 35, 36, or 37, wherein a defective endogenous dystrophin gene of the host cell or a defective portion thereof is edited to provide the synthetic nucleic acid molecule within the host cell's X-chromosome.

Embodiment 39. Use of (i) the synthetic nucleic acid molecule of any one of embodiments 1 to 21; (ii) the lentiviral vector of embodiment 22; (iii) the AAV vector of embodiment 23; (iv) the composition of any one of embodiments 25 to 28; or (iv) the host cell of any one of embodiments 29 to 33 for making a composition for administration to a subject suffering from Duchenne muscular dystrophy (DMD), Becker muscular dystrophy (BMD) or X-linked dilated cardiomyopathy (XLDC).

Embodiment 40. Use of (i) the synthetic nucleic acid molecule of any one of embodiments 1 to 21; (ii) the lentiviral vector of embodiment 22; (iii) the AAV vector of embodiment 23; (iv) the composition of any one of embodiments 25 to 28; or (iv) the host cell of any one of embodiments 29 to 33 for treating a subject suffering from Duchenne muscular dystrophy (DMD), Becker muscular dystrophy (BMD) or X-linked dilated cardiomyopathy (XLDC), or for ameliorating one or more adverse effects of DMD, BMD, or XLDC.

Embodiment 41. A synthetic nucleic acid molecule encoding a synthetic mini-dystrophin gene or micro-dystrophin gene encoding a synthetic, non-full length dystrophin protein comprising: (i) an N-terminal (NT) domain of the dystrophin protein or a modified N-terminal domain of the dystrophin protein; (ii) at least two membrane binding motifs (MBM) independently selected from the group consisting of an MBM of an R1-R2-R3 membrane binding domain (MBD), an MBM of a CR membrane binding domain, and an MBM of a CT membrane binding domain; (iii) an MBM of an R10-R11-R12 MBD; and (iv) an nNOS binding domain of R16-R17 or an nNOS binding domain of R16-R17 that is operably linked to a syntrophin PDZ domain; wherein the dystrophin domains and the MBM are arranged from N to C terminus in the order in which they occur in a wild-type dystrophin protein and are operably linked.

Embodiment 42. A synthetic nucleic acid molecule comprising a sequence encoding a fusion protein comprising a nNOS binding domain of dystrophin R16-R17 that is operably linked to a syntrophin PDZ domain.

Embodiment 43. A single recombinant adeno-associated virus (AAV) vector comprising the nucleic acid molecule of embodiment 41 or 42, wherein said nucleic acid molecule is operably linked to an expression cassette and viral inverted terminal repeats (ITRs) in the AAV.

Embodiment 44. A dual recombinant AAV vector system, comprising two AAV vectors, wherein one of the two AAV vectors comprises a part of the nucleic acid molecule of embodiment 41 or 42, and the other vector comprises the remaining part of said nucleic acid molecule, wherein the two vectors further comprise sequences that permit recombination with each other to produce said nucleic acid in full length, and wherein the nucleic acid in full length is operably linked to an expression cassette and viral ITRs.

Embodiment 45. A lentiviral vector comprising the synthetic nucleic acid molecule of embodiment 41 or 42, wherein the nucleic acid molecule is operably linked to an expression cassette, 5' and 3' long terminal repeats (LTR), and a psi sequence in the lentiviral vector.

Embodiment 46. A fusion protein comprising dystrophin nNOS binding domain of R16-R17 that is operably linked to a syntrophin PDZ domain.

Embodiment 47. A composition comprising (i) the synthetic nucleic acid molecule of embodiment 41 or 42, the vector of embodiment 43, 44, or 45, or the protein of embodiment 46; and (ii) a pharmaceutically acceptable carrier.

Embodiment 48. An isolated host cell comprising the synthetic nucleic acid molecule of embodiment 41 or 42, or the vector of embodiment 43, 44, or 45.

Embodiment 49. A method for the treating or ameliorating one or more adverse effects of Duchenne muscular dystrophy (DMD), age-related muscle atrophy, cancer cachexia, or other neuromuscular disorders characterized by loss of sarcolemmal neuronal nitric oxide synthase (nNOS) activity in a subject in need thereof comprising the step of administering to the subject a therapeutically effective amount of: (i) the synthetic nucleic acid molecule of any one of embodiments 41 or 42; (ii) the lentiviral vector of embodiment 45; (iii) the AAV vector of embodiment 43 or 44; (iv) the composition of embodiment 47; or (iv) the host cell of embodiment 48 to a subject in need thereof.

Embodiment 50. The method of embodiment 49, wherein the administration is by injection into muscle, systemic delivery, or local delivery.

EXAMPLES

The following examples are included to demonstrate various embodiments. It will be appreciated by those of skill in the art that the techniques disclosed in the following examples represent techniques discovered by the Applicants to function well. However, those of skill in the art should, in light of the instant disclosure, appreciate that many changes can be made in the specific embodiments that are disclosed, while still obtaining like or similar results, without departing from the scope of the disclosure.

Example 1

Identification of Dystrophin R1-3, R10-12 and CT as New Dystrophin MBDs

Figure 5:
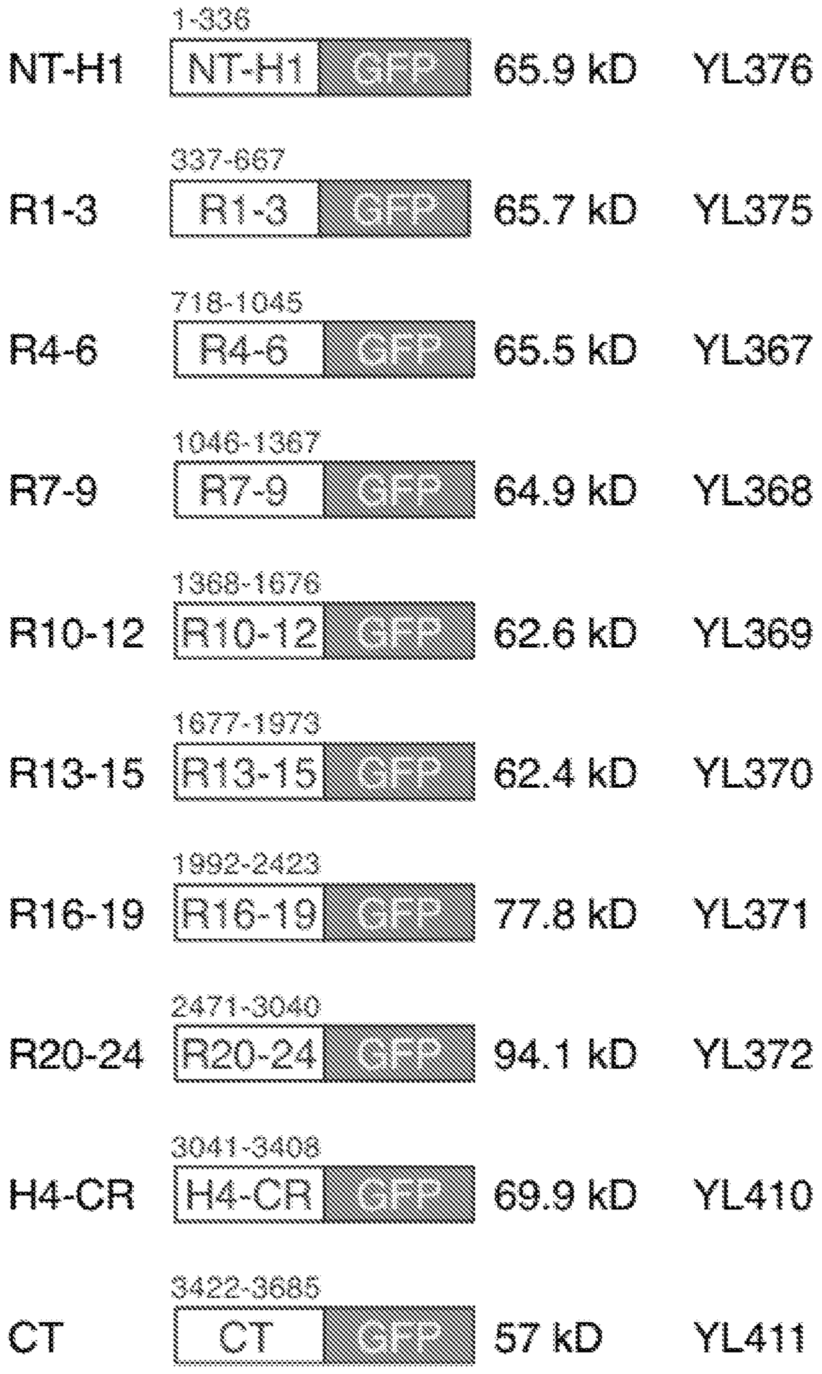
FIG. 5. Cartoon illustration of ten GFP-fused dystrophin subdomains used in the study. The full-length human dystrophin molecule is split into ten subdomains. The numerical number range above each cartoon illustration refers to amino acid sequence numbering in the full-length human dystrophin protein. The predicted molecular weight of each fusion protein is marked. The YL numbers refer to the construct name in the Duan/Lai laboratory.

To thoroughly understand how dystrophin interacts with the sarcolemma, we performed a comprehensive screening in mouse muscle. According to the fact that dystrophin has four functional domains and its mid-rod domain can be further divided into sub-regions (14), we split the full-length human dystrophin protein into ten subdomains, including NT-H1, R1-3, R4-6, R7-9, R10-12, R13-15, R16-19, R20-24, H4-CR and CT. We fused each subdomain with a green fluorescent protein (GFP) tag and individually expressed them in the tibialis anterior (TA) muscle of dystrophin-null mdx mice by adeno-associated virus (AAV)-mediated gene transfer (FIG. 5).

Figure 6:
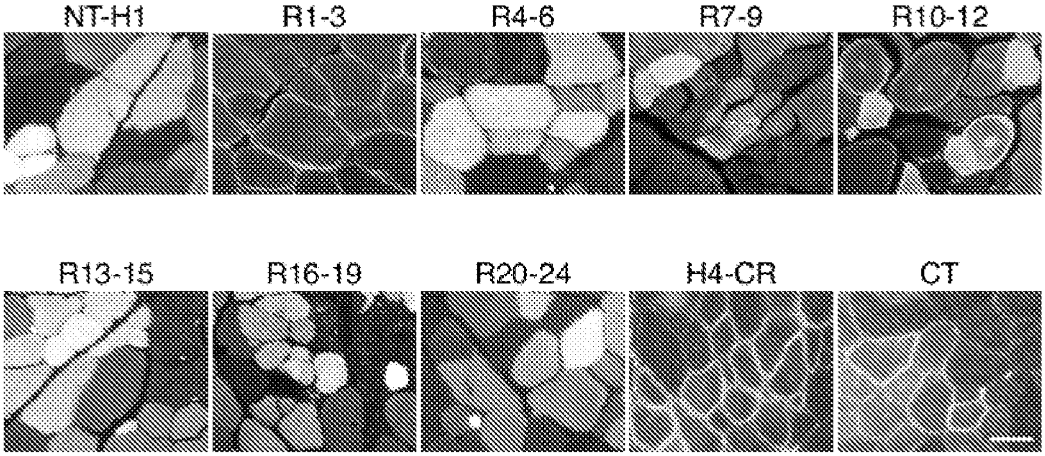
FIG. 6. Dystrophin R1-3, R10-12, CR and CT are independent membrane-binding domains. Full-length human dystrophin was split into ten subdomains and each subdomain fused with a GFP tag. The fusion proteins were individually expressed in mdx muscle by AAV gene transfer. Representative GFP photomicrographs of each indicated dystrophin subdomain are shown. Dystrophin R1-3, H4-CR and CT were exclusively localized at the sarcolemma. R10-12 was found at the sarcolemma and in the cytosol. NT-H1, R4-6, R7-9, R13-15, R16-19 and R20-24 were exclusively localized in the cytosol. Scale bar: 50 μm.

To determine subcellular localizations of each dystrophin subdomain, we visualized the GFP signal under a fluorescence microscope (FIG. 6). In line with the literature, we observed sarcolemmal localization of the H4-CR subdomain. Unexpectedly, we found that subdomains R1-3 and CT were exclusively restricted at the muscle cell membrane. Subdomains NT-H1, R4-6, R7-9, R13-15, R16-19, and R20-24 were only detected in the cytosol. Interestingly, the R10-12 subdomain was found both at the sarcolemma and in the cytoplasm (FIG. 6).

Figure 7:
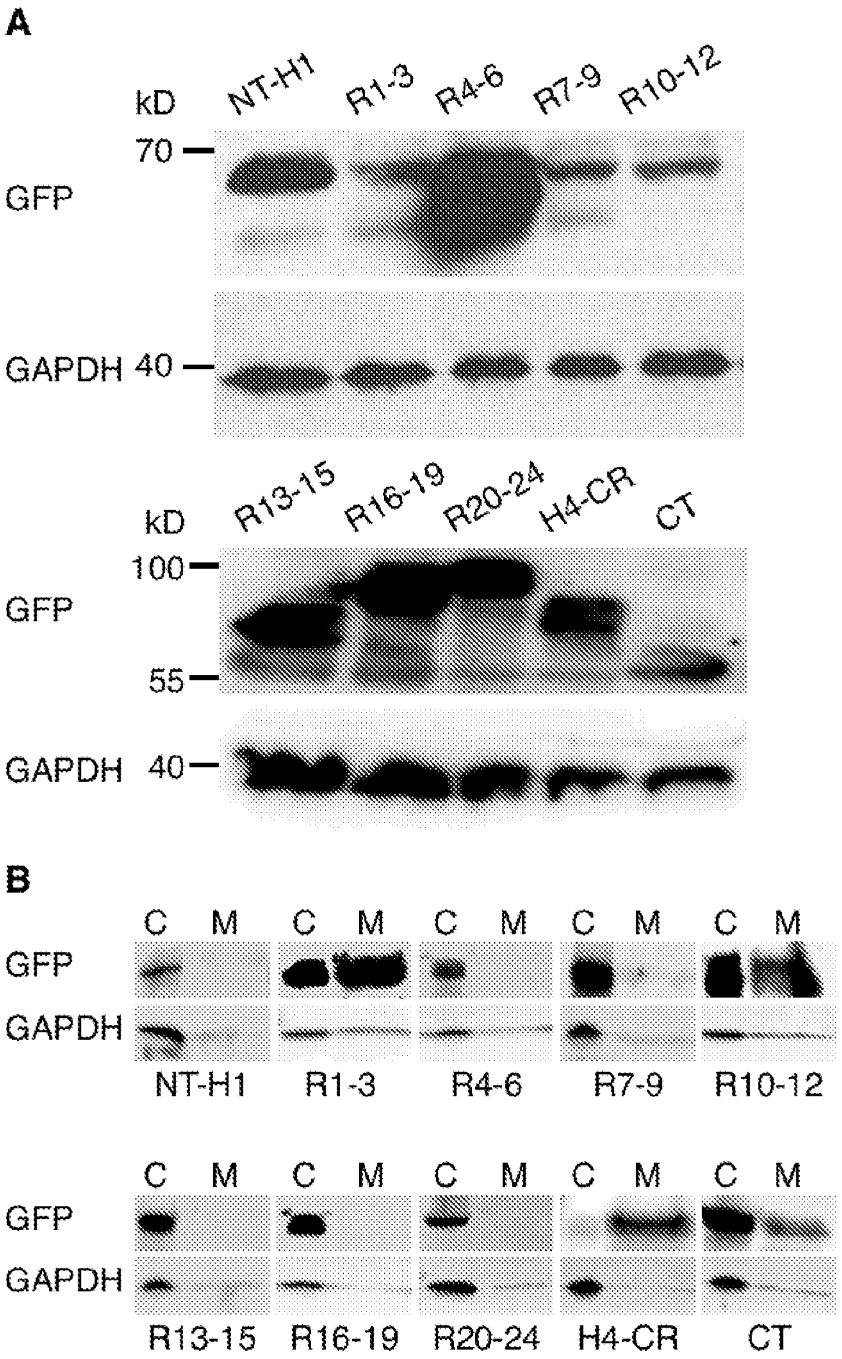
FIG. 7. Microsomal western blot suggests the association of R1-3, R10-12, CR and CT with the sarcolemma. A. Whole muscle lysate western blots revealing AAV-mediated expression of GFP-fused dystrophin subdomains in mdx muscle. B. Detection of dystrophin R1-3, R10-12, CR and CT in the membrane fraction by microsomal western blots. GAPDH marks the cytosolic fraction. C, cytosolic fraction; M, membrane fraction.

To confirm these intriguing observations, we performed immunoblot with whole muscle lysates and microsomal preparations (FIG. 7). In whole muscle lysates, we found efficient expression of all ten dystrophin subdomains (FIG. 7A). However, only subdomains R1-3, R10-12, CR and CT were detected in membrane-enriched microsomal preparations (FIG. 7B). These data are in agreement with immunostaining results suggesting that these subdomains are indeed dystrophin MBDs.

Figure 8:
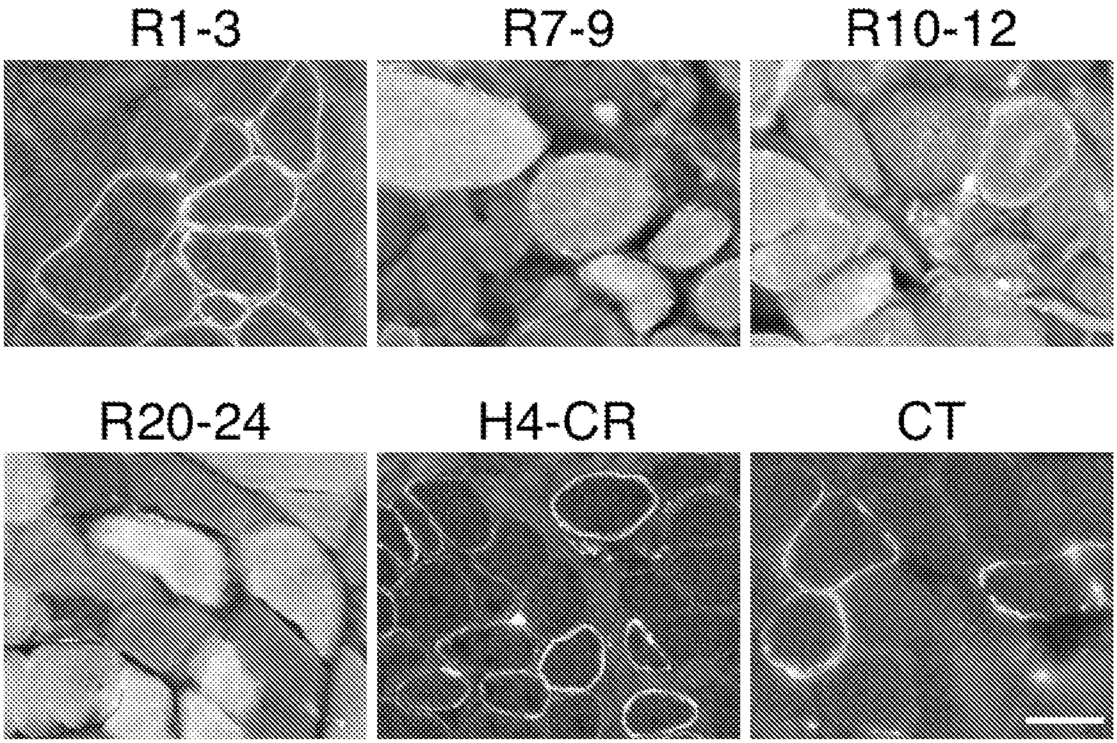
FIG. 8. Dystrophin R1-3, R10-12, CR and CT bind to the sarcolemma in canine muscle. Indicated GFP fusion dystrophin subdomains were expressed in dystrophic dog muscle by AAV gene transfer. Representative GFP photomicrographs show the membrane binding of R1-3, R10-12, CR and CT and cytosolic localization of R7-9 and R20-24. R10-12 is also seen in the cytosol. Scale bar: 50 μm.

Preservation of the membrane-binding property of R1-3, R10-12, CR and CT in canine muscle. To examine whether the membrane-binding property of R1-3, R10-12, CR and CT is conserved in different species, next we delivered the corresponding AAV vectors to dystrophic dog muscle by local injection. As controls, we also injected R7-9 and R20-24 AAV vectors. Two months later, we examined GFP expression under a fluorescence microscope. Similar to what we saw in mdx muscle, R1-3, CR and CT subdomains were exclusively localized at the muscle membrane, while the R10-12 subdomain was found both at the sarcolemma and in the cytoplasm. Subdomains R7-9 and R20-24, which localized exclusively in the cytosol in mdx muscle, were only detected in the cytosol of dystrophic dog muscle (FIG. 8)

Figure 9:
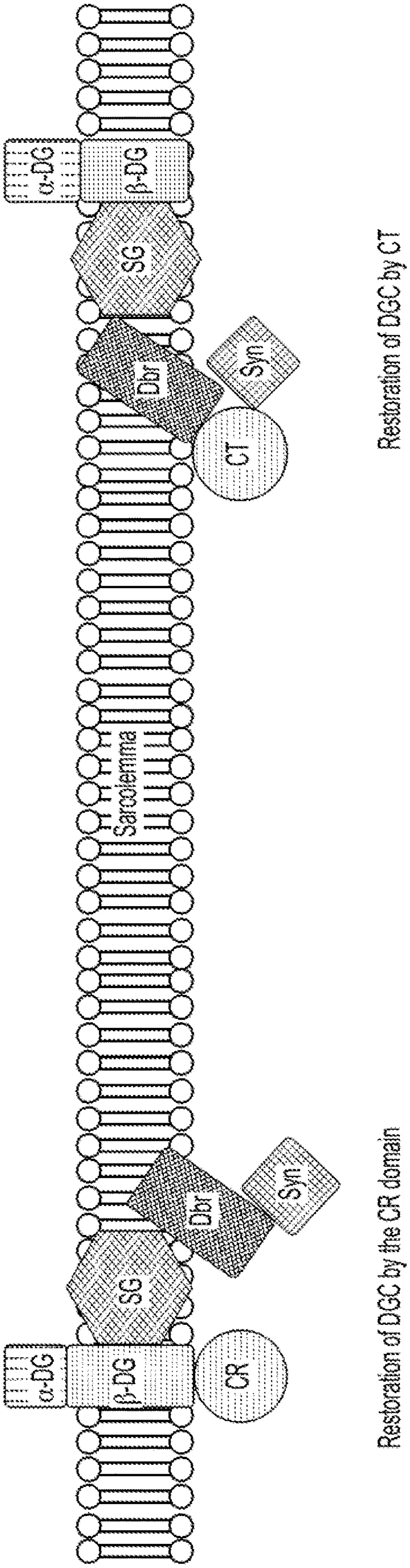
FIG. 9. The hypothetical mechanism of CT-mediated DGC restoration. Left side cartoon illustrates the CR domain mediated DGC restoration. Right side cartoon illustrates the hypothetical mechanism of CT-mediated DGC restoration. Specifically, direct membrane binding of the CT domain restores syntrophin and dystrobrevin to the sarcolemma (24, 25). Membrane-localized syntrophin and dystrobrevin then recruit sarcoglycans and dystroglycan to the sarcolemma (26-29). DG, dystroglycan; SG, sarcoglycans; Dbr, dystrobrevin; Syn, syntrophin.
Figure 10:
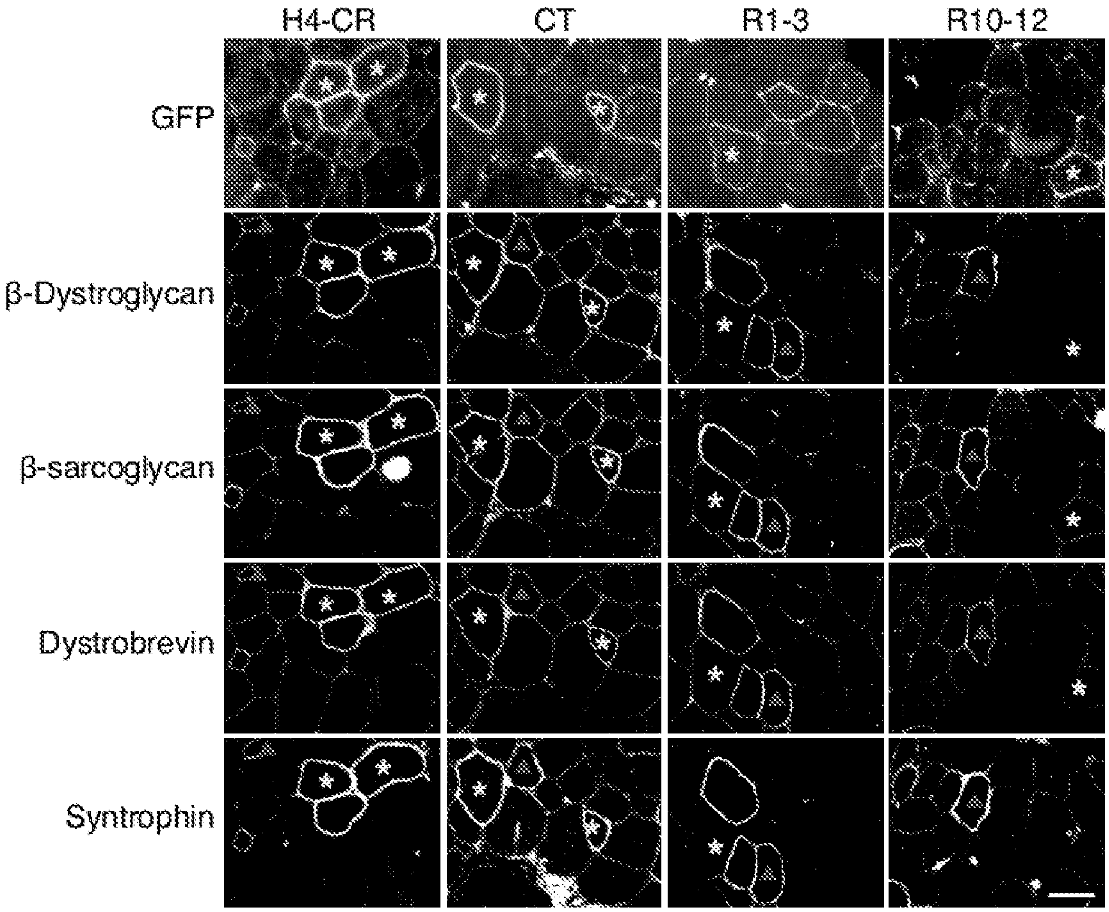
FIG. 10. Dystrophin CT restores the DGC at the sarcolemma. Representative serial section photomicrographs of GFP and immunostaining for β-dystroglycan, β-sarcoglycan, dystrobrevin and syntrophin in mdx muscle expressing the indicated GFP-dystrophin subdomain fusion proteins. Asterisk, the GFP-positive myofiber in serial sections; triangle, the GFP-negative revertant fiber in serial sections. GFP signals co-localize with DGC components in myofibers transduced by the H4-CR and CT but not R1-3 and R10-12 subdomain AAV vectors. Scale bar: 50 μm.

Independent restoration of the DGC by the CR domain and CT. In the canonical model (FIGS. 1 and 9), the CR domain is solely responsible for nucleating dystroglycan, sarcoglycans, dystrobrevin and syntrophin into the DGC at the sarcolemma (15-18). To determine whether the newly identified MBDs had similar functions, we evaluated DGC components on serial muscle sections by immunostaining (FIG. 10). As expected, the H4-CR subdomain successfully restored β-dystroglycan, β-sarcoglycan, dystrobrevin and syntrophin to the sarcolemma. Myofibers that were transduced with the CT subdomain AAV vector also resulted in sarcolemmal localization of these DGC components. In muscles infected with R1-3 and R10-12 AAV vectors, DGC components were detected in GFP-negative revertant fibers but not in transduced GFP-positive myofibers (FIG. 10).

Figure 3:
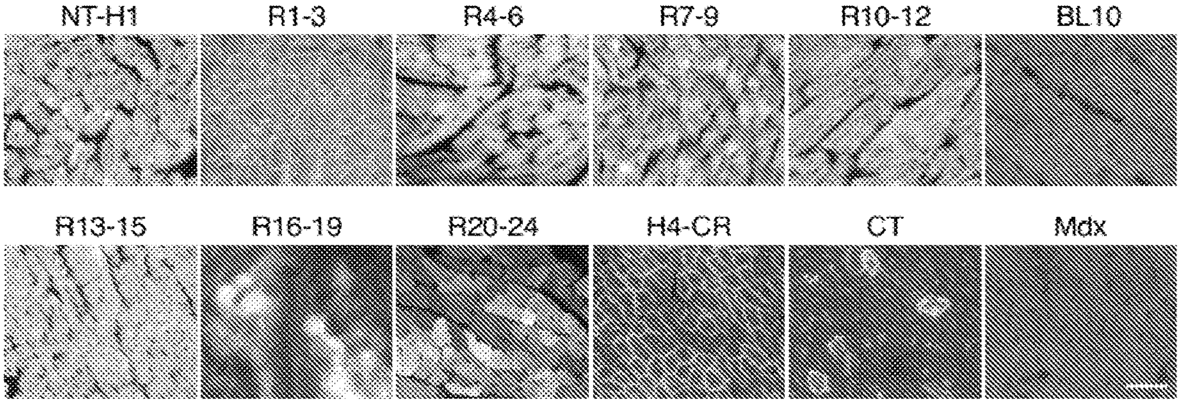
FIG. 3. Dystrophin R1-3, CR and CT bind to the sarcolemma in the heart. Indicated GFP fusion dystrophin subdomains were delivered to the mdx heart by systemic AAV injection. Uninjected BL10 and mdx hearts were used as negative controls. Subdomain H4-CR and CT showed membrane localization. Subdomain R1-3 was found in the intercalated disk and cytosol. Remaining subdomains were only seen in the cytosol. Scale bar: 50 μm.

Conservation of the membrane-binding property of R1-3, CR and CT in cardiac muscle. To determine whether our findings in skeletal muscle can be extended to cardiac muscle, we delivered GFP-fusion subdomain AAV vectors via the tail vein (FIG. 3). Compared with un-injected BL10 and mdx controls, systemic AAV injection resulted in robust GFP signals in the myocardium. Several different patterns were observed. The H4-CR subdomain was restricted at the sarcolemma while subdomains NT-H1, R4-6, R10-12, R13-15, R16-19 showed exclusive cytosolic expression. The R1-3 subdomain was found in the cytosol and the intercalated disk. In the mice infected with the CT-GFP AAV vector, we only detected a few GFP positive cardiomyocytes. Interestingly, GFP signals in these cells were found predominantly at the sarcolemma (FIG. 3).

DISCUSSION

Figure 11A:
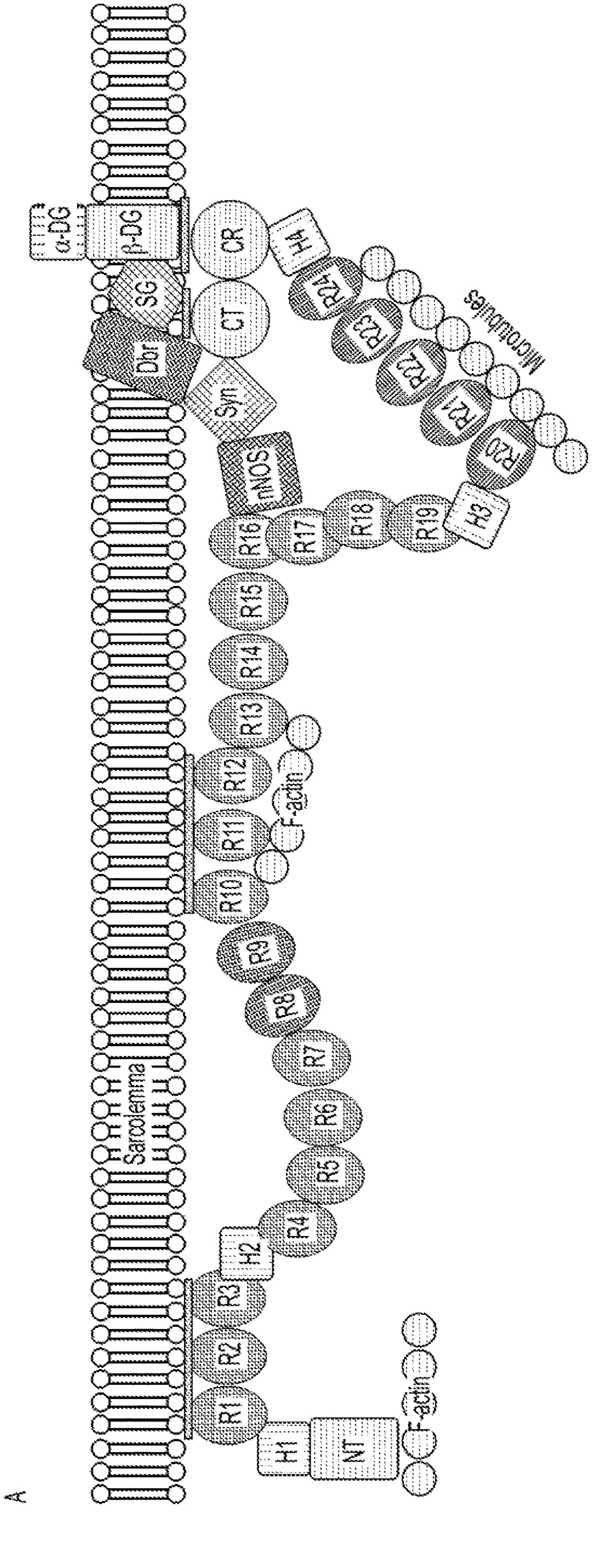
FIG. 11. A new model of dystrophin-sarcolemma interaction. A. In muscle, dystrophin binds to the sarcolemma through four independent membrane-binding subdomains; B. In the heart, dystrophin binds to the sarcolemma through three independent membrane-binding domains. These subdomains are marked by thick red lines.
Figure 11B:
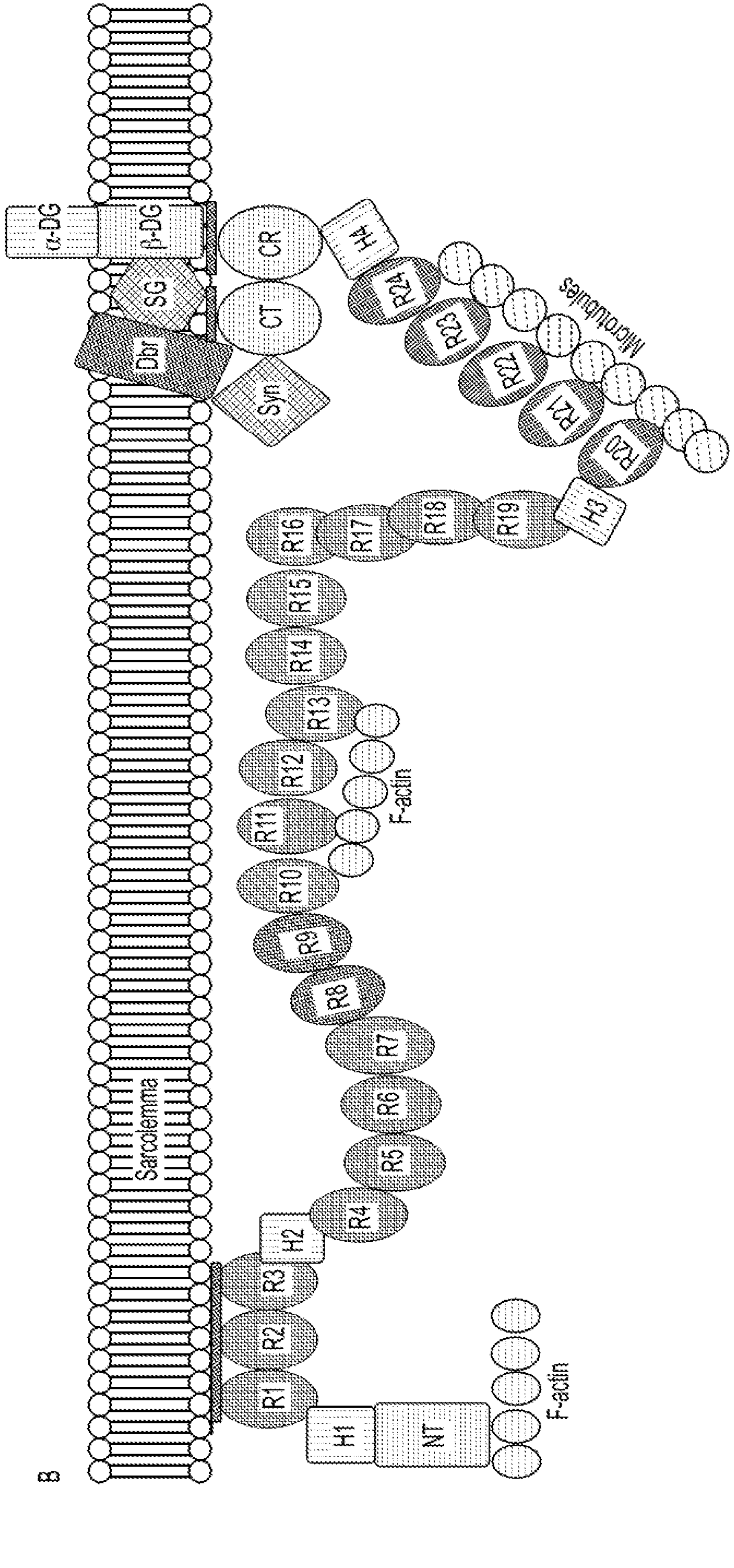

In this study, we performed the first comprehensive in vivo evaluation of the subcellular localizations of dystrophin subdomains. We demonstrated that in addition to the CR domain, dystrophin contains several highly conserved MBDs that can independently interact with the sarcolemma. These newly identified MBDs are R1-3, R10-12 and CT (FIG. 11). The CT subdomain bound to the sarcolemma in both skeletal muscle and cardiac muscle. Further it restored the DGC. Subdomain R1-3 showed exclusive membrane binding in skeletal muscle (FIG. 11A) but a preference for the intercalated disk in the heart (FIG. 11B). Subdomain R10-12 only demonstrated partial membrane localization in skeletal muscle (FIG. 11A).

Figure 2:
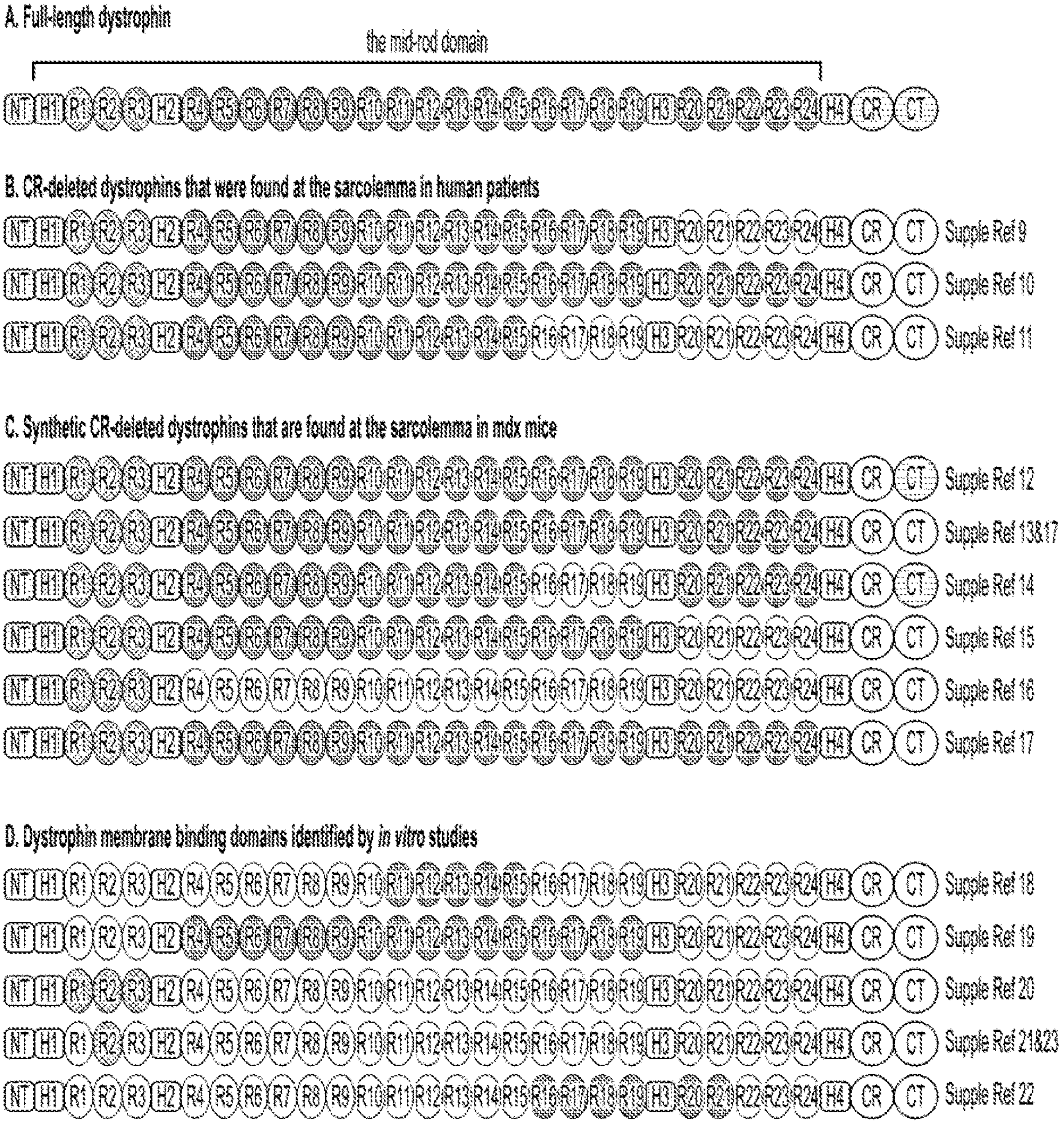
FIG. 2. Evidence of dystrophin sarcolemmal binding in the absence of the CR domain. A, Cartoon illustration of the structure of full-length dystrophin. B, Cartoon illustration of CR-deleted dystrophins that were found at the sarcolemma in patients (9-11). C, Cartoon illustration of synthetic CR-deleted dystrophin fragments that showed sarcolemmal localization in mdx mice (12-17). D, Cartoon illustration dystrophin membrane binding domains identified by in vitro interaction assays (18-23). Related references are marked next to the cartoon illustrations and the full citation is available in Supplementary References provided herein. Filled shapes: domains present; open shapes: domains absent.

Interaction with the sarcolemma is central to how dystrophin protects muscle. A wealth of molecular, biochemical and structural studies has provided unequivocal proof that the CR domain anchors dystrophin to the sarcolemma via the formation of the DGC (7-9). Hence it has been quite puzzling why dystrophins that lack the CR domain still appear to bind to the sarcolemma in some atypical patients (11-13). Studies performed in mdx mice suggest that these puzzling patient observations can well be true. Of notice, forced expression of fragmented dystrophins that lack the CR domain has been repeatedly detected at the sarcolemma in mdx mice (FIG. 2C) (19-24). Collectively, it is reasonable to hypothesize that dystrophin can carry additional membrane localization domain(s).

To better understand dystrophin-sarcolemma interaction, investigators have turned to the artificial in vitro systems. These studies identified a number of potential regions capable of membrane binding such as R2, R1-3, R4-19, R11-15, R16-21 (FIG. 2D) (14, 25-30). Essentially, 21 out of 24 spectrin-like repeats in the rod domain were found to carry the membrane binding property in these in vitro studies. Such a broad range makes it almost impossible to pinpoint the identity of true dystrophin MBDs. Considering the fact that in vivo performance of dystrophin spectrin-like repeats cannot be accurately predicted by in vitro analysis (31), it becomes even more challenging to characterize the CR domain-independent dystrophin-sarcolemma interaction in test tubes. Here we took a systematic and unbiased approach with an emphasis on the in vivo interaction in rodents and large mammals. We found four structurally defined regions in dystrophin that are capable of interacting with the sarcolemma. These include the well-studied CR domain and three new MBDs (two in the rod domain and one in CT). While R1-3 and R10-12 have been implicated in some in vitro studies, direct binding of CT to the sarcolemma has never been reported. Intriguingly, CT also restores the DGC (FIG. 10). It is intriguing that we observed striking differences in the membrane binding behavior of the newly identified rod domain MBDs. Specifically, R1-3 is not restricted to the sarcolemma in the heart and R10-12 has no membrane binding activity in the heart (FIG. 3). This is reminiscent of different nNOS-binding properties of dystrophin in the muscle and the heart (32, 33). Collectively, these data suggest that dystrophin can have different functional roles in the muscle and the heart.

The mechanism(s) by which these newly identified MBDs bind to the sarcolemma await future investigations. It is possible that electrostatic and/or hydrophobic interactions can play a role. However, considering what is known about other spectrin family proteins, we suspect that such interactions can likely involve specified membrane domains (such as lipid rafts) and palmitoylation (34).

Restoration of the DGC by CT is another unexpected finding in this study. We speculate that CT can utilize its syntrophin/dystrobrevin binding motifs to recruit syntrophin and dystrobrevin first. Subsequently, these two proteins scaffold sarcoglycans and dystroglycan to the complex (FIG. 9) (35-38).

Another area that requires further analysis is the kinetic mode of interaction between different MBDs and the sarcolemma. A recent study in the zebrafish suggests that dystrophin can associate with the sarcolemma either via stable tight interaction or via reversible dynamic shuttling between the sarcolemma and the cytosol (39). While additional studies are needed, the results of our microsomal preparation western blot seem to hint that the CR domain is responsible for stable membrane binding (GFP signals were barely detected in the cytosolic fraction) and three newly discovered MBDs can contribute to dynamic membrane binding (abundant GFP signals also presented in the cytosol) (FIG. 7B).

There are a few limitations in our study. First, we have not included hinges 2 and 3 in our constructs. Due to the structural properties of hinges (proline-rich, neither α-helix nor β-sheet), we suspect that these hinge regions can play a nominal role in membrane binding. Nevertheless, future studies are needed to confirm this. Second, we have used an over-expression system in our studies and also the fragmented dystrophin domains are not in their natural protein environment. It remains to be determined whether the membrane binding properties of the newly discovered MBDs are preserved under physiological concentration of dystrophin in wild type animals.

Taken together, we have discovered a new model for dystrophin membrane binding (FIG. 11). Our results offer insights into dystrophin function, DMD pathogenesis and gene therapy.

MATERIALS AND METHODS

Animals. All animal experiments were approved by the Animal Care and Use Committee of the University of Missouri, and the animal use and handling were strictly in accordance with the National Institutes of Health guidelines. Dystrophin-null mdx mice were purchased from The Jackson Laboratory (Bar Harbor, Me.). Dystrophin-deficient dogs were generated in house by artificial insemination.

AAV production and delivery. The GFP gene was fused in-frame to the C-terminal ends of the human dystrophin subdomains (FIG. 5). The fusion constructs were cloned into the cis AAV packaging constructs by PCR and confirmed by sequencing. Expression was driven by the cytomegalovirus promoter and the SV40 poly-adenylation signal. Y731F AAV-9 vectors were generated by transient transfection and purified through two rounds of CsC1 gradient ultracentrifugation (40, 41). The viral titer was determined by quantitative PCR.

AAV vectors were delivered by intramuscular injection to limb muscles to adult mdx mice ($4\text{-}7\times10^{11}$ vg particles/muscle) and adult dystrophic dogs ($0.8\text{-}4\times10^{14}$ vg particles/muscle). In dog studies, we applied 5-week transient immune suppression with cyclosporine and mycophenolate mofetil according to our published protocol (42).

Muscle harvesting, microscopic examination and western blot. Eight weeks after injection, animals were euthanized and muscles were harvested according to Liadaki et al through serial sucrose gradient to preserve the GFP signal (43). GFP was visualized directly under the fluorescein isothiocyanate channel using a fluorescence microscope.

Immunostianing was performed as we published before (31, 44). Whole muscle lysates were generated as we published before (31, 44). The cytosolic and microsomal preparations were obtained with the Plasma Membrane Protein Extraction kit (ab65400, Abcam). Muscle lysates were resolved in a 6% sodium dodecyl sulfate polyacrylamide gel and transferred to a polyvinylidene difluoride membrane. Antibodies used in immunostaining and western blot are listed in Table S1.

TABLE 1

Antibodies used in the study.

| Antigen | Host | Catalog # | Company | Dilution | Experiment |
|---|---|---|---|---|---|
| β-Dystroglycan | Mouse | NCL-B-DG | Novocastra | 1:50 | IF |
| Syntrophin | Mouse | ab11425 | Abcam | 1:200 | IF |
| β-Sarcoglycan | Mouse | NCL-B-SARC | Novocastra | 1:50 | IF |
| Dystrobrevin | Mouse | 610766 | BD Bioscience | 1:200 | IF |
| GFP | Mouse | 33-2600 | Invitrogen | 1:100 | WB |
| GAPDH | Mouse | MAB374 | Millipore | 1:5,000 | WB |

IF: Immunofluorescence staining; WB: western blot.

Example 2

Molecular Mechanisms for Membrane Binding of R1-3, R10-12 and the CT Domain

The data in Example 1 showed unequivocal evidence that R1-3, R10-12 and CT localize to the sarcolemma on their own. Two mechanisms can result in membrane localization: (A) direct binding to the membrane lipid bilayer via S-palmitoylation and (B) through interaction with other transmembrane proteins (e.g. the binding of the dystrophin CR-domain to β-dystroglycan). S-palmitoylation-mediated mechanism has been shown for other spectrin super-family proteins such as β-spectrin (Das, A. K. et al., *J. Biol. Chem.* 272, 11021-11025 (1997); Mariani et al., *J. Biol. Chem.* 268, 12996-13001 (1993)). Specifically, S-palmitoylation involves the addition of palmitate (a 16-carbon saturated fatty acid) to the cysteine residues of the target proteins through a reversible thioester linkage during the process of posttranslational modification (Linder, M. E. et al., *Nat. Rev. Mol. Cell. Biol.* 8, 74-84 (2007)). Insertion of palmitate to the lipid bilayer brings the target proteins to the plasma membrane.

Figure 14:
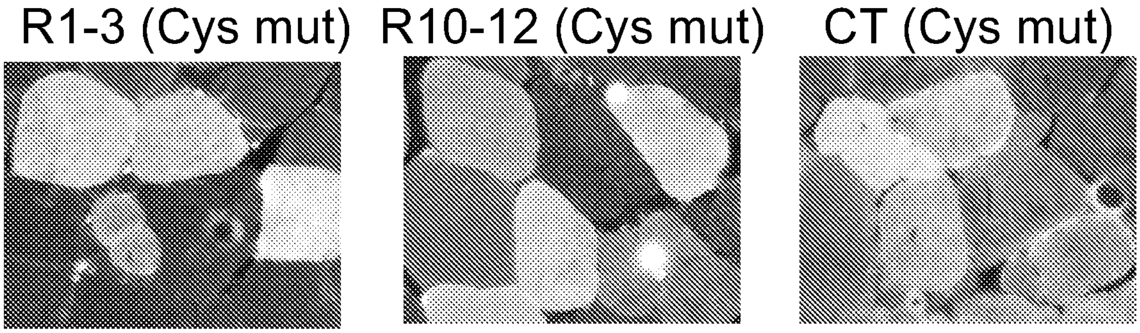
FIG. 14. Shows that cysteine mutations (C to S mutation) disrupt membrane binding of R1-3, R10-12 and CT. In R10-12, cysteine mutations also causes protein aggregates. Images shown as the GFP signal. Cys mut: cysteine mutant.

To distinguish these two potential mechanisms (direct binding via S-palmitoylation and indirect membrane binding via other membrane proteins), we examined the cysteine residues in new MBDs, and found that cysteine residues are very conserved in dystrophin R1-3, R10-12 and CT between human and mouse dystrophin (FIG. 12), indicating that cysteine residues can have an important role in the dystrophin function. In silico screening of palmitoylated sites with the CSS-Palm 2.0 program, a software for prediction of palmitoylated sites (Oku, S. et al., *J. Biol. Chem.* (2013); Ren, J. et al., *Protein Eng Des Sel* 21, 639-644 (2008)), successfully identified some palmitoylated sites in R1-3 and R10-12 (FIG. 13). Then we carried out a pilot study in which we mutated all cysteine residues in R1-3, R10-12 and the CT domain to serine (FIG. 14). Cysteine-to-serine mutation has been used by others to abolish S-palmitoylation (Topinka, J. R., et al., *Neuron* 20, 125-134 (1998); Yanai, A. et al. *Nat. Neurosci.* 9, 824-831 (2006)). We hypothesized that if S-palmitoylation mediated mechanism is responsible for sarcolemma anchoring of R1-3, R10-12 and the CT domain, cysteine-to-serine mutation should abolish S-palmitoylation and result in cytosolic location of R1-3, R10-12 and the CT domain. We made AAV vectors to express cysteine-to-serine mutated R1-3, R10-12 and the CT domain GFP fusion proteins. Following intramuscular injection to the muscle of mdx mice, we only detected cytosolic GFP signal (FIG. 14). This is in sharp contrast to what we see in FIG. 6. These results strongly suggest that S-palmitoylation is likely the predominant molecular mechanism for membrane localization of R1-3, R10-12 and the CT domain.

There are a total of four cysteine residues in R1-3, two in R10-12, and one in the CT domain. There are located in R1 (C433), R2 (C544), R3 (C569 and C650), R11 (C1505), R12 (C1569) and CT (C3476) (FIG. 12). In our preliminary study (FIG. 14), we found that mutation of all cysteine residues in each fragment abolished sarcolemmal binding.

Example 3

Figure 15:
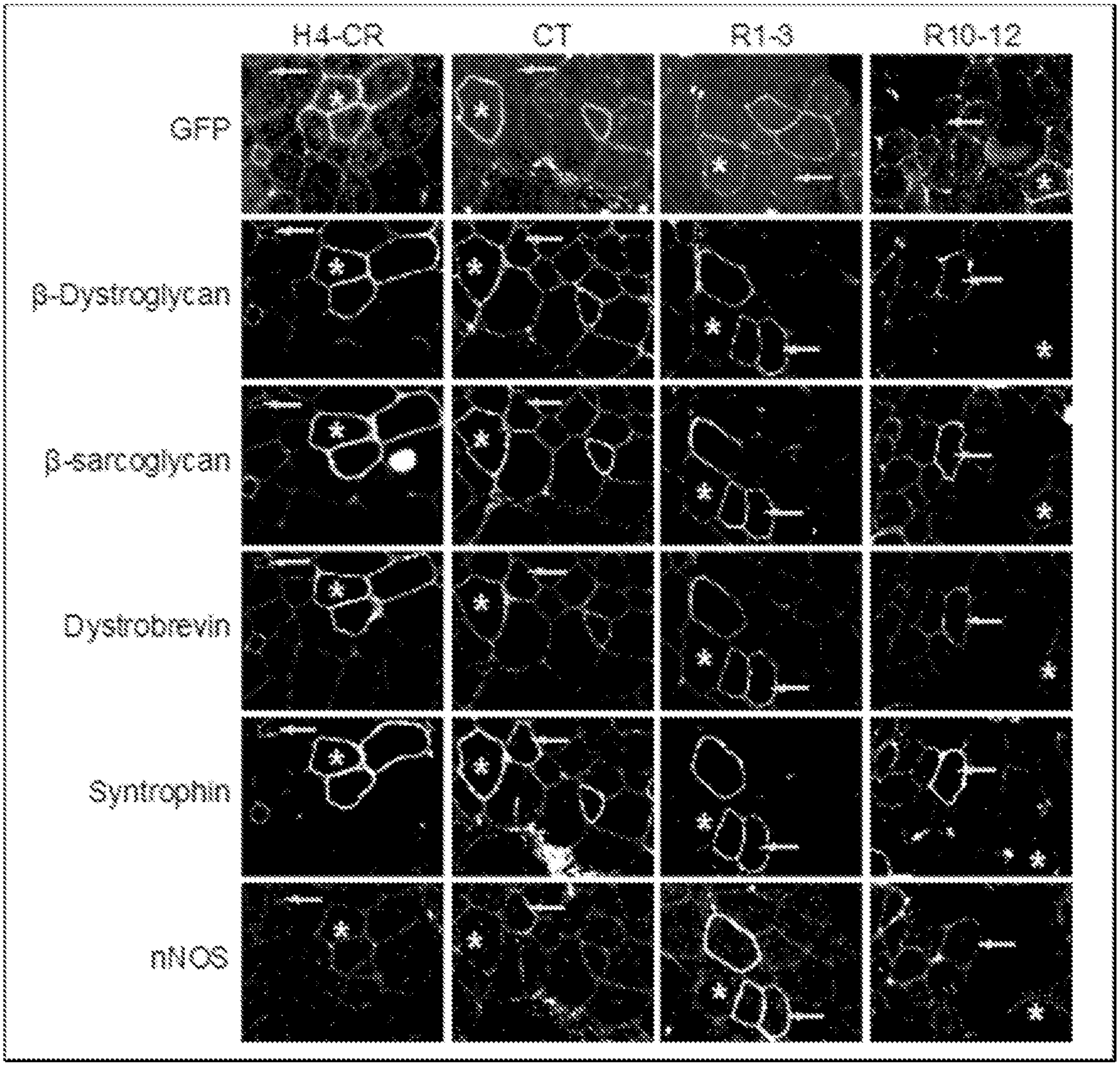
FIG. 15. Both CR and CT domain are associated with the DGC components. The DGC staining was performed in the sections expressed with H4-CR.GFP, CT.GFP, R1-3.GFP and R10-12.GFP. Both CR and CT domain are associated with the DGC at the muscle membrane, while R1-3 and R10-12 are not co-localized with the DGC at the sarcolemma. White asterisk: the GFP-positive fiber; arrow: the revertant fiber.

Further Identification of Protein Binding Partners, Membrane Binding Motifs (MBM), Membrane Binding Repeats, and Membrane Binding Sub-Domains As the first step to identify protein partners of our newly discovered MBDs, we performed immunofluorescence staining using antibodies against several DGC components. These included β-dystroglycan, β-sarcoglycan, dystrobrevin, syntrophin and nNOS. We also included H4-CR.GFP as a control. We have previously shown that nNOS-binding requires R16/17,(Lai, Y. et al., *J. Clin. Invest.* 119, 624-635 (2009)) or an nNOS binding domain of R16/17 (Lai, Y., et al., *Proc. Natl. Acad. Sci. USA* 110, 525-530 (2013). As a consequence, none of the MBDs was able to restore sarcolemmal nNOS expression. Previous studies suggest that the interaction of the CR domain with β-dystroglycan is sufficient for restoration of the DGC components (Crawford, G. E. et al., *J. Cell Biol.* 150, 1399-1410 (2000); Yue, Y. et al., *Mol Ther* 14, 79-87 (2006)). As expected, H4-CR restored all DGC components. We also found that R1-3 and R10-12 did not interact with the DGC components. The CT domain by itself is associated with all the DGC components at the muscle membrane (FIG. 15).

Figure 16:
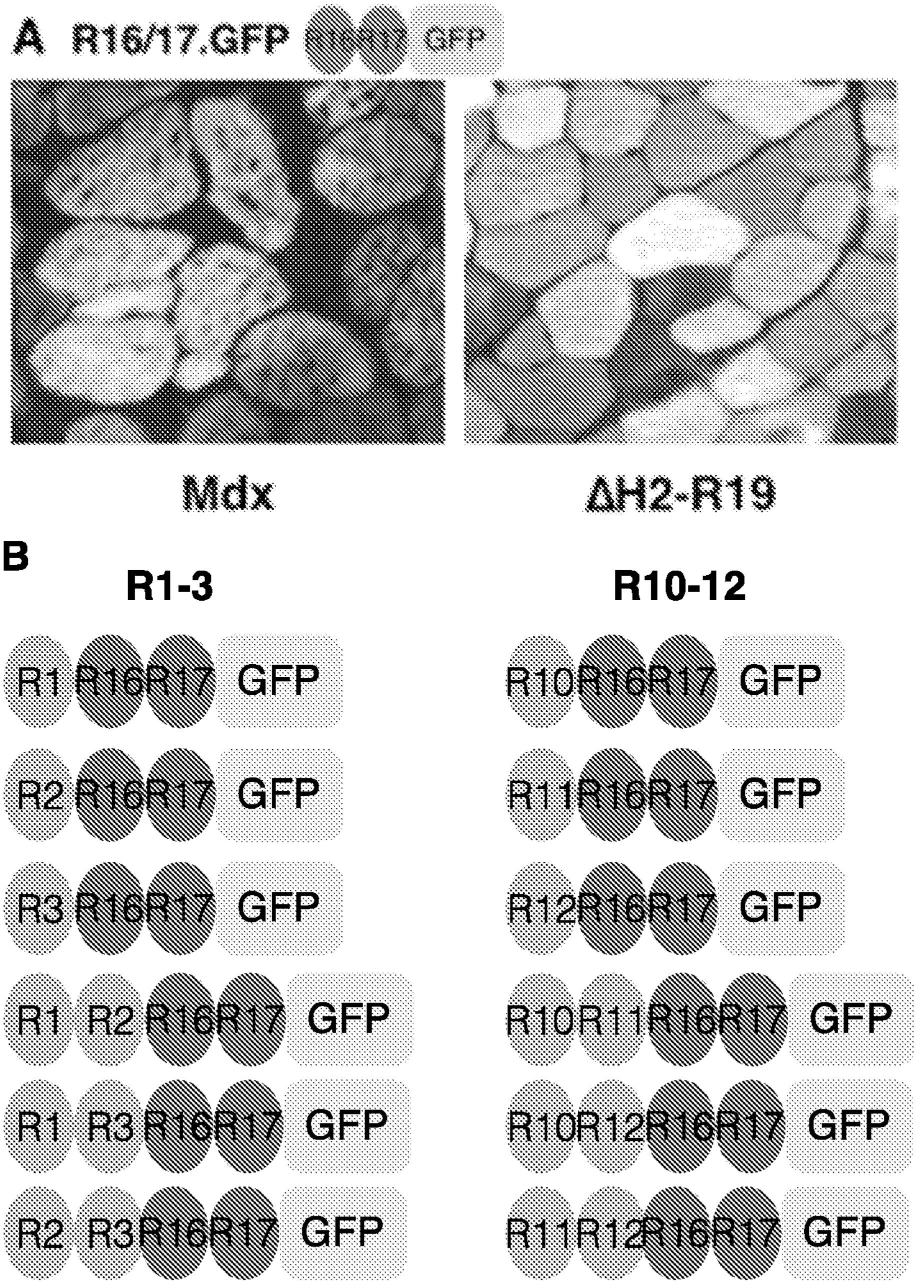
FIG. 16. The constructs for detecting whether individual repeats from R1-3 and R10-12 maintain the membrane-binding ability. A. Cytosolic distribution of R16/17.GFP in the muscle of mdx and ΔH2-R19 mini-dystrophin transgenic mice. B. The construct design for the example.

A typical feature of dystrophin membrane binding is that dystrophin MBDs are confined to two regions. Two MBDs R1-3 and R10-12 are located at the mid-rod domain, while the other two MBDs CR and CT are at the C-terminal part of dystrophin (FIG. 16). Through our preliminary data, both C-terminal MBDs (cMBDs), CR and CT, are associated with the DGC, while both rod MBDs (rMBDs), R1-3 and R10-12, are not co-localized with the components of the DGC (FIG. 17), suggesting that rMBDs and cMBDs have different functional roles. Dystrophin stabilizes and strengthens the sarcolemma by two different mechanisms: the axis from the ECM to intracellular cytoskeleton, and the membrane association from newly identified MBDs. Membrane binding of the CR domain establishes the axis from the ECM to intracellular cytoskeleton, and, in certain contexts and embodiments, the CR domain is involved in dystrophin function (Rafael, J. A. et al., *J. Cell Biol.* 134, 93-102 (1996)). In vitro studies have indicated that membrane binding of rMBDs is also important for membrane stability (Sarkis, J. et al., *FASEB* 1 27, 359-367 (2013); Sarkis, J. et al., *J. Biol. Chem.* (2011)). Both rMBDs are in close proximity to the muscle membrane and actin cytoskeleton. R1-3, is near the N-terminus of dystrophin, which interacts with F-actin, while R10-12 overlaps with the actin-binding domain R11-15 (FIG. 3). Simultaneous binding of R11-15 to phospholipid monolayer and F-actin considerably contributes to the stiffness and stability of the lipid monolayer (Sarkis, J. et al., *FASEB J.* 27, 359-367 (2013); Sarkis, J. et al., *J. Biol. Chem.* (2011)). So it is highly likely that the functional role of R1-3 and R10-12 is to tether actin cytoskeleton to the muscle membrane, and thereby strengthen the muscle membrane.

We will generate micro- and mini-dystrophin AAV vectors. Membrane binding of the rMBDs in truncated dystrophins will be disrupted either by cysteine mutations or by incorporating cytosolic rod domains of dystrophin. We will deliver AAV vectors to the tibialis anterior (TA) muscle of Cmah/mdx mice, examine membrane integrity by Evans blue dye uptake, and evaluate TA contractile properties and muscle histopathology. Also we will compare the function of two rMBDs: R1-3 and R101-2, in the context of truncated dystrophins to determine whether two rMBDs have equivalent function.

Figure 18:
FIG. 18. The constructs with partial deletion of the CT domain for detecting the membrane-binding motif in CT. The CT domain tested here is from amino acid 3422 to 3685. The Roman numerals indicate the partial CT domains with different boundaries. The boundary of the constructs is labeled by the number of amino acid. These partial CT domains will be fused to GFP and expressed by AAV gene transfer.

We will use two well-characterized micro-and mini-dystrophin genes as the backbones. The ΔR4-R23/ΔCT microgene and The ΔH2-R19 mini-gene have been shown to improve muscle function and correct dystrophic pathology in the dystrophic animal models (Harper, S. Q. et al., *Nat. Med.* 8, 253-261 (2002); Liu, M. et al., *Mol Ther* 11, 245-256 (2005); Lai, Y. et al., *Nat. Biotechnol.* 23, 1435-1439 (2005)). Both truncated dystrophins contain one rMBD, R1-3, and one cMBD, the CR domain. The ΔH2-R19 mini-dystrophin also carries another cMBD: the CT domain (FIG. 18). We will make three forms of constructs for the microgene including (1) original R1-3, (2) cysteine-mutated R1-3 and (3) replacement of R1-3 by R4-6. We will also make a similar set of constructs for the ΔH2-R19 minigene. Cysteine mutation or replacement with R4-6 will abolish the membrane binding of the rMBD, R1-3. Therefore, in the resulting truncated dystrophins, only the function of the axis from the ECM to cytoskeleton is maintained, and membrane binding from the rod domain is eliminated (FIG. 18). Experimental mice and gene delivery. We will use Cmah/mdx double knock out mice, which have a more severe phenotype and shorter life span than mdx mice (Chandrasekharan, K. et al., *Sci Transl Med* 2, 42ra54 (2010)). Microgenes will be delivered to the TA muscle of Cmah/mdx mice by the single AAV vectors, while mini-dystrophins will be delivered by over-lapping AAV vectors as reported before (Odom, G. L. et al., *Mol Ther* 19, 36-45 (2011)). Function of truncated dystrophins and their cysteine mutants will be determined and compared. We will investigate membrane integrity by Evans blue dye uptake, measure muscle force generation and the resistance to eccentric contraction, and examine muscle histopathology, including central nucleation, myofiber size, cross section area, fibrosis and inflammation infiltration, as our published protocols (Lai, Y. et al., *J. Clin. Invest.* 119, 624-635 (2009); Lai, Y. et al., *Nat. Biotechnol.* 23, 1435-1439 (2005); Lai, Y. et al., *Hum. Mol. Genet.* 23, 3189-3199 (2014)). The experiments outlined above will determine whether membrane binding of R1-3 is important for dystrophin function. To investigate the functional role of another rMBD, R10-12, we will compare it to R1-3 in the context of truncated dystrophins.

Both rMBDs R1-3 and R10-12 have lipid-binding properties, and are in close proximity to the actin-binding domains. However, there are some different aspects between R1-3 and R10-12. First, the rMBD R1-3 is located at the beginning of the rod domain, while the rMBD R10-12 is in the middle of the rod domain. Second, R1-3 is exclusively located at the muscle membrane, while R10-12 is found at both the muscle membrane and cytosol (FIGS. 8 and 10). Third, all therapeutically effective truncated dystrophins only carry a partial or complete R1-3 but not R10-12. It remains unclear whether the difference between R1-3 and R10-12 represents different functional roles.

Figure 19:
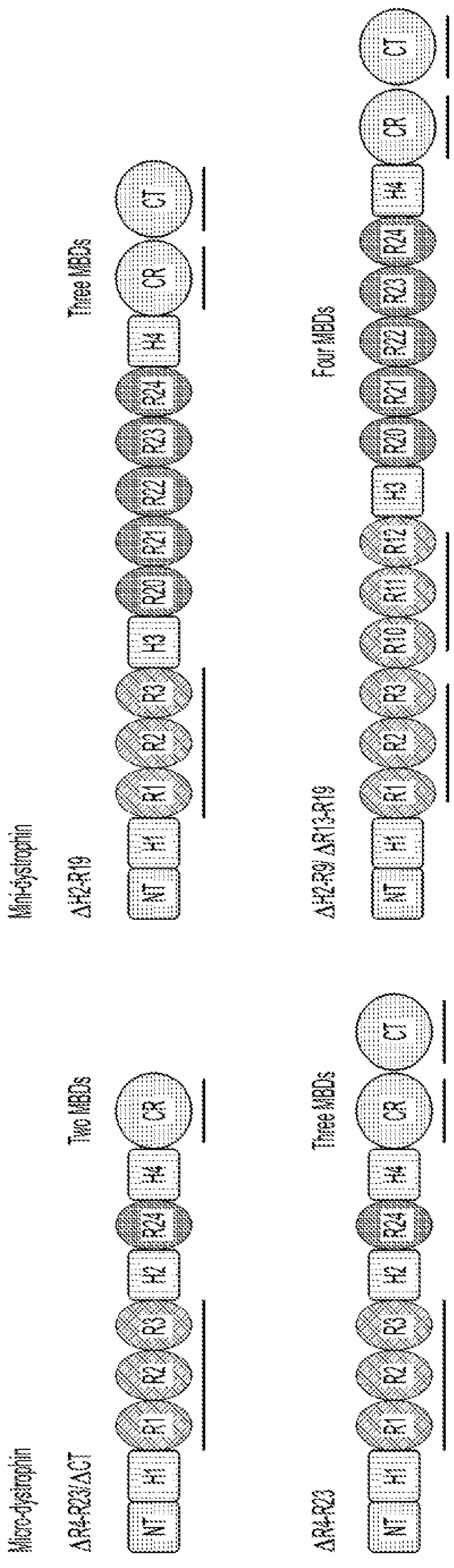
FIG. 19. The new micro- and mini-dystrophins. The original ΔR4-R23/ΔCT only contains two MBDs. We will generate ΔR4-R23 micro-dystrophin with three MBDs. The mini-dystrophin ΔH2-R19 contains three MBDs. We will add R10-12 to ΔH2-R19 minigene to make ΔH2-R9/ΔR13-R19 new minigene with four MBDs. The MBDs are marked by underlining.

We choose ΔH2-R23/ΔCT+H3 and ΔH2-R19 micro-and mini-gene as the backbones (FIG. 19). ΔH2-R23/ΔCT+H3 is an enhanced version of ΔR4-R23/ΔCT, in which H2 was replaced with H3 (Banks, G. B. et al., *PLoS Genet.* 6, e1000958 (2010)). R1-3 in ΔH2-R23/ΔCT+H3 will be replaced with R10-12 to generate ΔR1-R9/ΔR13-R23/ΔCT+H3. In ΔH2-R19, we will replace R1-3 with R10-12 to generate ΔR1-R9/ΔR13-R19 mini-dystrophin. To have a fair comparison, the other components of truncated dystrophins are the same (FIG. 19).

We will use AAV gene transfer to express ΔH2-R23/ΔCT+H3, ΔR1-R9/ΔR13-R23/ΔCT+H3, ΔH2-R19 and ΔR1-R9/ΔR13-R19 in the TA muscles of Cmah/mdx mice. The ability of the truncated dystrophins to generate muscle force, maintain membrane integrity and improve histopathology of the dystrophic muscle will be measured as outlined above. These studies will tell us whether R1-3 and R10-12 have equivalent function in micro-and mini-dystrophins.

Dystrophin CR domain not only anchor to β-dystroglycan to form the axis from the ECM to intracellular cytoskeleton, but can assemble the components of DGC at the muscle membrane. Dystrophin deficiency disassembles the DGC components at the muscle membrane. Hence, restoration of the DGC components to the sarcolemma is one criterion for therapeutic outcome of truncated dystrophins.

The non-muscle dystrophin isoform Dp116 contains both cMBDs (CR and CT domain), but is deficient of both rMBDs and actin-binding domains. So Dp116 is unable to interact with F-actin. Due to the presence of both cMBDs, it can restore the DGC. Obviously, Dp116 maintains the DGC function, and loses the mechanical function to connect the ECM and cytoskeleton. In the transgenic mice expressing Dp116, dystrophic histopathology and mechanical function of the muscle were not improved. But restoration of the DGC by Dp116 is found to be crucial for growth and maintenance of muscle mass when Dp116 is expressed in the muscle of dystrophin/utrophin double knockout mice (u-dko) (Judge, L. M. et al., *J. Cell Sci.* 119, 1537-1546 (2006); Judge, L. M. et al., *Hum. Mol. Genet.* 20, 4978-4990 (2011)). These studies suggest that the mechanical function of the CR domain to connect the ECM with cytoskeleton is important for preventing dystrophic pathology, while restoration of the DGC by the CR domain is critical for muscle mass.

Figure 17:
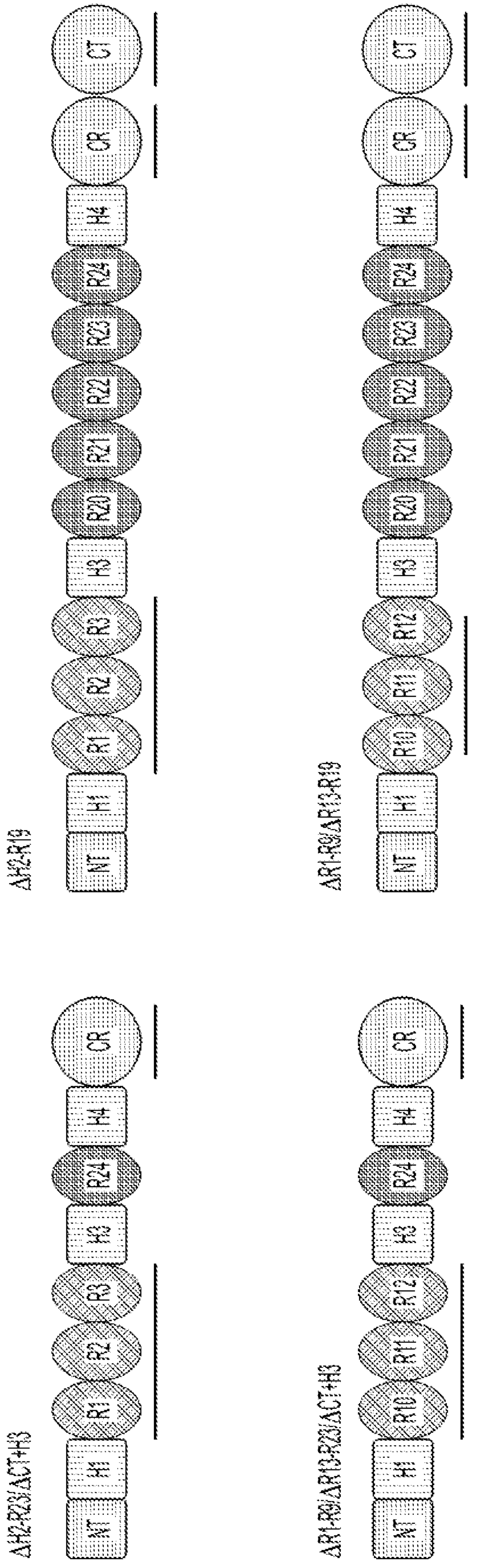
FIG. 17. Comparison of the functional roles of R1-3 and R10-12. R1-3 is replaced with R10-12 in micro-and mini-dystrophin. The membrane binding is marked by underlining.

Truncated dystrophins without the CR domain cannot prevent dystrophic pathology, despite the presence of the other three MBDs, suggesting that the CT domain cannot compensate for mechanical function of the CR domain. Through our preliminary data, we found that either CR or CT domain alone can restore the DGC components at the muscle membrane (FIG. 17). We will determine if the CT domain can compensate for the CR domain in terms of the function in muscle mass.

Figure 20:
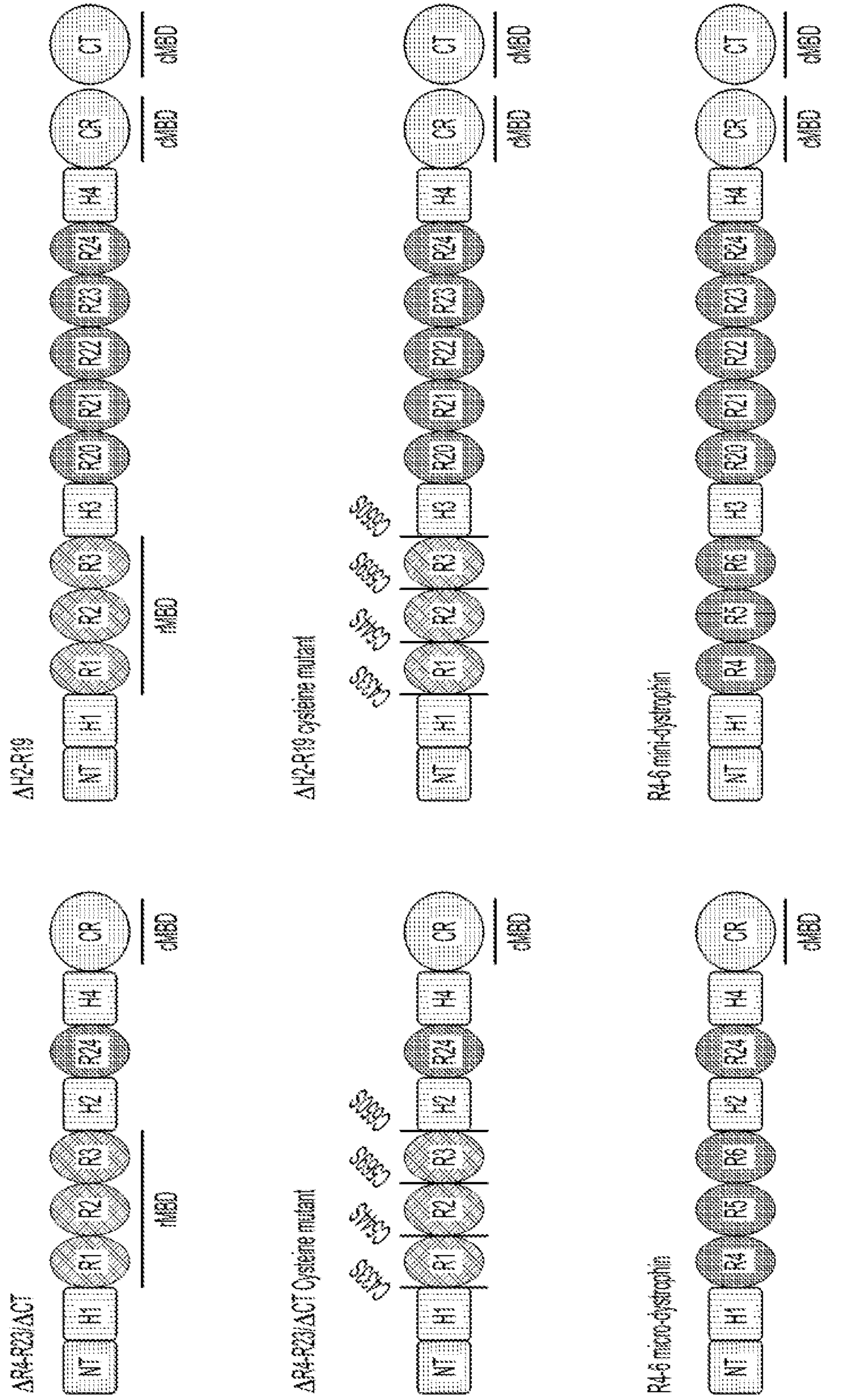
FIG. 20. Membrane binding of the rMBD, R1-3 was disrupted by cysteine mutations, or by replacement with R4-6 in micro-and mini-dystrophin. The membrane binding is marked by red underline.

We will examine the function of the CT domain in the context of micro-dystrophins. We will use ΔR4-R23/ΔCT microgene as the backbone, and replace the CR domain with the CT domain (FIG. 20).

Experimental mice and gene delivery. We will deliver AAV.ΔR4-R23/ΔCR and AAV.ΔR4-R23/ΔCT microgenes to utrophin/dystrophin double knock-out (u-dko) mice. Since u-dko mice have a short life span, we will perform systemic delivery of AAV viruses to neonatal u-dko mice.

Outcome measurement. Two months following virus injection, the body weight of u-dko mice and muscle mass of TA and Gastro muscles will be recorded. The DGC components will be evaluated by immunostaining and western blot. Contractile properties of TA muscle will be measured.

Both cMBDs, the CR and CT domain, are located at the C-terminal end of dystrophin and can restore the DGC. In certain contexts and embodiments, CR domain is involved in dystrophin function. However, the functional significance of the CT domain is contradictory. Although CT deletion has negligible consequences in transgenic mdx mice (Rafael, J. A. et al., *J. Cell Biol.* 134, 93-102 (1996)), in human patients, partial or complete CT deletion can cause severe DMD phenotype (Suminaga, R. et al., *Pediatr Res* 56, 739-743 (2004); Prior, T. W. et al., *Am. J. Hum. Genet.* 57, 22-33 (1995)), indicating that CT can have important functional roles in human. In this aim, we will address a specific functional role of the CT domain in muscle mass, which will gain more insight into the function of the CT domain.

Despite the identification of R1-3, R10-12 and CT as the new MBDs of dystrophin, it is unclear whether these domains are the smallest region required for membrane binding. In spectrin, lipid-binding motif and ankyrin-binding domain have been mapped to repeats 14 and 15 of β-spectrin (Ipsaro, J. J. et al., *Blood* 113, 5385-5393 (2009); Ipsaro, J. J. et al., *Blood* 115, 4093-4101 (2010); Bok, E. et al., *Cell Biol Int* 31, 1482-1494 (2007)). These results tremendously promote the efforts to solve the structure of repeats 14 and 15 of β-spectrin, which provides the structural and molecular perspective for the interactions of β-spectrin repeats 14 and 15 with lipids and ankyrin (Ipsaro, J. J. et al., *Blood* 113, 5385-5393 (2009); Ipsaro, J. J et al., *Blood* 115, 4093-4101 (2010)). We expect that mapping membrane-binding motifs in dystrophin R1-3, R10-12 and CT should be helpful for the future studies to reveal the structure of dystrophin MBDs, and facilitate our understanding of molecular basis of dystrophin membrane binding.

Figure 21:
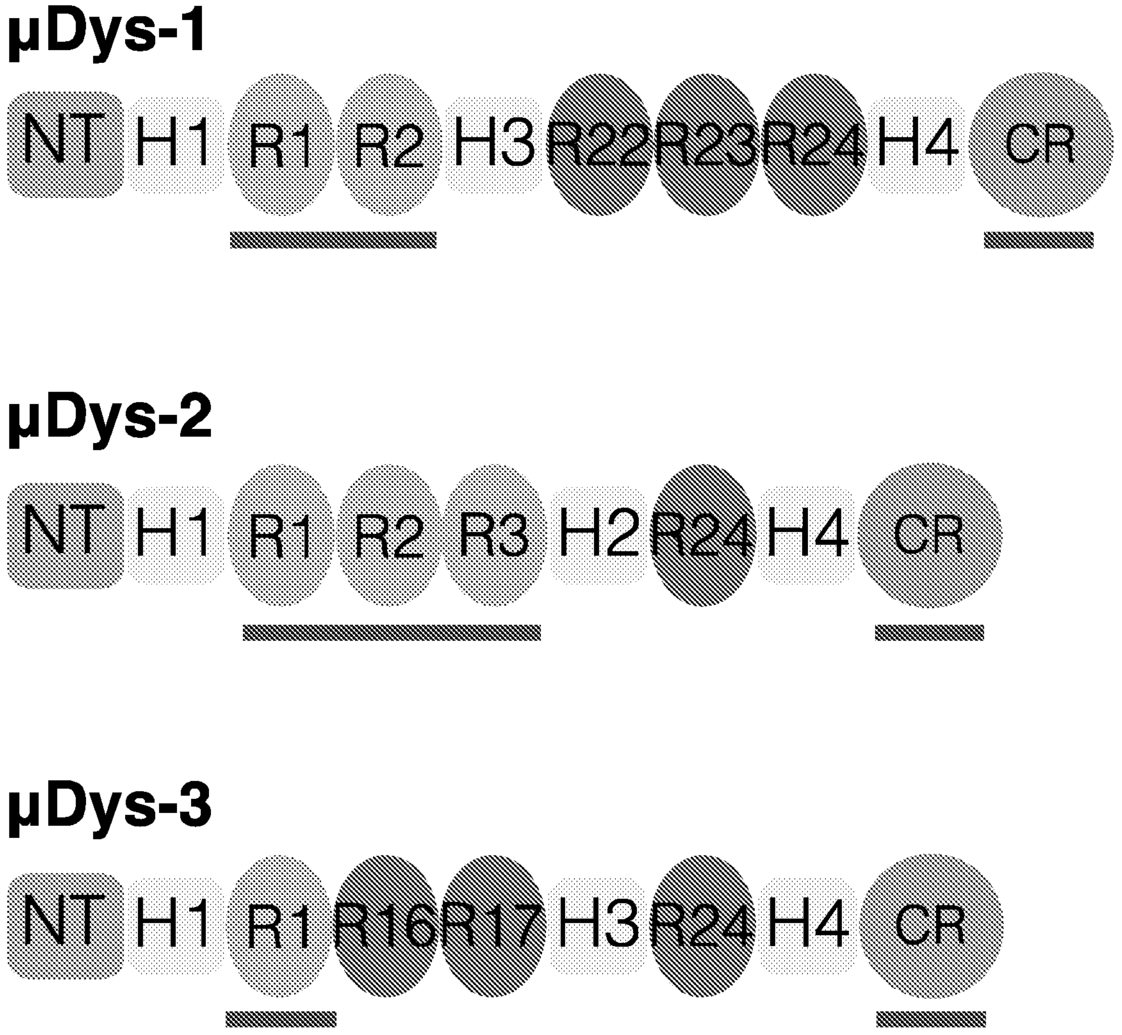
FIG. 21. Currently available micro-dystrophins used in a clinical trial (μDys-1; Mendell, J. R. et al. *N. Engl. J. Med.* 363, 1429-1437 (2010)) or in large animal models (μDys-2; Wang, Z. et al., *Mol Ther* 20, 1501-1507 (2012) and μDys-3; Yue, Y. et al. *Hum. Mol. Genet.* 24, 5880-5890 (2015)). They contain a partial or complete rMBD and a complete cMBD, indicated by underlining.
Figure 22:
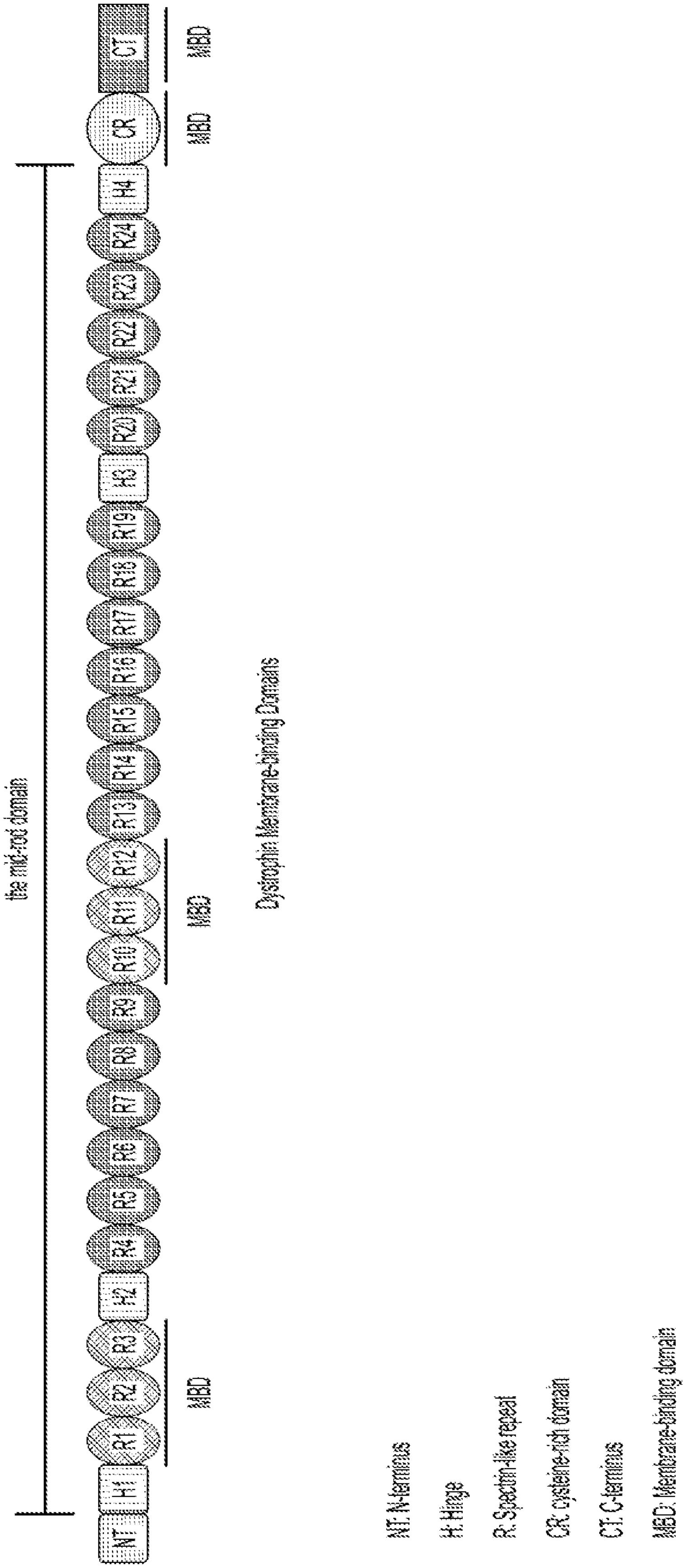
FIG. 22. Schematic diagram of dystrophin and its membrane binding domains.

To date, there exist three functional micro-dystrophins tested in canine dystrophic models and the clinical trial. Only ΔR4-R23/ΔCT micro-dystrophin contains a complete region of R1-3, while ΔR2-R15/ΔR18-R23/ΔCT (Lai, Y. et al., *J. Clin. Invest.* 119, 624-635 (2009)) and Δ3900 (Wang, B. et al., *Proc. Natl. Acad. Sci. USA* 97, 13714-13719 (2000)) micro-dystrophin carry only R1 or R1-2, respectively (FIG. 21). But muscle force comparison revealed that there is no apparent difference regarding muscle force improvement between ΔR4-R23/ΔCT and ΔR2-R15/ΔR18-R23/ΔCT, suggesting that a partial region of R1-3 possibly maintains the ability of membrane binding. Mapping membrane-binding motifs in R1-3 will help clarify this issue.

Identification of membrane-binding motifs in R1-3, R10-12, and CT will be important for the development of DMD gene therapy. Given the packaging limit of AAV vectors, the main focus of engineering truncated dystrophins will be maximizing dystrophin function in a minimal sequence. Hence, shortening dystrophin MBDs will be useful for DMD gene therapy.

Both R1-3 and R10-12 are composed of three spectrin-like repeats. First we ask whether the single repeat or bi-repeats of R1-3 and R10-12 maintain the ability of membrane binding. To address this issue, we will split R1-3 and R10-12 into smaller individual repeats, and use AAV.R16/17.GFP construct as the backbone, since our previous study has shown that R16/17.GFP is expressed in the cytosol of myofibers, and R16/17 are an important component of the microgene (Lai, Y. et al., *Proc. Natl. Acad. Sci. USA* 110, 525-530 (2013)). And we will fuse R1, R2, R3, R1-2, R2-3, R1,3 or R10, R11, R12, R10-11, R11-12, R10,12 to R16/17.GFP (FIG. 16), and exploit AAV gene transfer to express the GFP fusion proteins in the muscle of msz 4cv mice. Membrane binding of the GFP fusion proteins will be determined by the GFP signal and immunostaining with the epitope-specific antibodies. If the single repeat or bi-repeats maintain the membrane-binding ability, they will target the R16/17.GFP to the muscle membrane. The information gathered from these studies will help us determine which repeats in R1-3 and R10-12 have the ability of membrane binding, and will clarify whether the partial R1-3 in some micro-dystrophins conserves membrane binding.

Those repeats with the ability of membrane binding are named as membrane-binding repeats. Each spectrin-like repeat consists of three α-helices. Next, we will proceed to narrow down the membrane-binding motifs to the helices of the membrane-binding repeats. In our previous study, we successfully determined a 10-amino-acid nNOS-binding motif in the first helix of R17, and also found that two upstream and downstream helices that flank nNOS-binding motif are also required for nNOS binding since the flanking helices frame the nNOS-binding motif and make it accessible to nNOS binding (Lai, Y. et al., *Proc. Natl. Acad. Sci. USA* 110, 525-530 (2013)). Here, we will use the same strategy to decide the membrane-binding motifs in membrane-binding repeats.

Figure 23:
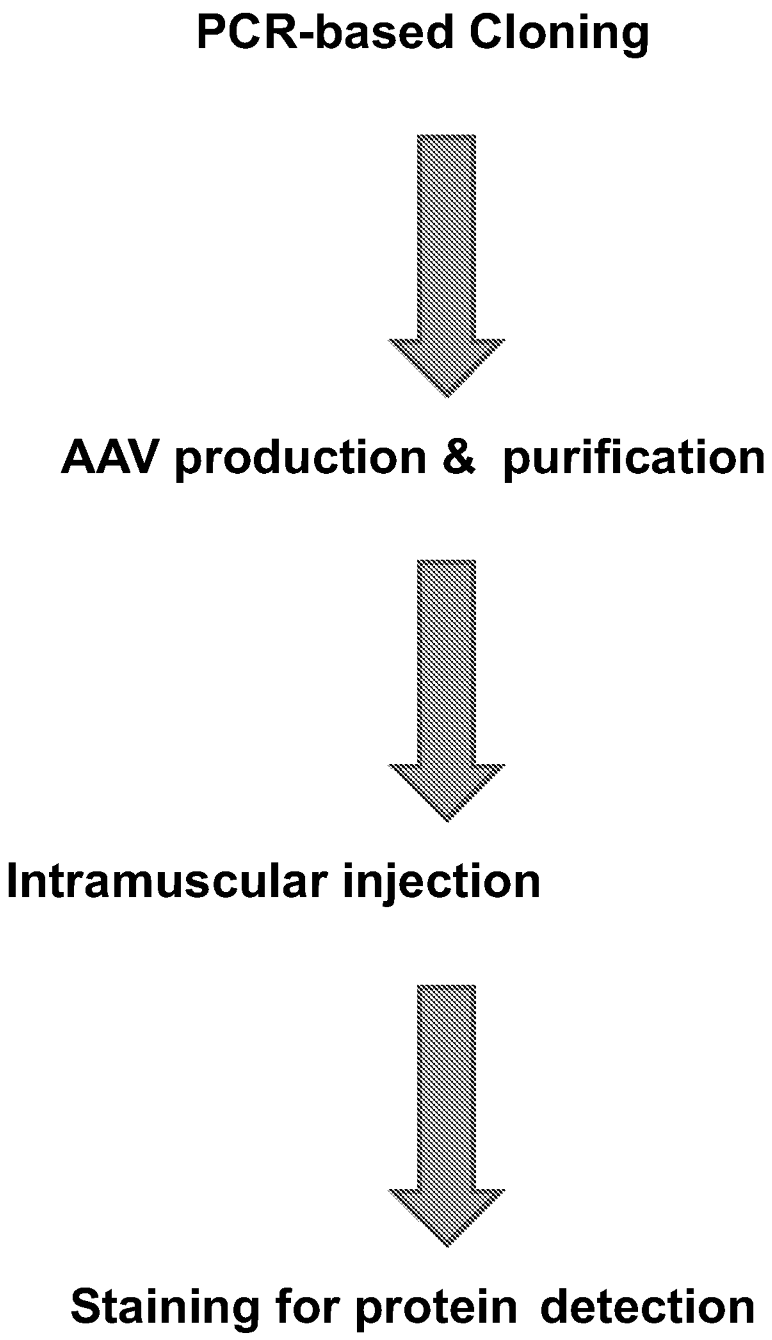
FIG. 23. Methodology for evaluating synthetic mini-dystrophin gene or micro-dystrophin gene constructs.

We will choose AAV constructs that contain membrane-binding repeats as the backbones (FIGS. 19, 20, and 21). Like our previous study, we will replace the individual helix in the membrane-binding repeats with the corresponding helix from R16 to determine which helices in the membrane-binding repeats are involved in membrane binding. For the helices that are involved in membrane binding, we will split each helix into 4-5 parts, each part containing 9-10 amino acids, and replace each part with the corresponding region from R16. Then we will express these mutants by AAV gene transfer in the TA muscle of mdx 4cv mice, and determine the membrane binding of these mutants by the GFP signal and immunostaining. An example of a methodology used to test various constructs is shown (FIG. 23). These studies will further narrow down the membrane-binding motifs in the membrane-binding repeats of R1-3 and R10-12.

We will use the deletion strategy to identify the membrane-binding motif in the CT domain. The construct AAV.CT.GFP shown in FIG. 5 will be used as the backbone. Different partial deletions of the CT domain will be introduced to AAV.CT.GFP construct as outlined in FIG. 18. We will use AAV gene transfer to deliver these constructs to the TA muscle of mdx 4cv mice. The membrane localization of the GFP fusion proteins will be determined by the GFP signal. If we decide which part of the CT domain is responsible for membrane binding, we will split this part into three smaller motifs, and narrow down the membrane-binding region to the smallest motif.

Example 4

Construction of New Dystrophin MBDs into Micro- and Mini-Dystrophin Synthetic Genes and Insertion of Same into AAV Vectors In vitro studies have shown that membrane association from newly discovered MBDs is important for dystrophin function (Sarkis, J. et al., *FASEB J.* 27, 359-367 (2013); Sarkis, J. et al., *J. Biol. Chem.* (2011)). However, currently available micro-dystrophins contain two MBDs: partial or complete R1-3 and the CR domain, while mini-dystrophins ΔH2-R19 and ΔH2-R15 carry three MBDs: R1-3, CR and CT, suggesting that the membrane-binding ability of truncated dystrophins is compromised. Here, we will generate new dystrophin AAV vectors by adding more MBDs.

For initial testing, we will use the ΔR4-R23/ΔCT microgene as the backbone, since ΔR4-R23/ΔCT microgene is the only microgene containing the complete MBD, R1-3 (FIG. 21). The micro-dystrophins are packaged by the single AAV vector, which has a packaging limit of about 4.9 kb. The original size of ΔR4-R23/ΔCT AAV vector is about 4.8 kb, including 3.6 kb micro-dystrophin cDNA, a 523 bp CMV promoter, a 206 bp SV40 PolyA site, 0.3 kb AAV ITRs, and other sequences for 5' and 3' untranslated regions (UTR) and multiple cloning sites. We will free up space for an additional MBD by shortening transcription regulation elements and sequences for UTRs and cloning sites. A shortened muscle-specific promoter and a synthetic PolyA site (49 bp) (Levitt, N. et al., *Genes Dev.* 3, 1019-1025 (1989)) will replace the CMV promoter and SV40 PolyA site. Also the sequences for UTRs and the cloning sites will be shortened by engineering the shorter UTRs, and including the cloning sites into the UTRs. To make the total size of micro-dystrophin AAV vector about 4.9 kb, these changes allow us to add >700 bp more bps in the ΔR4-R23/ΔCT micro-dystrophin. Since each spectrin-like repeat is about 330 bps and the CT domain is about 792 bps, the spared space can hold two more repeats or one more repeat and half of the CT domain or the whole CT domain. Since the shortest membrane-binding regions are first being identified, only the CT domain can be added to microgenes. For the first test, we will add the CT domain into ΔR4-R23/ΔCT micro-dystrophin without affecting the packaging efficiency of AAV vectors. So the resultant microgene ΔR4-R23 contains three MBDs (FIG. 19).

ΔH2-R19 mini-dystrophin contains three MBDs: R1-3, CR and CT domain. It can restore full muscle force but only partially recover heart hemodynamic function (Bostick, B. et al., *Mol Ther* 17, 253-261 (2009)). So we will use ΔH2-R19 mini-dystrophin as the backbone, and engineer R10-12 into ΔH2-R19 mini-dystrophin to make a new mini-dystrophin with four MBDs (FIG. 19).

These two constructs are two examples for how we will engineer new dystrophin AAV vectors by adding more MBDs into dystrophin AAV vectors. The list of micro-and mini-dystrophin AAV vectors can be expanded once the smallest membrane-binding region is identified from the preceding studies. For example, if rMBDs, R1-3 and R10-12, could be reduced to the single repeat, we can make the micro-dystrophin with two rMBDs and one cMBD, the CR domain. If one half of the CT domain can be trimmed, we could even make new micro-dystrophin AAV vector containing all four MBDs. If the membrane-binding motifs can be reduced to the helices, we can generate a hybrid repeat. For example, R16/17 are essential for nNOS binding. The first helix of R16 can be replaced without affecting nNOS binding. We can engineer the membrane-binding motif from R1-3 or R10-12 into the first helix of R16 to generate a hybrid repeat with two functions.

To examine therapeutic efficacy of new micro- and mini-dystrophins in murine and canine dystrophic models, we will deliver new dystrophin AAV vectors to Cmah/mdx mice and DMD dogs and examine therapeutic efficacy of these new dystrophin AAV vectors. All new dystrophin AAV vectors will be tested in Cmah/mdx first. Contractile properties of TA muscle, ECG and hemodynamic function, membrane integrity and muscle histopathology will be examined as outlined above. From the functional results, one best microgene and one best minigene will be selected for further testing in DMD dogs.

The therapeutic efficacy of new micro- and mini-dystrophins will be tested in DMD dogs. A series of functional studies in canine dystrophic models, including measurements of single muscle force, cardiac function and blood flow (Yang, H. T. et al. *PLoS One* 7, e44438 (2012); Fine, D. M. et al., *Neuromuscul Disord* 21, 453-461 (2011)) can be performed. Micro- and mini-dystrophin AAV vectors will be delivered to 5-6 DMD dogs, respectively. For virus injection in DMD dogs, a transient immunosuppression protocol will be administered. And AAV vectors will be injected to the Extensor Carpi Ulnaris (ECU) muscle of DMD dogs by intramuscular (IM) injection. After five to six months, force generation and the resistance to eccentric contraction of ECU muscle will be evaluated (Yang, H. T. et al., *PLoS One* 7, e44438 (2012); Shin, J. H. et al., *Mol Ther* 21, 750-757 (2013)). Histopathology will be investigated as proposed in the mouse studies.

Despite the role of cysteine residues in membrane binding of R1-3, R10-12 and the CT domain, the shortest membrane-binding region is still unknown. In this aim, we will identify membrane-binding motifs by AAV gene transfer. Hence, the membrane-binding motifs derived from this study will be highly relevant to DMD gene therapy. A previous study has shown that the single repeat R2 has lipid-binding ability (Le Rumeur, E. et al. *Biochim. Biophys. Acta* 1768, 648-654 (2007)) suggesting that the individual repeat from R1-3 can bind to the muscle membrane. So it is likely that the R1-3 membrane-binding region can be shortened.

Currently available truncated dystrophins are not fully functional. We will generate a series of new dystrophin AAV vectors that contain more MBDs to improve their therapeutic effects. First we will examine therapeutic effects of new dystrophin AAV vectors in the mouse model. Only after we confirm that new dystrophin AAV vectors perform better than original dystrophin AAV vectors, we will proceed to test the best candidates in the canine dystrophic model.

Example 5

Restoration of Sarcolemmal nNOS in mdx Mice by Dystrophin Spectrin-Like Repeats 16 and 17 and Syntrophin PDZ Fusion Protein Duchenne Muscular Dystrophy (DMD) is a genetic disorder that affects sarcolemmal localization of neuronal nitric oxide synthase (nNOS). Sarcolemmal nNOS is required for muscle cells to function properly. In DMD patients, a deficiency in the dystrophin protein leads to a reduction in sarcolemmal nNOS and syntrophin. From a previous study (Lai, Yi, et al. *Journal of Clinical Investigation* (2009): 624-35), recruitment of sarcolemmal nNOS is dependent on dystrophin spectrin-like repeats 16 and 17 (R16/17) and syntrophin PDZ domain.

Muscle wasting diseases such as Duchenne muscular dystrophy (DMD) affect sarcolemmal localization of neuronal nitric oxide synthase (nNOS). Sarcolemmal nNOS is required for muscle cells to function properly. Sarcolemmal localization of nNOS is dependent on its simultaneous binding to dystrophin spectrin-like repeats 16 and 17 (R16/17) and syntrophin PDZ domain. DMD is characterized by a deficiency in dystrophin. In DMD, loss of dystrophin leads to the reduction or loss of syntrophin at the sarcolemma, which further results in the loss of sarcolemmal nNOS. Loss of sarcolemmal neuronal nitric oxide synthase (nNOS) is a salient pathogenic feature in muscle wasting conditions/diseases such as age-related muscle atrophy, cancer cachexia, Duchenne muscular dystrophy (DMD) and many other neuromuscular disorders.

In a previous study, dystrophin R16/17 was expressed in the muscle of a truncated dystrophin transgenic mouse, where syntrophin is present at the membrane. The results showed that sarcolemmal nNOS was recovered successfully, indicating that dystrophin R16/17 and syntrophin PDZ are required for sarcolemmal nNOS.

Figure 24:
FIG. 24. The construct design of AAV.R16/17.Syn.GFP-.Pal. To induce the expression of R16/17.Syn PDZ.GFP.Pal in the muscle, we will engineer an AAV construct. Syntrophin PDZ domain is fused to the C-terminus of dystrophin R16/17. We add green fluorescent protein (GFP) as the tag to help detection of R16/17.Syn fusion protein. Pal is the signal for membrane targeting. The expression of R16/17.Syn.GFP.Pal is driven by CMV promoter and SV40 polyA. ITR (inverted terminal repeat) is the sequence for AAV virus production.

In this study, we engineered an adeno-associated virus (AAV) vector that can express a dystrophin R16/17-syntrophin PDZ fusion protein. We tested whether the expression of the fusion protein restored sarcolemmal nNOS in the muscle of mcbc mice, the DMD mouse model (FIG. 23). PCR-based cloning was used to clone syntrophin PDZ into the AAV.R16/17.GFP.Pal backbone to produce AAV.R16/17.Syn.GFP.Pal construct (FIG. 24). In the vector, a hinge region (GGSG) was inserted between R16/17 and syn PDZ. GFP is a tag that helps detect the R16/17.Syn protein. Pal is the signal for membrane targeting. The AAV plasmid DNA was amplified to produce large amounts of DNA for virus production.

We then performed a local injection of the virus into six, ~3.5 month old mdx mice. Each mouse received $1.4*10^{12}$ viral genome particles (vg) into the tibialis anterior and $2.2*10^{12}$ vg into the gastrocnemius muscles. Three weeks later, we harvested the muscle tissues. First, we confirmed the expression of the R16/17-syntrophin PDZ fusion protein in the muscle by fluorescence microscopy for the GFP signal. Then we performed immunostaining and nNOS activity staining to examine if the expression of R16/17-syntrophin PDZ fusion protein can restore sarcolemmal nNOS.

Figure 25:
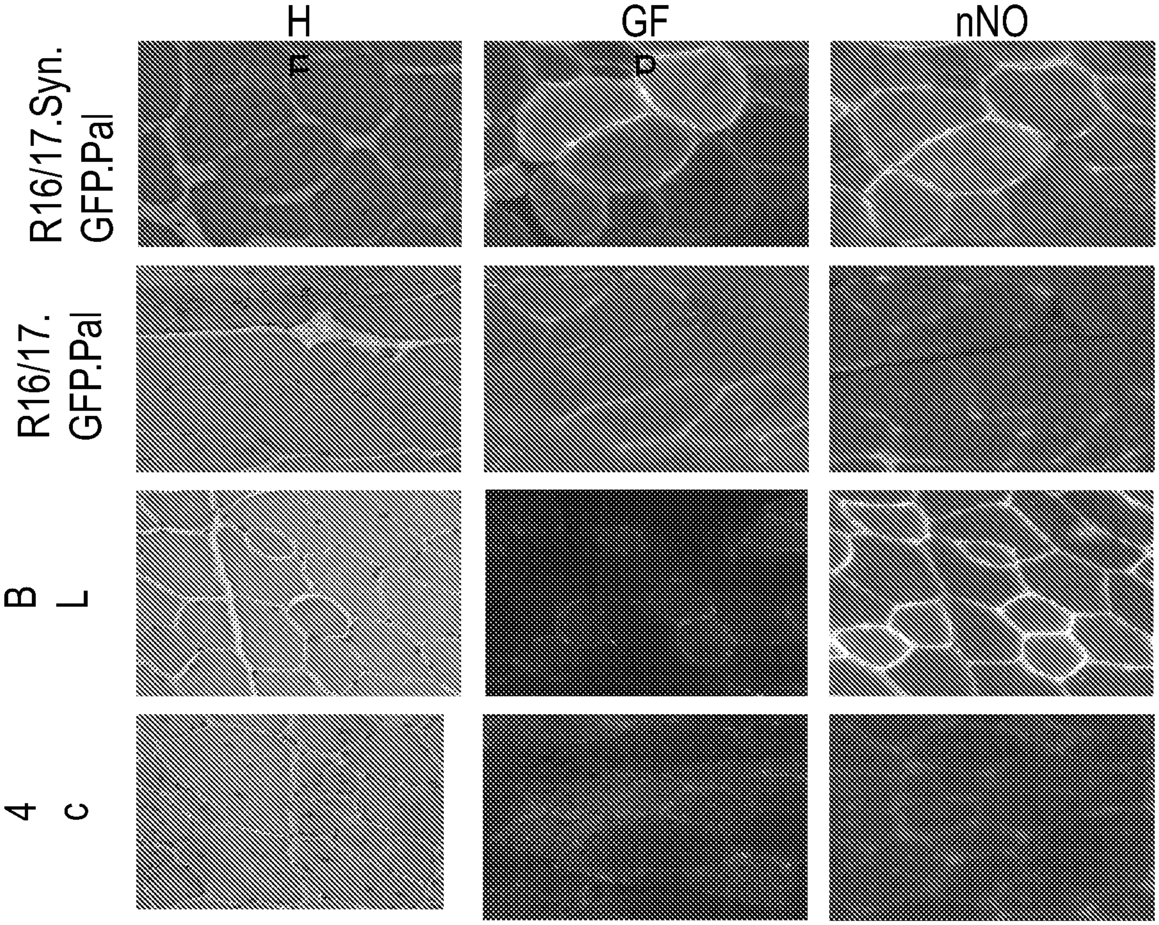
FIG. 25. Sarcolemmal nNOS was recovered successfully in a mdx mouse with the use of the R16/17-syntrophin PDZ fusion protein. Illustrated above are the expression levels of nNOS in different mice controls.
Figure 26:
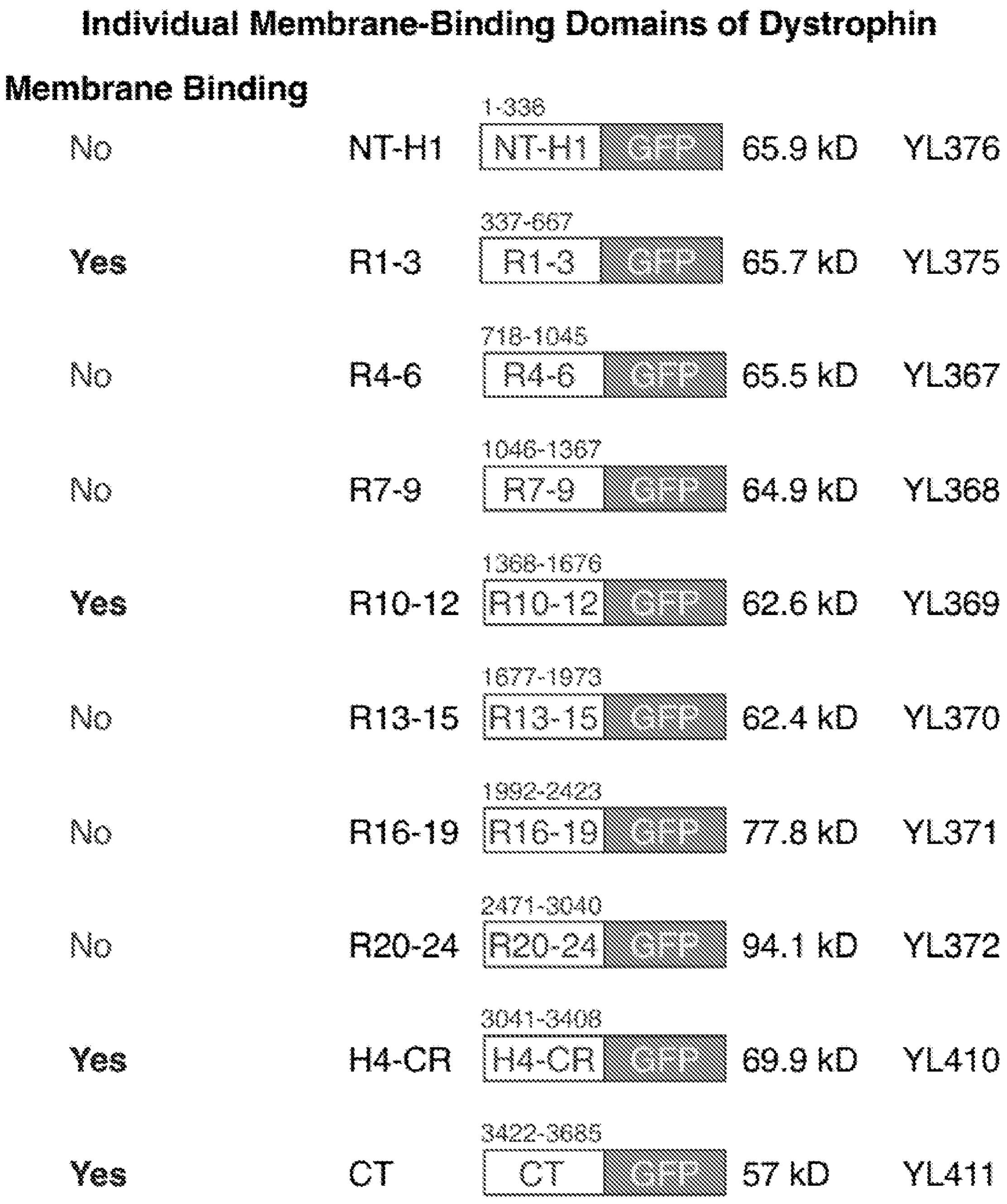
FIG. 26. Schematic diagram of dystrophin domains that do or do not exhibit membrane binding.

Our results show that sarcolemmal nNOS was recovered successfully with the use of R16/17-syntrophin PDZ fusion protein (FIG. 25). Further testing will be done to examine the therapeutic effects of restoring sarcolemmal nNOS. Restoration of sarcolemmal nNOS has therapeutic use for multiple neuromuscular disorders, such as DMD, and other muscle wasting conditions such as age/inactivity-related muscle atrophy and cancer cachexia.

DMD is a disorder that is characterized by degeneration and regeneration of muscle tissues and premature death most commonly due to cardiac or respiratory failure. In patients suffering from DMD, sarcolemmal nNOS is either reduced or completely lost. Sarcolemmal nNOS plays a crucial role in the upkeep of muscle tissues.

The results from this project show that it is possible to introduce sarcolemmal localization of nNOS in mdx mice with the use of a viral vector. Our next step is to see whether or not the R16/17-syntrophin PDZ fusion protein can recruit nNOS in DBA/mdx mice, a more severe phenotype mouse model of DMD.

Example 6

Description of Sequences Provided in the Sequence Listing

A description of sequences provided herewith in the electronic sequence listing file "17UMC006_SEQ LST_TC167044_ST25.txt" follows below.

SEQ ID NO: 1:
Full-length human dystrophin protein sequence

SEQ ID NO: 2:
Full-length dystrophin coding region

SEQ ID NO: 3:
.DELTA.17-48 (mini-dystrophin with 8.5 repeats and 3 hinges) (This minigene does not carry R16 or R17. It cannot restore nNOS)

SEQ ID NO: 4:
.DELTA.H2-R19 (mini-dystrophin with 8 repeats and 3 hinges) (This minigene does not carry R16 or R17. It cannot restore nNOS)

SEQ ID NO: 5:
.DELTA.H2-R17 (mini-dystrophin with 10 repeats and 3 hinges) (This minigene does not carry R16 or R17. It cannot restore nNOS)

SEQ ID NO: 6:
.DELTA.H2-R16 (mini-dystrophin with 11 repeats and 3 hinges) (This minigene carries R17 but not R16. It cannot restore nNOS)

SEQ ID NO: 7:
.DELTA.H2-R15 (mini-dystrophin with 12 repeats and 3 hinges) (This minigene carries both R16 and R17. It can restore nNOS)

SEQ ID NO: 8:
.DELTA.H2-R15/.DELTA.R18-19 (mini-dystrophin with 10 repeats and 3 hinges) (This minigene carries both R16 and R17. It can restore nNOS)

SEQ ID NO: 9:
.DELTA.H2-R15/.DELTA.17-19 (mini-dystrophin with 9 repeats and 3 hinges) (This minigene carries R16 but not R17. It cannot restore nNOS)

SEQ ID NO: 10:
.DELTA.H2-R15/.DELTA.0 (mini-dystrophin with 12 repeats and 3 hinges, no C-terminal domain) (This minigene carries both R16 and R17. It can restore nNOS)

SEQ ID NO: 11:
.DELTA.R2-R15/.DELTA.H3-R23/.DELTA.C (micro-dystrophin with 6 repeats and 2 hinges, no C-terminal domain) (This microgene carries both R16 and R17. It can restore nNOS)

SEQ ID NO: 12:
.DELTA.R3-R15/.DELTA.R18-23/.DELTA.C (micro-dystrophin with 5 repeats and 2 hinges, no C-terminal domain) (This microgene carries both R16 and R17. It can restore nNOS)

SEQ ID NO: 13:
.DELTA.R2-R15/.DELTA.R18-23/.DELTA.C (micro-dystrophin with 4 repeats and 2 hinges, no C-terminal domain) (This microgene carries both R16 and R17. It can restore nNOS)

-continued

SEQ ID NO: 14:
.DELTA.R3-R15/.DELTA.R17-23/.DELTA.C (micro-dystrophin with 4 repeats and 2 hinges, no C-terminal domain) (This microgene carries R16 but not R17. It cannot restore nNOS)

SEQ ID NO: 15:
AV.CMV..DELTA.R2-15/.DELTA.R18-23/.DELTA.C (This AAV vector contains four repeats and two hinges. It carries both R16 and R17 and it can restore nNOS)

SEQ ID NO: 16:
AV.CMV..DELTA.R3-15/.DELTA.R18-23/.DELTA.C (This AAV vector contains five repeats and two hinges. It carries both R16 and R17 and it can restore nNOS)

SEQ ID NO: 17:
Human dystrophin domain sequence N-terminal domain

SEQ ID NO: 18:
Hinge 1

SEQ ID NO: 19:
Repeat 1

SEQ ID NO: 20:
Repeat 2

SEQ ID NO: 21:
Repeat 3

SEQ ID NO: 22:
Hinge 1

SEQ ID NO: 23:
Repeat 4

SEQ ID NO: 24:
Repeat 5

SEQ ID NO: 25:
Repeat 6

SEQ ID NO: 26:
Repeat 7

SEQ ID NO: 27:
Repeat 8

SEQ ID NO: 28:
Repeat 9

SEQ ID NO: 29:
Repeat 10

SEQ ID NO: 30:
Repeat 11

SEQ ID NO: 31:
Repeat 12

SEQ ID NO: 32:
Repeat 13

SEQ ID NO: 33:
Repeat 14

SEQ ID NO: 34:
Repeat 15

SEQ ID NO: 35:
Repeat 16

SEQ ID NO: 36:
Repeat 17

SEQ ID NO: 37:
Repeat 18

-continued

SEQ ID NO: 38:
Repeat 19

SEQ ID NO: 39:
Hinge 3

SEQ ID NO: 40:
Repeat 20

SEQ ID NO: 41:
Repeat 21

SEQ ID NO: 42:
Repeat 22

SEQ ID NO: 43:
Repeat 23

SEQ ID NO: 44:
Repeat 24

SEQ ID NO: 45:
Hinge 4

SEQ ID NO: 46:
Cysteine-rich domain

SEQ ID NO: 47:
C-terminal domain

SEQ ID NO: 48:
Full-length canine dystrophin DNA sequence

SEQ ID NO: 49:
Full-length canine dystrophin protein sequence

SEQ ID NO: 50:
N-terminal domain from 1 aa to 252 aa; total 252 aa of full length human dystrophin protein of 3685 aa)

SEQ ID NO: 51:
Mid-rod domain (from 253 aa to 3112 aa; total 2860 aa of full length human dystrophin protein of 3685 aa)

SEQ ID NO: 52:
Cysteine-rich domain (from 3113 aa to 3408 aa; total 296 aa of full length human dystrophin protein of 3685 aa)

SEQ ID NO: 53:
C-terminal domain (from 3409 aa to 3695 aa; total 277 aa of full length human dystrophin protein of 3685 aa)

SEQ ID NO: 54:
LLNSRWECLRVASME

SEQ ID NO: 55:
QRLTEEQCLFSAWLS

SEQ ID NO: 56:
WLDNFARCWDNLVQK

SEQ ID NO: 57:
CLKLSRKM

SEQ ID NO: 58
R16 peptide sequence (first alpha-helix underlined):
EISYVPSTYLTEITHVSQALLEVEQLLNAPDLCAKDFEDLFKQEESLKNIK

DSLQQSSGRIDIIHSKKTAALQSATPVERVKLQEALSQLDFQWEKVNKMYK

DRQGRFDR

SEQ ID NO: 59
first alpha-helix of R16:
PSTYLTEITHVSQALLEVEQL

-continued

SEQ ID NO: 60
(R10-R11-R12 peptide; MBM underlined):
SIQSAQETEKSLHLIQESLTFIDKQLAAYIADKVDAAQMPQEAQKIQSDLT

SHEISLEEMKKHNQGKEAAQRVLSQIDVAQKKLQDVSMKFRLFQKPANFEL

RLQESKMILDEVKMHLPALETKSVEQEVVQSQLNHCVNLYKSLSEVKSEVE

MVIKTGRQIVQKKQTENPKELDERVTALKLHYNELGAKVTERKQQLEKCLK

LSRKMRKEMNVLTEWLAATDMELTKRSAVEGMPSNLDSEVAWGKATQKEIE

KQKVHLKSITEVGEALKTVLGKKETLVEDKLSLLNSNWIAVTSRAEEWLNL

LLE

SEQ ID NO: 61
(R1-R2-R3 peptide; MBM underlined):
SEVNLDRYQTALEEVLSWLLSAEDTLQAQGEISNDVEVVKDQFHTHEGYMM

DLTAHQGRVGNILQLGSKLIGTGKLSEDEETEVQEQMNLLNSRWECLRVAS

MEKQSNLHRVLMDLQNQKLKELNDWLTKTEERTRKMEEEPLGPDLEDLKRQ

VQQHKVLQEDLEQEQVRVNSLTHMVVVVDESSGDHATAALEEQLKVLGDRW

ANICRWTEDRWVLLQDILLKWQRLTEEQCLFSAWLSEKEDAVNKIHTTGFK

DQNEMLSSLQKLAVLKADLEKKKQSMGKLYSLKQDLLSTLKNKSVTQKTEA

WLDNFARCWDNLVQKLEKSTAQISQ

SEQ ID NO: 62:
GGSG

SEQ ID NO: 63:
GGGS

SEQ ID NO: 64:
GGGGS

SEQ ID NO: 65:
GSAT

SEQ ID NO: 66:
(PDZ domain of mouse syntrophin)

SEQ ID NO: 67:
(PDZ Domain of Human syntrophin)

REFERENCES

1. Straub, V., Rafael, J. A., Chamberlain, J. S. and Campbell, K. P. (1997) Animal models for muscular dystrophy show different patterns of sarcolemmal disruption. *J. Cell Biol.,* 139, 375-385.
2. Petrof, B. J., Shrager, J. B., Stedman, H. H., Kelly, A. M. and Sweeney, H. L. (1993) Dystrophin protects the sarcolemma from stresses developed during muscle contraction. *Proc. Natl. Acad. Sci. USA,* 90, 3710-3714.
3. Hoffman, E. P., Brown, R. H. J. and Kunkel, L. M. (1987) Dystrophin: the protein product of the Duchenne muscular dystrophy locus. *Cell,* 51, 919-928.
4. Koenig, M. and Kunkel, L. M. (1990) Detailed analysis of the repeat domain of dystrophin reveals four potential hinge segments that can confer flexibility *J. Biol. Chem.,* 265, 4560-4566.
5. Amann, K. J., Renley, B. A. and Ervasti, J. M. (1998) A cluster of basic repeats in the dystrophin rod domain binds F-actin through an electrostatic interaction. *J. Biol. Chem.,* 273, 28419-28423.
6. Rybakova, I. N., Amann, K. J. and Ervasti, J. M. (1996) A new model for the interaction of dystrophin with F-actin. *J. Cell Biol.,* 135, 661-672.

7. Campbell, K. P. and Kahl, S. D. (1989) Association of dystrophin and an integral membrane glycoprotein. *Nature,* 338, 259-262.
8. Jung, D., Yang, B., Meyer, J., Chamberlain, J. S. and Campbell, K. P. (1995) Identification and characterization of the dystrophin anchoring site on beta-dystroglycan. *J. Biol. Chem.,* 270, 27305-27310.
9. Huang, X., Poy, F., Zhang, R., Joachimiak, A., Sudol, M. and Eck, M. J. (2000) Structure of a WW domain containing fragment of dystrophin in complex with beta-dystroglycan. *Nat. Struct. Biol.,* 7, 634-638.
10. Ervasti, J. M. and Campbell, K. P. (1991) Membrane organization of the dystrophin-glycoprotein complex. *Cell,* 66, 1121-1131.
11. Helliwell, T. R., Ellis, J. M., Mountford, R. C., Appleton, R. E. and Morris, G. E. (1992) A truncated dystrophin lacking the C-terminal domains is localized at the muscle membrane. *Am. J. Hum. Genet.,* 50, 508-514.
12. Hoffman, E. P., Garcia, C. A., Chamberlain, J. S., Angelini, C., Lupski, J. R. and Fenwick, R. (1991) Is the carboxyl-terminus of dystrophin required for membrane association? A novel, severe case of Duchenne muscular dystrophy. *Ann. Neurol.,* 30, 605-610.
13. Recan, D., Chafey, P., Leturcq, F., Hugnot, J. P., Vincent, N., Tome, F., Collin, H., Simon, D., Czernichow, P., Nicholson, L. V. and et, A. (1992) Are cysteine-rich and COOH-terminal domains of dystrophin critical for sarcolemmal localization? *J. Clin. Invest.,* 89, 712-716.
14. Le Rumeur, E., Winder, S. J. and Hubert, J. F. (2010) Dystrophin: more than just the sum of its parts. *Biochim. Biophys. Acta,* 1804, 1713-1722.
15. Cox, G. A., Sunada, Y., Campbell, K. P. and Chamberlain, J. S. (1994) Dp71 can restore the dystrophin-associated glycoprotein complex in muscle but fails to prevent dystrophy. *Nat. Genet.,* 8, 333-339.
16. Crawford, G. E., Faulkner, J. A., Crosbie, R. H., Campbell, K. P., Froehner, S. C. and Chamberlain, J. S. (2000) Assembly of the dystrophin-associated protein complex does not require the dystrophin COOH-terminal domain *J. Cell Biol.,* 150, 1399-1410.
17. Rapaport, D., Greenberg, D. S., Tal, M., Yaffe, D. and Nudel, U. (1993) Dp71, the nonmuscle product of the Duchenne muscular dystrophy gene is associated with the cell membrane. *FEBS Lett.,* 328, 197-202.
18. Judge, L. M., Haraguchiln, M. and Chamberlain, J. S. (2006) Dissecting the signaling and mechanical functions of the dystrophin-glycoprotein complex *J. Cell Sci.,* 119, 1537-1546.
19. Rafael, J. A., Cox, G. A., Corrado, K., Jung, D., Campbell, K. P. and Chamberlain, J. S. (1996) Forced expression of dystrophin deletion constructs reveals structure-function correlations. *J. Cell Biol.,* 134, 93-102.
20. Fritz, J. D., Danko, I., Roberds, S. L., Campbell, K. P., Latendresse, J. S. and Wolff, J. A. (1995) Expression of deletion-containing dystrophins in mdx muscle: implications for gene therapy and dystrophin function. *Pediatr Res,* 37, 693-700.
21. Maconochie, M. K., Simpkins, A. H., Damien, E., Coulton, G., Greenfield, A. J. and Brown, S. D. (1996) The cysteine-rich and C-terminal domains of dystrophin are not required for normal costameric localization in the mouse. *Transgenic Res,* 5, 123-130.
22. Gardner, K. L., Kearney, J. A., Edwards, J. D. and Rafael-Fortney, J. A. (2006) Restoration of all dystrophin protein interactions by functional domains in trans does not rescue dystrophy. *Gene Ther,* 13, 744-751.
23. Barnabei, M. S., Sjaastad, F. V., Townsend, D., Bedada, F. B. and Metzger, J. M. (2015) Severe dystrophic cardiomyopathy caused by the enteroviral protease 2A-mediated C-terminal dystrophin cleavage fragment. *Sci Transl Med,* 7, 294ra106.
24. Dunckley, M. G., Wells, K. E., Piper, T. A., Wells, D. J. and Dickson, G. (1994) Independent localization of dystrophin N- and C-terminal regions to the sarcolemma of mdx mouse myofibres in vivo. *J. Cell Sci.,* 107, 1469-1475.
25. Hir, S. A., Raguenes-Nicol, C., Paboeuf, G., Nicolas, A., Le Rumeur, E. and Vie, V. (2014) Cholesterol favors the anchorage of human dystrophin repeats 16 to 21 in membrane at physiological surface pressure. *Biochim. Biophys. Acta,* 1838, 1266-1273.
26. DeWolf, C., McCauley, P., Sikorski, A. F., Winlove, C. P., Bailey, A. I., Kahana, E., Pinder, J. C. and Gratzer, W. B. (1997) Interaction of dystrophin fragments with model membranes. *Biophys. J.,* 72, 2599-2604.
27. Le Rumeur, E., Fichou, Y., Pottier, S., Gaboriau, F., Rondeau-Mouro, C., Vincent, M., Gallay, J. and Bondon, A. (2003) Interaction of dystrophin rod domain with membrane phospholipids. Evidence of a close proximity between tryptophan residues and lipids. *J. Biol. Chem.,* 278, 5993-6001.
28. Le Rumeur, E., Pottier, S., Da Costa, G., Metzinger, L., Mouret, L., Rocher, C., Fourage, M., Rondeau-Mouro, C. and Bondon, A. (2007) Binding of the dystrophin second repeat to membrane di-oleyl phospholipids is dependent upon lipid packing. *Biochim. Biophys. Acta,* 1768, 648-654.
29. Legardinier, S., Hubert, J. F., Le Bihan, O., Tascon, C., Rocher, C., Raguenes-Nicol, C., Bondon, A., Hardy, S. and Le Rumeur, E. (2008) Sub-domains of the dystrophin rod domain display contrasting lipid-binding and stability properties. *Biochim. Biophys. Acta,* 1784, 672-682.
30. Legardinier, S., Raguenes-Nicol, C., Tascon, C., Rocher, C., Hardy, S., Hubert, J. F. and Le Rumeur, E. (2009) Mapping of the lipid-binding and stability properties of the central rod domain of human dystrophin. *J. Mol. Biol.,* 389, 546-558.
31. Lai, Y., Zhao, J., Yue, Y. and Duan, D. (2013) alpha2 and alpha3 helices of dystrophin R16 and R17 frame a microdomain in the alpha1 helix of dystrophin R17 for neuronal NOS binding. *Proc. Natl. Acad. Sci. USA,* 110, 525-530.
32. Johnson, E. K., Zhang, L., Adams, M. E., Phillips, A., Freitas, M. A., Froehner, S. C., Green-Church, K. B. and Montanaro, F. (2012) Proteomic analysis reveals new cardiac-specific dystrophin-associated proteins. *PLoS One,* 7, e43515.
33. Lai, Y., Thomas, G. D., Yue, Y., Yang, H. T., Li, D., Long, C., Judge, L., Bostick, B., Chamberlain, J. S., Terjung, R. L. and Duan, D. (2009) Dystrophins carrying spectrin-like repeats 16 and 17 anchor nNOS to the sarcolemma and enhance exercise performance in a mouse model of muscular dystrophy. *J. Clin. Invest.,* 119, 624-635.
34. Bennett, V. and Lorenzo, D. N. (2016) An Adaptable Spectrin/Ankyrin-Based Mechanism for Long-Range Organization of Plasma Membranes in Vertebrate Tissues. *Curr Top Membr,* 77, 143-184.
35. Yoshida, M., Hama, H., Ishikawa-Sakurai, M., Imamura, M., Mizuno, Y., Araishi, K., Wakabayashi-Takai, E., Noguchi, S., Sasaoka, T. and Ozawa, E. (2000) Biochemical evidence for association of dystrobrevin with the sarcoglycan-sarcospan complex as a basis for understanding sarcoglycanopathy. *Hum. Mol. Genet.,* 9, 1033-1040.

36. Suzuki, A., Yoshida, M. and Ozawa, E. (1995) Mammalian alpha 1- and beta 1-syntrophin bind to the alternative splice-prone region of the dystrophin COOH terminus. *J. Cell Biol.,* 128, 373-381.
37. Yang, B., Jung, D., Rafael, J. A., Chamberlain, J. S. and Campbell, K. P. (1995) Identification of alpha-syntrophin binding to syntrophin triplet, dystrophin, and utrophin. *J. Biol. Chem.,* 270, 4975-4978.
38. Bunnell, T. M., Jaeger, M. A., Fitzsimons, D. P., Prins, K. W. and Ervasti, J. M. (2008) Destabilization of the dystrophin-glycoprotein complex without functional deficits in alpha-dystrobrevin null muscle. *PLoS One,* 3, e2604.
39. Bajanca, F., Gonzalez-Perez, V., Gillespie, S. J., Beley, C., Garcia, L., Theveneau, E., Sear, R. P. and Hughes, S. M. (2015) In vivo dynamics of skeletal muscle Dystrophin in zebrafish embryos revealed by improved FRAP analysis. *Elife,* 4, e06541.
40. Shin, J. H., Yue, Y. and Duan, D. (2012) Recombinant adeno-associated viral vector production and purification. *Methods Mol. Biol.,* 798, 267-284.
41. Zhong, L., Li, B., Mah, C. S., Govindasamy, L., Agbandje-McKenna, M., Cooper, M., Herzog, R. W., Zolotukhin, I., Warrington, K. H. J., Weigel-Van Aken, K. A. et al. (2008) Next generation of adeno-associated virus 2 vectors: point mutations in tyrosines lead to high-efficiency transduction at lower doses. *Proc. Natl. Acad. Sci. USA,* 105, 7827-7832.
42. Shin, J. H., Yue, Y., Srivastava, A., Smith, B., Lai, Y. and Duan, D. (2012) A Simplified Immune Suppression Scheme Leads to Persistent Micro-dystrophin Expression in Duchenne Muscular Dystrophy Dogs. *Hum. Gene Ther.,* 23, 202-209.
43. Liadaki, K., Luth, E. S. and Kunkell, L. M. (2007) Co-detection of GFP and dystrophin in skeletal muscle tissue sections. *BioTechniques,* 42, 699-700.
44. Lai, Y., Zhao, J., Yue, Y., Wasala, N. B. and Duan, D. (2014) Partial restoration of cardiac function with APDZ nNOS in aged mdx model of Duchenne cardiomyopathy. *Hum. Mol. Genet.,* 23, 3189-3199.

SUPPLEMENTARY REFERENCES

1. Suzuki, A., Yoshida, M., Yamamoto, H. and Ozawa, E. (1992) Glycoprotein-binding site of dystrophin is confined to the cysteine-rich domain and the first half of the carboxy-terminal domain. *FEBS Lett.,* 308, 154-160.
2. Suzuki, A., Yoshida, M., Hayashi, K., Mizuno, Y., Hagiwara, Y. and Ozawa, E. (1994) Molecular organization at the glycoprotein-complex-binding site of dystrophin. Three dystrophin-associated proteins bind directly to the carboxy-terminal portion of dystrophin. *Eur. J. Biochem.,* 220, 283-292.
3. Campbell, K. P. and Kahl, S. D. (1989) Association of dystrophin and an integral membrane glycoprotein. *Nature,* 338, 259-262.
4. Jung, D., Yang, B., Meyer, J., Chamberlain, J. S. and Campbell, K. P. (1995) Identification and characterization of the dystrophin anchoring site on beta-dystroglycan. *J. Biol. Chem.,* 270, 27305-27310.
5. Huang, X., Poy, F., Zhang, R., Joachimiak, A., Sudol, M. and Eck, M. J. (2000) Structure of a WW domain containing fragment of dystrophin in complex with beta-dystroglycan. *Nat. Struct. Biol.,* 7, 634-638.
6. Ishikawa-Sakurai, M., Yoshida, M., Imamura, M., Davies, K. E. and Ozawa, E. (2004) ZZ domain is essentially required for the physiological binding of dystrophin and utrophin to beta-dystroglycan. *Hum. Mol. Genet.,* 13, 693-702.
7. Draviam, R. A., Wang, B., Li, J., Xiao, X. and Watkins, S. C. (2006) Mini-dystrophin efficiently incorporates into the dystrophin protein complex in living cells. *J Muscle Res Cell Motil,* 27, 53-67.
8. Einbond, A. and Sudol, M. (1996) Towards prediction of cognate complexes between the WW domain and proline-rich ligands. *FEBS Lett.,* 384, 1-8.
9. Recan, D., Chafey, P., Leturcq, F., Hugnot, J. P., Vincent, N., Tome, F., Collin, H., Simon, D., Czernichow, P., Nicholson, L. V. and et, A. (1992) Are cysteine-rich and COOH-terminal domains of dystrophin critical for sarcolemmal localization? *J. Clin. Invest.,* 89, 712-716.
10. Hoffman, E. P., Garcia, C. A., Chamberlain, J. S., Angelini, C., Lupski, J. R. and Fenwick, R. (1991) Is the carboxyl-terminus of dystrophin required for membrane association? A novel, severe case of Duchenne muscular dystrophy. *Ann. Neurol.,* 30, 605-610.
11. Helliwell, T. R., Ellis, J. M., Mountford, R. C., Appleton, R. E. and Morris, G. E. (1992) A truncated dystrophin lacking the C-terminal domains is localized at the muscle membrane. *Am. J. Hum. Genet.,* 50, 508-514.
12. Rafael, J. A., Cox, G. A., Corrado, K., Jung, D., Campbell, K. P. and Chamberlain, J. S. (1996) Forced expression of dystrophin deletion constructs reveals structure-function correlations. *J. Cell Biol.,* 134, 93-102.
13. Maconochie, M. K., Simpkins, A. H., Damien, E., Coulton, G., Greenfield, A. J. and Brown, S. D. (1996) The cysteine-rich and C-terminal domains of dystrophin are not required for normal costameric localization in the mouse. *Transgenic Res,* 5, 123-130.
14. Gardner, K. L., Kearney, J. A., Edwards, J. D. and Rafael-Fortney, J. A. (2006) Restoration of all dystrophin protein interactions by functional domains in trans does not rescue dystrophy. *Gene Ther,* 13, 744-751.
15. Barnabei, M. S., Sjaastad, F. V., Townsend, D., Bedada, F. B. and Metzger, J. M. (2015) Severe dystrophic cardiomyopathy caused by the enteroviral protease 2A-mediated C-terminal dystrophin cleavage fragment. *Sci Transl Med,* 7, 294ra106.
16. Dunckley, M. G., Wells, K. E., Piper, T. A., Wells, D. J. and Dickson, G. (1994) Independent localization of dystrophin N- and C-terminal regions to the sarcolemma of mdx mouse myofibres in vivo. *J. Cell Sci.,* 107, 1469-1475.
17. Fritz, J. D., Danko, I., Roberds, S. L., Campbell, K. P., Latendresse, J. S. and Wolff, J. A. (1995) Expression of deletion-containing dystrophins in mdx muscle: implications for gene therapy and dystrophin function. *Pediatr Res,* 37, 693-700.
18. Sarkis, J., Hubert, J. F., Legrand, B., Robert, E., Cheron, A., Jardin, J., Hitti, E., Le Rumeur, E. and Vie, V. (2011) Spectrin-like repeats 11-15 of human dystrophin show adaptations to a lipidic environment. *J. Biol. Chem.,* 286, 30481-30491.
19. Legardinier, S., Raguenes-Nicol, C., Tascon, C., Rocher, C., Hardy, S., Hubert, J. F. and Le Rumeur, E. (2009) Mapping of the lipid-binding and stability properties of the central rod domain of human dystrophin. *J. Mol. Biol.,* 389, 546-558.
20. Legardinier, S., Hubert, J. F., Le Bihan, O., Tascon, C., Rocher, C., Raguenes-Nicol, C., Bondon, A., Hardy, S. and Le Rumeur, E. (2008) Sub-domains of the dystrophin rod domain display contrasting lipid-binding and stability properties. *Biochim. Biophys. Acta,* 1784, 672-682.

21. Le Rumeur, E., Pottier, S., Da Costa, G., Metzinger, L., Mouret, L., Rocher, C., Fourage, M., Rondeau-Mouro, C. and Bondon, A. (2007) Binding of the dystrophin second repeat to membrane di-oleyl phospholipids is dependent upon lipid packing. *Biochim. Biophys. Acta,* 1768, 648-654.

22. Hir, S. A., Raguenes-Nicol, C., Paboeuf, G., Nicolas, A., Le Rumeur, E. and Vie, V. (2014) Cholesterol favors the anchorage of human dystrophin repeats 16 to 21 in membrane at physiological surface pressure. *Biochim. Biophys. Acta,* 1838, 1266-1273.

23. Le Rumeur, E., Fichou, Y., Pottier, S., Gaboriau, F., Rondeau-Mouro, C., Vincent, M., Gallay, J. and Bondon, A. (2003) Interaction of dystrophin rod domain with membrane phospholipids. Evidence of a close proximity between tryptophan residues and lipids. *J. Biol. Chem.,* 278, 5993-6001.

24. Suzuki, A., Yoshida, M. and Ozawa, E. (1995) Mammalian alpha 1- and beta 1-syntrophin bind to the alternative splice-prone region of the dystrophin COOH terminus. *J. Cell Biol.,* 128, 373-381.

25. Yang, B., Jung, D., Rafael, J. A., Chamberlain, J. S. and Campbell, K. P. (1995) Identification of alpha-syntrophin binding to syntrophin triplet, dystrophin, and utrophin. *J. Biol. Chem.,* 270, 4975-4978.

26. Yoshida, M., Hama, H., Ishikawa-Sakurai, M., Imamura, M., Mizuno, Y., Araishi, K., Wakabayashi-Takai, E., Noguchi, S., Sasaoka, T. and Ozawa, E. (2000) Biochemical evidence for association of dystrobrevin with the sarcoglycan-sarcospan complex as a basis for understanding sarcoglycanopathy. *Hum. Mol. Genet.,* 9, 1033-1040.

27. Cox, G. A., Sunada, Y., Campbell, K. P. and Chamberlain, J. S. (1994) Dp71 can restore the dystrophin-associated glycoprotein complex in muscle but fails to prevent dystrophy. *Nat. Genet.,* 8, 333-339.

28. Rapaport, D., Greenberg, D. S., Tal, M., Yaffe, D. and Nudel, U. (1993) Dp71, the nonmuscle product of the Duchenne muscular dystrophy gene is associated with the cell membrane. *FEBS Lett.,* 328, 197-202.

29. Judge, L. M., Haraguchiln, M. and Chamberlain, J. S. (2006) Dissecting the signaling and mechanical functions of the dystrophin-glycoprotein complex *J. Cell Sci.,* 119, 1537-1546.

The inclusion of various references herein is not to be construed as any admission by the Applicant that the references constitute prior art. Applicants expressly reserve their right to challenge any allegations of unpatentability of inventions disclosed herein over the references included herein.

Having illustrated and described the principles of the present disclosure, it should be apparent to persons skilled in the art that the disclosure can be modified in arrangement and detail without departing from such principles.

Although the materials and methods of this disclosure have been described in terms of various embodiments and illustrative examples, it will be apparent to those of skill in the art that variations can be applied to the materials and methods described herein without departing from the concept, spirit and scope of the disclosure. All such similar substitutes and modifications apparent to those skilled in the art are deemed to be within the spirit, scope and concept of the disclosure as defined by the appended claims or otherwise disclosed herein.

The invention claimed is:

1. A synthetic nucleic acid molecule encoding a synthetic mini-dystrophin gene or micro-dystrophin gene encoding a synthetic, non-full length dystrophin protein comprising: (i) an N-terminal (NT) domain of the dystrophin protein or a modified N-terminal domain of the dystrophin protein; and (ii) at least two membrane binding motifs (MBM) independently selected from the group consisting of (a) an MBM of an R1-R2 membrane binding domain (MBD), wherein the MBM of R1-R2 comprises a cysteine residue corresponding to the conserved cysteine residue of the S-palmitoylation site peptide of SEQ ID NO: 54, (b) an MBM of an R11-R12 MBD, wherein the MBM of R11-R12 comprises a cysteine residue corresponding to the conserved cysteine residue of the S-palmitoylation site peptide of SEQ ID NO: 57, (c) an MBM of a CR membrane binding domain, and (d) an MBM of a CT membrane binding domain; wherein the domains and the MBM are arranged from N to C terminus in the order in which they occur in a wild-type dystrophin protein and are operably linked.

2. The synthetic nucleic acid molecule of claim 1, wherein the MBM of R1-R2 comprises an at least one S palmitoylation site peptide of SEQ ID NO: 54.

3. The synthetic nucleic acid molecule of claim 1, wherein: (i) R3 repeat or R2-R3 repeats are absent from the non-full length dystrophin protein; or (ii) the R1, R2, R3, R1 and R2, R2 and R3, or R1, R2, and R3 repeats are present in the non-full length dystrophin protein.

4. The synthetic nucleic acid molecule of claim 1, wherein the MBM of R11-R12 comprises an S-palmitoylation site peptide of SEQ ID NO:57.

5. The synthetic nucleic acid molecule of claim 1, wherein: (i) the MBM of the CR membrane binding domain is absent, or (ii) wherein the CR membrane binding domain is absent.

6. The synthetic nucleic acid of claim 1, wherein: (i) at least one domain and at least one MBM are operably linked with a hinge region selected from the group consisting of a synthetic hinge, a semi-synthetic hinge, dystrophin H1, dystrophin H2, dystrophin H3, dystrophin H4, and variants thereof; or (ii) the dystrophin H1 hinge or a variant thereof operably links the C-terminus of the NT domain to the N-terminus of an MBM or domain containing an MBM, wherein the dystrophin H2 hinge or a variant thereof operably links the C-terminus of a MBM or domain containing an MBM to the N-terminus of another MBM or domain containing another MBM, wherein the dystrophin H3 hinge or a variant thereof operably links the C-terminus of an MBM or domain containing an MBM to the N-terminus of another MBM or domain containing another MBM, wherein the dystrophin H4 hinge or a variant thereof operably links the C-terminus of an MBM to the N-terminus of the CR MBM or the CR domain, or any combination thereof.

7. The synthetic nucleic acid molecule of claim 1, wherein: (i) the mini- or micro-dystrophin gene is between 5 kb to about 8 kb in length or less than 5 kb in length, respectively; or (ii) the mini- or micro-dystrophin gene is operably linked to a heterologous promoter, a heterologous 5' untranslated region (UTR), a heterologous 3' UTR, a heterologous polyadenylation site, or any combination thereof.

8. The synthetic nucleic acid molecule of claim 1, wherein said molecule is integrated within an endogenous dystrophin gene locus in an X-chromosome.

9. A lentiviral vector comprising the synthetic nucleic acid molecule of claim 1, wherein the nucleic acid molecule is operably linked to an expression cassette, 5' and 3' long terminal repeats (LTR), and a psi sequence in the lentiviral vector.

10. A single recombinant adeno-associated virus (AAV) vector comprising the nucleic acid of claim 1, wherein said nucleic acid molecule is operably linked to an expression cassette and viral inverted terminal repeats (ITRs) in the AAV.

11. A dual recombinant AAV vector system, comprising two AAV vectors, wherein one of the two AAV vectors comprises a part of the nucleic acid molecule of claim 1, and the other vector comprises the remaining part of said nucleic acid molecule, wherein the two vectors further comprise sequences that permit recombination with each other to produce said nucleic acid in full length, and wherein the nucleic acid in full length is operably linked to an expression cassette and viral ITRs.

12. A composition comprising the synthetic nucleic acid molecule of claim 1 and a pharmaceutically acceptable carrier.

13. The composition of claim 12, wherein: (i) the nucleic acid molecule is operably linked to an expression cassette, 5' and 3' long terminal repeats (LTR), and a psi sequence in a lentiviral vector; or (ii) the nucleic acid molecule is operably linked to an expression cassette and viral inverted terminal repeats (ITRs) in an AAV.

14. An isolated host cell comprising the synthetic nucleic acid molecule of claim 1.

15. The host cell of claim 14, wherein said nucleic acid molecule is integrated within an endogenous dystrophin gene locus in a chromosome of the host cell.

16. The host cell of claim 14, wherein: (i) the nucleic acid molecule is operably linked to an expression cassette, 5' and 3' long terminal repeats (LTR), and a psi element in a lentiviral vector: or (ii) said nucleic acid molecule is operably linked to an expression cassette and ITRs in an AAV.

17. The host cell of claim 14, wherein the host cell is a myogenic stem cell.

18. A method for the treating or ameliorating one or more adverse effects of Duchenne muscular dystrophy (DMD), Becker muscular dystrophy (BMD) or X-linked dilated cardiomyopathy (XLDC) in a subject in need thereof comprising the step of administering to the subject a therapeutically effective amount of the synthetic nucleic acid molecule of claim 1.

19. The method of claim 18, wherein the administration is by injection into muscle or systemic delivery.

20. The method of claim 18, wherein the synthetic nucleic acid is administered via an isolated host cell comprising said synthetic nucleic acid molecule and wherein the host cell is a stem cell or myogenic stem cell.

21. The method of claim 18, wherein the synthetic nucleic acid is administered via an isolated host cell comprising said synthetic nucleic acid molecule and wherein the host cell is derived from an autologous cell of the subject.

22. The method of claim 18, wherein a defective endogenous dystrophin gene of the host cell or a defective portion thereof is edited to provide the synthetic nucleic acid molecule within the host cell's X-chromosome.

23. The method of claim 18, wherein the synthetic nucleic acid molecule is administered via a lentiviral vector comprising the synthetic nucleic acid molecule, and wherein the nucleic acid molecule is operably linked to an expression cassette, 5' and 3' long terminal repeats (LTR), and a psi sequence in the lentiviral vector.

24. The method of claim 18, wherein the synthetic nucleic acid molecule is administered via a single recombinant adeno-associated virus (AAV) vector comprising said synthetic nucleic acid molecule, and wherein said nucleic acid molecule is operably linked to an expression cassette and viral inverted terminal repeats (ITRs) in the AAV.

* * * * *

UNITED STATES PATENT AND TRADEMARK OFFICE

CERTIFICATE OF CORRECTION

| | | |
|---|---|---|
| PATENT NO. | : 11,202,840 B2 | Page 1 of 1 |
| APPLICATION NO. | : 16/311236 | |
| DATED | : December 21, 2021 | |
| INVENTOR(S) | : Dongsheng Duan et al. | |

It is certified that error appears in the above-identified patent and that said Letters Patent is hereby corrected as shown below:

In the Specification

Column 1, Line 19, cancel the text beginning with "This invention was made with government support" to and ending "has certain rights in the invention." in Column 1, Line 23, and insert the following paragraph:
--This invention was made with government support under grant numbers NS090634 and AR067985 awarded by the National Institutes of Health. The government has certain rights in the invention.--

Signed and Sealed this
Fifth Day of July, 2022

Katherine Kelly Vidal

Katherine Kelly Vidal
*Director of the United States Patent and Trademark Office*